US009359407B2

(12) United States Patent
Rikihisa

(10) Patent No.: US 9,359,407 B2
(45) Date of Patent: Jun. 7, 2016

(54) *EHRLICHIA EWINGII* PROTEINS, NUCLEIC ACIDS, AND METHODS OF THEIR USE

(71) Applicant: The Ohio State University Research Foundation, Columbus, OH (US)

(72) Inventor: Yasuko Rikihisa, Worthington, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 14/301,931

(22) Filed: Jun. 11, 2014

(65) Prior Publication Data

US 2014/0341943 A1 Nov. 20, 2014

Related U.S. Application Data

(62) Division of application No. 12/115,490, filed on May 5, 2008, now Pat. No. 8,784,828.

(60) Provisional application No. 61/016,348, filed on Dec. 21, 2007, provisional application No. 60/916,227, filed on May 4, 2007.

(51) Int. Cl.

| | |
|---|---|
| *G01N 33/569* | (2006.01) |
| *A61K 38/04* | (2006.01) |
| *C07K 7/08* | (2006.01) |
| *C07K 14/29* | (2006.01) |
| *A61K 38/00* | (2006.01) |

(52) U.S. Cl.
CPC . *C07K 7/08* (2013.01); *A61K 38/04* (2013.01); *C07K 14/29* (2013.01); *G01N 33/56911* (2013.01); *A61K 38/00* (2013.01); *G01N 2333/29* (2013.01)

(58) Field of Classification Search

CPC .................... G01N 33/56911; G01N 2469/20; G01N 2333/29; G01N 33/54306; G01N 2333/20; G01N 33/54313; G01N 33/54353; G01N 33/54366; G01N 33/54386; G01N 33/54393; G01N 33/558; G01N 33/56983; G01N 33/587; G01N 33/685

See application file for complete search history.

(56) References Cited

U.S. PATENT DOCUMENTS

| | | | |
|---|---|---|---|
| 4,478,914 | A | 10/1984 | Giese |
| 5,401,656 | A | 3/1995 | Dawson et al. |
| 5,413,931 | A | 5/1995 | Dawson et al. |
| 5,789,176 | A | 8/1998 | Dawson et al. |
| 5,869,335 | A | 2/1999 | Munderloh et al. |
| 6,025,338 | A | 2/2000 | Barbet et al. |
| 6,207,169 | B1 | 3/2001 | Reed et al. |
| 6,231,869 | B1 | 5/2001 | Reed |
| 6,306,394 | B1 | 10/2001 | Murphy et al. |
| 6,392,023 | B1 | 5/2002 | Walker |
| 6,432,649 | B1 | 8/2002 | Stich et al. |
| 6,436,399 | B1 | 8/2002 | Rikihisa et al. |
| 6,544,517 | B1 | 4/2003 | Rikihisa et al. |
| 6,893,640 | B2 | 5/2005 | Rikihisa et al. |
| 6,923,963 | B2 | 8/2005 | Rikihisa et al. |
| 7,063,846 | B2 | 6/2006 | Rikihisa et al. |
| 7,183,060 | B2 * | 2/2007 | O'Connor, Jr. ................ 435/7.1 |
| 7,332,171 | B2 * | 2/2008 | Walker et al. ............. 424/234.1 |
| 8,784,828 | B2 | 7/2014 | Rikihisa et al. |
| 2004/0265333 | A1 | 12/2004 | Rikihisa et al. |
| 2009/0155825 | A1 | 6/2009 | Beall |
| 2011/0182925 | A1 | 7/2011 | Krah, III et al. |
| 2014/0162256 | A1 | 6/2014 | Rikihisa et al. |

FOREIGN PATENT DOCUMENTS

| | | |
|---|---|---|
| WO | 98/14584 | 4/1998 |
| WO | 98/16554 | 4/1998 |
| WO | 98/49312 | 11/1998 |
| WO | 99/13720 | 3/1999 |
| WO | 99/52370 | 10/1999 |
| WO | 00/32745 | 6/2000 |
| WO | 01/58466 | 8/2001 |
| WO | 01/80897 | 11/2001 |
| WO | 2008/112007 | 9/2008 |
| WO | 2008/137881 | 11/2008 |
| WO | 2010/126993 | 11/2010 |
| WO | 2014/089061 | 6/2014 |

OTHER PUBLICATIONS

Frutos, et al., "Comparative Genomic Analysis of Three Strains of *Ehrlichia ruminantium* Reveals an Active Process of Genome Size Plasticity," Journal of Bacteriology, vol. 188, No. 7, 2006, pp. 2533-2542.

Hotopp, et al., "Comparative Genomics of Emerging Human Ehrlichiosis Agents," Public Library of Science Genetics, vol. 2, Issues e21, 2006, pp. 208-223.

Philipp, et al., "A Decline in C6 Antibody Titer Occurs in Successfully Treated Patients with Culture-Confirmed Early Localized or Early Disseminated Lyme Borreliosis," Clinical and Diagnostic Laboratory Immunology, vol. 12, No. 9, 2005, pp. 1069-1074.

International Search Report and Written Opinion, dated Mar. 10, 2014, in connection with related International Application No. PCT/US2013/072850.

(Continued)

*Primary Examiner* — Padma V Baskar

(74) *Attorney, Agent, or Firm* — Meunier Carlin & Curfman LLC

(57) ABSTRACT

The novel omp-1 gene cluster encoding twenty one *Ehrlichia ewingii* (EE) proteins was isolated and sequenced completely. This invention relates to isolated *E. ewingii* (EE) polypeptides, isolated polynucleotides encoding EE polypeptides, probes, primers, isolated antibodies and methods of their production, immunogenic compositions and vaccines, as well as methods of using the EE polypeptides, antibodies, probes, and primers for the purpose of diagnosis, therapy and production of vaccines against *E. ewingii.*

27 Claims, 16 Drawing Sheets

(56) References Cited

OTHER PUBLICATIONS

Adelman et al., In Vitro Deletional Mutagenesis for Bacterial production of the 20,000-Dalton Form of Human Pituitary Growth Hormone, DNA 2:183-193 (1983).
Anderson et al. Ehrlichia ewingii sp. nov., the etiologic agent of canine granulocytic ehrlichiosis. Int J Syst Bacteriol. Apr. 1992;42(2):299-302.
Anziani et al., Experimental transmission of a granulocytic form of the tribe Ehrlichieae by Dermacentor variabilis and Amblyomma americanum to dogs, Am. J. Vet. Res., 151(6):929-931 (1990).
Altschul et al., Basic Local Alignment Search Tool, J. Mol. Biol. 215:403-410 (1990).
Bagos et al., PRED-TMBB: a web server for predicting the topology of β-barrel outer membrane proteins, Nucleic Acids Res 32:W400-W404 (2004).
Buller et al. Ehrlichia ewingii, a newly recognized agent of human ehrlichiosis. N. Engl J Med. Jul. 15, 1999;341(3):148-55.
Chen et al., Identification of a granulocytotropic Ehrlichia species as the etiologic agent of human disease, J. Clin. Microbiol., 32:589-595 (1994).
Crea et al., Chemical synthesis of genes for human insulin, Proc. Natl. Acad. Sci. (USA), 75:5765-5769 (1978).
Crocquet-Valdes et al. Analysis of ehrlichial p28 gene expression in a murine model of persistent infection. Ann N Y Acad Sci. 2005 1063:420-4.
Dawson et al., Serologic Diagnosis of Human Ehrlichiosis Using Two Ehrlichia canis Isolates, J. Infectious Disease, 163:564-567 (1991).
Dhingra et al., ASAP: Amplification, sequencing & annotation of plastomes, BMC Genomics, 6:176 (2005).
Dumler et al. Ehrlichioses in humans: epidemiology, clinical presentation, diagnosis, and treatment. Clin Infect Dis. Jul. 15. 2007;45 Suppl 1:S45-51.
Eremeeva et al., Differentiation among spotted fever group rickettsiae species by analysis of restriction fragment length polymorphism of PCR-amplified DNA, J. Clin. Microbial., 32:803-810 (1994).
Ewing et al. A new strain of Ehrlichia canis. J Am Vet Med Assoc. 1971 159(12):1771-4.
GenBank Accession No. AF287961 2001.
GenBank Accession No. AF287962 2001.
GenBank Accession No. AF287963 2001.
GenBank Accession No. AF287964 2001.
GenBank Accession No. AF287966 2001.
GenBank Accession No. DQ365879 2006.
GenBank Accession No. DQ902688 2007.
GenBank Accession No. EF116932 2008.
Goldman et al., Granulocytic Ehrlichiosis in Dogs from North Carolina and Virginia, J. Vet. Intern. Med., 12:61-70 (1998).
Gusa et al., Identification of a p28 Gene in Ehrlichia ewingii: Evaluation of Gene for Use as a Target for a Species-Specific PCR Diagnostic Assay, J. Clin. Microbiol., 39(11):3871-3876 (2001).
Heerden et al. Characterization of a major outer membrane protein multigene family in Ehrlichia ruminantium. Gene. 2004 330:159-68.
Holmes, PMSA specific antibodies and their diagnostic and therapeutic use, Exp. Opin. Invest. Drugs, 10(3):511-519 (2001).
International Search Report for PCT/US2008/062714, mailed Jan. 19, 2009.
Kawahara et al., Characterization of Ehrlichial Organisms Isolated from a Wild Mouse, J. Clin. Microbial., 31(1):89-96 (1993).
Lederman et al., A single amino acid substitution in a common African allele of the CD4 molecule ablates binding of the monoclonal antibody, OKT4, Mol. Immunol., 28(11):1171-1181 (1991).
Li et al., β-Endorphin omission analogs: Dissociation of immunoreactivity from other biological activities, Proc. Natl. Acad. Sci. United States, 77(6):3211-3214 (1980).
Lidell et al. Predominance of Ehrlichia ewingii in Missouri dogs. J Clin Microbiol. 2003 41(10):4617-22.
Liu et al., Chimeric mouse-human IgG1 antibody that can mediate lysis of cancer cells, Proc. Natl. Acad. Sci. USA, 84:3439-3443 (1987).
Logan et al., The development of Cowdria Ruminantium in neutrophils, Onderstepoort J. Vet. Res., 54(3):197-204 (1987).
Mavromatis et al., The Genome of the Obligately Intracellular Bacterium Ehrlichia canis Reveals Themes of Complex Membrane Structure and Immune Evasion Strategies, J. Bacteriol., 188(11):4015-4023 (2006).
Ndip et al. Ehrlichial infection in Cameroonian canines by Ehrlichia canis and Ehrlichia ewingii. Vet Microbiol. Nov. 30, 2005;111(1-2):59-66. Epub Sep. 21, 2005.
Neer et al., Consensus Statement on Ehrlichial Disease of Small Animals from the Infectious Disease Study Group of the ACVIM, J. Vet. Intern. Med., 16:309-315 (2002).
Ohashi et al., Immunodominant Major Outer Membrane Proteins of Ehrlichia chaffeensis Are Encoded by a Polymorphic Multigene Family, Infection and Immunity, 66(1):132-139 (1998).
Ohashi et al., Analysis of Transcriptionally Active Gene Clusters of Major Outer Membrane Protein Multigene Family in Ehrlichia canis and E. chaffeensis, Infection and Immunity, 69(4):2083-2091 (2001).
Rikihisa et al. Analyses of Ehrlichia canis and a canine granulocytic Ehrlichia infection. J Clin Microbiol. Jan. 1992;30(1):143-8.
Rikihisa et al. Western immunoblot analysis of Ehrlichia chaffeensis, E. canis, or E. ewingii infections in dogs and humans. J Clin Microbiol. Sep. 1994;32(9):2107-12.
Rikihisa et al. Molecular characterization of Aegyptianella pullorum (Rickettsiales, Anaplasmataceae). J Clin Microbiol. Nov. 2003;41(11):5294-7.
Ohashi et al., Cloning and Characterization of Multigenes Encoding the Immunodominant 30-Kilodalton Major Outer Membrane Proteins of Ehrlichia canis and Application of the Recombinant Protein for Serodiagnosis, J. Clin. Microbiol., 36(9):2671-2680 (1998).
Rutherford et al., Artemis: Sequence Visualization and Annotation, Bioinformatics, 16(10):944-945 (2000).
Stockham et al., Evaluation of granulocytic ehrlichiosis in dogs of Missouri, including serologic status to Ehrlichia canis, Ehrlichia equi, and Borrelia burgdorferi, Am. J. Vet. Res., 53(1):63-68 (1992).
Stockham et al., Experimental Transmission of Granulocytic Ehrlichial Organisms in Dogs, Vet. Clinical Pathology, 19(4):99-104 (1990).
Uilenberg, Heartwater (Cowdria ruminatium Infection): Current Status, Advances in Vet. Sci. and Comparative Med., 27:427-480 (1983b).
Ulmanen et al., Transcription and translation of foreign genes in Bacillus subtilis by the aid of a secretion vector, J. Bacteriol., 162(1):176-182 (1985).
Unver et al., Western and Dot Blotting Analyses of Ehrlichia chaffeensis Indirect Fluorescent-Antibody Assay-Positive and—Negative Human Sear by Using Native and Recombinant, J. of Clinical Microbiol., 37(12):3888-3895 (1999).
Van Heerden et al., Characterization of a major outer membrane protein multigene family in Ehrlichia ruminantium, Gene, 330:159-168 (2004).
Vieira et al., Production of Singe-Stranded Plasid DNA, Meth. Enzymol., 153:3-11 (1987).
Yabsley et al. Ehrlichia ewingii infection in white-tailed deer (Odocoileus virginianus) Emerg Infect Dis. Jul. 2008;8(7):668-71.
Aguero-Rosenfeld, M.E., et al., "Human Granulocytic Ehrlichiosis: A Case Series from a Medical Center in New York State," Annals of Internal Medicine, vol. 125, Issue 11, 1996, pp. 904-908.
Aguero-Rosenfeld, M.E., et al., "Serology of Culture-Confirmed Cases of Human Granulocytic Ehrlichiosis," J Clin Microbiol, vol. 38, 2000, pp. 635-638.
Aguirre, D.H., et al., "Transmission of Anaplasma marginale with Adult Boophilus Microplus ticks Fed as Nymphs on Calves with Different Levels of Rickettsaemia," Parasite, vol. 1, 1994, pp. 405-407.
Alberti, A., et al., "Equine and Canine Anaplasma phagocytophilum Strains Isolated on the Island of Sardinia (Italy) Are Phylogenetically Related to Pathogenic Strains from the United States," Appl Environ Microbiol, vol. 71, 2005, pp. 6418-6422.
Alleman, A.R., et al., "Anaplasma marginale Major Surface Protein 3 Is Encoded by a Polymorphic Multigene Family," Infection and Immunity, vol. 65, No. 1, 1997, pp. 156-163.

(56) References Cited

OTHER PUBLICATIONS

Anderson, B.E., et al., "*Ehrlichia chaffeensis*, a New Species Associated with Human Ehrlichiosis," Journal of Clinical Microbiology, vol. 29, No. 12, Dec. 1991, pp. 2838-2842.
Anderson, B.E., et al., "*Amblyomma Americanum*: A Potential Vector of Human Ehrlichiosis," Am. J. Trop. Med. Hyg, vol. 49, No. 2, 1993, pp. 239-244.
Asanovich, K.M., et al., "Antigenic Diversity of Granulocytic *Ehrlichia* isolates from Humans in Wisconsin and New York and a Horse in California," J. Infect Dis., vol. 176, 1997, pp. 1029-1034.
Bakken, J.S., et al., "Clinical and Laboratory Characteristics of Human Granulocytic Ehrlichiosis," Journal of the American Medical Association, vol. 275, No. 3, 1996, pp. 199-205.
Bakken, J.S., et al., "Serological Evidence of Human Granulocytic Ehrlichiosis in Norway," Eur. J. Clin. Microbiol. Infect. Dis., vol. 15, No. 10, 1996, pp. 829-832.
Barbet, A.F., "Recent developments in the molecular biology of anaplasmosis," Veterinary Parasitology, vol. 57, 1995, pp. 43-49.
Barbet, A.F., et al., "Antigenic Variation of *Anaplasma marginale* by Expression of MSP2 Mosaics," Infect Immun, vol. 68, No. 11, 2000, pp. 6133-6138.
Barbet, A.F., et al., "Antigenic variation of *Anaplasma marginale*: Major Surface Protein 2 Diversity during Cyclic Transmission between Ticks and Cattle," Infect Immun, vol. 69, No. 5, 2001, pp. 3057-3066.
Barbet, A.F., et al., "Expression of Multiple Outer Membrane Protein Sequence Variants from a Single Genomic Locus of *Anaplasma phagocytophilum*," Infect Immun, vol. 71, No. 4, 2003, pp. 1706-1718.
Barbet, A.F., et al., "Identification of functional promoters in the *msp2* expression loci of *Anaplasma marginale* and *Anaplasma phagocytophilum*," Gene, vol. 353, 2005, pp. 89-97.
Barbet, A.F., et al., "Structure of the Expression Site Reveals Global Diversity in MSP2 (P44) Variants in *Anaplasma phagocytophilum*," Infect and Immun, vol. 74, No. 11, 2006, pp. 6429-6437.
Barbour, A.G., "Antigenic Variation of a Relapsing Fever *Borrelia* species," Annu. Rev. Microbiol., vol. 44, 1990, pp. 155-171.
Bollon, A.P., "DNA Transformation Efficiency of Various Bacterial and Yeast Host-Vector Systems," Journal of Clinical Hematology and Oncology, vol. 10, Nos. 2 and 3, Apr.-Jul., 1980, pp. 39-48.
Brayton, K.A., et al., "Antigenic variation of *Anaplasma marginale* msp2 occurs by combinatorial gene conversion," Mol Microbiol, vol. 43, No. 5, 2002, pp. 1151-1159.
Brayton, K.A., et al., "Complete genome sequencing of *Anaplasma marginale* reveals that the surface is skewed to two superfamilies of outer membrane proteins," Proc Natl Acad Sci U.S.A., vol. 102, 2005, pp. 844-849.
Breitschwerdt, E.B., et al., "Doxycycline Hyclate Treatment of Experimental Canine Ehrlichiosis Followed by Challenge Inoculation with Two *Ehrlichia canis* Strains," Antimicrobial Agents and Chemotherapy, vol. 42, No. 2, Feb. 1998, pp. 362-368.
Breitschwerdt, E.B., et al., "Sequential Evaluation of Dogs Naturally Infected with *Ehrlichia canis, Ehrlichia chaffeensis, Ehrlichia equi, Ehrlichia ewingii*, or *Bartonella vinsonii*," Journal of Clinical Microbiology, vol. 36, No. 9, Sep. 1998, pp. 2645-2651.
Bremer, W.G., et al., "Transstadial and intrastadial experimental transmission of *Ehrlichia canis* by male *Rhipicephalus sanguineus*," Veterinary Parasitology, vol. 131, 2005, pp. 95-105.
Broach, J.R., "The Yeast Plasmid 2μ Circle," Cell, vol. 28, Feb. 1982, pp. 203-204.
Brouqui, P., et al., "Antigenic characterization of ehrlichiae: protein immunoblotting of *Ehrlichia canis, Ehrlichia sennetsu*, and *Ehrlichia risticii*," Journal of Clinical Microbiology, vol. 30, No. 5, 1992, pp. 1062-1066.
Brouqui, P., et al., "Serologic Diagnosis of Human Monocytic Ehrlichiosis by Immunoblot Analysis," Clinical and Diagnostic Laboratory Immunology, vol. 1, No. 6, 1994, pp. 645-649.
Brouqui, P., et al., "Human granulocytic ehrlichiosis in Europe," The Lancet, vol. 346, 1995, pp. 782-783.
Brown, G.K., et al., "Detection of *Ehrlichia platys* in dogs in Australia," Aust Vet J, vol. 79, 2001, pp. 554-558.
Buck, G.A., et al., "Design Strategies and Performance of Custom DNA Sequencing Primers," Biotechniques, vol. 27, No. 3, Sep. 1999, pp. 528-536.
Cardoso, L., et al., "Molecular detection of *Anaplasma platys* and *Ehrlichia canis* in dogs from the North of Portugal," Vet J., vol. 183, Issue 2, Feb. 2010, pp. 232-233.
Carver, T.J., et al., "ACT: the Artemis comparison tool," Bioinformatics, vol. 21, No. 16, 2005, pp. 3422-3423.
Chaichanasiriwithaya, W., et al., "Antigenic, Morphologic, and Molecular Characterization of new *Ehrlichia resiticii* Isolates," Journal of Clinical Microbiology, vol. 38, No. 12, 1994, pp. 3026-3033.
Chang, W.L., et al., "Specific Amplification of *Ehrlichia platys* DNA from Blood Specimens by Two-Step PCR," J Clin Microbiol, vol. 34, No. 12, 1996, pp. 3142-3146.
Chen, S.M., et al., "Analysis and Ultrastructure Localization of *Ehrlichia chaffeensis* Proteins with Monoclonal Antibodies," Am J Trop Med Hyg, vol. 54, No. 4, 1996, pp. 405-412.
Chen, S.M., et al., "Antigenic Diversity Among Strains of *Ehrlichia chaffeensis*," Proceedings of the International Symposium of Rickettsiae and Rickettsial Diseases, Slovak Academy of Sciences, Sep. 1-6, 1996, pp. 329-334.
Chen, S.M., et al., Genetic and Antigenic Diversity of *Ehrlichia chaffeensis*: Comparative Analysis of a Novel Human Strain from Oklahoma and Previously Isolated Strains, J. Infect. Dis., vol. 175, Apr. 1997, pp. 856-863.
Chen, S.M., et al., "Western Immunoblotting Analysis of the Antibody Responses of Patients with Human Monocytotropic Ehrlichiosis to Different Strains of *Ehrlichia chaffeensis* and *Ehrlichia canis*," Clinical and Diagnostic Laboratory Immunology, vol. 4, No. 6, Nov. 1997, pp. 731-735.
Coughlin, R.T., et al., "Transmission, Isolation, and Cultivation of Granulocytic *Ehrlichia* Resulting from Infection of Dogs by Adult *Ixodes scapularis* Collected from Eastern United States," Abstract 52 In Abstracts of 21$^{st}$ Semi-annual meeting of the American Society for Rickettsiology and Rickettsial diseases, Albany, NY, 1996, one page.
Crea, R., et al., "Chemical synthesis of genes for human insulin," Proc. Natl. Acad. Sci. USA, vol. 75, No. 12, 1978, pp. 5765-5769.
Dawson, J.E., et al., "Isolation and Characterization of an *Ehrlichia* sp. from a Patient Diagnosed with Human Ehrlichiosis," Journal of Clinical Microbiology, vol. 29, No. 12, Dec. 1991, pp. 2741-2745.
Dawson, J.E., et al., "Ehrlichia-like 16S rDNA Sequence from Wild White-Tailed Deer (*odocoileus virginianus*)," J. Parasitol., vol. 82, No. 1, 1996, pp. 52-58.
Dawson, J.E., et al., "Polymerase chain reaction evidence of *Ehrlichia chaffeensis*, an etiologic agent of human ehrlichiosis, in dogs from southeast Virginia," Am. J. Vet. Res., vol. 57, No. 8, 1996, pp. 1175-1179.
Dawson, J.E., et al., "The Interface Between Research and the Diagnoses of an Emerging Tick-borne Disease, Human Ehrlichiosis Due to *Ehrlichia chaffeensis*," Archives of Journal of Medicine, vol. 156, No. 2, 1996, pp. 137-142.
Dumler, J.S., et al., "Isolation and Characterization of a New Strain of *Ehrlichia chaffeensis* from a Patient with Nearly Fatal Monocytic Ehrlichiosis," Journal of Clinical Microbiology, vol. 33, No. 7, Jul. 1995, pp. 1704-1711.
Dumler, J.S., et al., "Serologic Cross-Reactions among *Ehrlichia equi, Ehrlichia phagocytophila*, and Human Granulocytic Ehrlichia," J Clin Microbiol, vol. 33, No. 5, 1995, pp. 1098-1103.
Dumler, J.S., et al., "Human Granulocytic Ehrlichiosis in Wisconsin and Minnesota: A Frequent Infection with the Potential for Persistence," Journal of Infectious Diseases, vol. 173, 1996, pp. 1027-1030.
Dumler, J.S., et al., "Reorganization of genera in the families *Rickettsiaceae* and *Anaplasmataceae* in the order *Rickettsiales*: unification of some species of *Ehrlichia* with *Anaplasma, Cowdria* with *Ehrlichia* and *Ehrlichia* with *Neorickettsia*, descriptions of six new species combinations and designation of *Ehrlichia equi* and 'HE agent' as subjective synonyms of *Ehrlichia phagocytophila*," Int J Syst Evol Microbiol, vol. 51, 2001, pp. 2145-2165.
Eid, G., et al., "Expression of Major Surface Protein 2 Antigenic Variants during Acute *Anaplasma marginale* Rickettsemia," Infect and Immun, vol. 64, No. 3, 1996, pp. 836-841.

(56) References Cited

OTHER PUBLICATIONS

EMBL Accession No. AY040556, Anaplasma central clone 337 major surface protein-2 gene, complete cds. 1203 bps sequence, Feb. 5, 2002, retrieved from the internet at http://www.ebi.ac.uk/Tools/dbfetch/dbfetch?db=embl&id=AY040556&f.. on Sep. 10, 2012, pp. 2-3.

EMBL Accession No. DQ363749, Anaplasma central RecJ gene, partial cds. 4219 bps sequence, Feb. 12, 2006, retrieved from the internet at http:www.ebi.ac.uk/Tools/dbfetch/dbfetch?db=embl&id=DQ363749&f.. on Sep. 10, 2012, pp. 2-3.

Emini, E.A., et al., "Induction of Hepatitis: A Virus-Neutralizing Antibody by a Virus-Specific Synthetic Peptide," Journal of Virology, vol. 55, No. 3, 1985, pp. 836-839.

Eng, T.R., et al., "Epidemiologic, Clinical, and Laboratory Findings of Human Ehrlichiosis in the United States, 1988," JAMA, vol. 264, 1990, pp. 2251-2258.

Eremeeva, M., et al., "Differentiation among Spotted Fever Group Rickettsiae Species by Analysis of Restriction Fragment Length Polymorphism of PCR-Amplified DNA," Journal of Clinical Microbiology, vol. 32, No. 3, 1994, pp. 803-810.

Ewing, S.A., et al., "Human Infection with *Ehrlichia canis*," The New England Journal of Medicine, vol. 317, No. 14, Oct. 1, 1987, pp. 899-900.

Ewing, S.A., et al., "Experimental Transmission of *Ehrlichia chaffeensis* (Rickettsiales: Ehrlichieae) Among White-Tailed Deer by *Amblyomma americanum* (Acari: lsodidae)," Journal of Medical Entomology, vol. 32, No. 3, May, 1995, pp. 368-374.

Ewing, S.A., et al., "Dogs Infected with a Human Granulocytotropic *Ehrlichia* spp. (Rickettsiales: Ehrlichieae)," Journal of Medical Entomology, vol. 34, No. 6, 1997, pp. 710-718.

Felek, S., et al., "Transcriptional Analysis of *p30* Major Outer Membrane Protein Genes of *Ehrlichia canis* in Naturally Infected Ticks and Sequence Analysis of *p30-10* of *E. Canis* from Diverse Geographic Regions," Journal of Clinical Microbiology, vol. 41, No. 2, Feb. 2003, pp. 886-888.

Felek, S., et al., "Sequence Analysis of *p44* Homologs Expressed by *Anaplasma phagocytophilum* in Infected Ticks Feeding on Naïve Hosts and in Mice Infected by Tick Attachment," Infect and Immun, vol. 72, No. 2, 2004, pp. 659-666.

Felsenstein, J., "Phylip-Phylogeny Inference Package (version 3.2)," Cladistics, vol. 5, 1989, pp. 164-166.

Ferreira, R.F., et al., "*Anaplasma platys* Diagnosis in Dogs: Comparison Between Morphological and Molecular Tests," Intern J Appl Res Vet Med, vol. 5, 2007, pp. 113-119.

French, T.W., et al., "Serologic diagnosis of infectious cyclic thrombocytopenia in dogs using an indirect fluorescent antibody test," Am J Vet Res, vol. 44, 1983, pp. 2407-2411.

French, D.M., et al., "Expression of *Anaplasma marginale* Major Surface Protein 2 Variants during Persistent Cyclic Rickettsemia," Infect Immun, vol. 66, No. 3, 1998, pp. 1200-1207.

Ganta, R.R., et al., "Differential Clearance and Immune Responses to Tick Cell-Derived versus Macrophage Culture-Derived *Ehrlichia chaffeensis* in Mice," Infect Immun, vol. 75, No. 1, 2007, pp. 135-145.

Gilman, M.Z., et al., "Isolation of sigma-28-specific promoters from *Bacillus subtilis* DNA," Gene, vol. 32, 1984, pp. 11-20.

Gold, L., et al., "Translational Initiation in Prokaryotes," Ann. Rev. Microbiol., vol. 35, 1981, pp. 365-403.

Goodman, J.L., et al., Direct Cultivation of the Causative Agent of Human Granulocytic Ehrlichiosis, The New England Journal of Medicine, vol. 334, No. 4, 1996, pp. 209-215.

Greig, B., et al., "Geographic, Clinical, Serologic, and Molecular Evidence of Granulocytic Ehrlichiosis, a Likely Zoonotic Disease, in Minnesota and Wisconsin dogs," J Clin Microbiol, vol. 34, No. 1, 1996, pp. 44-48.

Grover, D.L., et al., "Detection of *Ehrlichia canis* in *Rhipicephalus sanguineus* with a p30—based PCR Assay," 79th Conference of Research Workers in Animal Diseases, Chicago, Illinois, Nov. 7-9, 1999.

Groves, M.G., "Transmission of *Ehrlichia canis* to Dogs by Ticks (*Rhipicephalus sanguineus*)," Am J Vet Res, vol. 36, No. 7, Jul. 1975, pp. 937-940.

Haas, R., et al., "The Repertoire of Silent Pilus Genes in *Neisseria gonorrhoeae*; Evidence for Gene Conversion," Cell, vol. 44, 1986, pp. 107-115.

Hair, J.A., et al., "Behavioral ecology of *Amblyomma americanum*," Chapter 18, Morphology, Physiology, and Behavioral Biology of Ticks, Ellis Horwood Limited, 1986, pp. 406-427.

Hamer, D.H., et al., "Regulation In Vivo of a Coned Mammalian Gene: Cadmium Induces the Transcriptio of a Mouse Metallothionein Gene in SV40 Vectors," Journal of Molecular and Applied Genetics, vol. 1, 1982, pp. 273-288.

Hardalo, C.J., et al., "Human Granulocytic Ehrlichiosis in Connecticut: Report of a Fatal Case," Clinical Infectious Diseases, vol. 21, 1995, pp. 910-914.

Harlow, E., "Antibodies: A Laboratory Manual," Cold Spring Harbor Laboratory, 1988, 152 pages.

Harvey, J.W., et al., "Cyclic thrombocytopenia induced by a Rickettsia-like agent in dogs," J Infect Dis, vol. 137, 1978, pp. 182-188.

Heberling, R.L., et al., "Rapid Dot-Immunobinding Assay on Nitrocellulose for Viral Antibodies," Journal of Clinical Microbiology, vol. 23, No. 1, 1986, pp. 109-113.

Hildebrandt, P.K., "Pathology of Canine Ehrlichiosis (Tropical Canine Pancytopenia)," Am. J. Vet. Res., vol. 34, No. 10, Oct. 1973, pp. 1309-1320.

Hodzic, E., et al., "Acquisition and Transmission of the Agent of Human Granulocytic Ehrlichiosis by *Ixodes scapularis* Ticks," Journal of Clinical Microbiology, vol. 36, No. 12, Dec. 1998, pp. 3574-3578.

Hsieh, T., et al., "Changes in Expression of the 44-Kilodalton Outer Surface Membrane Antigen (*p44* kD) for Monitoring Progression of Infection and Antimicrobial Susceptibility of the Human Granulocytic Ehrlichiosis (HGE) agent in HL-60 Cells," Biochem Biophys Res Commun, vol. 257, 1999, pp. 351-355.

Hua, P., et al., "Canine Ehrlichiosis Caused Simultaneously by *Ehrlichia canis* and *Ehrlichia platys*," Microbiol Immunol, vol. 44, No. 9, 2000, pp. 737-739.

Huang, H., et al., "Prevalence and Molecular Analysis of *Anaplasma platys* from Dogs in Lara, Venezuela," Brazilian J. Microbiol, vol. 36, 2005, pp. 211-216.

Huang, H., et al., "Porin Activity of *Anaplasma phagocytophilum* Outer Membrane Fraction and Purified P44," J Bacteriol, vol. 189, No. 5, 2007, pp. 1998-2006.

IJdo, J.W., et al., "The Early Humoral Response in Human Granulocytic Ehrlichiosis," The Journal of Infectious Diseases, vol. 176, 1997, pp. 687-692.

IJdo, J.W., et al., "Cloning of the Gene Encoding the 44-Kilodalton Antigen of the Agent of Human Granulocytic Ehrlichiosis and Characterization of the Humoral Response," Infection and Immunity, vol. 66, No. 7, 1998, pp. 3264-3269.

ljdo, J.W., et al., "Serodiagnosis of Human Granulocytic Ehrlichiosis by a Recombinant HGE-44-Based Enzyme-Linked Immunosorbent Assay," J Clin Microbiol, vol. 37, No. 11, 1999, pp. 3540-3544.

Inokuma, H., et al., "Detection of *Ehrlichia platys* DNA in Brown Dog Ticks (*Rhipicephalus sanguineus*) in Okinawa Island, Japan," J Clin Microbiol, vol. 38, No. 11, 2000, pp. 4219-4221.

Inokuma, H., et al., "Demonstration of *Anaplasma* (*Ehrlichia*) *platys* inclusions in peripheral blood platelets of a dog in Japan," Vet Parasitol, vol. 110, 2002, pp. 145-152.

Inokuma, H., et al., "Determination of the Nucleotide Sequences of Heat Shock Operon *groESL* and the Citrate Synthase Gene (*gitA*) of *Anaplasma* (*Ehrlichia*) *platys* for Phylogenetic and Diagnostic Studies," Clin Diagn Lab Immunol, vol. 9, No. 5, 2002, pp. 1132-1136.

lqbal, Z., et al., "Application of the polymerase chain reaction for the detection of *Ehrlichia canis* in tissues of dogs," Veterinary Microbiology, vol. 42, 1994, pp. 281-287.

lqbal, Z., et al., "Comparison of PCR with Other Tests for Early Diagnosis of Canine Ehrlichiosis," Journal of Clinical Microbiology, vol. 32, No. 7, Jul. 1994, pp. 1658-1662.

lqbal, Z., et al., "Reisolation of *Ehrlichia canis* from Blood and Tissues of Dogs after Doxycycline Treatment," Journal of Clinical Microbiology, vol. 32, No. 7, Jul. 1994, pp. 1644-1649.

(56) References Cited

OTHER PUBLICATIONS

Jameson, B.A., et al., "The antigenic index: a novel algorithm for predicting antigen determinants," CABIOS, vol. 4, No. 1, 1988, pp. 181-186.
Jeanteur, D., et al., "The bacterial porin superfamily: sequence alignment and structure prediction," Mol Microbiol, vol. 5, No. 9, Sep. 1991, pp. 2153-2164.
Kelly, P.J., et al., "Serological evidence for antigenic relationships between *Ehrlichia canis* and *Cowdria ruminatium*," Research in Veterinary Science, vol. 56, No. 2, 1994, pp. 170-174.
Kim, H.Y., et al., "Characterization of monoclonal antibodies to the 44-kilodalton major outer membrane protein of the human granulocytic ehrlichiosis agent," J Clin Microbiol, vol. 36, 1998, pp. 3278-3284.
Kocan, K.M., et al., "Persistence of *Anaplasma marginale* Rickettsiales: Anaplasmataceae) in Male *Dermacentor andersoni* (Acari: Ixodidae) Transferred Successively from Infected to Susceptible Calves," Journal of Medical Entomology, vol. 29, No. 4, Jul. 1992, pp. 657-668.
Kocan, K.M., et al., "Development of *Anaplasma marginale* in male *Dermacentor andersoni* transferred from parasitemic to susceptible cattle," Am J Vet Res, vol. 53, No. 4, Apr. 1992, pp. 499-507.
Kocan, K.M., et al., "Development of *Anaplasma marginale* in salivary glands of male *Dermacentor andersoni*," Am J Vet Res, vol. 54, No. 1, Jan. 1993, pp. 107-112.
Koehler, J.E., et al., "Overexpression and surface localization of the *chlamydia trachomatis* major outer membrane protein in *Escherichia coli*," Molecular Microbiology, vol. 6, No. 9, 1992, pp. 1087-1094.
Kuehn, N. F., et al., "Clinical and hematologic findings in canine ehrlichiosis," Journal of the American Veterinary Medical Association, vol. 186, No. 4, Feb. 1985, pp. 355-358.
Kumagai, Y., et al., "Expression and Porin Activity of P28 and OMP-1F during Intracellular *Ehrlichia chaffeensis* Development," J Bacteriol, vol. 190, No. 10, 2008, pp. 3597-3605.
Kyte, J., et al., "A Simple Method for Displaying the Hydropathic Character of a Protein," J. Mol. Biol., vol. 157, 1982, pp. 105-132.
Lewis, G.E., "The Brown Dog Tick *Rhipicephalus sanguineus* and the Dog as Experimental Hosts of *Ehrlichia canis*," Dec. 1977, Am J Vet Res, vol. 38, No. 12, pp. 1953-1955.
Lin, Q., et al., "Analysis of Sequences and Loci of *p44* Homologs Expressed by *Anaplasma phagocytophila* in Acutely Infected Patients," J Clin Microbiol, vol. 40, No. 8, 2002, pp. 2981-2988.
Lin, Q., et al., "Mechanisms of Variable *p44* Expression by *Anaplasma phagocytophilum*," Infect Immun, vol. 71, No. 10, 2003, pp. 5650-5661.
Lin, Q., et al., "Establishment of Cloned *Anaplasma phagocytophilum* and Analysis of *p44* Gene Conversion within an Infected Horse and Infected SCID Mice," Infect Immun, vol. 73, No. 8, 2005, pp. 5106-5114.
Lin, Q., et al., "Analysis of Involvement of the RecF Pathway in a *p44* Recombination in *Anaplasma phagocytophilum* and in *Escherichia coli* by Using a Plasmid Carrying the *p44* Expression and *p44* Donor Loci," Infect Immun, vol. 74, No. 4, 2006, pp. 2052-2062.
Lockhart, J.M., "Site-Specific Geographic Association Between *Amblyomma americanum* (Acari: Ixodidae) and *Ehrlichia chaffeensis*-Reactive (Rickettsiales: Ehrlichieae) Antibodies in White-Tailed Deer," J. Med. Entomology, vol. 33, No. 1, 1996, pp. 153-158.
Madigan, J.E., "Transmission and Passage in Horses of the Agent of Human Granulocytic Ehrlichiosis," Journal of Infectious Diseases, vol. 172, 1995, pp. 1141-1144.
Madigan, J.E., et al., "Equine Granulocytic Ehrlichiosis in Connecticut Caused by an Agent Resembling the Human Granulocytotropic Ehrlichia," Journal of Clinical Microbiology, vol. 34, No. 2, 1996, pp. 434-435.
Maeda, M.D., K., et al., "Human Infection with *Ehrlichia canis*, a Leukocytic Rickettsia," N. Engl. J. Med., vol. 316, 1987, pp. 853-856.
Mahan, S.M., et al., "An immunoblotting diagnostic assay for heartwater based on the immunodominant 32-kilodalton protein of *Cowdria ruminantium* detects false positive in the field sera," Journal of Clinical Microbiology, vol. 31, No. 10, 1993, pp. 2729-2737.
Maniatis, T., "Recombinant DNA Procedures in the Study of Eukaryotic Genes," Cell Biology, vol. 3, 1980, pp. 564-608.
Mathew, J.S., et al., "Characterization of a new isolate of *Ehrlichia platys* (Order *Rickettsiales*) using electron microscopy and polymerase chain reaction," Vet Parasitol, vol. 68, 1997, pp. 1-10.
Mathew, J.S., et al., "Efficacy of a modified polymerase chain reaction assay for detection of *Ehrlichia canis* infection," J Vet Diagn Invest, vol. 12, 2000, pp. 456-459.
Matthewman, L.A., et al., "Reactivity of sera collected from dogs in Mutare, Zimbabwe, to antigens of *ehrlichia canis* and *cowdria ruminantium*," The Veterinary Record, vol. 134, No. 19, May 7, 1994, pp. 498-499.
McBride, J.W., et al., "Molecular characterization of a new 28-kilodalton protein gene and a multigene locus encoding five homologous 28-kilodalton immunodominant outer member proteins of *Ehrlichia canis*," Chapter 1, Rickettsiae and Rickettsial Diseases at the Turn of the Third Millennium, 1999, pp. 43-47.
McBride, J.W., et al., "Molecular Cloning of the Gene for a Conserved Major Immunoreactive 28-kilodalton Protein of *Ehrlichia canis*: a Potential Serodiagnostic Antigen," Clinical and Diagnostic Laboratory Immunology, vol. 6, No. 3, 1999, pp. 392-399.
McBride, J.W., et al., "A conserved, transcriptionally active *p28* multigene locus of *Ehrlichia canis*," Gene, vol. 254, 2000, pp. 245-252.
McBride, J.W., et al., "Immunodiagnosis of *Ehrlichia canis* infection with Recombinant Proteins," Journal of Clinical Microbiology, vol. 39, No. 1, Jan. 2001, pp. 315-322.
McDade, J.E., "Ehrlichiosis—A Disease of Animals and Humans," J. Infect Dis., vol. 161, No. 4, 1990, pp. 609-617.
McKnight, S.L., "Functional Relationships between Transcriptional Control Signals of the Thymidine Kinase Gene of Herpes Simplex Virus," Cell, vol. 31, Dec. 1982, pp. 355-365.
Miller, D.W., et al., "An Insect Baculovirus Host-Vector System for High-Level Expression of Foreign Genes," Genetic Engineering, Principles and Methods, vol. 8, 1979, pp. 277-298.
Morrison, D.F., et al., "Comparison of commercial IFA and PCR kits for detection of *Ehrlichia canis* in canine blood from clinical cases," Dept. of Vet. Prevent. Medicine, The Ohio State University, Conference of research workers in animal disease, Chicago, 2000.
Murphy, G.L., et al., "A molecular and serologic survey of *Ehrlichia canis, E. chaffeensis*, and *E. ewingii* in dogs and ticks from Oklahoma," Veterinary Parasitology, vol. 79, 1998, pp. 325-339.
Murphy, C.I., et al., "Major Antigenic Proteins of the Agent of Human Granulocytic Ehrlichiosis are Encoded by Members of a Multigene Family," Infection and Immunity, vol. 66, No. 8, 1998, pp. 3711-3718.
Mylonakis, M.E., et al., Chronic canine ehrlichiosis (*Ehrlichia canis*): a retrospective study of 19 natural cases, J Am Anim Hosp Assoc, vol. 40, 2004, pp. 174-184.
Nadelman, R.B., et al., "Simultaneous Human Granulocytic Ehrlichiosis and Lyme Borreliosis," The New England Journal of Medicine, vol. 337, No. 1, 1997, pp. 27-30.
Nelson, C.M., et al., "Whole genome transcription profiling of *Anaplasma phagocytophilum* in human and tick host cells by tiling array analysis," BMC Genomics, vol. 9, 2008, p. 364, 16 pages.
Oberle, S.M., et al., "Derivation of the complete *msp4* gene sequence of *Anaplasma marginale* without cloning," Gene, vol. 136, 1993, pp. 291-294.
Ohashi, N., et al., "Immunoprotective 28-kDa outer membrane protein of *Ehrlichia chaffeensis* is a member of multi-sized protein antigen family," In Abstracts of the 97th General Meeting of the American Society for Microbiology, D-80, May 4, 1997, p. 221.
Ohashi, N., et al., "Cloning, Sequencing, and Overexpression of *Ehrlichia canis* Immunoreactive Protein Gene Homologous to Members of *Ehrlichia Chaffeensis omp-1* Gene Family," Abstract D-28, General Meeting of the American Society for Microbiology, Atlanta, Georgia, May 17-21, 1998, p. 217.
Ohashi, N., et al., "Characterization of *p30* Multigene Family of *Ehrlichia canis*," Abstract D/B-126, 99th General Meeting of the American Society for Microbiology, Chicago, Illinois, May 30-Jun. 3, 1999, p. 233.

(56) References Cited

OTHER PUBLICATIONS

Palmer, G.H., et al., "Immunization of Cattle with a 36-Kilodalton Surface Protein Induces Protection against Homologous and Heterologous *Anaplasma marginale* Challenge," Infection and Immunity, vol. 56, No. 6, 1988, pp. 1526-1531.

Palmer, G.H., et al., "The Immunoprotective *Anaplasma marginale* Major Surface Protein 2 is Encoded by a Polymorphic Multigene Family," Infection and Immunity, vol. 62, No. 9, Sep. 1994, pp. 3808-3816.

Palmer, G.H., et al., "Insights into mechanisms of bacterial antigenic variation derived from the complete genome sequence of *Anaplasma marginale*," Ann NY Acad Sci, vol. 1078, 2006, pp. 15-25.

Palmer, G.H., et al., "Nothing is permanent but change —antigenic variation in persistent bacterial pathogens," Cell Microbiol, vol. 11, No. 12, 2009, pp. 1697-1705.

Park, J., et al., "Major Surface Protein 2 of *Anaplasma phagocytophilum* Facilitates Adherences to Granulocytes," Infect Immun, vol. 71, No. 7, 2003, pp. 4018-4025.

Perez, M., et al., "*Ehrlichia canis*-Like Agent Isolated from a Man in Venezuela: Antigenic and Genetic Characterization," Journal of Clinical Microbiology, Sep. 1996, vol. 34, No. 9, Sep. 1996, pp. 2133-2139.

Poitout, F.M., et al, "Genetic Variants of *Anaplasma phagocytophilum* Infecting Dogs in Western Washington State," J Clin Microbiol, vol. 43, No. 2, 2005, pp. 796-801.

Pollock, R.M., "Determination of Protein-DNA Sequence Specificity by PCR-Assisted Binding-Site Selection," Current Protocols in Molecular Biology, 1996, Supplement 33, 2000, 15 pages.

Pretorius, A-M, et al., "Serological survey for antibodies reactive with *Ehrlichia canis* and *E. chaffeensis* in dogs from the Bloemfontein area, South Africa," Tydskr.S.Afr.vet.Ver., vol. 69, No. 4, 1998, pp. 126-128.

Pusterla, N., et al., "Granulocytic Ehrlichiosis in Two Dogs in Switzerland," J Clin Microbiol, vol. 35, No. 9, 1997, pp. 2307-2309.

Pusterla, N., et al., "Identification of a Granulocytic *Ehrlichia* Strain Isolated from a Horse in Switzerland and Comparison with Other Rickettsiae of the *Ehrlichia phagocytophila* Genogroup," Journal of Clinical Microbiology, vol. 36, No. 7, 1998, pp. 2035-2037.

Rechav, Y., et al., "Evidence for Attachment Pheromones in the Cayenne Tick (Acari: Ixodidae)," J. Med. Entomol., vol. 34, No. 2, 1997, pp. 234-237.

Reddy, G., et al., "Sequence Heterogeneity of the Major Antigenic Protein 1 Genes from *Cowdria ruminantium* Isolates from Different Geographical Areas," Clinical and Diagnostic Laboratory Immunology, vol. 3, No. 4, 1996, pp. 417-422.

Reddy, G., et al., "A Family of 28 kDa Variant Surface Antigen Genes of the tribe *Ehrlichiae*: Does it play a role in immune evasion?" Abstract Annual Meeting of ASRRD, Sep. 23, 1997, two pages.

Reddy, G., et al., "Molecular characterization of a 28 kDa Surface Antigen Gene Family of the Tribe Ehrlichiae," Biochemical and Biophysical Research Communications, vol. 247, Jun. 1998, pp. 636-643.

Reddy, G.R., et al., "Variability in the 28-kDa Surface Antigen Protein Multigene Locus of Isolates of the Emerging Disease Agent *Ehrlichia chaffeensis* Suggests that it plays a role in Immune Evasion," Mol. Cell. Biology Research Communications, vol. 1, 1999, pp. 167-175.

Rikihisa, Y., "The Tribe *Ehrlichieae* and Ehrlichial Diseases," Clinical Microbiology Reviews, vol. 4, No. 3, Jul. 1991, pp. 286-308.

Rikihisa, Y., et al., "C-Reactive Protein and α1-Acid Glycoprotein Levels in Dogs Infected with *Ehrlichia canis*," Journal of Clinical Microbiology, vol. 32, No. 4, 1994, pp. 912-917.

Rikihisa, Y., et al., "Ehrlichiosis," Journal of Clinical Microbiology, vol. 22, No. 4, 1995, 15 pages.

Rikihisa, Y., "Rickettsiae and Rickettsial Diseases," In Proceedings of the 5$^{th}$ International Symposium on Rickettsiae and Rickettsial Diseases, Bratislava, Slovak Republic, Sep. 1-6, 1996, pp. 272-286.

Rikihisa, Y., et al., "Ultrastructural and Antigenic Characterization of a Granulocytic Ehrlichiosis Agent Directly Isolated and Stably Cultivated from a Patient in New York State," Journal of Infectious Diseases, vol. 175, 1997, pp. 210-213.

Rikihisa, Y., "Clinical and biological aspects of infections caused by *Ehrlichia chaffeensis*," Microbes and Infection, vol. 1, 1999, pp. 367-376.

Rikihisa, Y., "Ehrlichiae of Veterinary Importance," In Rickettsiae and rickettsial diseases at the turn of the third millennium, D. Raoult, P. Brouqui, Ed., 1999, pp. 393-404.

Roux, K.H., et al., "One-step optimization using touchdown and stepdown PCR," Methods Mol Biol, vol. 67, 1997, pp. 39-45.

Rurangirwa, F.R., et al., "Restriction of major surface protein 2 (MSP2) variants during tick transmission of the ehrlichia *Anaplasma marginale*," Proc Natl Acad Sci U.S.A., vol. 96, Mar. 1999, pp. 3171-3176.

Sainz, A., et al., "*Ehrlichia platys* Infection and disease in dogs in Spain," J Vet Diagn Invest, vol. 11, 1999, pp. 382-384.

Sambrook, J., et al., "Molecular Cloning: A Laboratory Manual," 2$^{nd}$ edition, Cold Spring Harbor Laboratory Press, 1989, cover page, contents pp. xi-xxxviii, Chapters 2, 5 and 6, 160 pages.

Sanogo, Y.O., et al., "First evidence of *Anaplasma platys* in *Rhipicephalus sanguineus* (Acari: Ixodida) collected from dogs in Africa," Onderstepoort J Vet Res, vol. 70, 2003, pp. 205-212.

Scherf, A., et al., "Antigenic variation in malaria: in situ switching, relaxed and mutually exclusive transcription of var genes during intra-erythrocytic development in *Plasmodium falciparum*," The EMBO Journal, vol. 17, No. 18, 1998, pp. 5418-5426.

Seidman, C.E., "Introduction of Plasmid DNA into Cells," Current Protocols in Molecular Biology, Supplement 37, 1997, 31 pages.

Shaw, D.R., et al., "Mouse/Human Chimeric Antibodies to a Tumor-Associated Antigen: Biologic Activity of the Four Human IgG Subclasses," Articles, vol. 80, No. 19, 1988, pp. 1553-1559.

Simpson, R.M., et al., "Evaluation of *Rhipicephalus sanguineus* as a potential biologic vector of *Ehrlichia platys*," Am J Vet Res, vol. 52, 1991, pp. 1537-1541.

Singu, V., et al., "*Ehrlichia chaffeensis* Expresses Macrophage- and Tick Cell-Specific 28—Kilodalton Outer Membrane Proteins," Infect Immun, vol. 73, No. 1, 2005, pp. 79-87.

Smith, R.D., et al., "Development of *Ehrlichia canis*, Causative Agent of Canine Ehrlichiosis, in the Tick *Rhipicephalus sanguineus* and Its Differentiation from a Symbiotic Rickettsia," American Journal of Veterinary Research, vol. 37, No. 2, 1976, pp. 119-126.

Sonenshine, D.E., "Biology of Ticks," vol. 1, Oxford University Press, Inc., 1991, 66 pages.

Sparagano, O.A., et al., "Molecular detection of *Anaplasma platys* in dogs using polymerase chain reaction and reverse line blot hybridization," J Vet Diagn Invest, vol. 15, 2003, pp. 527-534.

St. Geme, III, J.W., et al., "Characterization of the Genetic Locus Encoding *Haemophilus influenza* Type b Surface Fibrils," Journal of Bacteriology, vol. 178, No. 21, 1996, pp. 6281-6287.

Standaert, S.M., et al., "Primary Isolation of *Ehrlichia chaffeensis* from Patients with Febrile Illnesses: Clinical and Molecular Characteristics," Journal of Infectious Diseases, vol. 181, 2000, pp. 1082-1088.

Stern, A., et al., "Opacity Genes in *Neisseria gonorrheae*: Control of Phase and Antigenic Variation," Cell, vol. 47, 1986, pp. 61-71.

Stich, R.W., et al., "Transstadial and attempted transovarial transmission of *Anaplasma marginale* by *Dermacentor variabilis*," Am. J. Vet. Res., vol. 50, No. 8, 1989, pp. 1377-1380.

Stich, R.W., et al., "Preliminary Development of A Polymerase Chain Reaction Assay for *Anaplasma marginale* in Ticks," Biotechnology Techniques, vol. 5, No. 4, 1991, pp. 269-274.

Stich, R.W., et al., "Detection of *Anaplasma marginale* in *Dermacentor* species ticks with the polymerase chain reaction," Thesis presented to Oklahoma State University, Jul. 1992, 156 pages.

Stich, R.W., et al., "Detection of *Anaplasma marginale* (Rickettsiales: Anaplasmataceae) in Secretagogue-Induced Oral Secretions of *Dermacentor andersoni* (Acari: Ixodidae) with the Polymerase Chain Reaction," Journal of Mededical Entomology, vol. 30, No. 4, 1993, pp. 789-794.

Stich, et al., "A Polymerase Chain Reaction Assay for *Ehrlichia canis*," 3$^{rd}$ International Conference, Ticks and Tick-Borne Pathogens: Into the 21$^{st}$ Century, Hotel Academia, High Tatra Mountains, Slovakia, Aug. 30-Sep. 3, 1999, p. 40.

(56) References Cited

OTHER PUBLICATIONS

Stich, R.W., et al., "Detection of *Ehrlichia canis* in Canine Carrier Blood and in Individual Experimentally Infected Ticks with a *p30*-Based PCR Assay," Journal of Clinical Microbiology, vol. 40, No. 2, 2002, pp. 540-546.
Stiller, D., et al., "Detection of colonies of *Anaplasma marginale* in salivary glands of three *Dermacentor* spp infected as nymphs or adults," Am. J. Vet Res., vol. 50, No. 8, 1989, pp. 1381-1385.
Stiller, D., et al., "Recent developments in elucidating tick vector relationships for anaplasmosis and equine piroplasmosis," Veterinary Parasitology, vol. 57, 1995, pp. 97-108.
Storey, J.R., et al., "Molecular Cloning and Sequencing of Three Granulocytic *Ehrlichia* Genes Encoding High-Molecular-Weight Immunoreactive Proteins," Infection and Immunity, vol. 66, No. 4, 1998, pp. 1356-1363.
Suksawat, J., et al., "Coinfection with Three *Ehrlichia* Species in Dogs from Thailand and Venezuela with Emphasis on Consideration of 16S Ribosomal DNA Secondary Structure," J Clin Microbiol, vol. 39, No. 1, 2001, pp. 90-93.
Sulsona, C.R., et al., "The *map1* Gene of *Cowdria ruminantium* Is a Member of a Multigene Family Containing Both Conserved and Variable Genes," Biochemical and Biophysical Research Communications, vol. 257, 1999, pp. 300-305.
Sumption, K.J., et al., "Human ehrlichiosis in the UK," The Lancet, vol. 364, 1995, pp. 1487-1488.
Tajima, T., et al, "Comparison of Two Recombinant Major Outer Membrane Proteins of the Human Granulocytic Ehrlichiosis Agent for Use in an Enzyme-Linked Immunosorbent Assay," Clin Diagn Lab Immunol, vol. 7, No. 4, 2000, pp. 652-657.
Telford, III, S.R., et al., "Perpetuation of the agent of human granulocytic ehrlichiosis in a deer tick-rodent cycle," Proc. Natl. Acad. Sci. USA, vol. 93, 1996, pp. 6209-6214.
Unver, et al., "Dot Immunoblot Assay for Canine Ehrlichiosis: Using Recombinant Major Protein Antigen of *Ehrlichia Canis*," Abstract D-29, 98th General Meeting of the American Society for Microbiology, Atlanta, Georgia, May 17-21, 1998.
Unver, A., et al., "Transcriptional Analysis of *p30* Major Outer Membrane Multigene Family of *Ehrlichia canis* in Dogs, Ticks, and Cell Culture at Different Temperatures," Infection and Immunity, vol. 69, No. 10, 2001, pp. 6172-6178.
Unver, A., et al., "Analysis of 16S rRNA gene sequences of *Ehrlichia canis, Anaplasma platys*, and *Wolbachia* species from canine blood in Japan," Ann NY Acad Sci, vol. 990, 2003, pp. 692-698.
Urakami, H., et al., "Serodiagnosis of Scrib Typhus with Antigens Immobilized on Nitrocellulose Sheet," Journal of Clinical Microbiology, vol. 27, No. 8, 1989, pp. 1841-1846.
van Vliet, A., et al., "Molecular Cloning, Sequence Analysis, and Expression of the Gene Encoding the Immunodominant 32-Kilodalton Protein of *Cowdria ruminantium*," Infect Immun, vol. 62, No. 4, 1994, pp. 1451-1456.
Vanhamme, L., et al., "Control of Gene Expression in Trypanosomes," Microbiological Reviews, vol. 59, No. 2, 1995, pp. 223-240.
Voytek, M.A., et al., "Detection of ammonium-oxidizing bacteria of the beta-subclass of the class Proteobacteria in aquatic samples with the PCR," Applied and Environmental Microbiology, vol. 61, No. 4, 1995, pp. 1444-1450.
Walker, D.H., et al., "Emergence of the Ehrlichioses as Human Health Problems," Emerging Infectious Diseases, vol. 2, No. 1, 1996, pp. 18-29.
Walker, D.H., et al., "Emerging Bacterial Zoonotic and Vector-Borne Diseases: Ecological and Epidemiological Factors," Journal of the American Medical Association, vol. 275, No. 6, 1996, pp. 463-469.
Wang, X., et al., "Rapid Sequential Changeover of Expressed *p44* Genes during the Acute Phase of *Anaplasma phagocytophilum* Infection in Horses," Infect and Immun, vol. 72, No. 12, 2004, pp. 6852-6859.
Wang, X., et al., "*Anaplasma phagocytophilum p44* mRNA Expression Is Differentially Regulated in Mammalian and Tick Host Cells: Involvement of the DNA Binding Protein ApxR," J Bacteriol, vol. 189, No. 23, 2007, pp. 8651-8659.
Wen, B., et al., "Comparison of Nested PCR with Immunofluorescent-Antibody Assay for Detection of *Ehrlichia canis* Infection in Dogs Treated with Doxycycline," Journal of Clinical Microbiology, vol. 35, No. 7, 1997, pp. 1852-1855.
Whitlock, J.E., et al., "Prevalence of *Ehrlichia chaffeensis* (Rickettsiales: Rickettsiaceae) in *Amblyomma americanum* (Acari: Ixodidae) from the Georgia Coast and Barrier Islands," Journal of Medical Entomology, vol. 37, No. 2, 2000, pp. 276-280.
Wormser, G.P., et al., Human Granulocytic Ehrlichiosis—New York, MMWR Morbidity and Mortality Weekly Report, vol. 44, No. 32, 1995, four pages.
Wormser, G.P., et al., "False-positive Lyme disease serology in human granulocytic ehrlichiosis," The Lancet, vol. 347, 1996, pp. 981-982.
Yamamoto, S., et al., "Detection of Antibody to *Ehrlichia canis* in Dogs," J. Japanese Med. Assoc., vol. 47, 1994, pp. 765-767.
Yu, X-J, et al., "Sequence and characterization of an *Ehrlichia chaffeensis* gene encoding 314 amino acids highly homologous to the NAD a enzyme," FEMS Microbiol Let, vol. 154, No. 1, 1997, pp. 53-58.
Yu, X-J, et al., "Characterization of the genus-common outer member proteins in *Ehrlichia*," Rickettsiae and Rickettsial Diseases at the Turn of the Third Millennium, 1999, pp. 103-107.
Yu, X-J, et al., "Genetic Diversity of the 28-Kilodalton Outer Membrane Protein Gene in Human Isolates of *Ehrlichia chaffeensis*," Journal of Clinical Microbiology, vol. 37, No. 4, 1999, pp. 1137-1143.
Yu, X., et al., "Characterization of the complete transcriptionally active *Ehrlichia chaffeensis* 28 kDa outer membrane protein multigene family," Gene, vol. 248, 2000, pp. 59-68.
Yu, X., et al., "Phylogenetic relationships of *Anaplasma marginale* and '*Ehrlichia platys*' to other Ehrlichia species determined by GroEL amino acid sequences," Int J Syst Evol Microbiol, vol. 51, 2001, pp. 1143-1146.
Zaugg, J.L., et al., "Transmission of *Anaplasma marginale* Theiler by males of *Dermacentor andersoni* Stiles fed on an Idaho field-infected, chronic carrier cow," Am. J. Vet Res., vol. 47, No. 10, 1986, pp. 2269-2271.
Zhang, J-R., et al., "Antigenic Variation in Lyme Disease Borreliae by Promiscuous Recombination of VMP-like Sequence Cassettes," Cell, vol. 89, 1997, pp. 275-285.
Zhang, Y., et al., "Binding of Outer Membrane Proteins of *Ehrlichia chaffeensis* to DH82 Cells," Abstract D-79, 97th General Meeting of the American Society for Microbiology, Miami, May 4-8, 1997, one page.
Zhang, C., et al., "Identification of 19 Polymorphic Major Outer Membrane Protein Genes and Their Immunogenic Peptides in *Ehrlichia ewingii* for Use in a Serodiagnostic Assay," Clin Vaccine Immunol, vol. 15, No. 3, 2008, pp. 402-411.
Zhi, N., et al., "Comparison of Major Antigenic Proteins of Six Strains of the Human Granulocytic Ehrlichiosis Agent by Western Immunoblot Analysis," Journal of Clinical Microbiology, vol. 35, No. 10, 1997, pp. 2606-2611.
Zhi, N., et al., "Cloning and Expression of the 44-Kilodalton Major Outer Membrane Protein Gene of the Human Granulocytic Ehrlichiosis Agent and Application of the Recombinant Protein to Serodiagnosis," J Clin Microbiol, vol. 36, No. 6, 1998, pp. 1666-1673.
Zhi, N., et al., "Multiple *p44* genes encoding major outer membrane proteins are expressed in the human granulocytic ehrlichiosis agent," J Biol Chem, vol. 274, 1999, pp. 17828-178236.
Zhi, N., et al., "Characterization of the Expressed Genes in *p44* Multigene Family Encoding Major Antigenic Outer Membrane Proteins of the Human Granulocytic Ehrlichiosis Agent in HL-60 cells," Abstract D/B-124, 99th General Meeting American Society for Microbiology, Chicago, Illinois, May 30-Jun. 3, 1999, p. 233.
Zhi, N., et al., "Transcript Heterogeneity of the *p44* Multigene Family in a Human Granulocytic Ehrlichiosis Agent Transmitted by Ticks," Infect Immun, vol. 70, No. 3, 2002, pp. 1175-1184.
European Search Report, dated Feb. 21, 2005, in connection with European Patent Application No. 98949384.6, 7 pages.

(56) References Cited

OTHER PUBLICATIONS

International Search Report, dated Feb. 25, 1999, in connection with International Application No. PCT/US1998/019600, 4 pages.
International Search Report, dated Sep. 24, 2012, received in connection with corresponding International Application No. PCT/US2012/031580, 6 pages.
International Preliminary Report on Patentability and Written Opinion, dated Oct. 1, 2013, received in connection with corresponding International Application No. PCT/US2012/031580, 8 pages.
GenBank Accession No. AF021338, Feb. 19, 1998, retrieved from the internet at http://www.ncbi.nlm.nih.gov/nuccore/AF021338.1?report=genbank on Jan. 21, 2016.
GenBank Accession No. AF029322, Aug. 13, 1998, retrieved from the internet at http://www.ncbi.nlm.nih.gov/nuccore/af029322 on Jan. 21, 2016.
GenBank Accession No. AF029323, Aug. 13, 1998, retrieved from the internet at http://www.ncbi.nlm.nih.gov/nuccore/af029323 on Jan. 21, 2016.
GenBank Accession No. AF037599, Jul. 17, 1998 retrieved from the internet at http://www.ncbi.nlm.nih.gov/nuccore/af037599 on Jan. 21, 2016.
GenBank Accession No. AF059181, Jul. 4, 1998 retrieved from the internet at http://www.ncbi.nlm.nih.gov/nuccore/AF059181.1?report=genbank on Jan. 21, 2016.
GenBank Accession No. AF062761, Jul. 18, 1998 retrieved from the internet at http://www.ncbi.nlm.nih.gov/nuccore/AF062761.1?report=genbank on Jan. 21, 2016.
GenBank Accession No. AF068234, May 24, 2000 retrieved from the internet at http://www.ncbi.nlm.nih.gov/nuccore/af068234 on Jan. 21, 2016.
GenBank Accession No. AF077732, Jun. 19, 2001 retrieved from the internet at http://www.ncbi.nlm.nih.gov/nuccore/af077732 on Jan. 21, 2016.
GenBank Accession No. AF077732.1, Dec. 13, 1999 retrieved from the internet at http://www.ncbi.nlm.nih.gov/nuccore/af077732.1 on Jan. 21, 2016.
GenBank Accession No. AF077733, Jun. 20, 2001 retrieved from the internet at http://www.ncbi.nlm.nih.gov/nuccore/af077733 on Jan. 21, 2016.
GenBank Accession No. AF077733.1, Dec. 13, 1999 retrieved from the internet at http://www.ncbi.nlm.nih.gov/nuccore/af077733.1 on Jan. 21, 2016.
GenBank Accession No. AF077734, Jun. 20, 2001 retrieved from the internet at http://www.ncbi.nlm.nih.gov/nuccore/af077734 on Jan. 21, 2016.
GenBank Accession No. AF077734.1, Dec. 13, 1999 retrieved from the internet at http://www.ncbi.nlm.nih.gov/nuccore/af077734.1 on Jan. 21, 2016.
GenBank Accession No. AF077735, Dec. 13, 1999 retrieved from the internet at http://www.ncbi.nlm.nih.gov/nuccore/af077735 on Jan. 21, 2016.
GenBank Accession No. AF077735.1, Dec. 13, 1999 retrieved from the internet at http://www.ncbi.nlm.nih.gov/nuccore/af077735.1 on Jan. 21, 2016.
GenBank Accession No. AF078553, Apr. 2, 2001 retrieved from the internet at http://www.ncbi.nlm.nih.gov/nuccore/af078553 on Jan. 21, 2016.
GenBank Accession No. AF078554, Oct. 26, 1998 retrieved from the internet at http://www.ncbi.nlm.nih.gov/nuccore/AF078554.1?report=genbank on Jan. 21, 2016.
GenBank Accession No. AF078555, Oct. 26, 1998 retrieved from the internet at http://www.ncbi.nlm.nih.gov/nuccore/AF078555.1?report=genbank on Jan. 21, 2016.
GenBank Accession No. AF082744, Sep. 18, 2000 retrieved from the internet at http://www.ncbi.nlm.nih.gov/nuccore/af082744 on Jan. 21, 2016.
GenBank Accession No. AF082744.1, Jul. 26, 2000 retrieved from the internet at http://www.ncbi.nlm.nih.gov/nuccore/af082744.1 on Jan. 21, 2016.
GenBank Accession No. AF082745, Jul. 26, 2000 retrieved from the internet at http://www.ncbi.nlm.nih.gov/nuccore/af082745 on Jan. 21, 2016.
GenBank Accession No. AF082745.1, Jul. 26, 2000 retrieved from the internet at http://www.ncbi.nlm.nih.gov/nuccore/af082745.1 on Jan. 21, 2016.
GenBank Accession No. AF082746, Jul. 26, 2000 retrieved from the internet at http://www.ncbi.nlm.nih.gov/nuccore/af082746 on Jan. 21, 2016.
GenBank Accession No. AF082746.1, Jul. 26, 2000 retrieved from the internet at http://www.ncbi.nlm.nih.gov/nuccore/af082746.1 on Jan. 21, 2016.
GenBank Accession No. AF082747, Jul. 26, 2000 retrieved from the internet at http://www.ncbi.nlm.nih.gov/nuccore/af082747 on Jan. 21, 2016.
GenBank Accession No. AF082747.1, Jul. 26, 2000 retrieved from the internet at http://www.ncbi.nlm.nih.gov/nuccore/af082747.1 on Jan. 21, 2016.
GenBank Accession No. AF082748, Jul. 26, 2000 retrieved from the internet at http://www.ncbi.nlm.nih.gov/nuccore/af082748 on Jan. 21, 2016.
GenBank Accession No. AF082748.1, Jul. 26, 2000 retrieved from the internet at http://www.ncbi.nlm.nih.gov/nuccore/af082748.1 on Jan. 21, 2016.
GenBank Accession No. AF082749, Jul. 26, 2000 retrieved from the internet at http://www.ncbi.nlm.nih.gov/nuccore/af082749 on Jan. 21, 2016.
GenBank Accession No. AF082749.1, Jul. 26, 2000 retrieved from the internet at http://www.ncbi.nlm.nih.gov/nuccore/af082749.1 on Jan. 21, 2016.
GenBank Accession No. AF082750, Jul. 26, 2000 retrieved from the internet at http://www.ncbi.nlm.nih.gov/nuccore/af082750 on Jan. 21, 2016.
GenBank Accession No. AF082750.1, Jul. 26, 2000 retrieved from the internet at http://www.ncbi.nlm.nih.gov/nuccore/af082750.1 on Jan. 21, 2016.
GenBank Accession No. AF107766, Mar. 18, 1999 retrieved from the internet at http://www.ncbi.nlm.nih.gov/nuccore/af107766 on Jan. 21, 2016.
GenBank Accession No. AF107767, Mar. 18, 1999 retrieved from the internet at http://www.ncbi.nlm.nih.gov/nuccore/af107767 on Jan. 21, 2016.
GenBank Accession No. AF125274, Apr. 20, 1999 retrieved from the internet at http://www.ncbi.nlm.nih.gov/nuccore/af125274 on Jan. 21, 2016.
GenBank Accession No. AF125275, Apr. 20, 1999 retrieved from the internet at httb://www.ncbi.nlm.nih.gov/nuccore/af125275 on Jan. 21, 2016.
GenBank Accession No. AF125276, Apr. 20, 1999 retrieved from the internet at httb://www.ncbi.nlm.nih.gov/nuccore/af125276 on Jan. 21, 2016.
GenBank Accession No. AF125277, Apr. 20, 1999 retrieved from the internet at http://www.ncbi.nlm.nih.gov/nuccore/af125277 on Jan. 21, 2016.
GenBank Accession No. AF125278, Apr. 20, 1999 retrieved from the internet at http://www.ndbi.nlm.nih.gov/nuccore/af125278 on Jan. 21, 2016.
GenBank Accession No. AF125279, Apr. 20, 1999 retrieved from the internet at http://www.ncbi.nlm.nih.gov/nuccore/af125279 on Jan. 21, 2016.
GenBank Accession No. AF135254, Jun. 30, 1999 retrieved from the internet at http://www.ncbi.nlm.nih.gov/nuccore/af135254 on Jan. 21, 2016.
GenBank Accession No. AF135255, Jun. 30, 1999 retrieved from the internet at http://www.ncbi.nlm.nih.gov/nuccore/af135255 on Jan. 21, 2016.
GenBank Accession No. AF135256, Jun. 30, 1999 retrieved from the internet at http://www.ncbi.nlm.nih.gov/nuccore/af135256 on Jan. 21, 2016.
GenBank Accession No. AF135257, Jun. 30, 1999 retrieved from the internet at http://www.ncbi.nlm.nih.gov/nuccore/AF135257.1?report=genbank on Jan. 21, 2016.

(56) References Cited

OTHER PUBLICATIONS

GenBank Accession No. AF135258, Jun. 30, 1999 retrieved from the internet at http://www.ncbi.nlm.nih.gov/nuccore/af135258 on Jan. 21, 2016.
GenBank Accession No. AF135259, Jun. 30, 1999 retrieved from the internet at http://www.ndbi.nlm.nih.gov/nuccore/af135259 on Jan. 21, 2016.
GenBank Accession No. AF135260, Jun. 30, 1999 retrieved from the internet at http://www.ncbi.nlm.nih.gov/nuccore/af135260 on Jan. 21, 2016.
GenBank Accession No. AF135261, Jun. 30, 1999 retrieved from the internet at http://www.ncbi.nlm.nih.gov/nuccore/af135261 on Jan. 21, 2016.
GenBank Accession No. AF135262, Jun. 30, 1999 retrieved from the internet at http://www.ncbi.nlm.nih.gov/nuccore/af135262 on Jan. 21, 2016.
GenBank Accession No. AF135263, Jun. 30, 1999 retrieved from the internet at http://www.ncbi.nlm.nih.gov/nuccore/af135263 on Jan. 21, 2016.
GenBank Accession No. AF230642, Jun. 1, 2000 retrieved from the internet at http://www.ncbi.nlm.nih.gov/nuccore/af230642 on Jan. 21, 2016.
GenBank Accession No. AF287965, Nov. 6, 2001 retrieved from the internet at http://www.ncbi.nlm.nih.gov/nuccore/af287965 on Jan. 21, 2016.
GenBank Accession No. AF324792, Apr. 11, 2001 retrieved from the internet at http://www.ncbi.nlm.nih.gov/nuccore/af324792 on Jan. 21, 2016.
GenBank Accession No. L01987, Mar. 17, 1994 retrieved from the internet at http://www.ncbi.nlm.nih.gov/nuccore/l01987 on Jan. 21, 2016.
GenBank Accession No. U07862, Jan. 6, 1995 retrieved from the internet at http://www.ncbi.nlm.nih.gov/nuccore/u07862 on Jan. 21, 2016.
GenBank Accession No. U36193, Aug. 8, 1996 retrieved from the internet at httb://www.ncbi.nlm.nih.gov/nuccore/u36193 on Jan. 21, 2016.
GenBank Accession No. U50830, Jul. 14, 1996 retrieved from the internet at httb://www.ncbi.nlm.nih.gov/nuccore/u50830 on Jan. 21, 2016.
GenBank Accession No. U50831, Jul. 14, 1996 retrieved from the internet at httb://www.ncbi.nlm.nih.gov/nuccore/u50831 on Jan. 21, 2016.
GenBank Accession No. U50832, Jul. 14, 1996 retrieved from the internet at httb://www.ncbi.nlm.nih.gov/nuccore/u50832 on Jan. 21, 2016.
GenBank Accession No. U50833, Jul. 14, 1996 retrieved from the internet at httb://www.ncbi.nlm.nih.gov/nuccore/u50833 on Jan. 21, 2016.
GenBank Accession No. U50834, Jul. 14, 1996 retrieved from the internet at http://www.ncbi.nlm.nih.gov/nuccore/u50834 on Jan. 21, 2016.
GenBank Accession No. U50835, Jul. 14, 1996 retrieved from the internet at http://www.ncbi.nlm.nih.gov/nuccore/u50835 on Jan. 21, 2016.
GenBank Accession No. U72291, Apr. 2, 2001, retrieved from the internet at http://www.ncbi.nlm.nih.gov/nuccore/U72291 on Jan. 21, 2016.
GenBank Accession No. X74250, Sep. 9, 2004 retrieved from the internet at http://www.ncbi.nlm.nih.gov/nuccore/x74250 on Jan. 21, 2016.

\* cited by examiner

SEQUENCE LISTING

<160> NUMBER OF SEQ ID NOS: 323

<210> SEQ ID NO 1
<211> LENGTH: 24126
<212> TYPE: DNA
<213> ORGANISM: Ehrlichia ewingii

<400> SEQUENCE: 1
gtcaaaacca actcgcaaac aagttaggaa ttactttcca acaagtacaa aaatatgaga 60
aaggaacaaa ccgtatagtt attagcagac tatatcagct tgcaagcgta cttaacgttg 120
aagtaagaga tataatgtta aaactacagg aagatctaaa aaatatctcg tgtgacaacg 180
atgttgtatc tataccacat ctaaaagata atgaagataa atttatcccg gaacttcacg 240
acaataaaat agatagcaaa gaggttttaa tgatggttag agcgtatact tgtataaaaa 300
atgaaaaagt acgtaacata atctacaatc tagttaaggc attatctgtg gataattaat 360
taagtaatta atattgagtt ataggattat acatcacatc tagattatta atatgtaatt 420
tgttgcaaga attataaatg tattatataa cactaaatta ttacttaata cactatcact 480
atgtagagtg tgtattctaa gttatatact aacaaaccag tttattgact gggcatatta 540
tttttgacct aaggcatgat ttttactaat attaaattta ttgtatagtt ttggatagta 600
ttatgattaa attctcaagt gtaggagtta cactttcttt agcaacattg ctctcacata 660
atgcattatc atcaccaatt cctatagatt tctccaatga aagcgaaatg gtaggtttct 720
acgcaagtgc gcattacaat ctagaacttc ccatgttcag tccaatatct gtaaaataca 780
aatccactgg taattcagaa gctgataaat cggaaaaaga gttaactcta tttaccttaa 840
aagaaagcac tcaagcacca gatttcacaa aaaaagaaac attcaatgat aaaagcgggt 900
acaaaccagt atacaacaga aattatactg ggttttctgg agccgttgga tattcaggag 960
gtggcataag agtggaaata gaaggagcat tcacaagatt tgatgttgac aagcaaaagc 1020
acacccatcc agataatcat aggtacttcg cttcctgtac agaacaagag atgaaacccg 1080
ctcagcaaaa tggaagcagc aaagatggta attatgtagt aatgaaaaac gaaggattta 1140
aagctatttc tttaacattt aatgtttgtt acgacatgat agtcagtaat tcttctttaa 1200
taccaagtgc ttgtgttggc ataggacaag gaatcactaa tttcctagga gcaacaaaca 1260
ttcacaccat atttcaagct aagctaggtt taggattttc aatttcacca aaaactattt 1320
tgtttgctaa tgggtattac gtaaaaacaa aggatgatgc ttttacaaat ctcacagttc 1380
aatatcctgt taaattaaca agtcctccta cccatataga tccagtagtt tatttccact 1440
cagattattg tggaggtgaa gtaggtctta gatttatttt ataaattatt ttagagcagt 1500
taatatagtc accatatttt ttagagcata tcaaagtgtt taagttattt tttgcttcat 1560

```
taaatcacta gttcctgtac ttaaacatta taggccaaag tcatattatt aacaacatat    1620
taactgggtg atacattttt tattctcaac ttacaacaat gcttaacaaa tattagctgg    1680
ttttaccaag caacacaatt tacaacacta aataatgaat cacaaaacaa ccatatatgt    1740
tacttccttt tatcaattaa gtataaaaaa atttcaaata gaggtagaag aaattgttaa    1800
caacagaaat tactttatta taaaatacta ttttaaactt aataataaac caacttaata    1860
tttaataagt tgttttttt atttgactaa aaattattta tagaataaaa cacttaaata    1920
ctgtcatatt ttactataac agtatttaaa ttgtgctgta tttaactagt tgttggtgct    1980
ttttagcatt ttgctttttt ggatacaatt gatgtgtagt tattttagaa atattatata    2040
aggtttaagt atatgagtta taagaaggtt attttctgga ttatattatt tcttacacca    2100
ggtgcttctt tatcacaagg gttaaatgat aatattttta aaactttta tgttggtgtt    2160 caatataaac ctgctataca tcatttatca catcttatca ttaaggagac atcaaaagat    2220
actataggaa tatttgcatt aaaaaagat gcctcattac ctacggatat taaaaagaat    2280
agtaatttaa atattaggta caacccacac tatgaaaata ataattctgg gttttcaggt    2340
ctgctaggat atcattataa taacaatttt aggatagaat ctgaaatttc ttatgaaatt    2400 tttccttta aaaatgaagg ttataaaatt accggtgttg aacaacattt tgcactagca    2460
agtgagttag atactaatgg taatcaacca aaaacagaca agtacgttac tataataaat    2520
gatggcatta gagctacctc agtattgatt aatgcttgtt atgatggtat tgatattaaa    2580
aaaaataata tagtagtata ttcatgtatt ggacttggag cagacatagt agatttctta    2640
agcaagtata atacaaagtt gtcatatcaa gggaaactag gactaagtta tccaatttcc    2700
ctcaaaataa tacttttgc agaaggttac tatcatggac tcttaggcaa tgtattcaac    2760
aatgtacctg ttaattatcc tactgacaac aatacaacaa agactactgt gtcagctatt    2820
ttaaatatta gatattatgg tggaagtgta ggagtaagat ttatattata aaaatatttt    2880
tgacaatttt tatttatcgt tttatatgta tgtaggtata aataaaaatt agtgtgttta    2940
cttgattgag ttaatatgtt taaggttatg ctatgagtaa tagaaagtta tataatadat    3000
ctttattatt ctccatttccc acttcttgtt tattttgtt ttttcaccac tcaagtcatg    3060
taaatgcatt aaattttagt atttccaact atcttaacag gtataacaat atctttaaca    3120
cagaagataa caaaccgctg aatagtcaag taaatacttc ttttatgttc atcacaagaa    3180
caattaagtc ttcagcaaga aaaactaaag gaatagtaga agacttttgt agaaacagca    3240
atgttttaac gaagaagcta gttccggatt tatatacaaa gacagtacga agaattatta    3300 gtattttaa tgagatcaag ctaaatcata taatttctta tttaactgct tttactagtt    3360
ttagaatggt tacatctcaa taccatgaag taatgagtaa ttttaaaggc ttatttatta    3420
attgttctct taacataata gacaaacgta atttcaagtc tatcatttct ggcattaatt    3480
attttgatag agaaattaga tgcttacttt ctcaaagtta caattattaa ggtttatatt    3540
atgaattatg cgaaggtttt tatattaatg tttgtaaatac ttttcttacc ttcatcatcc    3600
ctattagcct tagagaataa tctctctgga ggtgtaggtc atatctatat aagtggacag    3660
tacaaaccga gtattccaca atttaataaa ttttcaatgg aggaagctac tattggagca    3720
gtaattccaa aatcttttaaa gcaagatgca gaagatataa cactcagtat actcgcatta    3780
tccacaaatt tcacattacc ttatgatcct aaatacaaga agagtttact aggattaggt    3840
ggtactatag gttatgcaat aaacaatttt agaatagaac ttgaaacatt ttatgaaaag    3900
ttcaatgtaa gcgcccctag tgggtatgat gacaatattt atgcatattt tagcatagaa    3960
```

```
gttccacagt taaggagcct tccttatcat tacactatga aaatactgg tatcatcttg    4020 tcacctgttc tagcaaacat atgttatgat atcaacaaaa aacaactgag aaatgtatct    4080
ccctacttat gtcttgggtt tggagtagat ctaatcgatt tcttgataa agtaagtttt    4140 aagttttctt atcaagctaa acttggtgtt agttacttga tcaccaaa tctagcattt    4200 tttattgatg gatcttttca taggcatcta ggaaatcaat ttagtgatct actactagat    4260
tatcctagtt attatcgtag tcttactagc ctcagtgata atgatcctaa tcgcattcta    4320
ccatttacta gcgcatcagc aaagcttaat attaattttt ttagtgctaa tattggtatc    4380
aggtttattt tttgataatg agttatgttt atgaaaaagt tatattattt aaattttaca    4440
gtattagtac taacagtata tctctttcca agctttgttt tttcaatgca aggtaggagt    4500
aatattactg gatcttacat tacagtaagt tatcagccat ctatgtcaaa ttttagaaat    4560
tttcatatca aagaaactaa ctttgataca aaggacccaa ttgggttaat aagatctgca    4620
agaagtactg aacctagtgt tttaaaaatt aatactcatt tttataaacc ccaacaaagt    4680
gattcttaca agtcttatgg aaatgattta ttagggttta gcacatctat tggattattg    4740
gtaaaaaact taaggatgga atttgaaggg tcatacaaaa aatttgatat aaaacgcctc    4800
gtaaattatg catctagaga tggtcatagg tactttgcca ttcccagaga tacattcttt    4860
aataattcaa ttccatatgc atttaatgct tatacagtag caaaaaataa tggattatct    4920
attatttcta acatgataaa tttgtgttat gaatcaataa aatataacaa tttcatgcct    4980
tatatatgtt taggtgctgg aggagatttt atagaacttt ttgattctat gagaataaaa    5040
tttgcttatc aaggaaaatt aggagttagc tatcctctta cctcaaattt agttctcgct    5100
atcagtgggc aatatcacaa agtcgtagga gataaattta agtttttacc tctcatgctt    5160
tcaccttcta cacctagaag aagaataacct cctcaaagta gttcagaagt acaagatgca    5220
actggattat taactcttga tttagggtat tttagtgctg atattggatt aaggtttatg    5280
ttttagttgt ttaacattaa gtgtagatat atgaacaata aaaaaagtca tgttatatgc    5340
atgttaattt ttctattatt acctatgaag tctttctcag tattgataga tactacagag    5400
aaagactacg cttccaatgt atatattagc agccaatata agccaagttt ttctaatttt    5460
agaagttttt caatacagga aattaattct aaaacaaaaa attcaatagc tcttgaaaag    5520
ccaattgaat cgaatagtaa tatattaaaa tcaaatgctc atataattgt tcctcataat    5580
atacaatttc aagataatac aattagtttt agtggagctg ttgggtactc ttctaaagga    5640
ttaagattag aattagaaag tgcttatgaa gaattttata caaagagct taatagttct    5700 tcactaataa gctcaaataa tcattataca caattatatg aagctaattt tcaaaatttt    5760
gctacaagta gactatctat tacttctttc ataatcaata cttgttatga cattttaatt    5820
ggtagttcac cagtaatgcc atatatatgc acaggcattg gtggagatat aatcaggctt    5880
ttcaatacaa catatcttaa atttgcatat caaggtaaat ttggtataag ttatccgtta    5940
aataataata ttatactgtt ttctgacata tactatcatg agattatagg acaagagttt    6000
gaaaatttgt atacacaata tgtatctggt ataaatagtc tccaagaaat tacgtcagta    6060
ccagctagtt ttaatattgg atattttggc agtgaaatag gagtaaggtt tatatttaat    6120
aagcaataaa aagggcatat atgagaaaaa aaatctattc tataaatgta atattagtct    6180
ttactttact tcttttatct atccagtcgt ttgcaatatc tatagataat aatataattg    6240
accaaaatct tggcttatat ttaagtgcac aatacaaacc aagcatttcc cattttaaaa    6300
```

-continued

```
attttttcagt gcaagaagtt aataagaagg tagatttaat tgctcttaaa aatgatgtta   6360
cacatattac agaagagata cttaaagatc ctacaaactt taatactcac tatagtgcaa   6420
aatttaaaaa tagtttcaca ggtttcagtg gcgcagttgg ttattattct gctcaaggtc   6480
caaggttaga agttgagggt ttctatgaaa attttgatat aacagactgt agtaactgca   6540
caataaatga tgccaacaga tatttagcac tagctcgcga aaaagataac aatcaagttc   6600
aaccaaaagc acatgattcc agcagtactg acagcaataa tagtagtaat aatactaaga   6660
aatcttactt tactttcatg aaaaacaatg gaatatctat cgcatctgtt atgatcaacg   6720
gctgttatga tttttctttg aataatataa aaatatcacc ttatgtatgt gcaggcattg   6780
gaggggattt tatagaattc tttgaggtaa tgcatattaa attttcttat caaggtaagt   6840
taggagttag ttatttaata tctccttcca ttagcttatt tgttgatgga tattatcata   6900
gtgtaataaa taataaattt aaaaacttgc atgttacata tgcatatata ctaaaagatt   6960
cacctaccat tacttctgca atagctcagc ttaacattgg atactttggt ggtgaagttg   7020
gattaaggtt tgtatttttaa ataataatga aataagggga ttttctatga gcaataaaaa   7080
aaaatttact atagggacag tgttggtatc tttgctagct tttctaccta cttactcttt   7140
ttcagcacct ataagcaata attctgaaga taatattttt ggcttatata ttgcaggaca   7200
atataggcca ggtgtttctc atttttctgg ctttggagta acagaaacta attttgccac   7260
acaaaaatta atgagagtta aaaaagattc taaagaagga cttccaaata tacttaaaag   7320
caaagataat ttcacagaac catatgttgc aaaatttcaa gataatgcag ttagttttag   7380
cggtgctatt ggttattctt accctgaagg tctaagatta gaaatagaag gttcttacga   7440
aacatttgat gttaaagatc ctaaagattg ttcagtaaaa gatgctttta gacatttagc   7500
tctagtacgt gaattagata caggtctttc catgcctaaa gaaaaaaaat atactgttat   7560
gagaaataat ggattatcta ttgcatcaat tctaattaat ggttgttatg attttgattt   7620
tgataatcta atagtatctc cttatgtatg cttaggtata ggtgaagact ttattgaatt   7680
ttttgatgtt ttgcatatta aatttgctta tcaaggtaag ttaggtatta gctacgagtt   7740
atctcctaga atcaacgtat tgccgatgg ttattatcat aaggtaatag gcaatcagtt   7800
caagaaccta aatgtcaatc atgttgttga attagatgac tttcctaaag tcacctctgc   7860
agtagctaca cttaatgttg gatactttgg tggtgaagtt ggtgtaaggt ttatatttta   7920
acaatataac acataggaaa gtcttttatg agttgtgaaa aaaaattttg ttacagtaaa   7980
aagcatatta tcttctttat tactactgtt tcttctgtac aatcttttc agcatcttta   8040 aacaatgctg aagatcataa agacttttac ctatatgtta ttctatacat atcctataac   8100
tttttttgta ttatcaggtt aataacagta aaagatagtc atttttttc tattaacaca   8160 agttcttata atttatgctt ggaaaaacat aagaatgaca ttagcttcag caaaatacta   8220
ggtgttttta caaaaacaat tcatagctat aacattggag attcccatga aaggtttaat   8280
gctgaaaatc ttcggaacag tttaacgaaa gataaatatc ttacttcaga acaagaagta   8340
aatgattata acatcattag tgccataaaa aatagtgggc tttatctatt aatagagata   8400 cttttttaaca tatattacat aattattggt agaaatttca ttcatctttt tgatattttta  8460 tgtatcaaat ctaccaatca aactgagctt agtattaact tactttccaa agctaatcta   8520
cctatcaata gattttacta tagaataaaa gataaccaac atgaaaattc aaaaattcat   8580
tacgctatta tcttatcaaa caacaagtat cttcaaaact ctttaggaga tactaagact   8640
aatacttatg gagtaagaag taatttttaat aatacataag ggaaatttttt atgagtaaca   8700
```

```
aaaaaatatt ttctataata gggcaagcac taacatgttt agtactattt tcacctattt    8760
actccttttc agaatcaaat cattatgata aatctttata tgttgctgga cagtacaaat    8820
caagcttatc tcatttcacc aattttttcag ttagagaaac tgatattaat actaaggggc   8880
tattcaagct cggacacggc gtgactcttg ttgaagaaga tataaagaac catttacagt    8940
tcacaattcc tcatagtgta gcatttaaaa acaattttgc aaattttagt gctgccgtcg    9000
gatatatctc ccctggaggc ccaagagttg aaatagaagg ttcctatgaa aattttgatg    9060
taaaggatct taaaaattgc acaatacaag atgcttgtag atatctatca ctagctagag    9120
aaatatgcaa agaaaatgat aaaccaacac ctaagaaaaa aaaatatgtt gtcatgagaa    9180
atgatggaat ttctattaca tctgttacta ttaatggctg ttatgatttt tccataaata    9240
aattacctaa aatatcacct tatatatgtg cagggtttgg tggagatttt atagaattt     9300 ttgattctgt acgtgtcaaa tttgcttatc aaagtaaatt aggtattaac tattcattat    9360
cttctaactt cattctattt gttgatgggt attaccacag agtaatagga aaccaattca    9420
agaatttaaa tgttcaaaac atgtttgata gtaatgaacc atacgttaca tctgcaatag    9480
ccactcttaa tattgaacac tttggcggtg ggtttggttt gagatttata ttttaaggag    9540
ttttatgaga aaaaaaagtt ttattataat aggaacagta ctaatatgtt tactgtcacc    9600
acctaatata tcttttttcag aagttattac gcataacgat aataaacacc ctggaatata   9660
tgtaagtggg caatacaaac caggaatttc ccatcttaga aagttttcag ttaaagaaac    9720
taacgccacc acagtacaat tagtaggact taattatact gctgcaccta ttgatgatat    9780
aaaaacaagt agtaagtttg acactcctta tacaatagca tttcaaaaca atatcatcag    9840
ctttagtgca gccataggtt attctcacgc taagggacta agaatcgaat tagaaggatc    9900
ttatgaagaa tttgatgtta cagatcctgg aaactataca ataaaagatg cttatcggta    9960
ttttgctata gctcgagaaa tgaacagtag tagtaacaat caacccaagg ataaacaatt   10020
cactgttatg agaaatgacg gagtttctat tgtatccttc atgtttaacg gttgctatga   10080
ttttcctttg ggtatcttag agatatcacc ttatatatgt gctggtattg gtggagatt   10140 tatagaattt tttgatgctc tacatataaa acctgcatac caaggcaagt taggacttaa   10200
ctatcctcta ttttccaaag ttagcttatt tattgatgga tattaccaca agtaataggt   10260
ccaacaattt aagcatttaa acgttcaaca cgttgttaca ttagatacac ctaaaattgc   10320
atctgtagta gctacacttg atgttagtta ctttggtggt gaaattggaa tgagacttat   10380
attttaggaa atattatgaa taataaaaaa atgttttcca taataggcat atcattatta   10440
gcaaatttgc tattgttgcc taatatgtct tttgctaaaa ataattacag ctatattaat   10500
ccagtgttat atataagtgg gcaatacagg ccaggagttt ctcactttag tcaattctca   10560
gtcagagaaa cccactatga tacacaacta ttagctgaac ttaaaaaaga ggtcggtagt   10620
gttactaaca ccgttataca agcctatgca aactacaatg ttcctagtca gccccctttc   10680
agccatactt atgttgcaga atttgaagat aacactatta gcttcagtgg agctgttggc   10740
ttttcttact ctgaaggtcc tagaatcgaa atagaatttt cttatgaaga attcgatgtt   10800
aagaattctg ggcattcttc aatagatgct catcgttact ttgctctatt gcgacactct   10860
aacaacggaa atactcaaca aaatcctttt gctgtaatga gaaataacgg gttatttatt   10920
ggatctgtag caataaatag ttgttatgat tttatcttag atgataccccc agctttacct   10980 tatgtctgcg gaggcattgg tggagatttt atagagttct tgacgagtt acacgtaaaa   11040
```

```
cttgcttacc aaggtaagat aggtatcagt tatcctatac actctaaagt cagcacgttt   11100
gttgatgtat attatcacag agtgataaac aataaattta aaaatttaca tgttcaatat   11160
gttaatacta ctacttcaca agctataaat cctcaaatca catccgcagt agctactctt   11220
aatgttggct attttggtat tgaaattgga gcaagattaa cctttttaatt aacaactaaa   11280 tacggaattt tatgaataat aaaaatagat ttactgcaat aggtgtagct ttaacatgtt   11340
tactgctatt accaaatgtc tcctttcag aaactacaat tattaatcaa ccatctggac   11400
tatatataag tggacaatat aaaccaagtg tttctgtatt tagcgatttt tcagtaaaag   11460
aagctaatgt tgcaacaaaa catttaatag cacttaaaaa gtctgttgat tctattaacg   11520
ccgaaaaagc aacacctcat aatcaaggcc ttggtaagcc agataatttt aacattcctt   11580
acaaagtaga attcgaagac aatgctgtta gttttagtgg agttatcggt tactctttc   11640 ctgaaggtcc aaggattgaa atagaaactt cttatgaaga atttgatgtt aaaaatcctg   11700
gaggttatac cttaaacgat gcttttcgat attttgcttt agcacgtgaa atagaaagtg   11760
atcagaataa attccaaccg aaaaatgcaa acagcaacag tagtaacaaa atttatcaca   11820
ctgtaatgag aaatgatggg ataagtgttt tatctaatat gatcaacatt tgttatgatt   11880
tttccttaga taatttacca gtactacctt acatatgcgg aggtacaggc gtagacacta   11940
tagaattctt tgattctttg catattaaac ttgcaggtca agctaagata ggtattactt   12000
atccattatc ttccaacatt aacctattcg ctggcgggta ctaccataaa gtaataggta   12060
accgatttaa aaacctaaaa gttcaacaca tagctgaact caatgacgct cctaaggtta   12120
catctgcagt agctacgctt aacatcagct attttggtgg tgaaattgga gcaagattta   12180
tattctaaat tgtaaacatt aaatatggaa atttctatga gcaataaaaa gaaactttt   12240 acaataagta cagcattata cttattatta tcacccaaca tatcttttc agaaactata   12300 gttgatgata tcgataggca atttaggtta tatattagtg gacaatataa accaagtctt   12360
tctgttttta gtaattttc agtaaaagaa accaacgtta caacaaaata tttaacagct   12420
cttaaaaagg atgctgatcc tactgaaaaa actggtagta caccctcatga gaaaggtctg   12480 ggaaagccag ataattttaa tattccttat aaggtagaat ttgaagacaa tgctgttagt   12540
tttagtggag ctgttggttt ttcttatcct gaaggtctaa gaattgaaat agaagcctct   12600
tatgaagaat tgatgttaa aaaccctgga ggctatacaa taagtaatgc ttttcggtat   12660
ttcgctttag tacgtgaatc agaaagtagt aaagaacctc aacccaaaaa tccgaacagc   12720
gctggcaaca acaaaatttt ccatactgta atgagaaatg atggagtagc tatttcatct   12780
attacaatca atggctgcta tgatttctct ttaagtcaat taccagtatt accttacata   12840
tgcggaggaa taggtataga cactatagac ttctttgatg cattacatat taagtttgca   12900
ggtcagggga aattaggtat tacttaccca ctatctggta acatcaactt attcgctgat   12960
ggatattacc ataaagtaat aagcaaccaa tttaaaaatt taaacgttca acatgtagct   13020
gaactcaatg atgatcctaa agttacatct gcagtagcta cactcaatat cagttatttt   13080
ggcggtgaaa ttggcgtaag gtacatattt taattaatta tttatgacaa cattaaacaa   13140
caagaaactg tttagttatg cagttttttg ttgtcgatag tgtttatta ataatacatt   13200 caaaaaggtt ttaccaagta atgagagatt gggtaagtgt tttatctaat atgatcaatg   13260
tttattatga gatttttctt tagacaatct ctagcactac cttgtatatg cagagacaca   13320
ggcgcagata ctataaattc ttgcatatta aacttgcagg tcaagctaag ataggtatta   13380 cttattttatt atctttcaac attagataat taaagttaat gtctgttaca tttatttta   13440
```

```
gcaataagaa aacagtaaca ttactttagt ttgtctaatt atactgctat gtgttgttta   13500
agaagtttta tatgtgttaa ctatatgaaa agtccatttt atactagaag ctttatgttc   13560
ttttaaaaag cttttattaa aaataaccaa agtcgatatc tattatattt gtttcaagga   13620
taggaaatca gtatattaca tccaaactca gcagagtact tttttaggta gaaataaaat   13680
aattaagtaa tccaataaat atgtcaatta aactgatata gtcatatatt tacatggtac   13740
tgagttgaat ttagagttat tcaaatatta tttatattat aaaagtttcc tatatagttc   13800
atatacaaaa ttgtcatgct atatagatga tactgtggta tatgaaggct ctaaatacag   13860
atttttcgaa ctttattctt aataaatcaa tactaaatta aatttcttta taagaatcac   13920
attatatact tgttagaaaa atacttttta atactatata tacttctatc tctacaatat   13980
atcagacgag taacttttaa gtatatggtt ttattcctgt taaacttttc gtacatagag   14040
tgttataggc aattctataa atactaatta atttaccatt ccatattatt taatatatgc   14100
tataatagaa taaattaaga atgtgaagtt gttttagtac attttaacat tagcaattta   14160
gaattatatc atttataatg ctttgcacct aatgagagcc acaggctttt ttttttatac   14220
taccaattaa atattacgat aaagcaaaaa attgcttcaa caattttttc attaactagt   14280
aggtaaactt aaactacaaa ttttattaaa attttatca taattattct aaatattaat   14340
taataagttg taattttaaa agaaaattta tattctagac ttgcttttct ttacttcttt   14400
tattattctt aagttattta ttatctttat ttaatatata aaaggtttat taacatgaat   14460
tacaataaaa ttttagtaag aagtgcatta atttcattaa tgacagtctt accataccag   14520
tcttttgcag atcctatgaa ttccaatgat gttagtatta atgacagtaa agaaggattt   14580
tatatcagtg caaaatatag cccaagcata ccatatatta gaaaattttc agctgtagaa   14640
acccctattg aaggagctat ttctccaact aagaaagttc ttggcctaaa caaaggcgga   14700
tctatagcaa attcccatga ttttagcaaa atagatccat cacttgattt ccataataac   14760
ctaatatcag ggttttcagg aagtatcggt tatgctatgg atggaccaag aatagaaatt   14820
gaagctacat atcaaaaatt tcacccgaaa aatccagaca ataatgacac tgatagtagt   14880
gaccattata aatattacgg tttatttcgt gaaggaacac cacaagaaga agaacatagg   14940
tatgtagtac ttaaaaatga agggttaact tttatgtcat taacagttaa tgcttgttat   15000
gacattgttg ctgaaggtat accttttata ccatatgcat gcgttggtat cggcagtgac   15060
ttgatcgaca tattcaatga taaaaattta aaatttgctt atcaaggaaa agttggtatt   15120
agctatccta ttacttcaga agtttctgca tttattggtg gatactacca tggaattata   15180
ggaaataagt ttaataaact acctgtaaag actcctgtaa cgttagacac agcaccacaa   15240
acaacttctg cttcagtaga acttgacact ggtttctttg gaggagaaat aggagtaagc   15300
tttagcttct aaattcacct tatttattgt tatacacaaa acaaatagtg ataaaaaatt   15360
tagcaattca taatagggaa aatatggaat tatttcaagt tttcccttat gttttttgtat   15420 tcctatacat ttaagaaaag tatttttacg gtacgtaaca ttaataaatt ataaatatta   15480
ctgttttaca taacaatatg ttaaattttc ttataaacat aattcatctt tttacataaa   15540
aaaatacctt ctagcttgct tttcttttac acttctacta ttgttaattt attttcacta   15600
ttaggtgtgt aatatgaatt gtaagaaaat ttttataaca agtgcactaa tgtcactagt   15660
atcttttata ccttgcatat cttttttctaa tccaatgcaa gataacaata ttgttggtaa   15720
tttttatgtt agtgggaaat atatgccaac tatatcacat tttgataatt tttctgctaa   15780
```

```
agaagataca atagaaacta ttgcaacatt tggtctatct aaaacttata atagatctag   15840
tcctatacat agtgactttta cagattcaaa atattcattt aaatatgaaa acaatccgtt   15900
cttaggcttt gcaggagctg ttggttattc aatggaagga ttaagactag agtttgaaat   15960
atcctatgaa aaattcgatg taaagaatcc agataatagt tacagcaatg gagcacatat   16020
gtattatgct ctatcaagaa aagataatgc taatatagga acaacaccac aagataaaaa   16080
atacgtttat attaaaaatg aaggactaac tgacatatca ctcatgttaa acgcatgcta   16140
tgatgtaata tctgaaggta tatcttttgt tccttatata tgtgcaggta ttggcagtga   16200 tttatatca atgtttgaca ttacaagtcc taaactttct taccaaggaa aactaggtat   16260
aagttactca ataaacccag aaatgtctgt ttttattggt ggacatttcc ataaagtaat   16320
aggcgatcaa tttaaagaca tcactcctct taaacctaat gggatagaaa atacaaccgc   16380
tactcatgta ctagtaacgc ttcatatgtg tcacttcggt gcagaaattg gaggtagatt   16440
cactttctaa acttacttta ttattgtcac acataaaaaa taaatttaaa ctaatttttat   16500 tattgctgta tcaaacaaaa acaatagtga caaaaagaca tagcaataag agagggggg   16560 gggggagaa agaatgcatt agaaatcaac aatttttact cattgccatg ataataaaat   16620
ctatatagac acatataaaa gatatatatc ttttatatgt tatgataata tattaaattt   16680
ttcttacaag aatcactacc attctgtact aaaaactaca ttctaacttg ctttttctttt   16740 acacttccac tattgttaat ttatttgtca ctattaggta taattatgaa ttgcaagaaa   16800 gttttttataa caagtgcact tatatcgttt atatgttttc taccaggagt atccttctcc   16860
aacacaatac aagataataa tatcgttggt aactttttaca tcagcggaaa gtacatgcca   16920
actgtatcac atttcggtaa ctttttctgca aagaagaaa aagcagagac taaaaaaaca   16980
tttggtttag aaaaaaatta tgatggagct aaaaatagaag ataatcaagt acagaacaaa   17040
tttaccattt caaattactc atttaaatat gaagacaacc cattttttagg ttttgctgga   17100 gccattggat attcaatgga aggtccaaga atagaacttg aagtatctta cgaaacattt   17160
aatgtaaaaa accaagacaa cagttacaaa aatgatgccc atatgtatta cctttttggca   17220 cgagaagttg atagttcttc gccaacaaaa cctcaagtta acaaatctgt cttgctcaaa   17280
aatgaaggtc taactgactt ttcaatcatg ctaaatgcat gttatgacat aataacagat   17340 aatataccctt tttccccttta tatatgtgca ggtgttggtg ctgatttagt gtcaatgttt   17400
aatagcataa atcctaaact tgcttaccaa ggaaaactag gtataagtta ctcaataagt   17460
ccagaagttt ctgcttttat tggtgggcac tttcataaag tgataggcaa tgaatttaaa   17520
gatattgcta ctatattacc tagcggttct agtattaagg ataatcaata tgcaatagta   17580
acacttagtg tatgtcattt tggtgtagaa attggtggaa gggtttcatt ttaattttaa   17640
agtaaattta tgagctacca gtttactaag caaatactat atagttttac tcagataaag   17700
tggtagtagg cactaaaatt taaaatagct agcaattata ttcataacta taagggttt   17760 atacatattg taattgttag ctaagctttg ttattacgaa acacaaacac atatctttcc   17820
tatatatggt cttgataaca taacaacttt ataacactta tctttatagg aaattatcta   17880
ccactcaata aatatactac aaaacaataa atctcaacag tttagaacta ttctgtaaat   17940
caaacatttc actatgatct tttactaaca tccttttctt cttttcctca taaggtacct   18000
agccaaacac catatgtaca ccactagtac acacctcaat aaacactaaa caccataaaa   18060
cctatgacaa aaagatgatt acctacctaa ataaacaac tttcactaaa actttaattg   18120
aggttacata cctataatat agcaatttat agccataaca tagataatgc cactacctttt   18180
```

```
aacacttcac ataaaaagcc ttataaacaa aatagagaat atctatcttg ttacaatctc    18240
ttaaaagaat agttatctac cacccataaa tacatatgaa atcttaccat cttccatgaa    18300
tataagatta acaccattaa agtaagactt gttgataaca taacgacttt ttacgaaaac    18360
aagacccatc cctacaacac tcttctacag ccagcaaagc tatttaattt ataaatgcaa    18420
acctaatacc aacttcacaa ccaaaatgat cagtatttaa attagcagaa gcagaagtaa    18480
tcttaggagc ttcttctata ctaggatgat aagcaatttc taccctctca tatttactgc    18540
ctacaacctt atgatagtaa ccacctccaa acaacataat attagacttt acagggtagt    18600
taacaccaaa cttaacttga taagaaaatt taggcaacga tattcctaaa aactttatgt    18660
aatctgcacc aacaccagca cacacatatg gagctaaagg aacatctcct ctggtaatat    18720
cataacagaa atttacattt agagatctat caataacacc attatttttcc aatactacaa    18780 acttttttact tgtaattgtt tcttcacgag ataatgcaaa aaacttatag ttattacttc    18840
cttcacgata aaactgtctt tcagactcaa aatgcgaata agaaccttca aattctattc    18900
tcatactatt aaagtaacac cccataacac cactaaaact attaaaacta cttgcataag    18960
taggatcata agcctgctta aaactagttt ctttagtaat atcagtagca tcataactta    19020
aagcaaaaat cttctttgtg agcccaggta ttgtttctgc agctgaaaaa ttactaaaat    19080
taggaacacc tactctatat tgagtaccaa cataaaaacc ccttttttct tcagaaacca    19140
ctacatcaga aaaagaacta tctggcaaaa aagaaaataa tgtacttaat gcaacactta    19200
gaacaaactt tttgtaattc attttttaat ccattaataa caaaaggtaa actacggtaa    19260
tctactatga caaagtatgt caagtcaagt aattgtacac aattataagt gttatacaaa    19320
caataaataa aattacaaaa aaatattttt cgtatcaatc agtataggtt ttatttcata    19380
gataataaaa acattaacaa aatattctat gtattatttt tcacatcaat taaaaaaatt    19440
gctactttaa taataaaaag cctatataaa tactttcata ccaatttcag ccccaaaata    19500
acctatatct aagttagcta atgccgaagt aaccttaggt gcataaaaga gatttcttgg    19560
atactgaaca ggaatattac tatattcatt gtcaattact ccatgataat atccatcaac    19620
aaataaagat atcctttcag atattaggta attaacacct actttagctt gggcagcaat    19680
tttaactttc acagtattaa agatactaat aatatctcct cctatcccta cacatgaaaa    19740
aggagtaata taagtattgt ttagcgtaaa atcataacaa atattcaaca taacagaatt    19800
taattctatt ccatcgtttt tcaaagtaac ataatttata tgttttgcag gaccatgtct    19860
atataatgca aaatatctat agttatcatc tacaatatgg cttttagtat cttgtacatc    19920 aaattttttca tagaaactct caagttctat tctgaaattt tgaaatgaat atccaatgaa    19980
aaaagataag ccaaaaaggc tattatcata ctttggcaca taatcttctg ataagtcaaa    20040
attatataga ttgtctacca atttatcagc actttctaat aaatcatgtt ttaaaccaac    20100
aacccgttca gtcgctacat catgcaaaat ctgtgtttct tctattgaaa aattattaaa    20160
aaaaggatga ctcaacttat ataaaacacc aaaagaaatt ggacttactt ggttagctaa    20220
agtatttgac atcccaaaag acatcgaggc ataaaaggt aggagtaatc ctaatcctgt    20280
tattgtagtt tttacaattt tatatttcat aatttatcac cttaaaaaat atagtacata    20340
cttaataatt tatttttaac taaaaaatta attagtctac aaataatatt aataatgag    20400 tttataatag ttaatactaa atgaaaaata tattaattat actataaaaa ttaatgttct    20460
tacgtaatat cacatcatta atacattaat atattaagta gaatgggtta ttcatattac    20520
```

```
ataataattt gggataattt ctactatatg gaaaacttttt aattataaag acaactttaa    20580
ataactctag aatttaactc aatattataa caccacatat tgattacttt aatctaatat    20640
aggcagcaca tttatctaga aatctaataa cttctctcca tctaaaaatg actaatgctc    20700
tactgtatta gtgccataca ttaacttttat aatacctgct taaacaattg ttacaggaat    20760
tttaatatta aaaacatatt aaaggttttc tcaaacaaca catcattatc tatagactaa    20820
tgctataaaa ctattctcgt tatctcaaga atacatgact taggccatct tttcgcatca    20880
acaactaaat aaagtatagc atatataaaa aaacaaatgt aaattacgat aatccagtac    20940
aataaatatc tcagccaagc aattatatat aatcctacag ggatacaaca actgataacg    21000
acacaaaaac tacttatttt tataacttat actttcaagt accacaacaa ttacaaattt    21060
atataaacta aatatgatat tattgcttta aaaataatt atcattcaag aataatacct    21120
aaataaatat tcttatacca acttcagaac ctaaataacc tatatccaac tcagccaata    21180
ctgaactacg agtagatgga aaaacaagaa cttttggata ttttacagaa atactactat    21240
attggttgcc aattatctta tgataataca tatccataaa taaaaatgcc ctttcagata    21300
ttctgtaatt aaatcccatt ttagcatgaa atgcaggttt aaatcttaca gcatcaaaga    21360
tattaataat atcttctcct attcctacac ataaaaaagg agtgagagaa gtattcttcc    21420
ctataaaatc gtagcaaata tttagtataa cagaataaag ttttactcca ttgtttatta    21480
aagtaacata atctgaattt aaattatctt gcttagataa agcaaaatac ctatagttat    21540
tatctataat gtgattttta gtatctctta catcaaagct ttcataaaga ccctcaagtt    21600
ctacttttaa gttttttaaat gaatatccaa ataaaaaaga taagccgtaa agactatttt    21660
tatattttgg aacgtagtct tctgaaaaat caaaattaga taaattttttt atagcttcat    21720
cagcatttat taaaatatca tttttcaatc caagaactct tttatttgct ataataccag    21780
atgtcaaatt tgtttctctg attaaaaaat gattaaaaaa aggagtactt aacttatatg    21840
aagcacttaa agaaacagat ttagtatgac tatcagaagc atctgatacc aaagatgctg    21900
aaaaagcctg gaaaggcaat aataacccaa gcattattat tgcaatttttt gtaattttgc    21960
atttcataac ttacttaccc tgaaaaacat agcatatatt tacaacttaa atacttctga    22020
ttaaaaaata ttgattgatc tgtaaaaaat tagacagcta atttataata attaattcta    22080
tatgaagaac gtattaataa taatataaag aaacaaacca gttaacgtac taccgtatta    22140
ttaatacacc catcgtagta catgcgtaat atagtataac atacgaaaaa gcattctaca    22200
taatcgatac tcaccaaatt ttatacaaaa gacaacttta aataacagtc aaaccatgta    22260
aacatattga aactttaaaa caactattta ttcggataat caaataactt atttcttctt    22320
atttaaaaat tactatttta ttatatcaat gtaacaatta cactttacat ttaatagatc    22380
gttataaata aatattacta agttcattaa atatcatata aaatactaat aataagttat    22440
gatcatatat aaatattacc tttactaata ctattcaact taataactta tcttatacct    22500
aatcacacat ataaaagacg tgcaaagatt acaacattaa gaatgttcaa atatcaaaaa    22560
aaaaaaatgc acttaattac cactaaacta ttgacttata caacaacaat ataacagtt    22620
aattcaccta ttaaacacta cttaattatg taaaaaacta ccaacaatac caataagtag    22680
tgtaaattct acatcacaac aagaaactta ctcatcaata aaatctattg catatacttt    22740
tatgtaaaga aaaaacatac cagataatca aaatcacagg ttacacaaaa cagaaaaaca    22800
aaaatctcgc taataactaa acattacctc gcatattctt tacctagcag aaaccaaata    22860
aaatgattgc tatatccaat attttaaaca caaaattttt atgtaaactt ccagataata    22920
```

```
ttagttattt ttttaaaaag aataaattta tgatttatga caaattatca tttgtataaa  22980
ataaaacata ttgttttctt tatcaatatg catataataa gtgttattaa taaatctagg  23040
taagtcataa tggatatttt tggtcacaat cttgacgctt acgtcgctac acttaatgca  23100
gagtacacag gaagcgttcc tgtacaagaa gatggcagtt ttgatgctac actaaatatt  23160
acggttgaag atctttatgg catatatgct cgtttttcgg gaactataca gcagcaacat  23220
ggaaaaagtt atctgaacta ttatcttgag gagagtacag attttccaga aattcctttc  23280
ttagcatcat acagcggcac agcaaaagtt ctcagtgaag atacagatac aggtctcatc  23340
tcttttgatg atattagcaa tggaatccac gtttcattct caacaaaaca acaagaaact  23400
ataagtagtg atagtataga agaagaagaa gaagaagaag cagcagcagc agcataagat  23460
aaagaaaaat tttttgtaac atcttacagg tttgtactat ctaataaggt aggtgcttaa  23520
gtttttctac ataggcacct actttataag tacattaaag tagattatat tttaagtgcc  23580
ttgcacagtt ttaaaaataa atacaaaata gagagcataa ctctacagca aaattcaggg  23640
tttactttta gagtctgtta ttctagtttc agcacaccat tatactaaaa cttaataaac  23700
agataaacta tgtactgatt ctttacaaat tatttacata gtatgtaaat atgcaatcac  23760
actacatgca aatgcgttaa ttttattgta cttttatctt atttaatcat ataattcaca  23820
acctaataaa ttaaatatca ttttattatg ctcagtattg cacaaaaaat ctttggctca  23880
gcaaataata gaacaataaa gtcattttac aaaatagtta acaacataaa tgcaatagaa  23940
catgaagttc aacttctttc taatgaatca ttaaagcaca aaactattga atttaaagaa  24000
gaactcaaac aaggtaaatc tctagatgac atattagtac cagcatttgc tgtagtaaga  24060
gaagctgcaa aaagagtatt aaatatgaga cactttgacg ttcaacttat aggaggaata  24120
gtctta                                                             24126
```

```
<210> SEQ ID NO 2
<211> LENGTH: 118
<212> TYPE: PRT
<213> ORGANISM: Ehrlichia ewingii

<400> SEQUENCE: 2

Gln Asn Gln Leu Ala Asn Lys Leu Gly Ile Thr Phe Gln Gln Val Gln
 1               5                  10                  15

Lys Tyr Glu Lys Gly Thr Asn Arg Ile Val Ile Ser Arg Leu Tyr Gln
            20                  25                  30

Leu Ala Ser Val Leu Asn Val Glu Val Arg Asp Ile Met Leu Lys Leu
        35                  40                  45

Gln Glu Asp Leu Lys Asn Ile Ser Cys Asp Asn Asp Val Val Ser Ile
    50                  55                  60

Pro His Leu Lys Asp Asn Glu Asp Lys Phe Ile Pro Glu Leu His Asp
65                  70                  75                  80

Asn Lys Ile Asp Ser Lys Glu Val Leu Met Met Val Arg Ala Tyr Thr
                85                  90                  95

Cys Ile Lys Asn Glu Lys Val Arg Asn Ile Ile Tyr Asn Leu Val Lys
            100                 105                 110

Ala Leu Ser Val Asp Asn
        115

<210> SEQ ID NO 3
<211> LENGTH: 293
<212> TYPE: PRT
```

-continued

<213> ORGANISM: Ehrlichia ewingii

<400> SEQUENCE: 3

Met Ile Lys Phe Ser Ser Val Gly Val Thr Leu Ser Leu Ala Thr Leu
1               5                   10                  15

Leu Ser His Asn Ala Leu Ser Ser Pro Ile Pro Ile Asp Phe Ser Asn
            20                  25                  30

Glu Ser Glu Met Val Gly Phe Tyr Ala Ser Ala His Tyr Asn Leu Glu
        35                  40                  45

Leu Pro Met Phe Ser Pro Ile Ser Val Lys Tyr Lys Ser Thr Gly Asn
    50                  55                  60

Ser Glu Ala Asp Lys Ser Glu Lys Glu Leu Thr Leu Phe Thr Leu Lys
65                  70                  75                  80

Glu Ser Thr Gln Ala Pro Asp Phe Thr Lys Lys Glu Thr Phe Asn Asp
                85                  90                  95

Lys Ser Gly Tyr Lys Pro Val Tyr Asn Arg Asn Tyr Thr Gly Phe Ser
            100                 105                 110

Gly Ala Val Gly Tyr Ser Gly Gly Ile Arg Val Glu Ile Glu Gly
        115                 120                 125

Ala Phe Thr Arg Phe Asp Val Asp Lys Gln Lys His Thr His Pro Asp
    130                 135                 140

Asn His Arg Tyr Phe Ala Ser Cys Thr Glu Gln Glu Met Lys Pro Ala
145                 150                 155                 160

Gln Gln Asn Gly Ser Ser Lys Asp Gly Asn Tyr Val Val Met Lys Asn
                165                 170                 175

Glu Gly Phe Lys Ala Ile Ser Leu Thr Phe Asn Val Cys Tyr Asp Met
            180                 185                 190

Ile Val Ser Asn Ser Ser Leu Ile Pro Ser Ala Cys Val Gly Ile Gly
        195                 200                 205

Gln Gly Ile Thr Asn Phe Leu Gly Ala Thr Asn Ile His Thr Ile Phe
    210                 215                 220

Gln Ala Lys Leu Gly Leu Gly Phe Ser Ile Ser Pro Lys Thr Ile Leu
225                 230                 235                 240

Phe Ala Asn Gly Tyr Tyr Val Lys Thr Lys Asp Asp Ala Phe Thr Asn
                245                 250                 255

Leu Thr Val Gln Tyr Pro Val Lys Leu Thr Ser Pro Pro Thr His Ile
            260                 265                 270

Asp Pro Val Val Tyr Phe His Ser Asp Tyr Cys Gly Gly Glu Val Gly
        275                 280                 285

Leu Arg Phe Ile Leu
    290

<210> SEQ ID NO 4
<211> LENGTH: 272
<212> TYPE: PRT
<213> ORGANISM: Ehrlichia ewingii

<400> SEQUENCE: 4

Met Ser Tyr Lys Lys Val Ile Phe Trp Ile Ile Leu Phe Leu Thr Pro
1               5                   10                  15

Gly Ala Ser Leu Ser Gln Gly Leu Asn Asp Asn Ile Phe Lys Asn Phe
            20                  25                  30

Tyr Val Gly Val Gln Tyr Lys Pro Ala Ile His His Leu Ser His Leu
        35                  40                  45

Ile Ile Lys Glu Thr Ser Lys Asp Thr Ile Gly Ile Phe Ala Leu Lys

```
                        50                  55                  60
Lys Asp Ala Ser Leu Pro Thr Asp Ile Lys Lys Asn Ser Asn Leu Asn
 65                  70                  75                  80

Ile Arg Tyr Asn Pro His Tyr Glu Asn Asn Asn Ser Gly Phe Ser Gly
                 85                  90                  95

Leu Leu Gly Tyr His Tyr Asn Asn Asn Phe Arg Ile Glu Ser Glu Ile
                100                 105                 110

Ser Tyr Glu Ile Phe Pro Leu Lys Asn Glu Gly Tyr Lys Ile Thr Gly
            115                 120                 125

Val Glu Gln His Phe Ala Leu Ala Ser Glu Leu Asp Thr Asn Gly Asn
        130                 135                 140

Gln Pro Lys Thr Asp Lys Tyr Val Thr Ile Ile Asn Asp Gly Ile Arg
145                 150                 155                 160

Ala Thr Ser Val Leu Ile Asn Ala Cys Tyr Asp Gly Ile Asp Ile Lys
                165                 170                 175

Lys Asn Asn Ile Val Val Tyr Ser Cys Ile Gly Leu Gly Ala Asp Ile
            180                 185                 190

Val Asp Phe Leu Ser Lys Tyr Asn Thr Lys Leu Ser Tyr Gln Gly Lys
        195                 200                 205

Leu Gly Leu Ser Tyr Pro Ile Ser Leu Lys Ile Ile Leu Phe Ala Glu
    210                 215                 220

Gly Tyr Tyr His Gly Leu Leu Gly Asn Val Phe Asn Asn Val Pro Val
225                 230                 235                 240

Asn Tyr Pro Thr Asp Asn Asn Thr Thr Lys Thr Thr Val Ser Ala Ile
                245                 250                 255

Leu Asn Ile Arg Tyr Tyr Gly Gly Ser Val Gly Val Arg Phe Ile Leu
            260                 265                 270

<210> SEQ ID NO 5
<211> LENGTH: 185
<212> TYPE: PRT
<213> ORGANISM: Ehrlichia ewingii

<400> SEQUENCE: 5

Met Ser Asn Arg Lys Leu Tyr Asn Lys Ser Leu Leu Phe Ser Phe Pro
 1               5                  10                  15

Thr Ser Cys Leu Phe Leu Phe Phe His His Ser Ser His Val Asn Ala
                20                  25                  30

Leu Asn Phe Ser Ile Ser Asn Tyr Leu Asn Arg Tyr Asn Asn Ile Phe
             35                  40                  45

Asn Thr Glu Asp Asn Lys Pro Leu Asn Ser Gln Val Asn Thr Ser Phe
         50                  55                  60

Met Phe Ile Thr Arg Thr Ile Lys Ser Ser Ala Arg Lys Thr Lys Gly
 65                  70                  75                  80

Ile Val Glu Asp Phe Cys Arg Asn Ser Asn Val Leu Thr Lys Lys Leu
                 85                  90                  95

Val Pro Asp Leu Tyr Thr Lys Thr Val Arg Arg Ile Ile Ser Ile Phe
            100                 105                 110

Asn Glu Ile Lys Leu Asn His Ile Ile Ser Tyr Leu Thr Ala Phe Thr
        115                 120                 125

Ser Phe Arg Met Val Thr Ser Gln Tyr His Glu Val Met Ser Asn Phe
    130                 135                 140

Lys Gly Leu Phe Ile Asn Cys Ser Leu Asn Ile Ile Asp Lys Arg Asn
145                 150                 155                 160
```

```
Phe Lys Ser Ile Ile Ser Gly Ile Asn Tyr Phe Asp Arg Glu Ile Arg
                165                 170                 175

Cys Leu Leu Ser Gln Ser Tyr Asn Tyr
            180                 185

<210> SEQ ID NO 6
<211> LENGTH: 284
<212> TYPE: PRT
<213> ORGANISM: Ehrlichia ewingii

<400> SEQUENCE: 6

Met Asn Tyr Ala Lys Val Phe Ile Leu Met Phe Val Ile Leu Phe Leu
  1               5                  10                  15

Pro Ser Ser Ser Leu Leu Ala Leu Glu Asn Asn Leu Ser Gly Gly Val
                 20                  25                  30

Gly His Ile Tyr Ile Ser Gly Gln Tyr Lys Pro Ser Ile Pro Gln Phe
             35                  40                  45

Asn Lys Phe Ser Met Glu Glu Ala Thr Ile Gly Ala Val Ile Pro Lys
         50                  55                  60

Ser Leu Lys Gln Asp Ala Glu Asp Ile Thr Leu Ser Ile Leu Ala Leu
 65                  70                  75                  80

Ser Thr Asn Phe Thr Leu Pro Tyr Asp Pro Lys Tyr Lys Lys Ser Leu
                 85                  90                  95

Leu Gly Leu Gly Gly Thr Ile Gly Tyr Ala Ile Asn Asn Phe Arg Ile
                100                 105                 110

Glu Leu Glu Thr Phe Tyr Glu Lys Phe Asn Val Ser Ala Pro Ser Gly
            115                 120                 125

Tyr Asp Asp Asn Ile Tyr Ala Tyr Phe Ser Ile Glu Val Pro Gln Leu
        130                 135                 140

Arg Ser Leu Pro Tyr His Tyr Thr Met Lys Asn Thr Gly Ile Ile Leu
145                 150                 155                 160

Ser Pro Val Leu Ala Asn Ile Cys Tyr Asp Ile Asn Lys Lys Gln Leu
                165                 170                 175

Arg Asn Val Ser Pro Tyr Leu Cys Leu Gly Phe Gly Val Asp Leu Ile
            180                 185                 190

Asp Phe Leu Asp Lys Val Ser Phe Lys Phe Ser Tyr Gln Ala Lys Leu
        195                 200                 205

Gly Val Ser Tyr Leu Ile Ser Pro Asn Leu Ala Phe Phe Ile Asp Gly
    210                 215                 220

Ser Phe His Arg His Leu Gly Asn Gln Phe Ser Asp Leu Leu Leu Asp
225                 230                 235                 240

Tyr Pro Ser Tyr Tyr Arg Ser Leu Thr Ser Leu Ser Asp Asn Asp Pro
                245                 250                 255

Asn Arg Ile Leu Pro Phe Thr Ser Ala Ser Ala Lys Leu Asn Ile Asn
            260                 265                 270

Phe Phe Ser Ala Asn Ile Gly Ile Arg Phe Ile Phe
        275                 280

<210> SEQ ID NO 7
<211> LENGTH: 293
<212> TYPE: PRT
<213> ORGANISM: Ehrlichia ewingii

<400> SEQUENCE: 7

Met Phe Met Lys Lys Leu Tyr Tyr Leu Asn Phe Thr Val Leu Val Leu
  1               5                  10                  15
```

-continued

Thr Val Tyr Leu Phe Pro Ser Phe Val Phe Ser Met Gln Gly Arg Ser
            20                  25                  30

Asn Ile Thr Gly Ser Tyr Ile Thr Val Ser Tyr Gln Pro Ser Met Ser
        35                  40                  45

Asn Phe Arg Asn Phe His Ile Lys Glu Thr Asn Phe Asp Thr Lys Asp
    50                  55                  60

Pro Ile Gly Leu Ile Arg Ser Ala Arg Ser Thr Glu Pro Ser Val Leu
65                  70                  75                  80

Lys Ile Asn Thr His Phe Tyr Lys Pro Gln Gln Ser Asp Ser Tyr Lys
                85                  90                  95

Ser Tyr Gly Asn Asp Leu Leu Gly Phe Ser Thr Ser Ile Gly Leu Leu
            100                 105                 110

Val Lys Asn Leu Arg Met Glu Phe Glu Gly Ser Tyr Lys Lys Phe Asp
        115                 120                 125

Ile Lys Arg Leu Val Asn Tyr Ala Ser Arg Asp Gly His Arg Tyr Phe
    130                 135                 140

Ala Ile Pro Arg Asp Thr Phe Phe Asn Asn Ser Ile Pro Tyr Ala Phe
145                 150                 155                 160

Asn Ala Tyr Thr Val Ala Lys Asn Asn Gly Leu Ser Ile Ile Ser Asn
                165                 170                 175

Met Ile Asn Leu Cys Tyr Glu Ser Ile Lys Tyr Asn Asn Phe Met Pro
            180                 185                 190

Tyr Ile Cys Leu Gly Ala Gly Gly Asp Phe Ile Glu Leu Phe Asp Ser
        195                 200                 205

Met Arg Ile Lys Phe Ala Tyr Gln Gly Lys Leu Gly Val Ser Tyr Pro
    210                 215                 220

Leu Thr Ser Asn Leu Val Leu Ala Ile Ser Gly Gln Tyr His Lys Val
225                 230                 235                 240

Val Gly Asp Lys Phe Lys Phe Leu Pro Leu Met Leu Ser Pro Ser Thr
                245                 250                 255

Pro Arg Arg Arg Ile Pro Pro Gln Ser Ser Ser Glu Val Gln Asp Ala
            260                 265                 270

Thr Gly Leu Leu Thr Leu Asp Leu Gly Tyr Phe Ser Ala Asp Ile Gly
        275                 280                 285

Leu Arg Phe Met Phe
    290

<210> SEQ ID NO 8
<211> LENGTH: 272
<212> TYPE: PRT
<213> ORGANISM: Ehrlichia ewingii

<400> SEQUENCE: 8

Met Asn Asn Lys Lys Ser His Val Ile Cys Met Leu Ile Phe Leu Leu
 1               5                  10                  15

Leu Pro Met Lys Ser Phe Ser Val Leu Ile Asp Thr Thr Glu Lys Asp
            20                  25                  30

Tyr Ala Ser Asn Val Tyr Ile Ser Ser Gln Tyr Lys Pro Ser Phe Ser
        35                  40                  45

Asn Phe Arg Ser Phe Ser Ile Gln Glu Ile Asn Ser Lys Thr Lys Asn
    50                  55                  60

Ser Ile Ala Leu Glu Lys Pro Ile Glu Ser Ser Asn Ile Leu Lys
65                  70                  75                  80

Ser Asn Ala His Ile Ile Val Pro His Asn Ile Gln Phe Gln Asp Asn
                85                  90                  95

-continued

Thr Ile Ser Phe Ser Gly Ala Val Gly Tyr Ser Ser Lys Gly Leu Arg
            100                 105                 110

Leu Glu Leu Glu Ser Ala Tyr Glu Glu Phe Tyr Thr Lys Glu Leu Asn
            115                 120                 125

Ser Ser Ser Leu Ile Ser Ser Asn Asn His Tyr Thr Gln Leu Tyr Glu
            130                 135                 140

Ala Asn Phe Gln Asn Phe Ala Thr Ser Arg Leu Ser Ile Thr Ser Phe
145                 150                 155                 160

Ile Ile Asn Thr Cys Tyr Asp Ile Leu Ile Gly Ser Ser Pro Val Met
                165                 170                 175

Pro Tyr Ile Cys Thr Gly Ile Gly Gly Asp Ile Ile Arg Leu Phe Asn
            180                 185                 190

Thr Thr Tyr Leu Lys Phe Ala Tyr Gln Gly Lys Phe Gly Ile Ser Tyr
            195                 200                 205

Pro Leu Asn Asn Asn Ile Ile Leu Phe Ser Asp Ile Tyr Tyr His Glu
            210                 215                 220

Ile Ile Gly Gln Glu Phe Glu Asn Leu Tyr Thr Gln Tyr Val Ser Gly
225                 230                 235                 240

Ile Asn Ser Leu Gln Glu Ile Thr Ser Val Pro Ala Ser Phe Asn Ile
                245                 250                 255

Gly Tyr Phe Gly Ser Glu Ile Gly Val Arg Phe Ile Phe Asn Lys Gln
            260                 265                 270

<210> SEQ ID NO 9
<211> LENGTH: 299
<212> TYPE: PRT
<213> ORGANISM: Ehrlichia ewingii

<400> SEQUENCE: 9

Met Arg Lys Lys Ile Tyr Ser Ile Asn Val Ile Leu Val Phe Thr Leu
1               5                   10                  15

Leu Leu Leu Ser Ile Gln Ser Phe Ala Ile Ser Ile Asp Asn Asn Ile
            20                  25                  30

Ile Asp Gln Asn Leu Gly Leu Tyr Leu Ser Ala Gln Tyr Lys Pro Ser
            35                  40                  45

Ile Ser His Phe Lys Asn Phe Ser Val Gln Glu Val Asn Lys Lys Val
50                  55                  60

Asp Leu Ile Ala Leu Lys Asn Asp Val Thr His Ile Thr Glu Glu Ile
65                  70                  75                  80

Leu Lys Asp Pro Thr Asn Phe Asn Thr His Tyr Ser Ala Lys Phe Lys
                85                  90                  95

Asn Ser Phe Thr Gly Phe Ser Gly Ala Val Gly Tyr Tyr Ser Ala Gln
            100                 105                 110

Gly Pro Arg Leu Glu Val Glu Gly Phe Tyr Glu Asn Phe Asp Ile Thr
            115                 120                 125

Asp Cys Ser Asn Cys Thr Ile Asn Asp Ala Asn Arg Tyr Leu Ala Leu
            130                 135                 140

Ala Arg Glu Lys Asp Asn Asn Gln Val Gln Pro Lys Ala His Asp Ser
145                 150                 155                 160

Ser Ser Thr Asp Ser Asn Ser Asn Asn Thr Lys Lys Ser Tyr
                165                 170                 175

Phe Thr Phe Met Lys Asn Asn Gly Ile Ser Ile Ala Ser Val Met Ile
            180                 185                 190

Asn Gly Cys Tyr Asp Phe Ser Leu Asn Asn Ile Lys Ile Ser Pro Tyr

```
            195                 200                 205
Val Cys Ala Gly Ile Gly Gly Asp Phe Ile Glu Phe Phe Glu Val Met
210                 215                 220

His Ile Lys Phe Ser Tyr Gln Gly Lys Leu Gly Val Ser Tyr Leu Ile
225                 230                 235                 240

Ser Pro Ser Ile Ser Leu Phe Val Asp Gly Tyr Tyr His Ser Val Ile
                245                 250                 255

Asn Asn Lys Phe Lys Asn Leu His Val Thr Tyr Ala Tyr Ile Leu Lys
                260                 265                 270

Asp Ser Pro Thr Ile Thr Ser Ala Ile Ala Gln Leu Asn Ile Gly Tyr
                275                 280                 285

Phe Gly Gly Glu Val Gly Leu Arg Phe Val Phe
290                 295

<210> SEQ ID NO 10
<211> LENGTH: 284
<212> TYPE: PRT
<213> ORGANISM: Ehrlichia ewingii

<400> SEQUENCE: 10

Met Ser Asn Lys Lys Phe Thr Ile Gly Thr Val Leu Val Ser Leu
1               5                   10                  15

Leu Ala Phe Leu Pro Thr Tyr Ser Phe Ser Ala Pro Ile Ser Asn Asn
                20                  25                  30

Ser Glu Asp Asn Ile Phe Gly Leu Tyr Ile Ala Gly Gln Tyr Arg Pro
                35                  40                  45

Gly Val Ser His Phe Ser Gly Phe Gly Val Thr Glu Thr Asn Phe Ala
            50                  55                  60

Thr Gln Lys Leu Met Arg Val Lys Lys Asp Ser Lys Glu Gly Leu Pro
65                  70                  75                  80

Asn Ile Leu Lys Ser Lys Asp Asn Phe Thr Glu Pro Tyr Val Ala Lys
                85                  90                  95

Phe Gln Asp Asn Ala Val Ser Phe Ser Gly Ala Ile Gly Tyr Ser Tyr
                100                 105                 110

Pro Glu Gly Leu Arg Leu Glu Ile Glu Gly Ser Tyr Glu Thr Phe Asp
            115                 120                 125

Val Lys Asp Pro Lys Asp Cys Ser Val Lys Asp Ala Phe Arg His Leu
130                 135                 140

Ala Leu Val Arg Glu Leu Asp Thr Gly Leu Ser Met Pro Lys Glu Lys
145                 150                 155                 160

Lys Tyr Thr Val Met Arg Asn Asn Gly Leu Ser Ile Ala Ser Ile Leu
                165                 170                 175

Ile Asn Gly Cys Tyr Asp Phe Asp Phe Asp Asn Leu Ile Val Ser Pro
                180                 185                 190

Tyr Val Cys Leu Gly Ile Gly Glu Asp Phe Ile Glu Phe Phe Asp Val
            195                 200                 205

Leu His Ile Lys Phe Ala Tyr Gln Gly Lys Leu Gly Ile Ser Tyr Glu
210                 215                 220

Leu Ser Pro Arg Ile Asn Val Phe Ala Asp Gly Tyr Tyr His Lys Val
225                 230                 235                 240

Ile Gly Asn Gln Phe Lys Asn Leu Asn Val Asn His Val Val Glu Leu
                245                 250                 255

Asp Asp Phe Pro Lys Val Thr Ser Ala Val Ala Thr Leu Asn Val Gly
                260                 265                 270
```

```
Tyr Phe Gly Gly Glu Val Gly Val Arg Phe Ile Phe
            275                 280
```

```
<210> SEQ ID NO 11
<211> LENGTH: 243
<212> TYPE: PRT
<213> ORGANISM: Ehrlichia ewingii

<400> SEQUENCE: 11
```

```
Met Ser Cys Glu Lys Lys Phe Cys Tyr Ser Lys His Ile Ile Phe
  1               5                  10                  15

Phe Ile Thr Thr Val Ser Ser Val Gln Ser Phe Ser Ala Ser Leu Asn
                 20                  25                  30

Asn Ala Glu Asp His Lys Asp Phe Tyr Leu Tyr Val Ile Leu Tyr Ile
             35                  40                  45

Ser Tyr Asn Phe Phe Cys Ile Ile Arg Leu Ile Thr Val Lys Asp Ser
 50                  55                  60

His Phe Phe Ser Ile Asn Thr Ser Ser Tyr Asn Leu Cys Leu Glu Lys
 65                  70                  75                  80

His Lys Asn Asp Ile Ser Phe Ser Lys Ile Leu Gly Val Phe Thr Lys
                 85                  90                  95

Thr Ile His Ser Tyr Asn Ile Gly Asp Ser His Glu Arg Phe Asn Ala
            100                 105                 110

Glu Asn Leu Arg Asn Ser Leu Thr Glu Asp Lys Tyr Leu Thr Ser Glu
        115                 120                 125

Gln Glu Val Asn Asp Tyr Asn Ile Ile Ser Ala Ile Lys Asn Ser Gly
    130                 135                 140

Leu Tyr Leu Leu Ile Glu Ile Leu Phe Asn Ile Tyr Tyr Ile Ile Ile
145                 150                 155                 160

Gly Arg Asn Phe Ile Thr Ser Phe Asp Ile Leu Cys Ile Lys Ser Thr
                165                 170                 175

Asn Gln Thr Glu Leu Ser Ile Asn Leu Leu Ser Lys Ala Asn Leu Pro
            180                 185                 190

Ile Asn Arg Phe Tyr Tyr Arg Ile Lys Asp Asn Gln His Glu Asn Ser
        195                 200                 205

Lys Ile His Tyr Ala Ile Ile Leu Ser Asn Asn Lys Tyr Leu Gln Asn
    210                 215                 220

Ser Leu Gly Asp Thr Lys Thr Asn Thr Tyr Gly Val Arg Ser Asn Phe
225                 230                 235                 240

Asn Asn Thr
```

```
<210> SEQ ID NO 12
<211> LENGTH: 281
<212> TYPE: PRT
<213> ORGANISM: Ehrlichia ewingii

<400> SEQUENCE: 12
```

```
Met Ser Asn Lys Lys Ile Phe Ser Ile Ile Gly Gln Ala Leu Thr Cys
  1               5                  10                  15

Leu Val Leu Phe Ser Pro Ile Tyr Ser Phe Ser Glu Ser Asn His Tyr
                 20                  25                  30

Asp Lys Ser Leu Tyr Val Ala Gly Gln Tyr Lys Ser Ser Leu Ser His
             35                  40                  45

Phe Thr Asn Phe Ser Val Arg Glu Thr Asp Ile Asn Thr Lys Gly Leu
 50                  55                  60

Phe Lys Leu Gly His Gly Val Thr Leu Val Glu Glu Asp Ile Lys Asn
```

```
                65                  70                  75                  80
        His Leu Gln Phe Thr Ile Pro His Ser Val Ala Phe Lys Asn Asn Phe
                            85                  90                  95

Ala Asn Phe Ser Ala Ala Val Gly Tyr Ile Ser Pro Gly Gly Pro Arg
                        100                 105                 110

Val Glu Ile Glu Gly Ser Tyr Glu Asn Phe Asp Val Lys Asp Leu Lys
                        115                 120                 125

Asn Cys Thr Ile Gln Asp Ala Cys Arg Tyr Leu Ser Leu Ala Arg Glu
        130                 135                 140

Ile Cys Lys Glu Asn Asp Lys Pro Thr Pro Lys Glu Lys Lys Tyr Val
        145                 150                 155                 160

Val Met Arg Asn Asp Gly Ile Ser Ile Thr Ser Val Thr Ile Asn Gly
                            165                 170                 175

Cys Tyr Asp Phe Ser Ile Asn Lys Leu Pro Lys Ile Ser Pro Tyr Ile
                        180                 185                 190

Cys Ala Gly Phe Gly Gly Asp Phe Ile Glu Phe Phe Asp Ser Val Arg
                        195                 200                 205

Val Lys Phe Ala Tyr Gln Ser Lys Leu Gly Ile Asn Tyr Ser Leu Ser
        210                 215                 220

Ser Asn Phe Ile Leu Phe Val Asp Gly Tyr Tyr His Arg Val Ile Gly
        225                 230                 235                 240

Asn Gln Phe Lys Asn Leu Asn Val Gln Asn Met Phe Asp Ser Asn Glu
                            245                 250                 255

Pro Tyr Val Thr Ser Ala Ile Ala Thr Leu Asn Ile Glu His Phe Gly
                        260                 265                 270

Gly Gly Phe Gly Leu Arg Phe Ile Phe
                        275                 280

<210> SEQ ID NO 13
<211> LENGTH: 280
<212> TYPE: PRT
<213> ORGANISM: Ehrlichia ewingii

<400> SEQUENCE: 13

Met Arg Lys Lys Ser Phe Ile Ile Ile Gly Thr Val Leu Ile Cys Leu
        1               5                   10                  15

Leu Ser Pro Pro Asn Ile Ser Phe Ser Glu Val Ile Thr His Asn Asp
                        20                  25                  30

Asn Lys His Pro Gly Ile Tyr Val Ser Gly Gln Tyr Lys Pro Gly Ile
                    35                  40                  45

Ser His Leu Arg Lys Phe Ser Val Lys Glu Thr Asn Ala Thr Thr Val
        50                  55                  60

Gln Leu Val Gly Leu Asn Tyr Thr Ala Ala Pro Ile Asp Asp Ile Lys
        65                  70                  75                  80

Thr Ser Ser Lys Phe Asp Thr Pro Tyr Thr Ile Ala Phe Gln Asn Asn
                            85                  90                  95

Ile Ile Ser Phe Ser Ala Ala Ile Gly Tyr Ser His Ala Lys Gly Leu
                        100                 105                 110

Arg Ile Glu Leu Glu Gly Ser Tyr Glu Glu Phe Asp Val Thr Asp Pro
                        115                 120                 125

Gly Asn Tyr Thr Ile Lys Asp Ala Tyr Arg Tyr Phe Ala Ile Ala Arg
        130                 135                 140

Glu Met Asn Ser Ser Ser Asn Asn Gln Pro Lys Asp Lys Gln Phe Thr
        145                 150                 155                 160
```

```
Val Met Arg Asn Asp Gly Val Ser Ile Val Ser Phe Met Phe Asn Gly
            165                 170                 175

Cys Tyr Asp Phe Pro Leu Gly Ile Leu Glu Ile Ser Pro Tyr Ile Cys
        180                 185                 190

Ala Gly Ile Gly Gly Asp Phe Ile Glu Phe Asp Ala Leu His Ile
        195                 200                 205

Lys Pro Ala Tyr Gln Gly Lys Leu Gly Leu Asn Tyr Pro Leu Phe Ser
210                 215                 220

Lys Val Ser Leu Phe Ile Asp Gly Tyr Tyr His Lys Val Ile Gly Gln
225                 230                 235                 240

Gln Phe Lys His Leu Asn Val Gln His Val Val Thr Leu Asp Thr Pro
            245                 250                 255

Lys Ile Ala Ser Val Val Ala Thr Leu Asp Val Ser Tyr Phe Gly Gly
            260                 265                 270

Glu Ile Gly Met Arg Leu Ile Phe
            275                 280

<210> SEQ ID NO 14
<211> LENGTH: 290
<212> TYPE: PRT
<213> ORGANISM: Ehrlichia ewingii

<400> SEQUENCE: 14

Met Asn Asn Lys Lys Met Phe Ser Ile Ile Gly Ile Ser Leu Leu Ala
1               5                   10                  15

Asn Leu Leu Leu Leu Pro Asn Met Ser Phe Ala Lys Asn Asn Tyr Ser
                20                  25                  30

Tyr Ile Asn Pro Val Leu Tyr Ile Ser Gly Gln Tyr Arg Pro Gly Val
            35                  40                  45

Ser His Phe Ser Gln Phe Ser Val Arg Glu Thr His Tyr Asp Thr Gln
        50                  55                  60

Leu Leu Ala Glu Leu Lys Lys Glu Val Gly Ser Val Thr Asn Thr Val
65                  70                  75                  80

Ile Gln Ala Tyr Ala Asn Tyr Asn Val Pro Ser Gln Ala Pro Phe Ser
                85                  90                  95

His Thr Tyr Val Ala Glu Phe Glu Asp Asn Thr Ile Ser Phe Ser Gly
            100                 105                 110

Ala Val Gly Phe Ser Tyr Ser Glu Gly Pro Arg Ile Glu Ile Glu Phe
        115                 120                 125

Ser Tyr Glu Glu Phe Asp Val Lys Asn Ser Gly His Ser Ser Ile Asp
130                 135                 140

Ala His Arg Tyr Phe Ala Leu Leu Arg His Ser Asn Asn Gly Asn Thr
145                 150                 155                 160

Gln Gln Asn Pro Phe Ala Val Met Arg Asn Asn Gly Leu Phe Ile Gly
                165                 170                 175

Ser Val Ala Ile Asn Ser Cys Tyr Asp Phe Ile Leu Asp Asp Thr Pro
            180                 185                 190

Ala Leu Pro Tyr Val Cys Gly Ile Gly Gly Asp Phe Ile Glu Phe
        195                 200                 205

Phe Asp Glu Leu His Val Lys Leu Ala Tyr Gln Gly Lys Ile Gly Ile
    210                 215                 220

Ser Tyr Pro Ile His Ser Lys Val Ser Thr Phe Val Asp Val Tyr Tyr
225                 230                 235                 240

His Arg Val Ile Asn Asn Lys Phe Lys Asn Leu His Val Gln Tyr Val
                245                 250                 255
```

```
Asn Thr Thr Thr Ser Gln Ala Ile Asn Pro Gln Ile Thr Ser Ala Val
            260                 265                 270

Ala Thr Leu Asn Val Gly Tyr Phe Gly Ile Glu Ile Gly Ala Arg Leu
        275                 280                 285

Thr Phe
    290

<210> SEQ ID NO 15
<211> LENGTH: 298
<212> TYPE: PRT
<213> ORGANISM: Ehrlichia ewingii

<400> SEQUENCE: 15

Met Asn Asn Lys Asn Arg Phe Thr Ala Ile Gly Val Ala Leu Thr Cys
 1               5                  10                  15

Leu Leu Leu Leu Pro Asn Val Ser Phe Ser Glu Thr Thr Ile Ile Asn
            20                  25                  30

Gln Pro Ser Gly Leu Tyr Ile Ser Gly Gln Tyr Lys Pro Ser Val Ser
        35                  40                  45

Val Phe Ser Asp Phe Ser Val Lys Glu Ala Asn Val Ala Thr Lys His
    50                  55                  60

Leu Ile Ala Leu Lys Lys Ser Val Asp Ser Ile Asn Ala Glu Lys Ala
65                  70                  75                  80

Thr Pro His Asn Gln Gly Leu Gly Lys Pro Asp Asn Phe Asn Ile Pro
                85                  90                  95

Tyr Lys Val Glu Phe Glu Asp Asn Ala Val Ser Phe Ser Gly Val Ile
            100                 105                 110

Gly Tyr Ser Phe Pro Glu Gly Pro Arg Ile Glu Ile Glu Thr Ser Tyr
        115                 120                 125

Glu Glu Phe Asp Val Lys Asn Pro Gly Gly Tyr Thr Leu Asn Asp Ala
    130                 135                 140

Phe Arg Tyr Phe Ala Leu Ala Arg Glu Ile Glu Ser Asp Gln Asn Lys
145                 150                 155                 160

Phe Gln Pro Lys Asn Ala Asn Ser Asn Ser Ser Asn Lys Ile Tyr His
                165                 170                 175

Thr Val Met Arg Asn Asp Gly Ile Ser Val Leu Ser Asn Met Ile Asn
            180                 185                 190

Ile Cys Tyr Asp Phe Ser Leu Asp Asn Leu Pro Val Leu Pro Tyr Ile
        195                 200                 205

Cys Gly Gly Thr Gly Val Asp Thr Ile Glu Phe Phe Asp Ser Leu His
    210                 215                 220

Ile Lys Leu Ala Gly Gln Ala Lys Ile Gly Ile Thr Tyr Pro Leu Ser
225                 230                 235                 240

Ser Asn Ile Asn Leu Phe Ala Gly Tyr Tyr His Lys Val Ile Gly
                245                 250                 255

Asn Arg Phe Lys Asn Leu Lys Val Gln His Ile Ala Glu Leu Asn Asp
            260                 265                 270

Ala Pro Lys Val Thr Ser Ala Val Ala Thr Leu Asn Ile Ser Tyr Phe
        275                 280                 285

Gly Gly Glu Ile Gly Ala Arg Phe Ile Phe
    290                 295

<210> SEQ ID NO 16
<211> LENGTH: 302
<212> TYPE: PRT
```

<213> ORGANISM: Ehrlichia ewingii

<400> SEQUENCE: 16

Met Glu Ile Ser Met Ser Asn Lys Lys Leu Phe Thr Ile Ser Thr
1               5                   10                  15

Ala Leu Tyr Leu Leu Ser Pro Asn Ile Ser Phe Ser Glu Thr Ile
            20                  25                  30

Val Asp Asp Ile Asp Arg Gln Phe Arg Leu Tyr Ile Ser Gly Gln Tyr
        35                  40                  45

Lys Pro Ser Leu Ser Val Phe Ser Asn Phe Ser Val Lys Glu Thr Asn
    50                  55                  60

Val Thr Thr Lys Tyr Leu Thr Ala Leu Lys Lys Asp Ala Asp Pro Thr
65                  70                  75                  80

Glu Lys Thr Gly Ser Thr Pro His Glu Lys Gly Leu Gly Lys Pro Asp
                85                  90                  95

Asn Phe Asn Ile Pro Tyr Lys Val Glu Phe Glu Asp Asn Ala Val Ser
            100                 105                 110

Phe Ser Gly Ala Val Gly Phe Ser Tyr Pro Glu Gly Leu Arg Ile Glu
        115                 120                 125

Ile Glu Ala Ser Tyr Glu Glu Phe Asp Val Lys Asn Pro Gly Gly Tyr
    130                 135                 140

Thr Ile Ser Asn Ala Phe Arg Tyr Phe Ala Leu Val Arg Glu Ser Glu
145                 150                 155                 160

Ser Ser Lys Glu Pro Gln Pro Lys Asn Pro Asn Ser Ala Gly Asn Asn
                165                 170                 175

Lys Ile Phe His Thr Val Met Arg Asn Asp Gly Val Ala Ile Ser Ser
            180                 185                 190

Ile Thr Ile Asn Gly Cys Tyr Asp Phe Ser Leu Ser Gln Leu Pro Val
        195                 200                 205

Leu Pro Tyr Ile Cys Gly Gly Ile Gly Ile Asp Thr Ile Asp Phe Phe
    210                 215                 220

Asp Ala Leu His Ile Lys Phe Ala Gly Gln Gly Lys Leu Gly Ile Thr
225                 230                 235                 240

Tyr Pro Leu Ser Gly Asn Ile Asn Leu Phe Ala Asp Gly Tyr Tyr His
                245                 250                 255

Lys Val Ile Ser Asn Gln Phe Lys Asn Leu Asn Val Gln His Val Ala
            260                 265                 270

Glu Leu Asn Asp Asp Pro Lys Val Thr Ser Ala Val Ala Thr Leu Asn
        275                 280                 285

Ile Ser Tyr Phe Gly Gly Glu Ile Gly Val Arg Tyr Ile Phe
    290                 295                 300

<210> SEQ ID NO 17
<211> LENGTH: 285
<212> TYPE: PRT
<213> ORGANISM: Ehrlichia ewingii

<400> SEQUENCE: 17

Met Asn Tyr Asn Lys Ile Leu Val Arg Ser Ala Leu Ile Ser Leu Met
1               5                   10                  15

Thr Val Leu Pro Tyr Gln Ser Phe Ala Asp Pro Met Asn Ser Asn Asp
            20                  25                  30

Val Ser Ile Asn Asp Ser Lys Glu Gly Phe Tyr Ile Ser Ala Lys Tyr
        35                  40                  45

Ser Pro Ser Ile Pro Tyr Ile Arg Lys Phe Ser Ala Val Glu Thr Pro 50 55 60

Ile Glu Gly Ala Ile Ser Pro Thr Lys Lys Val Leu Gly Leu Asn Lys
65 70 75 80

Gly Gly Ser Ile Ala Asn Ser His Asp Phe Ser Lys Ile Asp Pro Ser
85 90 95

Leu Asp Phe His Asn Asn Leu Ile Ser Gly Phe Ser Gly Ser Ile Gly
100 105 110

Tyr Ala Met Asp Gly Pro Arg Ile Glu Ile Glu Ala Thr Tyr Gln Lys
115 120 125

Phe His Pro Lys Asn Pro Asp Asn Asn Asp Thr Asp Ser Ser Asp His
130 135 140

Tyr Lys Tyr Tyr Gly Leu Phe Arg Glu Gly Thr Pro Gln Glu Glu Glu
145 150 155 160

His Arg Tyr Val Val Leu Lys Asn Glu Gly Leu Thr Phe Met Ser Leu
165 170 175

Thr Val Asn Ala Cys Tyr Asp Ile Val Ala Glu Gly Ile Pro Phe Ile
180 185 190

Pro Tyr Ala Cys Val Gly Ile Gly Ser Asp Leu Ile Asp Ile Phe Asn
195 200 205

Asp Lys Asn Leu Lys Phe Ala Tyr Gln Gly Lys Val Gly Ile Ser Tyr
210 215 220

Pro Ile Thr Ser Glu Val Ser Ala Phe Ile Gly Gly Tyr Tyr His Gly
225 230 235 240

Ile Ile Gly Asn Lys Phe Asn Lys Leu Pro Val Lys Thr Pro Val Thr
245 250 255

Leu Asp Thr Ala Pro Gln Thr Thr Ser Ala Ser Val Glu Leu Asp Thr
260 265 270

Gly Phe Phe Gly Gly Glu Ile Gly Val Ser Phe Ser Phe
275 280 285

<210> SEQ ID NO 18
<211> LENGTH: 278
<212> TYPE: PRT
<213> ORGANISM: Ehrlichia ewingii

<400> SEQUENCE: 18

Met Asn Cys Lys Lys Ile Phe Ile Thr Ser Ala Leu Met Ser Leu Val
1 5 10 15

Ser Phe Ile Pro Cys Ile Ser Phe Ser Asn Pro Met Gln Asp Asn Asn
20 25 30

Ile Val Gly Asn Phe Tyr Val Ser Gly Lys Tyr Met Pro Thr Ile Ser
35 40 45

His Phe Asp Asn Phe Ser Ala Lys Glu Asp Thr Ile Glu Thr Ile Ala
50 55 60

Thr Phe Gly Leu Ser Lys Thr Tyr Asn Arg Ser Ser Pro Ile His Ser
65 70 75 80

Asp Phe Thr Asp Ser Lys Tyr Ser Phe Lys Tyr Glu Asn Asn Pro Phe
85 90 95

Leu Gly Phe Ala Gly Ala Val Gly Tyr Ser Met Glu Gly Leu Arg Leu
100 105 110

Glu Phe Glu Ile Ser Tyr Glu Lys Phe Asp Val Lys Asn Pro Asp Asn
115 120 125

Ser Tyr Ser Asn Gly Ala His Met Tyr Tyr Ala Leu Ser Arg Lys Asp
130 135 140

```
Asn Ala Asn Ile Gly Thr Thr Pro Gln Asp Lys Lys Tyr Val Tyr Ile
145                 150                 155                 160

Lys Asn Glu Gly Leu Thr Asp Ile Ser Leu Met Leu Asn Ala Cys Tyr
                165                 170                 175

Asp Val Ile Ser Glu Gly Ile Ser Phe Val Pro Tyr Ile Cys Ala Gly
            180                 185                 190

Ile Gly Ser Asp Phe Ile Ser Met Phe Asp Ile Thr Ser Pro Lys Leu
        195                 200                 205

Ser Tyr Gln Gly Lys Leu Gly Ile Ser Tyr Ser Ile Asn Pro Glu Met
    210                 215                 220

Ser Val Phe Ile Gly Gly His Phe His Lys Val Ile Gly Asp Gln Phe
225                 230                 235                 240

Lys Asp Ile Thr Pro Leu Lys Pro Asn Gly Ile Glu Asn Thr Thr Ala
                245                 250                 255

Thr His Val Leu Val Thr Leu His Met Cys His Phe Gly Ala Glu Ile
            260                 265                 270

Gly Gly Arg Phe Thr Phe
        275

<210> SEQ ID NO 19
<211> LENGTH: 282
<212> TYPE: PRT
<213> ORGANISM: Ehrlichia ewingii

<400> SEQUENCE: 19

Met Asn Cys Lys Lys Val Phe Ile Thr Ser Ala Leu Ile Ser Phe Ile
 1               5                  10                  15

Cys Phe Leu Pro Gly Val Ser Phe Ser Asn Thr Ile Gln Asp Asn Asn
            20                  25                  30

Ile Val Gly Asn Phe Tyr Ile Ser Gly Lys Tyr Met Pro Thr Val Ser
        35                  40                  45

His Phe Gly Asn Phe Ser Ala Lys Glu Glu Lys Ala Glu Thr Lys Lys
    50                  55                  60

Thr Phe Gly Leu Glu Lys Asn Tyr Asp Gly Ala Lys Ile Glu Asp Asn
65                  70                  75                  80

Gln Val Gln Asn Lys Phe Thr Ile Ser Asn Tyr Ser Phe Lys Tyr Glu
                85                  90                  95

Asp Asn Pro Phe Leu Gly Phe Ala Gly Ala Ile Gly Tyr Ser Met Glu
            100                 105                 110

Gly Pro Arg Ile Glu Leu Glu Val Ser Tyr Glu Thr Phe Asn Val Lys
        115                 120                 125

Asn Gln Asp Asn Ser Tyr Lys Asn Asp Ala His Met Tyr Tyr Leu Leu
    130                 135                 140

Ala Arg Glu Val Asp Ser Ser Ser Pro Thr Lys Pro Gln Val Asn Lys
145                 150                 155                 160

Ser Val Leu Leu Lys Asn Glu Gly Leu Thr Asp Phe Ser Ile Met Leu
                165                 170                 175

Asn Ala Cys Tyr Asp Ile Ile Thr Asp Asn Ile Pro Phe Ser Pro Tyr
            180                 185                 190

Ile Cys Ala Gly Val Gly Ala Asp Leu Val Ser Met Phe Asn Ser Ile
        195                 200                 205

Asn Pro Lys Leu Ala Tyr Gln Gly Lys Leu Gly Ile Ser Tyr Ser Ile
    210                 215                 220

Ser Pro Glu Val Ser Ala Phe Ile Gly Gly His Phe His Lys Val Ile
225                 230                 235                 240
```

```
Gly Asn Glu Phe Lys Asp Ile Ala Thr Ile Leu Pro Ser Gly Ser Ser
                245                 250                 255

Ile Lys Asp Asn Gln Tyr Ala Ile Val Thr Leu Ser Val Cys His Phe
            260                 265                 270

Gly Val Glu Ile Gly Gly Arg Val Ser Phe
        275                 280

<210> SEQ ID NO 20
<211> LENGTH: 272
<212> TYPE: PRT
<213> ORGANISM: Ehrlichia ewingii

<400> SEQUENCE: 20

Met Asn Tyr Lys Lys Phe Val Leu Ser Val Ala Leu Ser Thr Leu Phe
  1               5                  10                  15

Ser Phe Leu Pro Asp Ser Ser Phe Ser Asp Val Val Ser Glu Glu
             20                  25                  30

Lys Arg Gly Phe Tyr Val Gly Thr Gln Tyr Arg Val Gly Val Pro Asn
         35                  40                  45

Phe Ser Asn Phe Ser Ala Ala Glu Thr Ile Pro Gly Leu Thr Lys Lys
 50                  55                  60

Ile Phe Ala Leu Ser Tyr Asp Ala Thr Asp Ile Thr Lys Glu Thr Ser
65                  70                  75                  80

Phe Lys Gln Ala Tyr Asp Pro Thr Tyr Ala Ser Ser Phe Asn Ser Phe
                 85                  90                  95

Ser Gly Val Met Gly Cys Tyr Phe Asn Ser Met Arg Ile Glu Phe Glu
            100                 105                 110

Gly Ser Tyr Ser His Phe Glu Ser Glu Arg Gln Phe Tyr Arg Glu Gly
        115                 120                 125

Ser Asn Asn Tyr Lys Phe Phe Ala Leu Ser Arg Glu Glu Thr Ile Thr
130                 135                 140

Ser Lys Lys Phe Val Val Leu Glu Asn Asn Gly Val Ile Asp Arg Ser
145                 150                 155                 160

Leu Asn Val Asn Phe Cys Tyr Asp Ile Thr Arg Gly Asp Val Pro Leu
                165                 170                 175

Ala Pro Tyr Val Cys Ala Gly Val Gly Ala Asp Tyr Ile Lys Phe Leu
            180                 185                 190

Gly Ile Ser Leu Pro Lys Phe Ser Tyr Gln Val Lys Phe Gly Val Asn
        195                 200                 205

Tyr Pro Val Lys Ser Asn Ile Met Leu Phe Gly Gly Tyr Tyr His
    210                 215                 220

Lys Val Val Gly Ser Lys Tyr Glu Arg Val Glu Ile Ala Tyr His Pro
225                 230                 235                 240

Ser Ile Glu Glu Ala Pro Lys Ile Thr Ser Ala Ser Ala Asn Leu Asn
                245                 250                 255

Thr Asp His Phe Gly Cys Glu Val Gly Ile Arg Phe Ala Phe Ile Asn
            260                 265                 270

<210> SEQ ID NO 21
<211> LENGTH: 282
<212> TYPE: PRT
<213> ORGANISM: Ehrlichia ewingii

<400> SEQUENCE: 21

Met Lys Tyr Lys Ile Val Lys Thr Thr Ile Thr Gly Leu Gly Leu Leu
  1               5                  10                  15
```

```
Leu Pro Phe Tyr Ala Ser Met Ser Phe Gly Met Ser Asn Thr Leu Ala
             20                  25                  30

Asn Gln Val Ser Pro Ile Ser Phe Gly Val Leu Tyr Lys Leu Ser His
         35                  40                  45

Pro Phe Phe Asn Asn Phe Ser Ile Glu Glu Thr Gln Ile Leu His Asp
     50                  55                  60

Val Ala Thr Glu Arg Val Val Gly Leu Lys His Asp Leu Leu Glu Ser
65                  70                  75                  80

Ala Asp Lys Leu Val Asp Asn Leu Tyr Asn Phe Asp Leu Ser Glu Asp
             85                  90                  95

Tyr Val Pro Lys Tyr Asp Asn Ser Leu Phe Gly Leu Ser Phe Phe Ile
             100                 105                 110

Gly Tyr Ser Phe Gln Asn Phe Arg Ile Glu Leu Glu Ser Phe Tyr Glu
             115                 120                 125

Lys Phe Asp Val Gln Asp Thr Lys Ser His Ile Val Asp Asp Asn Tyr
     130                 135                 140

Arg Tyr Phe Ala Leu Tyr Arg His Gly Pro Ala Lys His Ile Asn Tyr
145                 150                 155                 160

Val Thr Leu Lys Asn Asp Gly Ile Glu Leu Asn Ser Val Met Leu Asn
             165                 170                 175

Ile Cys Tyr Asp Phe Thr Leu Asn Asn Thr Tyr Ile Thr Pro Phe Ser
             180                 185                 190

Cys Val Gly Ile Gly Gly Asp Ile Ile Ser Ile Phe Asn Thr Val Lys
             195                 200                 205

Val Lys Ile Ala Ala Gln Ala Lys Val Gly Val Asn Tyr Leu Ile Ser
     210                 215                 220

Glu Arg Ile Ser Leu Phe Val Asp Gly Tyr Tyr His Gly Val Ile Asp
225                 230                 235                 240

Asn Glu Tyr Ser Asn Ile Pro Val Gln Tyr Pro Arg Asn Leu Phe Tyr
             245                 250                 255

Ala Pro Lys Val Thr Ser Ala Leu Ala Asn Leu Asp Ile Gly Tyr Phe
             260                 265                 270

Gly Ala Glu Ile Gly Met Lys Val Phe Ile
             275                 280

<210> SEQ ID NO 22
<211> LENGTH: 282
<212> TYPE: PRT
<213> ORGANISM: Ehrlichia ewingii

<400> SEQUENCE: 22

Met Lys Cys Lys Ile Thr Lys Ile Ala Ile Met Leu Gly Leu Leu
1                   5                  10                  15

Leu Pro Phe Gln Ala Phe Ser Ala Ser Leu Val Ser Asp Ala Ser Asp
             20                  25                  30

Ser His Thr Lys Ser Val Ser Leu Ser Ala Ser Tyr Lys Leu Ser Thr
         35                  40                  45

Pro Phe Phe Asn His Phe Leu Ile Arg Glu Thr Asn Leu Thr Ser Gly
     50                  55                  60

Ile Ile Ala Asn Lys Arg Val Leu Gly Leu Lys Asn Asp Ile Leu Ile
65                  70                  75                  80

Asn Ala Asp Glu Ala Ile Lys Asn Leu Ser Asn Phe Asp Phe Ser Glu
             85                  90                  95

Asp Tyr Val Pro Lys Tyr Lys Asn Ser Leu Tyr Gly Leu Ser Phe Leu
```

```
                    100                 105                 110
Phe Gly Tyr Ser Phe Lys Asn Leu Lys Val Glu Leu Glu Gly Leu Tyr
            115                 120                 125

Glu Ser Phe Asp Val Arg Asp Thr Lys Asn His Ile Ile Asp Asn Asn
        130                 135                 140

Tyr Arg Tyr Phe Ala Leu Ser Lys Gln Asp Asn Leu Asn Ser Asp Tyr
145                 150                 155                 160

Val Thr Leu Ile Asn Asn Gly Val Lys Leu Tyr Ser Val Ile Leu Asn
                165                 170                 175

Ile Cys Tyr Asp Phe Ile Gly Lys Asn Thr Ser Leu Thr Pro Phe Leu
            180                 185                 190

Cys Val Gly Ile Gly Glu Asp Ile Ile Asn Ile Phe Asp Ala Val Arg
        195                 200                 205

Phe Lys Pro Ala Phe His Ala Lys Met Gly Phe Asn Tyr Arg Ile Ser
210                 215                 220

Glu Arg Ala Phe Leu Phe Met Asp Met Tyr Tyr His Lys Ile Ile Gly
225                 230                 235                 240

Asn Gln Tyr Ser Ser Ile Ser Val Lys Tyr Pro Lys Val Leu Val Phe
                245                 250                 255

Pro Ser Thr Arg Ser Ser Val Leu Ala Glu Leu Asp Ile Gly Tyr Leu
            260                 265                 270

Gly Ser Glu Val Gly Ile Arg Ile Phe Ile
        275                 280

<210> SEQ ID NO 23
<211> LENGTH: 135
<212> TYPE: PRT
<213> ORGANISM: Ehrlichia ewingii

<400> SEQUENCE: 23

Met Asp Ile Phe Gly His Asn Leu Asp Ala Tyr Val Ala Thr Leu Asn
1               5                   10                  15

Ala Glu Tyr Thr Gly Ser Val Pro Val Gln Glu Asp Gly Ser Phe Asp
            20                  25                  30

Ala Thr Leu Asn Ile Thr Val Glu Asp Leu Tyr Gly Ile Tyr Ala Arg
        35                  40                  45

Phe Ser Gly Thr Ile Gln Gln Gln His Gly Lys Ser Tyr Leu Asn Tyr
    50                  55                  60

Tyr Leu Glu Glu Ser Thr Asp Phe Pro Glu Ile Pro Phe Leu Ala Ser
65                  70                  75                  80

Tyr Ser Gly Thr Ala Lys Val Leu Ser Glu Asp Thr Asp Thr Gly Leu
                85                  90                  95

Ile Ser Phe Asp Asp Ile Ser Asn Gly Ile His Val Ser Phe Ser Thr
            100                 105                 110

Lys Gln Gln Glu Thr Ile Ser Ser Asp Ser Ile Glu Glu Glu Glu Glu
        115                 120                 125

Glu Glu Ala Ala Ala Ala Ala
    130                 135

<210> SEQ ID NO 24
<211> LENGTH: 93
<212> TYPE: PRT
<213> ORGANISM: Ehrlichia ewingii

<400> SEQUENCE: 24

Met Leu Ser Ile Ala Gln Lys Ile Phe Gly Ser Ala Asn Asn Arg Thr
```

```
                1               5                   10                  15

Ile Lys Ser Phe Tyr Lys Ile Val Asn Asn Ile Asn Ala Ile Glu His
                            20                  25                  30

Glu Val Gln Leu Leu Ser Asn Glu Ser Leu Lys His Lys Thr Ile Glu
                        35                  40                  45

Phe Lys Glu Glu Leu Lys Gln Gly Lys Ser Leu Asp Asp Ile Leu Val
                    50                  55                  60

Pro Ala Phe Ala Val Val Arg Glu Ala Ala Lys Arg Val Leu Asn Met
            65                  70                  75                  80

Arg His Phe Asp Val Gln Leu Ile Gly Gly Ile Val Leu
                            85                  90

<210> SEQ ID NO 25
<211> LENGTH: 17
<212> TYPE: PRT
<213> ORGANISM: Ehrlichia ewingii

<400> SEQUENCE: 25

Ser Cys Thr Glu Gln Glu Met Lys Pro Ala Gln Gln Asn Gly Ser Ser
1               5                   10                  15

Lys

<210> SEQ ID NO 26
<211> LENGTH: 16
<212> TYPE: PRT
<213> ORGANISM: Ehrlichia ewingii

<400> SEQUENCE: 26

Glu Gln His Phe Ala Leu Ala Ser Glu Leu Asp Thr Asn Gly Asn Gln
1               5                   10                  15

<210> SEQ ID NO 27
<211> LENGTH: 17
<212> TYPE: PRT
<213> ORGANISM: Ehrlichia ewingii

<400> SEQUENCE: 27

Val Ser Ala Pro Ser Gly Tyr Asp Asp Asn Ile Tyr Ala Tyr Phe Ser
1               5                   10                  15

Ile

<210> SEQ ID NO 28
<211> LENGTH: 15
<212> TYPE: PRT
<213> ORGANISM: Ehrlichia ewingii

<400> SEQUENCE: 28

Phe Ala Ile Pro Arg Asp Thr Phe Phe Asn Asn Ser Ile Pro Tyr
1               5                   10                  15

<210> SEQ ID NO 29
<211> LENGTH: 16
<212> TYPE: PRT
<213> ORGANISM: Ehrlichia ewingii

<400> SEQUENCE: 29

Asn Ser Ser Ser Leu Ile Ser Ser Asn Asn His Tyr Thr Gln Leu Tyr
1               5                   10                  15

<210> SEQ ID NO 30
<211> LENGTH: 17
```

```
<212> TYPE: PRT
<213> ORGANISM: Ehrlichia ewingii

<400> SEQUENCE: 30

Lys Asp Asn Asn Gln Val Gln Pro Lys Ala His Asp Ser Ser Ser Thr
 1               5                  10                  15

Asp

<210> SEQ ID NO 31
<211> LENGTH: 15
<212> TYPE: PRT
<213> ORGANISM: Ehrlichia ewingii

<400> SEQUENCE: 31

Lys Asp Pro Lys Asp Cys Ser Val Lys Asp Ala Phe Arg His Leu
 1               5                  10                  15

<210> SEQ ID NO 32
<211> LENGTH: 15
<212> TYPE: PRT
<213> ORGANISM: Ehrlichia ewingii

<400> SEQUENCE: 32

Thr Glu Asp Lys Tyr Leu Thr Ser Glu Gln Glu Val Asn Asp Tyr
 1               5                  10                  15

<210> SEQ ID NO 33
<211> LENGTH: 15
<212> TYPE: PRT
<213> ORGANISM: Ehrlichia ewingii

<400> SEQUENCE: 33

Ile Cys Lys Glu Asn Asp Lys Pro Thr Pro Lys Glu Lys Lys Tyr
 1               5                  10                  15

<210> SEQ ID NO 34
<211> LENGTH: 17
<212> TYPE: PRT
<213> ORGANISM: Ehrlichia ewingii

<400> SEQUENCE: 34

Tyr Arg Tyr Phe Ala Ile Ala Arg Glu Met Asn Ser Ser Asn Asn
 1               5                  10                  15

Gln

<210> SEQ ID NO 35
<211> LENGTH: 12
<212> TYPE: PRT
<213> ORGANISM: Ehrlichia ewingii

<400> SEQUENCE: 35

Lys Asn Ser Gly His Ser Ser Ile Asp Ala His Arg
 1               5                  10

<210> SEQ ID NO 36
<211> LENGTH: 17
<212> TYPE: PRT
<213> ORGANISM: Ehrlichia ewingii

<400> SEQUENCE: 36

Ile Glu Ser Asp Gln Asn Lys Phe Gln Pro Lys Asn Ala Asn Ser Asn
 1               5                  10                  15

Ser
```

<210> SEQ ID NO 37
<211> LENGTH: 17
<212> TYPE: PRT
<213> ORGANISM: Ehrlichia ewingii

<400> SEQUENCE: 37

Ser Glu Ser Ser Lys Glu Pro Gln Pro Lys Asn Pro Asn Ser Ala Gly
1 5 10 15

Asn

<210> SEQ ID NO 38
<211> LENGTH: 16
<212> TYPE: PRT
<213> ORGANISM: Ehrlichia ewingii

<400> SEQUENCE: 38

Lys Tyr Tyr Gly Leu Phe Arg Glu Gly Thr Pro Gln Glu Glu Glu His
1 5 10 15

<210> SEQ ID NO 39
<211> LENGTH: 16
<212> TYPE: PRT
<213> ORGANISM: Ehrlichia ewingii

<400> SEQUENCE: 39

Ser Arg Lys Asp Asn Ala Asn Ile Gly Thr Thr Pro Gln Asp Lys Lys
1 5 10 15

<210> SEQ ID NO 40
<211> LENGTH: 16
<212> TYPE: PRT
<213> ORGANISM: Ehrlichia ewingii

<400> SEQUENCE: 40

Lys Ile Glu Asp Asn Gln Val Gln Asn Lys Phe Thr Ile Ser Asn Tyr
1 5 10 15

<210> SEQ ID NO 41
<211> LENGTH: 12
<212> TYPE: PRT
<213> ORGANISM: Ehrlichia ewingii

<400> SEQUENCE: 41

Gln Phe Tyr Arg Glu Gly Ser Asn Asn Tyr Lys Phe
1 5 10

<210> SEQ ID NO 42
<211> LENGTH: 14
<212> TYPE: PRT
<213> ORGANISM: Ehrlichia ewingii

<400> SEQUENCE: 42

Val Gln Asp Thr Lys Ser His Ile Val Asp Asp Asn Tyr Arg
1 5 10

<210> SEQ ID NO 43
<211> LENGTH: 15
<212> TYPE: PRT
<213> ORGANISM: Ehrlichia ewingii

<400> SEQUENCE: 43

Ser Lys Gln Asp Asn Leu Asn Ser Asp Tyr Val Thr Leu Ile Asn
1 5 10 15

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cgyatyatga gaggtatgag                                                 20

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aggrtctata tgttttggtg ct                                              22

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ttgyattggt atagggcaag ga                                              22

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ctcaaatttt ttaccraata aaccatg                                         27

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
crtattcatg tttaggrttt gg                                              22

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
agttgctawa gcaaartact c                                               21

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
tagaasttga agcttttat gag                                           23

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
gatataccrt trttttttgc tacag                                        25

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
aartwctttg ctataccacg ta                                           22

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
tctatttcta aycttggycc ttg                                          23

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
atrggycttr caamtgatgt tac                                          23

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
yttaytccar cttcaccacc a                                            21

-continued

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gcartagcwa cacttaatgt tg                                              22

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cctggtttat attgmccact t                                               21

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gagtatttyg gtrgtgaatt tgg                                             23

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
raaatctcct cctaktcctg c                                               21

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ctgtmatgag aaaygacggg tt                                              22

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tayyaatktc aacagaatca ayatc                                           25

<210> SEQ ID NO 62

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
caatayaaac ccagtgtttc tg                                            22

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
grataagtaa yacctaaytt acc                                           23

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tayrgtmaat ggctgctatg at                                            22

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
aagtgtagcw actgcrgatg t                                             21

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
taccatmaag taatrggcaa tca                                           23

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ayttctccgc caaagtatcc a                                             21

<210> SEQ ID NO 68
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gctcctcaaa ccacatctgc                                                  20

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
takggtttat agcktcaaac atg                                              23

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ttytcwcctt acatatgtgc ag                                               22

<210> SEQ ID NO 71
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
carttcatat ttacaccwga aakagtgaa                                        29

<210> SEQ ID NO 72
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gtwtttamwt tgtakkttta ctactgtt                                         28

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ctaytcttgg rccacccatt g                                                21

<210> SEQ ID NO 74
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 74
tagggtttgc aggagctatt g                                              21

<210> SEQ ID NO 75
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
aattttaggr yttrtagctt caaac                                          25

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
tatgygcagg trttggtact ga                                             22

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gawgcttctg ggcttatrga gt                                             22

<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
caaatcctaa aatttcttay caagga                                         26

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tyagtaattt ttcagctgaa gaaac                                          25

<210> SEQ ID NO 80
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 80
gcaaaaytgc ttgcatawgt ag                                              22

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
atttytcaga agartatgtt cca                                             23

<210> SEQ ID NO 82
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gagtmaaaaa ytttaayaat rtcttctc                                        28

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
aaaatatcca ttrtagctta cct                                             23

<210> SEQ ID NO 84
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
atgwtaaatt yatgyttaag ttgca                                           25

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
sccygtyttc atttcggata tc                                              22

<210> SEQ ID NO 86
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 86
gtactttgcc attcccagag a                                              21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gatctactcc aaacccaaga c                                              21

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ggaattactg ctccaatagt agc                                            23

<210> SEQ ID NO 89
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gttgatgggt attaccacag ag                                             22

<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
cacctagtat tttgctgaag ct                                             22

<210> SEQ ID NO 91
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
ttacttaccc actatctggt aac                                            23

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 92
taatttcccc tgacctgcaa ac                                            22

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
caaaccagtt tattgactgg gcat                                          24

<210> SEQ ID NO 94
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
caatcatgct aaatgcatgt tatgac                                        26

<210> SEQ ID NO 95
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ggatttatgc tattaaacat tgacac                                        26

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
ttcaagctaa gctaggttta gg                                            22

<210> SEQ ID NO 97
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
catattaact caatcaagta aacacac                                       27

<210> SEQ ID NO 98
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
cctcttacct caaatttagt tctc                                            24

<210> SEQ ID NO 99
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
ttcacctata cctaagcata cataag                                          26

<210> SEQ ID NO 100
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gtcatgctat atagatgata ctgtg                                           25

<210> SEQ ID NO 101
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tcccttatgt ttttgtattc ctatac                                          26

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
ccatccatag cataaccgat ac                                              22

<210> SEQ ID NO 103
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
ctgttatgag aaatgacgga gtttc                                           25

<210> SEQ ID NO 104
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 104
cgtacataga gtgttatagg caattc                                    26

<210> SEQ ID NO 105
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ggtttaagta tatgagttat aagaaggt                                  28

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
atgcacaggc attggtggag a                                         21

<210> SEQ ID NO 107
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
gtatatatgc atatgtaaca tgcaag                                    26

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
ggcatgtact ttccgctgat g                                         21

<210> SEQ ID NO 109
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
ctttactact ttctgattca cgtac                                     25

<210> SEQ ID NO 110
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
```
tgcttttatt ggtgggcact ttc                                              23

<210> SEQ ID NO 111
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111 taagttttt gcattatctc gtgaag                                            26

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
ttgcacaaaa aatctttggc tcag                                             24

<210> SEQ ID NO 113
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
attaacgcat ttgcatgtag tagtgtg                                          27

<210> SEQ ID NO 114
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
caaggaaaac taggtataag ttactc                                           26

<210> SEQ ID NO 115
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
aagactggta tggtaagact gtc                                              23

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
acaccccata acaccactaa aag                                                23

<210> SEQ ID NO 117
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
gtttgttaac taccctgtaa agtc                                               24

<210> SEQ ID NO 118
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gatagtacaa acctgtaaga tgttac                                             26

<210> SEQ ID NO 119
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
aacctaaatt gcctatcgat atcatc                                             26

<210> SEQ ID NO 120
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
tcaaccgtaa tatttagtgt agcatc                                             26

<210> SEQ ID NO 121
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
caatatggct tttagtatct tgtacatc                                           28

<210> SEQ ID NO 122
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
tacactactt attggtattg ttggtag                                            27

<210> SEQ ID NO 123
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 123
tatgttgttt ggaggtggtt actatc    26

<210> SEQ ID NO 124
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 124
cctatatcta agttagctaa tgccgaag    28

<210> SEQ ID NO 125
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 125
tttttgtttt tctgttttgt gtaacctgtg    30

<210> SEQ ID NO 126
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 126
ctgggcattc ttcaatagat gctc    24

<210> SEQ ID NO 127
<211> LENGTH: 505
<212> TYPE: DNA
<213> ORGANISM: Ehrlichia ewingii

<400> SEQUENCE: 127
ccaactgtat cacatttcgg taacttttct gcaaaagaag aaaaagcaga gactaaaaaa 60
acatttggtt tagaaaaaaa ttatgatgga gctaaaatag aagataatca agtacagaac 120
aaatttacca tttcaaatta ctcatttaaa tatgaagaca acccattttt aggttttgct 180
ggagccattg gatattcaat ggaaggtcca agaatagaac ttgaagtatc ttacgaaaca 240
tttaatgtaa aaaaccaaga caacagttac aaaaaatgatg cccatatgta ttaccttttg 300
gcacgagaag ttgatagttc ttcgccaaca aaacctcaag ttaacaaatc tgtcttgctc 360
aaaaatgaag gtctaactga cttttcaatc atgctaaatg catgttatga cataataaca 420
gataatatac ctttttcccc ttatatatgt gcaggtgttg gtgctgattt agtgtcaatg 480
tttaatagca taaatcctaa acttg 505

<210> SEQ ID NO 128
<211> LENGTH: 168
<212> TYPE: PRT
<213> ORGANISM: Ehrlichia ewingii

<400> SEQUENCE: 128

Pro Thr Val Ser His Phe Gly Asn Phe Ser Ala Lys Glu Glu Lys Ala
1               5                   10                  15

Glu Thr Lys L

```
                    20                  25                  30

Ile Glu Asp Asn Gln Val Gln Asn Lys Phe Thr Ile Ser Asn Tyr Ser
            35                  40                  45

Phe Lys Tyr Glu Asp Asn Pro Phe Leu Gly Phe Ala Gly Ala Ile Gly
        50                  55                  60

Tyr Ser Met Glu Gly Pro Arg Ile Glu Leu Glu Val Ser Tyr Glu Thr
65                  70                  75                  80

Phe Asn Val Lys Asn Gln Asp Asn Ser Tyr Lys Asn Asp Ala His Met
                85                  90                  95

Tyr Tyr Leu Leu Ala Arg Glu Val Asp Ser Ser Pro Thr Lys Pro
            100                 105                 110

Gln Val Asn Lys Ser Val Leu Leu Lys Asn Glu Gly Leu Thr Asp Phe
        115                 120                 125

Ser Ile Met Leu Asn Ala Cys Tyr Asp Ile Ile Thr Asp Asn Ile Ser
    130                 135                 140

Phe Ser Pro Tyr Ile Cys Ala Gly Val Gly Ala Asp Leu Val Ser Met
145                 150                 155                 160

Phe Asn Ser Ile Asn Pro Lys Leu
                165

<210> SEQ ID NO 131
<211> LENGTH: 505
<212> TYPE: DNA
<213> ORGANISM: Ehrlichia ewingii

<400> SEQUENCE: 131
ccaactgtat cacatttcgg taactttcct gcaaagaag  aaaaagcaga gactaaaaaa    60
acatttggtt tagaaaaaaa ttatgatgga gctaaaatag aagataatca agtacagaac   120
aaatttacca tttcaaatta ctcatttaaa tatgaagaca acccatttt  aggttttgct   180 ggagccattg gatattcaat ggaaggtcca agaatagaac ttgaagtatc ttacgaaaca   240
tttaatgtaa aaaccaaga caacagttac aaaaatgatg cccatatgta ttaccttttg   300
gcacgagaag ttgatagttc ttcgccaaca aaacctcaag ttaacaaatc tgtcttgctc   360
aaaaatgaag gtctaactga ctttcaatc atgctaaatg catgttatga cataataaca   420
gataatatac cttttccccc ttatatatgt gcaggtgttg gtgctgattt agtgtcaatg   480
tttaatagca taaatcctaa acttg                                         505

<210> SEQ ID NO 132
<211> LENGTH: 168
<212> TYPE: PRT
<213> ORGANISM: Ehrlichia ewingii

<400> SEQUENCE: 132

Pro Thr Val Ser His Phe Gly Asn Phe Ser Ala Lys Glu Glu Lys Ala
1               5                   10                  15

Glu Thr Lys Lys Thr Phe Gly Leu Glu Lys Asn Tyr Asp Gly Ala Lys
            20                  25                  30

Ile Glu Asp Asn Gln Val Gln Asn Lys Phe Thr Ile Ser Asn Tyr Ser
        35                  40                  45

Phe Lys Tyr Glu Asp Asn Pro Phe Leu Gly Phe Ala Gly Ala Ile Gly
    50                  55                  60

Tyr Ser Met Glu Gly Pro Arg Ile Glu Leu Glu Val Ser Tyr Glu Thr
65                  70                  75                  80

Phe Asn Val Lys Asn Gln Asp Asn Ser Tyr Lys Asn Asp Ala His Met
```

```
                    85                  90                  95
Tyr Tyr Leu Leu Ala Arg Glu Val Asp Ser Ser Pro Thr Lys Pro
                100                 105                 110

Gln Val Asn Lys Ser Val Leu Lys Asn Glu Gly Leu Thr Asp Phe
            115                 120                 125

Ser Ile Met Leu Asn Ala Cys Tyr Asp Ile Ile Thr Asp Asn Ile Pro
        130                 135                 140

Phe Ser Pro Tyr Ile Cys Ala Gly Val Gly Ala Asp Leu Val Ser Met
145                 150                 155                 160

Phe Asn Ser Ile Asn Pro Lys Leu
                165

<210> SEQ ID NO 133
<211> LENGTH: 505
<212> TYPE: DNA
<213> ORGANISM: Ehrlichia ewingii

<400> SEQUENCE:

145              150              155              160
Phe Asn Ser Ile Asn Pro Lys Leu
                165

<210> SEQ ID NO 135
<211> LENGTH: 505
<212> TYPE: DNA
<213> ORGANISM: Ehrlichia ewingii

<400> SEQUENCE: 135
ccaactgtat cacatttcgg taacttttct gcaaagaag aaaaagcaga gactaaaaaa      60
acatttggtt tagaaaaaaa ttatgatgga gctaaaatag aagataatca agtacagaac     120
aaatttacca tttcaaatta ctcatttaaa tatgaagaca acccattttt aggttttgct    180
ggagccattg gatattcaat ggaaggtccc agaatagaac ttgaagtatc ttacgaaaca    240
tttaatgtaa aaaccaaga caacagttac aaaaatgatg cccatatgta ttacctttg     300 gcacgagaag ttgatagttc ttcgccaaca aaacctcaag ttaacaaatc tgtcttgctc    360
aaaaatgaag gtctaactga cttttcaatc atgctaaatg catgttatga cataataaca    420
gataatatat cttttccccc ttatatatgt gcaggtgttg gtgctgatt agtgtcaatg    480 tttaatagca taaatcctaa acttg                                           505

<210> SEQ ID NO 136
<211> LENGTH: 168
<212> TYPE: PRT
<213> ORGANISM: Ehrlichia ewingii

<400> SEQUENCE: 136

Pro Thr Val Ser His Phe Gly Asn Phe Ser Ala Lys Glu Glu Lys Ala
 1               5                  10                  15

Glu Thr Lys Lys Thr Phe Gly Leu Glu Lys Asn Tyr Asp Gly Ala Lys
            20                  25                  30

Ile Glu Asp Asn Gln Val Gln Asn Lys Phe Thr Ile Ser Asn Tyr Ser
        35                  40                  45

Phe Lys Tyr Glu Asp Asn Pro Phe Leu Gly Phe Ala Gly Ala Ile Gly
    50                  55                  60

Tyr Ser Met Glu Gly Pro Arg Ile Glu Leu Glu Val Ser Tyr Glu Thr
65                  70                  75                  80

Phe Asn Val Lys Asn Gln Asp Asn Ser Tyr Lys Asn Asp Ala His Met
                85                  90                  95

Tyr Tyr Leu Leu Ala Arg Glu Val Asp Ser Ser Ser Pro Thr Lys Pro
            100                 105                 110

Gln Val Asn Lys Ser Val Leu Leu Lys Asn Glu Gly Leu Thr Asp Phe
        115                 120                 125

Ser Ile Met Leu Asn Ala Cys Tyr Asp Ile Ile Thr Asp Asn Ile Ser
    130                 135                 140

Phe Ser Pro Tyr Ile Cys Ala Gly Val Gly Ala Asp Leu Val Ser Met
145                 150                 155                 160

Phe Asn Ser Ile Asn Pro Lys Leu
                165

<210> SEQ ID NO 137
<211> LENGTH: 14
<212> TYPE: PRT
<213> ORGANISM: Ehrlichia ewingii

<400> SEQUENCE: 137

Ser Pro Ile Pro Ile Asp Phe Ser Asn Glu Ser Glu Met Val
1               5                   10

<210> SEQ ID NO 138
<211> LENGTH: 10
<212> TYPE: PRT
<213> ORGANISM: Ehrlichia ewingii

<400> SEQUENCE: 138

Gln Gly Leu Asn Asp Asn Ile Phe Lys Asn
1               5                   10

<210> SEQ ID NO 139
<211> LENGTH: 15
<212> TYPE: PRT
<213> ORGANISM: Ehrlichia ewingii

<400> SEQUENCE: 139

Leu Leu Ala Leu Glu Asn Asn Leu Ser Gly Gly Val Gly His Ile
1               5                   10                  15

<210> SEQ ID NO 140
<211> LENGTH: 13
<212> TYPE: PRT
<213> ORGANISM: Ehrlichia ewingii

<400> SEQUENCE: 140

Ser Phe Val Phe Ser Met Gln Gly Arg Ser Asn Ile Thr
1               5                   10

<210> SEQ ID NO 141
<211> LENGTH: 14
<212> TYPE: PRT
<213> ORGANISM: Ehrlichia ewingii

<400> SEQUENCE: 141

Val Leu Ile Asp Thr Thr Glu Lys Asp Tyr Ala Ser Asn Val
1               5                   10

<210> SEQ ID NO 142
<211> LENGTH: 13
<212> TYPE: PRT
<213> ORGANISM: Ehrlichia ewingii

<400> SEQUENCE: 142

Ala Ile Ser Ile Asp Asn Asn Ile Ile Asp Gln Asn Leu
1               5                   10

<210> SEQ ID NO 143
<211> LENGTH: 11
<212> TYPE: PRT
<213> ORGANISM: Ehrlichia ewingii

<400> SEQUENCE: 143

Pro Ile Ser Asn Asn Ser Glu Asp Asn Ile Phe
1               5                   10

<210> SEQ ID NO 144
<211> LENGTH: 9
<212> TYPE: PRT
<213> ORGANISM: Ehrlichia ewingii

<400> SEQUENCE: 144

Leu Asn Asn Ala Glu Asp His Lys Asp

```
<210> SEQ ID NO 145
<211> LENGTH: 9
<212> TYPE: PRT
<213> ORGANISM: Ehrlichia ewingii

<400> SEQUENCE: 145

Glu Ser Asn His Tyr Asp Lys Ser Leu
1               5

<210> SEQ ID NO 146
<211> LENGTH: 13
<212> TYPE: PRT
<213> ORGANISM: Ehrlichia ewingii

<400> SEQUENCE: 146

Glu Val Ile Thr His Asn Asp Asn Lys His Pro Gly Ile
1               5                   10

<210> SEQ ID NO 147
<211> LENGTH: 12
<212> TYPE: PRT
<213> ORGANISM: Ehrlichia ewingii

<400> SEQUENCE: 147

Ala Lys Asn Asn Tyr Ser Tyr Ile Asn Pro Val Leu
1               5                   10

<210> SEQ ID NO 148
<211> LENGTH: 11
<212> TYPE: PRT
<213> ORGANISM: Ehrlichia ewingii

<400> SEQUENCE: 148

Glu Thr Thr Ile Ile Asn Gln Pro Ser Gly Leu
1               5                   10

<210> SEQ ID NO 149
<211> LENGTH: 13
<212> TYPE: PRT
<213> ORGANISM: Ehrlichia ewingii

<400> SEQUENCE: 149

Glu Thr Ile Val Asp Asp Ile Asp Arg Gln Phe Arg Leu
1               5                   10

<210> SEQ ID NO 150
<211> LENGTH: 16
<212> TYPE: PRT
<213> ORGANISM: Ehrlichia ewingii

<400> SEQUENCE: 150

Ala Asp Pro Met Asn Ser Asn Asp Val Ser Ile Asn Asp Ser Lys Glu
1               5                   10                  15

<210> SEQ ID NO 151
<211> LENGTH: 8
<212> TYPE: PRT
<213> ORGANISM: Ehrlichia ewingii

<400> SEQUENCE: 151

Leu Val Ser Phe Ile Pro Cys Ile
1               5
```

<210> SEQ ID NO 152
<211> LENGTH: 8
<212> TYPE: PRT
<213> ORGANISM: Ehrlichia ewingii

<400> SEQUENCE: 152

```
Phe Ile Cys Glu Leu Pro Gly Val
 1               5
```

<210> SEQ ID NO 153
<211> LENGTH: 9
<212> TYPE: PRT
<213> ORGANISM: Ehrlichia ewingii

<400> SEQUENCE: 153

```
Asp Val Val Val Ser Glu Glu Lys Arg
 1               5
```

<210> SEQ ID NO 154
<211> LENGTH: 21
<212> TYPE: PRT
<213> ORGANISM: Ehrlichia ewingii

<400> SEQUENCE: 154

```
Phe Tyr Ala Ser Met Ser Phe Gly Met Ser Asn Thr Leu Ala Asn Gln
 1               5                   10                  15

Val Ser Pro Ile Ser
             20
```

<210> SEQ ID NO 155
<211> LENGTH: 15
<212> TYPE: PRT
<213> ORGANISM: Ehrlichia ewingii

<400> SEQUENCE: 155

```
Leu Val Ser Asp Ala Ser Asp Ser His Thr Lys Ser Val Ser Leu
 1               5                   10                  15
```

<210> SEQ ID NO 156
<211> LENGTH: 35
<212> TYPE: PRT
<213> ORGANISM: Ehrlichia ewingii

<400> SEQUENCE: 156

```
Tyr Lys Ser Thr Gly Asn Ser Glu Ala Asp Lys Ser Glu Lys Glu Leu
 1               5                   10                  15

Thr Leu Phe Thr Leu Lys Glu Ser Thr Gln Ala Pro Asp Phe Thr Lys
             20                  25                  30

Lys Glu Thr
         35
```

<210> SEQ ID NO 157
<211> LENGTH: 24
<212> TYPE: PRT
<213> ORGANISM: Ehrlichia ewingii

<400> SEQUENCE: 157

```
Ser Lys Asp Thr Ile Gly Ile Phe Ala Leu Lys Lys Asp Ala Ser Leu
 1               5                   10                  15

Pro Thr Asp Ile Lys Lys Asn Ser
             20
```

<210> SEQ ID NO 158
<211> LENGTH: 30
<212> TYPE: PRT
<213> ORGANISM: Ehrlichia ewingii

<400> SEQUENCE: 158

Met Glu Glu Ala Thr Ile Gly Ala Val Ile Pro Lys Ser Leu Lys Gln
 1               5                  10                  15

Asp Ala Glu Asp Ile Thr Leu Ser Ile Leu Ala Leu Ser Thr
            20                  25                  30

<210> SEQ ID NO 159
<211> LENGTH: 26
<212> TYPE: PRT
<213> ORGANISM: Ehrlichia ewingii

<400> SEQUENCE: 159

Phe Asp Thr Lys Asp Pro Ile Gly Leu Ile Arg Ser Ala Arg Ser Thr
 1               5                  10                  15

Glu Pro Ser Val Leu Lys Ile Asn Thr His
            20                  25

<210> SEQ ID NO 160
<211> LENGTH: 22
<212> TYPE: PRT
<213> ORGANISM: Ehrlichia ewingii

<400> SEQUENCE: 160

Ser Lys Thr Lys Asn Ser Ile Ala Leu Glu Lys Pro Ile Glu Ser Asn
 1               5                  10                  15

Ser Asn Ile Leu Lys Ser
            20

<210> SEQ ID NO 161
<211> LENGTH: 23
<212> TYPE: PRT
<213> ORGANISM: Ehrlichia ewingii

<400> SEQUENCE: 161

Lys Lys Val Asp Leu Ile Ala Leu Lys Asn Asp Val Thr His Ile Thr
 1               5                  10                  15

Glu Glu Ile Leu Lys Asp Pro
            20

<210> SEQ ID NO 162
<211> LENGTH: 25
<212> TYPE: PRT
<213> ORGANISM: Ehrlichia ewingii

<400> SEQUENCE: 162

Phe Ala Thr Gln Lys Leu Met Arg Val Lys Lys Asp Ser Lys Glu Gly
 1               5                  10                  15

Leu Pro Asn Ile Leu Lys Ser Lys Asp
            20                  25

<210> SEQ ID NO 163
<211> LENGTH: 32
<212> TYPE: PRT
<213> ORGANISM: Ehrlichia ewingii

<400> SEQUENCE: 163

Cys Ile Ile Arg Leu Ile Thr Val Lys Asp Ser His Phe Phe Ser Ile
 1               5                  10                  15

Asn Thr Ser Ser Tyr Asn Leu Cys Leu Glu Lys His Lys Asn Asp Ile
            20                  25                  30

<210> SEQ ID NO 164
<211> LENGTH: 26
<212> TYPE: PRT
<213> ORGANISM: Ehrlichia ewingii

<400> SEQUENCE: 164

Asp Ile Asn Thr Lys Gly Leu Phe Lys Leu Gly His Gly Val Thr Leu
1               5                   10                  15

Val Glu Glu Asp Ile Lys Asn His Leu Gln
            20                  25

<210> SEQ ID NO 165
<211> LENGTH: 24
<212> TYPE: PRT
<213> ORGANISM: Ehrlichia ewingii

<400> SEQUENCE: 165

Ala Thr Thr Val Gln Leu Val Gly Leu Asn Tyr Thr Ala Ala Pro Ile
1               5                   10                  15

Asp Asp Ile Lys Thr Ser Ser Lys
            20

<210> SEQ ID NO 166
<211> LENGTH: 35
<212> TYPE: PRT
<213> ORGANISM: Ehrlichia ewingii

<400> SEQUENCE: 166

His Tyr Asp Thr Gln Leu Leu Ala Glu Leu Lys Lys Glu Val Gly Ser
1               5                   10                  15

Val Thr Asn Thr Val Ile Gln Ala Tyr Ala Asn Tyr Asn Val Pro Ser
            20                  25                  30

Gln Ala Pro
        35

<210> SEQ ID NO 167
<211> LENGTH: 32
<212> TYPE: PRT
<213> ORGANISM: Ehrlichia ewingii

<400> SEQUENCE: 167

Val Ala Thr Lys His Leu Ile Ala Leu Lys Lys Ser Val Asp Ser Ile
1               5                   10                  15

Asn Ala Glu Lys Ala Thr Pro His Asn Gln Gly Leu Gly Lys Pro Asp
            20                  25                  30

<210> SEQ ID NO 168
<211> LENGTH: 32
<212> TYPE: PRT
<213> ORGANISM: Ehrlichia ewingii

<400> SEQUENCE: 168

Val Thr Thr Lys Tyr Leu Thr Ala Leu Lys Lys Asp Ala Asp Pro Thr
1               5                   10                  15

Glu Lys Thr Gly Ser Thr Pro His Glu Lys Gly Leu Gly Lys Pro Asp
            20                  25                  30

<210> SEQ ID NO 169

```
<211> LENGTH: 32
<212> TYPE: PRT
<213> ORGANISM: Ehrlichia ewingii

<400> SEQUENCE: 169
```

Pro Ile Glu Gly Ala Ile Ser Pro Thr Lys Lys Val Leu Gly Leu Asn
1               5                   10                  15

Lys Gly Gly Ser Ile Ala Asn Ser His Asp Phe Ser Lys Ile Asp Pro
            20                  25                  30

```
<210> SEQ ID NO 170
<211> LENGTH: 29
<212> TYPE: PRT
<213> ORGANISM: Ehrlichia ewingii

<400> SEQUENCE: 170
```

Asp Thr Ile Glu Thr Ile Ala Thr Phe Gly Leu Ser Lys Thr Tyr Asn
1               5                   10                  15

Arg Ser Ser Pro Ile His Ser Asp Phe Thr Asp Ser Lys
            20                  25

```
<210> SEQ ID NO 171
<211> LENGTH: 27
<212> TYPE: PRT
<213> ORGANISM: Ehrlichia ewingii

<400> SEQUENCE: 171
```

Ile Pro Gly Leu Thr Lys Lys Ile Phe Ala Leu Ser Tyr Asp Ala Thr
1               5                   10                  15

Asp Ile Thr Lys Glu Thr Ser Phe Lys Gln Ala
            20                  25

```
<210> SEQ ID NO 172
<211> LENGTH: 37
<212> TYPE: PRT
<213> ORGANISM: Ehrlichia ewingii

<400> SEQUENCE: 172
```

Gln Ile Leu His Asp Val Ala Thr Glu Arg Val Val Gly Leu Lys His
1               5                   10                  15

Asp Leu Leu Glu Ser Ala Asp Lys Leu Val Asp Asn Leu Tyr Asn Phe
            20                  25                  30

Asp Leu Ser Glu Asp
        35

```
<210> SEQ ID NO 173
<211> LENGTH: 30
<212> TYPE: PRT
<213> ORGANISM: Ehrlichia ewingii

<400> SEQUENCE: 173
```

Leu Thr Ser Gly Ile Ile Ala Asn Lys Arg Val Leu Gly Leu Lys Asn
1               5                   10                  15

Asp Ile Leu Ile Asn Ala Asp Glu Ala Ile Lys Asn Leu Ser
            20                  25                  30

```
<210> SEQ ID NO 174
<211> LENGTH: 11
<212> TYPE: PRT
<213> ORGANISM: Ehrlichia ewingii

<400> SEQUENCE: 174
```

-continued

Asp Lys Gln Lys His Thr His Pro Asp Asn His
1               5                   10

<210> SEQ ID NO 175
<211> LENGTH: 11
<212> TYPE: PRT
<213> ORGANISM: Ehrlichia ewingii

<400> SEQUENCE: 175

Glu Gly Tyr Lys Ile Thr Gly Val Glu Gln His
1               5                   10

<210> SEQ ID NO 176
<211> LENGTH: 16
<212> TYPE: PRT
<213> ORGANISM: Ehrlichia ewingii

<400> SEQUENCE: 176

Val Ser Ala Pro Ser Gly Tyr Asp Asp Asn Ile Tyr Ala Tyr Ser Ile
1               5                   10                  15

<210> SEQ ID NO 177
<211> LENGTH: 13
<212> TYPE: PRT
<213> ORGANISM: Ehrlichia ewingii

<400> SEQUENCE: 177

Ile Lys Arg Leu Val Asn Tyr Ala Ser Arg Asp Gly His
1               5                   10

<210> SEQ ID NO 178
<211> LENGTH: 19
<212> TYPE: PRT
<213> ORGANISM: Ehrlichia ewingii

<400> SEQUENCE: 178

Glu Leu Asn Ser Ser Ser Leu Ile Ser Ser Asn Asn His Tyr Thr Gln
1               5                   10                  15

Leu Tyr Glu

<210> SEQ ID NO 179
<211> LENGTH: 10
<212> TYPE: PRT
<213> ORGANISM: Ehrlichia ewingii

<400> SEQUENCE: 179

Ile Thr Asp Cys Ser Asn Cys Thr Ile Asn
1               5                   10

<210> SEQ ID NO 180
<211> LENGTH: 15
<212> TYPE: PRT
<213> ORGANISM: Ehrlichia ewingii

<400> SEQUENCE: 180

Lys Asp Pro Lys Asp Cys Ser Val Lys Asp Ala Phe Arg His Leu
1               5                   10                  15

<210> SEQ ID NO 181
<211> LENGTH: 15
<212> TYPE: PRT
<213> ORGANISM: Ehrlichia ewingii

<400> SEQUENCE: 181

```
Thr Glu Asp Lys Tyr Leu Thr Ser Glu Gln Glu Val Asn Asp Tyr
 1               5                  10                  15

<210> SEQ ID NO 182
<211> LENGTH: 8
<212> TYPE: PRT
<213> ORGANISM: Ehrlichia ewingii

<400> SEQUENCE: 182

Asp Leu Lys Asn Cys Thr Ile Gln
 1               5

<210> SEQ ID NO 183
<211> LENGTH: 9
<212> TYPE: PRT
<213> ORGANISM: Ehrlichia ewingii

<400> SEQUENCE: 183

Thr Asp Pro Gly Asn Tyr Thr Ile Lys
 1               5

<210> SEQ ID NO 184
<211> LENGTH: 12
<212> TYPE: PRT
<213> ORGANISM: Ehrlichia ewingii

<400> SEQUENCE: 184

Lys Asn Ser Gly His Ser Ser Ile Asp Ala His Arg
 1               5                  10

<210> SEQ ID NO 185
<211> LENGTH: 6
<212> TYPE: PRT
<213> ORGANISM: Ehrlichia ewingii

<400> SEQUENCE: 185

Thr Leu Asn Asp Ala Phe
 1               5

<210> SEQ ID NO 186
<211> LENGTH: 6
<212> TYPE: PRT
<213> ORGANISM: Ehrlichia ewingii

<400> SEQUENCE: 186

Thr Ile Ser Asn Ala Phe
 1               5

<210> SEQ ID NO 187
<211> LENGTH: 16
<212> TYPE: PRT
<213> ORGANISM: Ehrlichia ewingii

<400> SEQUENCE: 187

Lys Tyr Tyr Gly Leu Phe Arg Glu Gly Thr Pro Gln Glu Glu Glu His
 1               5                  10                  15

<210> SEQ ID NO 188
<211> LENGTH: 6
<212> TYPE: PRT
<213> ORGANISM: Ehrlichia ewingii

<400> SEQUENCE: 188

Ser Asn Gly Ala His Met
 1               5
```

<210> SEQ ID NO 189
<211> LENGTH: 12
<212> TYPE: PRT
<213> ORGANISM: Ehrlichia ewingii

<400> SEQUENCE: 189

Gln Phe Tyr Arg Glu Gly Ser Asn Asn Tyr Lys Phe
1               5                   10

<210> SEQ ID NO 190
<211> LENGTH: 14
<212> TYPE: PRT
<213> ORGANISM: Ehrlichia ewingii

<400> SEQUENCE: 190

Val Gln Asp Thr Lys Ser His Ile Val Asp Asp Asn Tyr Arg
1               5                   10

<210> SEQ ID NO 191
<211> LENGTH: 11
<212> TYPE: PRT
<213> ORGANISM: Ehrlichia ewingii

<400> SEQUENCE: 191

Arg Asp Thr Lys Asn His Ile Ile Asp Asn Asn
1               5                   10

<210> SEQ ID NO 192
<211> LENGTH: 20
<212> TYPE: PRT
<213> ORGANISM: Ehrlichia ewingii

<400> SEQUENCE: 192

Ser Cys Thr Glu Gln Glu Met Lys Pro Ala Gln Gln Asn Gly Ser Ser
1               5                   10                  15

Lys Asp Gly Asn
            20

<210> SEQ ID NO 193
<211> LENGTH: 12
<212> TYPE: PRT
<213> ORGANISM: Ehrlichia ewingii

<400> SEQUENCE: 193

Leu Asp Thr Asn Gly Asn Gln Pro Lys Thr Asp Lys
1               5                   10

<210> SEQ ID NO 194
<211> LENGTH: 15
<212> TYPE: PRT
<213> ORGANISM: Ehrlichia ewingii

<400> SEQUENCE: 194

Ser Ile Glu Val Pro Gln Leu Arg Ser Leu Pro Tyr His Tyr Thr
1               5                   10                  15

<210> SEQ ID NO 195
<211> LENGTH: 17
<212> TYPE: PRT
<213> ORGANISM: Ehrlichia ewingii

<400> SEQUENCE: 195

Ile Pro Arg Asp Thr Phe Phe Asn Asn Ser Ile Pro Tyr Ala Phe Asn
1               5                   10                  15

```
                1               5                  10                  15
Ala

<210> SEQ ID NO 196
<211> LENGTH: 10
<212> TYPE: PRT
<213> ORGANISM: Ehrlichia ewingii

<400> SEQUENCE: 196

Ala Asn Phe Gln Asn Phe Ala Thr Ser Arg
1               5                  10

<210> SEQ ID NO 197
<211> LENGTH: 32
<212> TYPE: PRT
<213> ORGANISM: Ehrlichia ewingii

<400> SEQUENCE: 197

Lys Asp Asn Asn Gln Val Gln Pro Lys Ala His Asp Ser Ser Thr
1               5                  10                  15

Asp Ser Asn Asn Ser Ser Asn Asn Thr Lys Lys Ser Tyr Phe Thr Phe
            20                  25                  30

<210> SEQ ID NO 198
<211> LENGTH: 12
<212> TYPE: PRT
<213> ORGANISM: Ehrlichia ewingii

<400> SEQUENCE: 198

Leu Asp Thr Gly Leu Ser Met Pro Lys Glu Lys Lys
1               5                  10

<210> SEQ ID NO 199
<211> LENGTH: 10
<212> TYPE: PRT
<213> ORGANISM: Ehrlichia ewingii

<400> SEQUENCE: 199

Val Asn Asp Tyr Asn Ile Ile Ser Ala Ile
1               5                  10

<210> SEQ ID NO 200
<211> LENGTH: 14
<212> TYPE: PRT
<213> ORGANISM: Ehrlichia ewingii

<400> SEQUENCE: 200

Ile Cys Lys Glu Asn Asp Lys Pro Thr Pro Lys Glu Lys Lys
1               5                  10

<210> SEQ ID NO 201
<211> LENGTH: 15
<212> TYPE: PRT
<213> ORGANISM: Ehrlichia ewingii

<400> SEQUENCE: 201

Met Asn Ser Ser Ser Asn Asn Gln Pro Lys Asp Lys Gln Phe Thr
1               5                  10                  15

<210> SEQ ID NO 202
<211> LENGTH: 13
<212> TYPE: PRT
<213> ORGANISM: Ehrlichia ewingii
```

-continued

```
<400> SEQUENCE: 202

His Ser Asn Asn Gly Asn Thr Gln Gln Asn Pro Phe Ala
1               5                   10

<210> SEQ ID NO 203
<211> LENGTH: 24
<212> TYPE: PRT
<213> ORGANISM: Ehrlichia ewingii

<400> SEQUENCE: 203

Ile Glu Ser Asp Gln Asn Lys Phe Gln Pro Lys Asn Ala Asn Ser Asn
1               5                   10                  15

Ser Ser Asn Lys Ile Tyr His Thr
            20

<210> SEQ ID NO 204
<211> LENGTH: 23
<212> TYPE: PRT
<213> ORGANISM: Ehrlichia ewingii

<400> SEQUENCE: 204

Ser Glu Ser Ser Lys Glu Pro Gln Pro Lys Asn Pro Asn Ser Ala Gly
1               5                   10                  15

Asn Asn Lys Ile Phe His Thr
            20

<210> SEQ ID NO 205
<211> LENGTH: 14
<212> TYPE: PRT
<213> ORGANISM: Ehrlichia ewingii

<400> SEQUENCE: 205

Lys Asp Asn Ala Asn Ile Gly Thr Thr Pro Gln Asp Lys Lys
1               5                   10

<210> SEQ ID NO 206
<211> LENGTH: 8
<212> TYPE: PRT
<213> ORGANISM: Ehrlichia ewingii

<400> SEQUENCE: 206

Glu Thr Ile Thr Ser Lys Lys Phe
1               5

<210> SEQ ID NO 207
<211> LENGTH: 8
<212> TYPE: PRT
<213> ORGANISM: Ehrlichia ewingii

<400> SEQUENCE: 207

His Gly Pro Ala Lys His Ile Asn
1               5

<210> SEQ ID NO 208
<211> LENGTH: 9
<212> TYPE: PRT
<213> ORGANISM: Ehrlichia ewingii

<400> SEQUENCE: 208

Ser Lys Gln Asp Asn Leu Asn Ser Asp
1               5

<210> SEQ ID NO 209
```

-continued

```
<211> LENGTH: 24
<212> TYPE: PRT
<213> ORGANISM: Ehrlichia ewingii

<400> SEQUENCE: 209

Thr Val Gln Tyr Pro Val Lys Leu Thr Ser Pro Pro Thr His Ile Asp
1               5                   10                  15

Pro Val Val Tyr Phe His Ser Asp
            20

<210> SEQ ID NO 210
<211> LENGTH: 16
<212> TYPE: PRT
<213> ORGANISM: Ehrlichia ewingii

<400> SEQUENCE: 210

Asn Tyr Pro Thr Asp Asn Asn Thr Thr Lys Thr Thr Val Ser Ala Ile
1               5                   10                  15

<210> SEQ ID NO 211
<211> LENGTH: 25
<212> TYPE: PRT
<213> ORGANISM: Ehrlichia ewingii

<400> SEQUENCE: 211

Leu Leu Asp Tyr Pro Ser Tyr Tyr Arg Ser Leu Thr Ser Leu Ser Asp
1               5                   10                  15

Asn Asp Pro Asn Arg Ile Leu Pro Phe
            20                  25

<210> SEQ ID NO 212
<211> LENGTH: 28
<212> TYPE: PRT
<213> ORGANISM: Ehrlichia ewingii

<400> SEQUENCE: 212

Pro Leu Met Leu Ser Pro Ser Thr Pro Arg Arg Ile Pro Pro Gln
1               5                   10                  15

Ser Ser Ser Glu Val Gln Asp Ala Thr Gly Leu Leu
            20                  25

<210> SEQ ID NO 213
<211> LENGTH: 14
<212> TYPE: PRT
<213> ORGANISM: Ehrlichia ewingii

<400> SEQUENCE: 213

Tyr Thr Gln Tyr Val Ser Gly Ile Asn Ser Leu Gln Glu Ile
1               5                   10

<210> SEQ ID NO 214
<211> LENGTH: 9
<212> TYPE: PRT
<213> ORGANISM: Ehrlichia ewingii

<400> SEQUENCE: 214

Thr Tyr Ala Tyr Ile Leu Lys Asp Ser
1               5

<210> SEQ ID NO 215
<211> LENGTH: 9
<212> TYPE: PRT
<213> ORGANISM: Ehrlichia ewingii
```

<400> SEQUENCE: 215

Asn His Val Val Glu Leu Asp Asp Phe
1               5

<210> SEQ ID NO 216
<211> LENGTH: 27
<212> TYPE: PRT
<213> ORGANISM: Ehrlichia ewingii

<400> SEQUENCE: 216

Ser Lys Ile His Tyr Ala Ile Ile Leu Ser Asn Asn Lys Tyr Leu Gln
1               5                   10                  15

Asn Ser Leu Gly Asp Thr Lys Thr Asn Thr Tyr
            20                  25

<210> SEQ ID NO 217
<211> LENGTH: 8
<212> TYPE: PRT
<213> ORGANISM: Ehrlichia ewingii

<400> SEQUENCE: 217

Gln Asn Met Phe Asp Ser Asn Glu
1               5

<210> SEQ ID NO 218
<211> LENGTH: 8
<212> TYPE: PRT
<213> ORGANISM: Ehrlichia ewingii

<400> SEQUENCE: 218

Gln His Val Val Thr Leu Asp Thr
1               5

<210> SEQ ID NO 219
<211> LENGTH: 12
<212> TYPE: PRT
<213> ORGANISM: Ehrlichia ewingii

<400> SEQUENCE: 219

Gln Tyr Val Asn Thr Thr Thr Ser Gln Ala Ile Asn
1               5                   10

<210> SEQ ID NO 220
<211> LENGTH: 9
<212> TYPE: PRT
<213> ORGANISM: Ehrlichia ewingii

<400> SEQUENCE: 220

Gln His Ile Ala Glu Leu Asn Asp Ala
1               5

<210> SEQ ID NO 221
<211> LENGTH: 9
<212> TYPE: PRT
<213> ORGANISM: Ehrlichia ewingii

<400> SEQUENCE: 221

Gln His Val Ala Glu Leu Asn Asp Asp
1               5

<210> SEQ ID NO 222
<211> LENGTH: 12
<212> TYPE: PRT
<213> ORGANISM: Ehrlichia ewingii -continued

<400> SEQUENCE: 222

Lys Thr Pro Val Thr Leu Asp Thr Ala Pro Gln Thr
1               5                   10

<210> SEQ ID NO 223
<211> LENGTH: 20
<212> TYPE: PRT
<213> ORGANISM: Ehrlichia ewingii

<400> SEQUENCE: 223

Asp Ile Thr Pro Leu Lys Pro Asn Gly Ile Glu Asn Thr Thr Ala Thr
1               5                   10                  15

His Val Leu Val
            20

<210> SEQ ID NO 224
<211> LENGTH: 17
<212> TYPE: PRT
<213> ORGANISM: Ehrlichia ewingii

<400> SEQUENCE: 224

Asp Ile Ala Thr Ile Leu Pro Ser Gly Ser Ser Ile Lys Asp Asn Gln
1               5                   10                  15

Tyr

<210> SEQ ID NO 225
<211> LENGTH: 15
<212> TYPE: PRT
<213> ORGANISM: Ehrlichia ewingii

<400> SEQUENCE: 225

Tyr Glu Arg Val Glu Ile Ala Tyr His Pro Ser Ile Glu Glu Ala
1               5                   10                  15

<210> SEQ ID NO 226
<211> LENGTH: 16
<212> TYPE: PRT
<213> ORGANISM: Ehrlichia ewingii

<400> SEQUENCE: 226

Glu Tyr Ser Asn Ile Pro Val Gln Tyr Pro Arg Asn Leu Phe Tyr Ala
1               5                   10                  15

<210> SEQ ID NO 227
<211> LENGTH: 20
<212> TYPE: PRT
<213> ORGANISM: Ehrlichia ewingii

<400> SEQUENCE: 227

Gln Tyr Ser Ser Ile Ser Val Lys Tyr Pro Lys Val Leu Val Phe Pro
1               5                   10                  15

Ser Thr Arg Ser
            20

<210> SEQ ID NO 228
<211> LENGTH: 282
<212> TYPE: PRT
<213> ORGANISM: Ehrlichia ewingii

<400> SEQUENCE: 228

Met Lys Cys Lys Ile Thr Lys Ile Ala Ile Ile Met Leu Gly Leu Leu
1               5                   10                  15

```
Leu Pro Phe Gln Ala Phe Ser Ala Ser Leu Val Ser Asp Ala Ser Asp
                20                  25                  30

Ser His Thr Lys Ser Val Ser Leu Ser Ala Ser Tyr Lys Leu Ser Thr
            35                  40                  45

Pro Phe Phe Asn His Phe Leu Ile Arg Glu Thr Asn Leu Thr Ser Gly
    50                  55                  60

Ile Ile Ala Asn Lys Arg Val Leu Gly Leu Lys Asn Asp Ile Leu Ile
65                  70                  75                  80

Asn Ala Asp Glu Ala Ile Lys Asn Leu Ser Asn Phe Asp Phe Ser Glu
                85                  90                  95

Asp Tyr Val Pro Lys Tyr Lys Asn Ser Leu Tyr Gly Leu Ser Phe Leu
            100                 105                 110

Phe Gly Tyr Ser Phe Lys Asn Leu Lys Val Glu Leu Glu Gly Leu Tyr
        115                 120                 125

Glu Ser Phe Asp Val Arg Asp Thr Lys Asn His Ile Ile Asp Asn Asn
130                 135                 140

Tyr Arg Tyr Phe Ala Leu Ser Lys Gln Asp Asn Leu Asn Ser Asp Tyr
145                 150                 155                 160

Val Thr Leu Ile Asn Asn Gly Val Lys Leu Tyr Ser Val Ile Leu Asn
                165                 170                 175

Ile Cys Tyr Asp Phe Ile Gly Lys Asn Thr Ser Leu Thr Pro Phe Leu
            180                 185                 190

Cys Val Gly Ile Gly Glu Asp Ile Ile Asn Ile Phe Asp Ala Val Arg
        195                 200                 205

Phe Lys Pro Ala Phe His Ala Lys Met Gly Phe Asn Tyr Arg Ile Ser
    210                 215                 220

Glu Arg Ala Phe Leu Phe Met Asp Met Tyr Tyr His Lys Ile Ile Gly
225                 230                 235                 240

Asn Gln Tyr Ser Ser Ile Ser Val Lys Tyr Pro Lys Val Leu Val Phe
                245                 250                 255

Pro Ser Thr Arg Ser Ser Val Leu Ala Glu Leu Asp Ile Gly Tyr Leu
            260                 265                 270

Gly Ser Glu Val Gly Ile Arg Ile Phe Ile
        275                 280

<210> SEQ ID NO 229
<211> LENGTH: 293
<212> TYPE: PRT
<213> ORGANISM: Ehrlichia ewingii

<400> SEQUENCE: 229

Met Ile Lys Phe Ser Ser Val Gly Val Thr Leu Ser Leu Ala Thr Leu
1               5                   10                  15

Leu Ser His Asn Ala Leu Ser Ser Pro Ile Pro Ile Asp Phe Ser Asn
                20                  25                  30

Glu Ser Glu Met Val Gly Phe Tyr Ala Ser Ala His Tyr Asn Leu Glu
            35                  40                  45

Leu Pro Met Phe Ser Pro Ile Ser Val Lys Tyr Lys Ser Thr Gly Asn
    50                  55                  60

Ser Glu Ala Asp Lys Ser Glu Lys Glu Leu Thr Leu Phe Thr Leu Lys
65                  70                  75                  80

Glu Ser Thr Gln Ala Pro Asp Phe Thr Lys Lys Glu Thr Phe Asn Asp
                85                  90                  95

Lys Ser Gly Tyr Lys Pro Val Tyr Asn Arg Asn Tyr Thr Gly Phe Ser
```

```
            100                 105                 110
Gly Ala Val Gly Tyr Ser Gly Gly Ile Arg Val Glu Ile Glu Gly
            115                 120                 125
Ala Phe Thr Arg Phe Asp Val Asp Lys Gln Lys His Thr His Pro Asp
130                 135                 140
Asn His Arg Tyr Phe Ala Ser Cys Thr Glu Gln Glu Met Lys Pro Ala
145                 150                 155                 160
Gln Gln Asn Gly Ser Ser Lys Asp Gly Asn Tyr Val Val Met Lys Asn
                165                 170                 175
Glu Gly Phe Lys Ala Ile Ser Leu Thr Phe Asn Val Cys Tyr Asp Met
            180                 185                 190
Ile Val Ser Asn Ser Ser Leu Ile Pro Ser Ala Cys Val Gly Ile Gly
        195                 200                 205
Gln Gly Ile Thr Asn Phe Leu Gly Ala Thr Asn Ile His Thr Ile Phe
    210                 215                 220
Gln Ala Lys Leu Gly Leu Gly Phe Ser Ile Ser Pro Lys Thr Ile Leu
225                 230                 235                 240
Phe Ala Asn Gly Tyr Tyr Val Lys Thr Lys Asp Asp Ala Phe Thr Asn
                245                 250                 255
Leu Thr Val Gln Tyr Pro Val Lys Leu Thr Ser Pro Thr His Ile
            260                 265                 270
Asp Pro Val Val Tyr Phe His Ser Asp Tyr Cys Gly Gly Glu Val Gly
        275                 280                 285
Leu Arg Phe Ile Leu
    290

<210> SEQ ID NO 230
<211> LENGTH: 272
<212> TYPE: PRT
<213> ORGANISM: Ehrlichia ewingii

<400> SEQUENCE: 230

Met Ser Tyr Lys Lys Val Ile Phe Trp Ile Ile Leu Phe Leu Thr Pro
1               5                   10                  15
Gly Ala Ser Leu Ser Gln Gly Leu Asn Asp Asn Ile Phe Lys Asn Phe
            20                  25                  30
Tyr Val Gly Val Gln Tyr Lys Pro Ala Ile His His Leu Ser His Leu
        35                  40                  45
Ile Ile Lys Glu Thr Ser Lys Asp Thr Ile Gly Ile Phe Ala Leu Lys
    50                  55                  60
Lys Asp Ala Ser Leu Pro Thr Asp Ile Lys Lys Asn Ser Asn Leu Asn
65                  70                  75                  80
Ile Arg Tyr Asn Pro His Tyr Glu Asn Asn Ser Gly Phe Ser Gly
                85                  90                  95
Leu Leu Gly Tyr His Tyr Asn Asn Phe Arg Ile Glu Ser Glu Ile
            100                 105                 110
Ser Tyr Glu Ile Phe Pro Leu Lys Asn Glu Gly Tyr Lys Ile Thr Gly
        115                 120                 125
Val Glu Gln His Phe Ala Leu Ala Ser Glu Leu Asp Thr Asn Gly Asn
    130                 135                 140
Gln Pro Lys Thr Asp Lys Tyr Val Thr Ile Ile Asn Asp Gly Ile Arg
145                 150                 155                 160
Ala Thr Ser Val Leu Ile Asn Ala Cys Tyr Asp Gly Ile Asp Ile Lys
                165                 170                 175
```

```
Lys Asn Asn Ile Val Val Tyr Ser Cys Ile Gly Leu Gly Ala Asp Ile
            180                 185                 190

Val Asp Phe Leu Ser Lys Tyr Asn Thr Lys Leu Ser Tyr Gln Gly Lys
        195                 200                 205

Leu Gly Leu Ser Tyr Pro Ile Ser Leu Lys Ile Ile Leu Phe Ala Glu
    210                 215                 220

Gly Tyr Tyr His Gly Leu Leu Gly Asn Val Phe Asn Asn Val Pro Val
225                 230                 235                 240

Asn Tyr Pro Thr Asp Asn Asn Thr Thr Lys Thr Thr Val Ser Ala Ile
                245                 250                 255

Leu Asn Ile Arg Tyr Tyr Gly Gly Ser Val Gly Val Arg Phe Ile Leu
            260                 265                 270

<210> SEQ ID NO 231
<211> LENGTH: 284
<212> TYPE: PRT
<213> ORGANISM: Ehrlichia ewingii

<400> SEQUENCE: 231

Met Asn Tyr Ala Lys Val Phe Ile Leu Met Phe Val Ile Leu Phe Leu
 1               5                  10                  15

Pro Ser Ser Ser Leu Leu Ala Leu Glu Asn Asn Leu Ser Gly Gly Val
            20                  25                  30

Gly His Ile Tyr Ile Ser Gly Gln Tyr Lys Pro Ser Ile Pro Gln Phe
        35                  40                  45

Asn Lys Phe Ser Met Glu Glu Ala Thr Ile Gly Ala Val Ile Pro Lys
    50                  55                  60

Ser Leu Lys Gln Asp Ala Glu Asp Ile Thr Leu Ser Ile Leu Ala Leu
 65                 70                  75                  80

Ser Thr Asn Phe Thr Leu Pro Tyr Asp Pro Lys Tyr Lys Lys Ser Leu
                85                  90                  95

Leu Gly Leu Gly Gly Thr Ile Gly Tyr Ala Ile Asn Asn Phe Arg Ile
            100                 105                 110

Glu Leu Glu Thr Phe Tyr Glu Lys Phe Asn Val Ser Ala Pro Ser Gly
        115                 120                 125

Tyr Asp Asp Asn Ile Tyr Ala Tyr Phe Ser Ile Glu Val Pro Gln Leu
    130                 135                 140

Arg Ser Leu Pro Tyr His Tyr Thr Met Lys Asn Thr Gly Ile Ile Leu
145                 150                 155                 160

Ser Pro Val Leu Ala Asn Ile Cys Tyr Asp Ile Asn Lys Lys Gln Leu
                165                 170                 175

Arg Asn Val Ser Pro Tyr Leu Cys Leu Gly Phe Gly Val Asp Leu Ile
            180                 185                 190

Asp Phe Leu Asp Lys Val Ser Phe Lys Phe Ser Tyr Gln Ala Lys Leu
        195                 200                 205

Gly Val Ser Tyr Leu Ile Ser Pro Asn Leu Ala Phe Phe Ile Asp Gly
    210                 215                 220

Ser Phe His Arg His Leu Gly Asn Gln Phe Ser Asp Leu Leu Leu Asp
225                 230                 235                 240

Tyr Pro Ser Tyr Tyr Arg Ser Leu Thr Ser Leu Ser Asp Asn Asp Pro
                245                 250                 255

Asn Arg Ile Leu Pro Phe Thr Ser Ala Ser Ala Lys Leu Asn Ile Asn
            260                 265                 270

Phe Phe Ser Ala Asn Ile Gly Ile Arg Phe Ile Phe
        275                 280
```

```
<210> SEQ ID NO 232
<211> LENGTH: 293
<212> TYPE: PRT
<213> ORGANISM: Ehrlichia ewingii

<400> SEQUENCE: 232

Met Phe Met Lys Lys Leu Tyr Tyr Leu Asn Phe Thr Val Leu Val Leu
1               5                   10                  15

Thr Val Tyr Leu Phe Pro Ser Phe Val Phe Ser Met Gln Gly Arg Ser
            20                  25                  30

Asn Ile Thr Gly Ser Tyr Ile Thr Val Ser Tyr Gln Pro Ser Met Ser
        35                  40                  45

Asn Phe Arg Asn Phe His Ile Lys Glu Thr Asn Phe Asp Thr Lys Asp
    50                  55                  60

Pro Ile Gly Leu Ile Arg Ser Ala Arg Ser Thr Glu Pro Ser Val Leu
65                  70                  75                  80

Lys Ile Asn Thr His Phe Tyr Lys Pro Gln Gln Ser Asp Ser Tyr Lys
                85                  90                  95

Ser Tyr Gly Asn Asp Leu Leu Gly Phe Ser Thr Ser Ile Gly Leu Leu
            100                 105                 110

Val Lys Asn Leu Arg Met Glu Phe Glu Gly Ser Tyr Lys Lys Phe Asp
        115                 120                 125

Ile Lys Arg Leu Val Asn Tyr Ala Ser Arg Asp Gly His Arg Tyr Phe
    130                 135                 140

Ala Ile Pro Arg Asp Thr Phe Phe Asn Asn Ser Ile Pro Tyr Ala Phe
145                 150                 155                 160

Asn Ala Tyr Thr Val Ala Lys Asn Asn Gly Leu Ser Ile Ile Ser Asn
                165                 170                 175

Met Ile Asn Leu Cys Tyr Glu Ser Ile Lys Tyr Asn Asn Phe Met Pro
            180                 185                 190

Tyr Ile Cys Leu Gly Ala Gly Gly Asp Phe Ile Glu Leu Phe Asp Ser
        195                 200                 205

Met Arg Ile Lys Phe Ala Tyr Gln Gly Lys Leu Gly Val Ser Tyr Pro
    210                 215                 220

Leu Thr Ser Asn Leu Val Leu Ala Ile Ser Gly Gln Tyr His Lys Val
225                 230                 235                 240

Val Gly Asp Lys Phe Lys Phe Leu Pro Leu Met Leu Ser Pro Ser Thr
                245                 250                 255

Pro Arg Arg Arg Ile Pro Pro Gln Ser Ser Ser Glu Val Gln Asp Ala
            260                 265                 270

Thr Gly Leu Leu Thr Leu Asp Leu Gly Tyr Phe Ser Ala Asp Ile Gly
        275                 280                 285

Leu Arg Phe Met Phe
    290

<210> SEQ ID NO 233
<211> LENGTH: 272
<212> TYPE: PRT
<213> ORGANISM: Ehrlichia ewingii

<400> SEQUENCE: 233

Met Asn Asn Lys Lys Ser His Val Ile Cys Met Leu Ile Phe Leu Leu
1               5                   10                  15

Leu Pro Met Lys Ser Phe Ser Val Leu Ile Asp Thr Thr Glu Lys Asp
            20                  25                  30
```

Tyr Ala Ser Asn Val Tyr Ile Ser Ser Gln Tyr Lys Pro Ser Phe Ser
35 40 45

Asn Phe Arg Ser Phe Ser Ile Gln Glu Ile Asn Ser Lys Thr Lys Asn
50 55 60

Ser Ile Ala Leu Glu Lys Pro Ile Glu Ser Asn Ser Asn Ile Leu Lys
65 70 75 80

Ser Asn Ala His Ile Ile Val Pro His Asn Ile Gln Phe Gln Asp Asn
85 90 95

Thr Ile Ser Phe Ser Gly Ala Val Gly Tyr Ser Ser Lys Gly Leu Arg
100 105 110

Leu Glu Leu Glu Ser Ala Tyr Glu Glu Phe Tyr Thr Lys Glu Leu Asn
115 120 125

Ser Ser Ser Leu Ile Ser Ser Asn Asn His Tyr Thr Gln Leu Tyr Glu
130 135 140

Ala Asn Phe Gln Asn Phe Ala Thr Ser Arg Leu Ser Ile Thr Ser Phe
145 150 155 160

Ile Ile Asn Thr Cys Tyr Asp Ile Leu Ile Gly Ser Ser Pro Val Met
165 170 175

Pro Tyr Ile Cys Thr Gly Ile Gly Gly Asp Ile Ile Arg Leu Phe Asn
180 185 190

Thr Thr Tyr Leu Lys Phe Ala Tyr Gln Gly Lys Phe Gly Ile Ser Tyr
195 200 205

Pro Leu Asn Asn Asn Ile Ile Leu Phe Ser Asp Ile Tyr Tyr His Glu
210 215 220

Ile Ile Gly Gln Glu Phe Glu Asn Leu Tyr Thr Gln Tyr Val Ser Gly
225 230 235 240

Ile Asn Ser Leu Gln Glu Ile Thr Ser Val Pro Ala Ser Phe Asn Ile
245 250 255

Gly Tyr Phe Gly Ser Glu Ile Gly Val Arg Phe Ile Phe Asn Lys Gln
260 265 270

<210> SEQ ID NO 234
<211> LENGTH: 299
<212> TYPE: PRT
<213> ORGANISM: Ehrlichia ewingii

<400> SEQUENCE: 234

Met Arg Lys Lys Ile Tyr Ser Ile Asn Val Ile Leu Val Phe Thr Leu
1 5 10 15

Leu Leu Leu Ser Ile Gln Ser Phe Ala Ile Ser Ile Asp Asn Asn Ile
20 25 30

Ile Asp Gln Asn Leu Gly Leu Tyr Leu Ser Ala Gln Tyr Lys Pro Ser
35 40 45

Ile Ser His Phe Lys Asn Phe Ser Val Gln Glu Val Asn Lys Lys Val
50 55 60

Asp Leu Ile Ala Leu Lys Asn Asp Val Thr His Ile Thr Glu Glu Ile
65 70 75 80

Leu Lys Asp Pro Thr Asn Phe Asn Thr His Tyr Ser Ala Lys Phe Lys
85 90 95

Asn Ser Phe Thr Gly Phe Ser Gly Ala Val Gly Tyr Tyr Ser Ala Gln
100 105 110

Gly Pro Arg Leu Glu Val Glu Gly Phe Tyr Glu Asn Phe Asp Ile Thr
115 120 125

Asp Cys Ser Asn Cys Thr Ile Asn Asp Ala Asn Arg Tyr Leu Ala Leu

```
                130                 135                 140
Ala Arg Glu Lys Asp Asn Asn Gln Val Gln Pro Lys Ala His Asp Ser
145                 150                 155                 160

Ser Ser Thr Asp Ser Asn Asn Ser Ser Asn Asn Thr Lys Lys Ser Tyr
                165                 170                 175

Phe Thr Phe Met Lys Asn Asn Gly Ile Ser Ile Ala Ser Val Met Ile
            180                 185                 190

Asn Gly Cys Tyr Asp Phe Ser Leu Asn Asn Ile Lys Ile Ser Pro Tyr
                195                 200                 205

Val Cys Ala Gly Ile Gly Gly Asp Phe Ile Glu Phe Phe Glu Val Met
            210                 215                 220

His Ile Lys Phe Ser Tyr Gln Gly Lys Leu Gly Val Ser Tyr Leu Ile
225                 230                 235                 240

Ser Pro Ser Ile Ser Leu Phe Val Asp Gly Tyr Tyr His Ser Val Ile
                245                 250                 255

Asn Asn Lys Phe Lys Asn Leu His Val Thr Tyr Ala Tyr Ile Leu Lys
            260                 265                 270

Asp Ser Pro Thr Ile Thr Ser Ala Ile Ala Gln Leu Asn Ile Gly Tyr
        275                 280                 285

Phe Gly Gly Glu Val Gly Leu Arg Phe Val Phe
    290                 295
```

<210> SEQ ID NO 235
<211> LENGTH: 284
<212> TYPE: PRT
<213> ORGANISM: Ehrlichia ewingii

<400> SEQUENCE: 235

```
Met Ser Asn Lys Lys Phe Thr Ile Gly Thr Val Leu Val Ser Leu
1               5                   10                  15

Leu Ala Phe Leu Pro Thr Tyr Ser Phe Ser Ala Pro Ile Ser Asn Asn
                20                  25                  30

Ser Glu Asp Asn Ile Phe Gly Leu Tyr Ile Ala Gly Gln Tyr Arg Pro
            35                  40                  45

Gly Val Ser His Phe Ser Gly Phe Gly Val Thr Glu Thr Asn Phe Ala
        50                  55                  60

Thr Gln Lys Leu Met Arg Val Lys Lys Asp Ser Lys Glu Gly Leu Pro
65                  70                  75                  80

Asn Ile Leu Lys Ser Lys Asp Asn Phe Thr Glu Pro Tyr Val Ala Lys
                85                  90                  95

Phe Gln Asp Asn Ala Val Ser Phe Ser Gly Ala Ile Gly Tyr Ser Tyr
            100                 105                 110

Pro Glu Gly Leu Arg Leu Glu Ile Glu Gly Ser Tyr Glu Thr Phe Asp
        115                 120                 125

Val Lys Asp Pro Lys Asp Cys Ser Val Lys Asp Ala Phe Arg His Leu
130                 135                 140

Ala Leu Val Arg Glu Leu Asp Thr Gly Leu Ser Met Pro Lys Glu Lys
145                 150                 155                 160

Lys Tyr Thr Val Met Arg Asn Asn Gly Leu Ser Ile Ala Ser Ile Leu
                165                 170                 175

Ile Asn Gly Cys Tyr Asp Phe Asp Phe Asp Asn Leu Ile Val Ser Pro
            180                 185                 190

Tyr Val Cys Leu Gly Ile Gly Glu Asp Phe Ile Glu Phe Phe Asp Val
        195                 200                 205
```

-continued

```
Leu His Ile Lys Phe Ala Tyr Gln Gly Lys Leu Gly Ile Ser Tyr Glu
    210                 215                 220

Leu Ser Pro Arg Ile Asn Val Phe Ala Asp Gly Tyr Tyr His Lys Val
225                 230                 235                 240

Ile Gly Asn Gln Phe Lys Asn Leu Asn Val Asn His Val Val Glu Leu
                245                 250                 255

Asp Asp Phe Pro Lys Val Thr Ser Ala Val Ala Thr Leu Asn Val Gly
            260                 265                 270

Tyr Phe Gly Gly Glu Val Gly Val Arg Phe Ile Phe
        275                 280

<210> SEQ ID NO 236
<211> LENGTH: 243
<212> TYPE: PRT
<213> ORGANISM: Ehrlichia ewingii
<400> SEQUENCE: 236

Met Ser Cys Glu Lys Lys Phe Cys Tyr Ser Lys Lys His Ile Ile Phe
1               5                   10                  15

Phe Ile Thr Thr Val Ser Ser Val Gln Ser Phe Ser Ala Ser Leu Asn
            20                  25                  30

Asn Ala Glu Asp His Lys Asp Phe Tyr Leu Tyr Val Ile Leu Tyr Ile
        35                  40                  45

Ser Tyr Asn Phe Phe Cys Ile Ile Arg Leu Ile Thr Val Lys Asp Ser
    50                  55                  60

His Phe Phe Ser Ile Asn Thr Ser Ser Tyr Asn Leu Cys Leu Glu Lys
65                  70                  75                  80

His Lys Asn Asp Ile Ser Phe Ser Lys Ile Leu Gly Val Phe Thr Lys
                85                  90                  95

Thr Ile His Ser Tyr Asn Ile Gly Asp Ser His Glu Arg Phe Asn Ala
            100                 105                 110

Glu Asn Leu Arg Asn Ser Leu Thr Glu Asp Lys Tyr Leu Thr Ser Glu
        115                 120                 125

Gln Glu Val Asn Asp Tyr Asn Ile Ile Ser Ala Ile Lys Asn Ser Gly
    130                 135                 140

Leu Tyr Leu Leu Ile Glu Ile Leu Phe Asn Ile Tyr Tyr Ile Ile Ile
145                 150                 155                 160

Gly Arg Asn Phe Ile Thr Ser Phe Asp Ile Leu Cys Ile Lys Ser Thr
                165                 170                 175

Asn Gln Thr Glu Leu Ser Ile Asn Leu Leu Ser Lys Ala Asn Leu Pro
            180                 185                 190

Ile Asn Arg Phe Tyr Tyr Arg Ile Lys Asp Asn Gln His Glu Asn Ser
        195                 200                 205

Lys Ile His Tyr Ala Ile Ile Leu Ser Asn Asn Lys Tyr Leu Gln Asn
    210                 215                 220

Ser Leu Gly Asp Thr Lys Thr Asn Thr Tyr Gly Val Arg Ser Asn Phe
225                 230                 235                 240

Asn Asn Thr

<210> SEQ ID NO 237
<211> LENGTH: 281
<212> TYPE: PRT
<213> ORGANISM: Ehrlichia ewingii
<400> SEQUENCE: 237

Met Ser Asn Lys Lys Ile Phe Ser Ile Ile Gly Gln Ala Leu Thr Cys
```

```
  1               5                  10                 15
Leu Val Leu Phe Ser Pro Ile Tyr Ser Phe Ser Glu Ser Asn His Tyr
                 20                 25                 30

Asp Lys Ser Leu Tyr Val Ala Gly Gln Tyr Lys Ser Ser Leu Ser His
                 35                 40                 45

Phe Thr Asn Phe Ser Val Arg Glu Thr Asp Ile Asn Thr Lys Gly Leu
         50                 55                 60

Phe Lys Leu Gly His Gly Val Thr Leu Val Glu Glu Asp Ile Lys Asn
 65                 70                 75                 80

His Leu Gln Phe Thr Ile Pro His Ser Val Ala Phe Lys Asn Asn Phe
                 85                 90                 95

Ala Asn Phe Ser Ala Ala Val Gly Tyr Ile Ser Pro Gly Gly Pro Arg
                100                105                110

Val Glu Ile Glu Gly Ser Tyr Glu Asn Phe Asp Val Lys Asp Leu Lys
                115                120                125

Asn Cys Thr Ile Gln Asp Ala Cys Arg Tyr Leu Ser Leu Ala Arg Glu
        130                135                140

Ile Cys Lys Glu Asn Asp Lys Pro Thr Pro Lys Glu Lys Lys Tyr Val
145                150                155                160

Val Met Arg Asn Asp Gly Ile Ser Ile Thr Ser Val Thr Ile Asn Gly
                165                170                175

Cys Tyr Asp Phe Ser Ile Asn Lys Leu Pro Lys Ile Ser Pro Tyr Ile
                180                185                190

Cys Ala Gly Phe Gly Gly Asp Phe Ile Glu Phe Phe Asp Ser Val Arg
                195                200                205

Val Lys Phe Ala Tyr Gln Ser Lys Leu Gly Ile Asn Tyr Ser Leu Ser
        210                215                220

Ser Asn Phe Ile Leu Phe Val Asp Gly Tyr Tyr His Arg Val Ile Gly
225                230                235                240

Asn Gln Phe Lys Asn Leu Asn Val Gln Asn Met Phe Asp Ser Asn Glu
                245                250                255

Pro Tyr Val Thr Ser Ala Ile Ala Thr Leu Asn Ile Glu His Phe Gly
                260                265                270

Gly Gly Phe Gly Leu Arg Phe Ile Phe
                275                280
```

<210> SEQ ID NO 238
<211> LENGTH: 280
<212> TYPE: PRT
<213> ORGANISM: Ehrlichia ewingii

<400> SEQUENCE: 238

```
Met Arg Lys Lys Ser Phe Ile Ile Gly Thr Val Leu Ile Cys Leu
 1               5                  10                 15

Leu Ser Pro Pro Asn Ile Ser Phe Ser Glu Val Ile Thr His Asn Asp
                 20                 25                 30

Asn Lys His Pro Gly Ile Tyr Val Ser Gly Gln Tyr Lys Pro Gly Ile
                 35                 40                 45

Ser His Leu Arg Lys Phe Ser Val Lys Glu Thr Asn Ala Thr Thr Val
         50                 55                 60

Gln Leu Val Gly Leu Asn Tyr Thr Ala Ala Pro Ile Asp Asp Ile Lys
 65                 70                 75                 80

Thr Ser Ser Lys Phe Asp Thr Pro Tyr Thr Ile Ala Phe Gln Asn Asn
                 85                 90                 95
```

```
Ile Ile Ser Phe Ser Ala Ala Ile Gly Tyr Ser His Ala Lys Gly Leu
            100                 105                 110

Arg Ile Glu Leu Glu Gly Ser Tyr Glu Glu Phe Asp Val Thr Asp Pro
        115                 120                 125

Gly Asn Tyr Thr Ile Lys Asp Ala Tyr Arg Tyr Phe Ala Ile Ala Arg
    130                 135                 140

Glu Met Asn Ser Ser Ser Asn Asn Gln Pro Lys Asp Lys Gln Phe Thr
145                 150                 155                 160

Val Met Arg Asn Asp Gly Val Ser Ile Val Ser Phe Met Phe Asn Gly
                165                 170                 175

Cys Tyr Asp Phe Pro Leu Gly Ile Leu Glu Ile Ser Pro Tyr Ile Cys
            180                 185                 190

Ala Gly Ile Gly Gly Asp Phe Ile Glu Phe Phe Asp Ala Leu His Ile
        195                 200                 205

Lys Pro Ala Tyr Gln Gly Lys Leu Gly Leu Asn Tyr Pro Leu Phe Ser
    210                 215                 220

Lys Val Ser Leu Phe Ile Asp Gly Tyr Tyr His Lys Val Ile Gly Gln
225                 230                 235                 240

Gln Phe Lys His Leu Asn Val Gln His Val Val Thr Leu Asp Thr Pro
                245                 250                 255

Lys Ile Ala Ser Val Val Ala Thr Leu Asp Val Ser Tyr Phe Gly Gly
            260                 265                 270

Glu Ile Gly Met Arg Leu Ile Phe
        275                 280

<210> SEQ ID NO 239
<211> LENGTH: 290
<212> TYPE: PRT
<213> ORGANISM: Ehrlichia ewingii

<400> SEQUENCE: 239

Met Asn Asn Lys Lys Met Phe Ser Ile Ile Gly Ile Ser Leu Leu Ala
 1               5                  10                  15

Asn Leu Leu Leu Leu Pro Asn Met Ser Phe Ala Lys Asn Asn Tyr Ser
            20                  25                  30

Tyr Ile Asn Pro Val Leu Tyr Ile Ser Gly Gln Tyr Arg Pro Gly Val
        35                  40                  45

Ser His Phe Ser Gln Phe Ser Val Arg Glu Thr His Tyr Asp Thr Gln
    50                  55                  60

Leu Leu Ala Glu Leu Lys Lys Glu Val Gly Ser Val Thr Asn Thr Val
65                  70                  75                  80

Ile Gln Ala Tyr Ala Asn Tyr Asn Val Pro Ser Gln Ala Pro Phe Ser
                85                  90                  95

His Thr Tyr Val Ala Glu Phe Glu Asp Asn Thr Ile Ser Phe Ser Gly
            100                 105                 110

Ala Val Gly Phe Ser Tyr Ser Glu Gly Pro Arg Ile Glu Ile Glu Phe
        115                 120                 125

Ser Tyr Glu Glu Phe Asp Val Lys Asn Ser Gly His Ser Ser Ile Asp
    130                 135                 140

Ala His Arg Tyr Phe Ala Leu Leu Arg His Ser Asn Asn Gly Asn Thr
145                 150                 155                 160

Gln Gln Asn Pro Phe Ala Val Met Arg Asn Asn Gly Leu Phe Ile Gly
                165                 170                 175

Ser Val Ala Ile Asn Ser Cys Tyr Asp Phe Ile Leu Asp Asp Thr Pro
            180                 185                 190
```

```
Ala Leu Pro Tyr Val Cys Gly Ile Gly Gly Asp Phe Ile Glu Phe
            195                 200                 205

Phe Asp Glu Leu His Val Lys Leu Ala Tyr Gln Gly Lys Ile Gly Ile
210                 215                 220

Ser Tyr Pro Ile His Ser Lys Val Ser Thr Phe Val Asp Val Tyr Tyr
225                 230                 235                 240

His Arg Val Ile Asn Asn Lys Phe Lys Asn Leu His Val Gln Tyr Val
            245                 250                 255

Asn Thr Thr Thr Ser Gln Ala Ile Asn Pro Gln Ile Thr Ser Ala Val
            260                 265                 270

Ala Thr Leu Asn Val Gly Tyr Phe Gly Ile Glu Ile Gly Ala Arg Leu
            275                 280                 285

Thr Phe
    290

<210> SEQ ID NO 240
<211> LENGTH: 298
<212> TYPE: PRT
<213> ORGANISM: Ehrlichia ewingii

<400> SEQUENCE: 240

Met Asn Asn Lys Asn Arg Phe Thr Ala Ile Gly Val Ala Leu Thr Cys
1               5                   10                  15

Leu Leu Leu Leu Pro Asn Val Ser Phe Ser Glu Thr Thr Ile Ile Asn
            20                  25                  30

Gln Pro Ser Gly Leu Tyr Ile Ser Gly Gln Tyr Lys Pro Ser Val Ser
        35                  40                  45

Val Phe Ser Asp Phe Ser Val Lys Glu Ala Asn Val Ala Thr Lys His
    50                  55                  60

Leu Ile Ala Leu Lys Lys Ser Val Asp Ser Ile Asn Ala Glu Lys Ala
65                  70                  75                  80

Thr Pro His Asn Gln Gly Leu Gly Lys Pro Asp Asn Phe Asn Ile Pro
                85                  90                  95

Tyr Lys Val Glu Phe Glu Asp Asn Ala Val Ser Phe Ser Gly Val Ile
            100                 105                 110

Gly Tyr Ser Phe Pro Glu Gly Pro Arg Ile Glu Ile Glu Thr Ser Tyr
        115                 120                 125

Glu Glu Phe Asp Val Lys Asn Pro Gly Gly Tyr Thr Leu Asn Asp Ala
130                 135                 140

Phe Arg Tyr Phe Ala Leu Ala Arg Glu Ile Glu Ser Asp Gln Asn Lys
145                 150                 155                 160

Phe Gln Pro Lys Asn Ala Asn Ser Asn Ser Ser Asn Lys Ile Tyr His
                165                 170                 175

Thr Val Met Arg Asn Asp Gly Ile Ser Val Leu Ser Asn Met Ile Asn
            180                 185                 190

Ile Cys Tyr Asp Phe Ser Leu Asp Asn Leu Pro Val Leu Pro Tyr Ile
        195                 200                 205

Cys Gly Gly Thr Gly Val Asp Thr Ile Glu Phe Phe Asp Ser Leu His
    210                 215                 220

Ile Lys Leu Ala Gly Ala Lys Ile Gly Ile Thr Tyr Pro Leu Leu Ser
225                 230                 235                 240

Ser Asn Ile Asn Leu Phe Ala Gly Gly Tyr Tyr His Lys Val Ile Gly
                245                 250                 255

Asn Arg Phe Lys Asn Leu Lys Val Gln His Ile Ala Glu Leu Asn Asp
```

-continued

```
                260                 265                 270
Ala Pro Lys Val Thr Ser Ala Val Ala Thr Leu Asn Ile Ser Tyr Phe
            275                 280                 285

Gly Gly Glu Ile Gly Ala Arg Phe Ile Phe
        290                 295

<210> SEQ ID NO 241
<211> LENGTH: 302
<212> TYPE: PRT
<213> ORGANISM: Ehrlichia ewingii

<400> SEQUENCE: 241

Met Glu Ile Ser Met Ser Asn Lys Lys Leu Phe Thr Ile Ser Thr
 1               5                  10                  15

Ala Leu Tyr Leu Leu Ser Pro Asn Ile Ser Phe Ser Glu Thr Ile
            20                  25                  30

Val Asp Asp Ile Asp Arg Gln Phe Arg Leu Tyr Ile Ser Gly Gln Tyr
 35                  40                  45

Lys Pro Ser Leu Ser Val Phe Ser Asn Phe Ser Val Lys Glu Thr Asn
     50                  55                  60

Val Thr Thr Lys Tyr Leu Thr Ala Leu Lys Lys Asp Ala Asp Pro Thr
 65                  70                  75                  80

Glu Lys Thr Gly Ser Thr Pro His Glu Lys Gly Leu Gly Lys Pro Asp
                 85                  90                  95

Asn Phe Asn Ile Pro Tyr Lys Val Glu Phe Glu Asp Asn Ala Val Ser
            100                 105                 110

Phe Ser Gly Ala Val Gly Phe Ser Tyr Pro Glu Gly Leu Arg Ile Glu
        115                 120                 125

Ile Glu Ala Ser Tyr Glu Glu Phe Asp Val Lys Asn Pro Gly Gly Tyr
    130                 135                 140

Thr Ile Ser Asn Ala Phe Arg Tyr Phe Ala Leu Val Arg Glu Ser Glu
145                 150                 155                 160

Ser Ser Lys Glu Pro Gln Pro Lys Asn Pro Asn Ser Ala Gly Asn Asn
                165                 170                 175

Lys Ile Phe His Thr Val Met Arg Asn Asp Gly Val Ala Ile Ser Ser
            180                 185                 190

Ile Thr Ile Asn Gly Cys Tyr Asp Phe Ser Leu Ser Gln Leu Pro Val
        195                 200                 205

Leu Pro Tyr Ile Cys Gly Gly Ile Gly Ile Thr Ile Asp Phe Phe
    210                 215                 220

Asp Ala Leu His Ile Lys Phe Ala Gly Gln Gly Lys Leu Gly Ile Thr
225                 230                 235                 240

Tyr Pro Leu Ser Gly Asn Ile Asn Leu Phe Ala Asp Gly Tyr Tyr His
                245                 250                 255

Lys Val Ile Ser Asn Gln Phe Lys Asn Leu Asn Val Gln His Val Ala
            260                 265                 270

Glu Leu Asn Asp Asp Pro Lys Val Thr Ser Ala Val Ala Thr Leu Asn
        275                 280                 285

Ile Ser Tyr Phe Gly Gly Glu Ile Gly Val Arg Tyr Ile Phe
    290                 295                 300

<210> SEQ ID NO 242
<211> LENGTH: 285
<212> TYPE: PRT
<213> ORGANISM: Ehrlichia ewingii
```

<400> SEQUENCE: 242

```
Met Asn Tyr Asn Lys Ile Leu Val Arg Ser Ala Leu Ile Ser Leu Met
1               5                   10                  15

Thr Val Leu Pro Tyr Gln Ser Phe Ala Asp Pro Met Asn Ser Asn Asp
            20                  25                  30

Val Ser Ile Asn Asp Ser Lys Glu Gly Phe Tyr Ile Ser Ala Lys Tyr
        35                  40                  45

Ser Pro Ser Ile Pro Tyr Ile Arg Lys Phe Ser Ala Val Glu Thr Pro
    50                  55                  60

Ile Glu Gly Ala Ile Ser Pro Thr Lys Lys Val Leu Gly Leu Asn Lys
65                  70                  75                  80

Gly Gly Ser Ile Ala Asn Ser His Asp Phe Ser Lys Ile Asp Pro Ser
                85                  90                  95

Leu Asp Phe His Asn Asn Leu Ile Ser Gly Phe Ser Gly Ser Ile Gly
            100                 105                 110

Tyr Ala Met Asp Gly Pro Arg Ile Glu Ile Glu Ala Thr Tyr Gln Lys
        115                 120                 125

Phe His Pro Lys Asn Pro Asp Asn Asn Asp Thr Asp Ser Ser Asp His
    130                 135                 140

Tyr Lys Tyr Tyr Gly Leu Phe Arg Glu Gly Thr Pro Gln Glu Glu Glu
145                 150                 155                 160

His Arg Tyr Val Val Leu Lys Asn Glu Gly Leu Thr Phe Met Ser Leu
                165                 170                 175

Thr Val Asn Ala Cys Tyr Asp Ile Val Ala Glu Gly Ile Pro Phe Ile
            180                 185                 190

Pro Tyr Ala Cys Val Gly Ile Gly Ser Asp Leu Ile Asp Ile Phe Asn
        195                 200                 205

Asp Lys Asn Leu Lys Phe Ala Tyr Gln Gly Lys Val Gly Ile Ser Tyr
    210                 215                 220

Pro Ile Thr Ser Glu Val Ser Ala Phe Ile Gly Gly Tyr Tyr His Gly
225                 230                 235                 240

Ile Ile Gly Asn Lys Phe Asn Lys Leu Pro Val Lys Thr Pro Val Thr
                245                 250                 255

Leu Asp Thr Ala Pro Gln Thr Thr Ser Ala Ser Val Glu Leu Asp Thr
            260                 265                 270

Gly Phe Phe Gly Gly Glu Ile Gly Val Ser Phe Ser Phe
        275                 280                 285
```

<210> SEQ ID NO 243
<211> LENGTH: 278
<212> TYPE: PRT
<213> ORGANISM: Ehrlichia ewingii

<400> SEQUENCE: 243

```
Met Asn Cys Lys Lys Ile Phe Ile Thr Ser Ala Leu Met Ser Leu Val
1               5                   10                  15

Ser Phe Ile Pro Cys Ile Ser Phe Ser Asn Pro Met Gln Asp Asn Asn
            20                  25                  30

Ile Val Gly Asn Phe Tyr Val Ser Gly Lys Tyr Met Pro Thr Ile Ser
        35                  40                  45

His Phe Asp Asn Phe Ser Ala Lys Glu Asp Thr Ile Glu Thr Ile Ala
    50                  55                  60

Thr Phe Gly Leu Ser Lys Thr Tyr Asn Arg Ser Ser Pro Ile His Ser
65                  70                  75                  80
```

```
Asp Phe Thr Asp Ser Lys Tyr Ser Phe Lys Tyr Glu Asn Asn Pro Phe
                85                  90                  95

Leu Gly Phe Ala Gly Ala Val Gly Tyr Ser Met Glu Gly Leu Arg Leu
            100                 105                 110

Glu Phe Glu Ile Ser Tyr Glu Lys Phe Asp Val Lys Asn Pro Asp Asn
        115                 120                 125

Ser Tyr Ser Asn Gly Ala His Met Tyr Tyr Ala Leu Ser Arg Lys Asp
    130                 135                 140

Asn Ala Asn Ile Gly Thr Thr Pro Gln Asp Lys Lys Tyr Val Tyr Ile
145                 150                 155                 160

Lys Asn Glu Gly Leu Thr Asp Ile Ser Leu Met Leu Asn Ala Cys Tyr
                165                 170                 175

Asp Val Ile Ser Glu Gly Ile Ser Phe Val Pro Tyr Ile Cys Ala Gly
            180                 185                 190

Ile Gly Ser Asp Phe Ile Ser Met Phe Asp Ile Thr Ser Pro Lys Leu
        195                 200                 205

Ser Tyr Gln Gly Lys Leu Gly Ile Ser Tyr Ser Ile Asn Pro Glu Met
    210                 215                 220

Ser Val Phe Ile Gly Gly His Phe His Lys Val Ile Gly Asp Gln Phe
225                 230                 235                 240

Lys Asp Ile Thr Pro Leu Lys Pro Asn Gly Ile Glu Asn Thr Thr Ala
                245                 250                 255

Thr His Val Leu Val Thr Leu His Met Cys His Phe Gly Ala Glu Ile
            260                 265                 270

Gly Gly Arg Phe Thr Phe
        275
```

<210> SEQ ID NO 244
<211> LENGTH: 282
<212> TYPE: PRT
<213> ORGANISM: Ehrlichia ewingii

<400> SEQUENCE: 244

```
Met Asn Cys Lys Lys Val Phe Ile Thr Ser Ala Leu Ile Ser Phe Ile
1               5                   10                  15

Cys Phe Leu Pro Gly Val Ser Phe Ser Asn Thr Ile Gln Asp Asn Asn
                20                  25                  30

Ile Val Gly Asn Phe Tyr Ile Ser Gly Lys Tyr Met Pro Thr Val Ser
            35                  40                  45

His Phe Gly Asn Phe Ser Ala Lys Glu Glu Lys Ala Glu Thr Lys Lys
        50                  55                  60

Thr Phe Gly Leu Glu Lys Asn Tyr Asp Gly Lys Ile Glu Asp Asn
65                  70                  75                  80

Gln Val Gln Asn Lys Phe Thr Ile Ser Asn Tyr Ser Phe Lys Tyr Glu
                85                  90                  95

Asp Asn Pro Phe Leu Gly Phe Ala Gly Ala Ile Gly Tyr Ser Met Glu
            100                 105                 110

Gly Pro Arg Ile Glu Leu Glu Val Ser Tyr Glu Thr Phe Asn Val Lys
        115                 120                 125

Asn Gln Asp Asn Ser Tyr Lys Asn Asp Ala His Met Tyr Tyr Leu Leu
    130                 135                 140

Ala Arg Glu Val Asp Ser Ser Pro Thr Lys Pro Gln Val Asn Lys
145                 150                 155                 160

Ser Val Leu Leu Lys Asn Glu Gly Leu Thr Asp Phe Ser Ile Met Leu
                165                 170                 175
```

```
Asn Ala Cys Tyr Asp Ile Ile Thr Asp Asn Ile Pro Phe Ser Pro Tyr
                180                 185                 190

Ile Cys Ala Gly Val Gly Ala Asp Leu Val Ser Met Phe Asn Ser Ile
            195                 200                 205

Asn Pro Lys Leu Ala Tyr Gln Gly Lys Leu Gly Ile Ser Tyr Ser Ile
    210                 215                 220

Ser Pro Glu Val Ser Ala Phe Ile Gly Gly His Phe His Lys Val Ile
225                 230                 235                 240

Gly Asn Glu Phe Lys Asp Ile Ala Thr Ile Leu Pro Ser Gly Ser Ser
                245                 250                 255

Ile Lys Asp Asn Gln Tyr Ala Ile Val Thr Leu Ser Val Cys His Phe
            260                 265                 270

Gly Val Glu Ile Gly Gly Arg Val Ser Phe
            275                 280

<210> SEQ ID NO 245
<211> LENGTH: 272
<212> TYPE: PRT
<213> ORGANISM: Ehrlichia ewingii

<400> SEQUENCE: 245

Met Asn Tyr Lys Lys Phe Val Leu Ser Val Ala Leu Ser Thr Leu Phe
1               5                   10                  15

Ser Phe Leu Pro Asp Ser Ser Phe Ser Asp Val Val Ser Glu Glu
                20                  25                  30

Lys Arg Gly Phe Tyr Val Gly Thr Gln Tyr Arg Val Gly Val Pro Asn
            35                  40                  45

Phe Ser Asn Phe Ser Ala Ala Glu Thr Ile Pro Gly Leu Thr Lys Lys
    50                  55                  60

Ile Phe Ala Leu Ser Tyr Asp Ala Thr Asp Ile Thr Lys Glu Thr Ser
65                  70                  75                  80

Phe Lys Gln Ala Tyr Asp Pro Thr Tyr Ala Ser Ser Phe Asn Ser Phe
                85                  90                  95

Ser Gly Val Met Gly Cys Tyr Phe Asn Ser Met Arg Ile Glu Phe Glu
            100                 105                 110

Gly Ser Tyr Ser His Phe Glu Ser Glu Arg Gln Phe Tyr Arg Glu Gly
        115                 120                 125

Ser Asn Asn Tyr Lys Phe Phe Ala Leu Ser Arg Glu Glu Thr Ile Thr
130                 135                 140

Ser Lys Lys Phe Val Val Leu Glu Asn Asn Gly Val Ile Asp Arg Ser
145                 150                 155                 160

Leu Asn Val Asn Phe Cys Tyr Asp Ile Thr Arg Gly Asp Val Pro Leu
                165                 170                 175

Ala Pro Tyr Val Cys Ala Gly Val Gly Ala Asp Tyr Ile Lys Phe Leu
            180                 185                 190

Gly Ile Ser Leu Pro Lys Phe Ser Tyr Gln Val Lys Phe Gly Val Asn
        195                 200                 205

Tyr Pro Val Lys Ser Asn Ile Met Leu Phe Gly Gly Tyr Tyr His
    210                 215                 220

Lys Val Val Gly Ser Lys Tyr Glu Arg Val Glu Ile Ala Tyr His Pro
225                 230                 235                 240

Ser Ile Glu Glu Ala Pro Lys Ile Thr Ser Ala Ser Ala Asn Leu Asn
                245                 250                 255

Thr Asp His Phe Gly Cys Glu Val Gly Ile Arg Phe Ala Phe Ile Asn
```

<210> SEQ ID NO 246
<211> LENGTH: 282
<212> TYPE: PRT
<213> ORGANISM: Ehrlichia ewingii

<400> SEQUENCE: 246

Met Lys Tyr Lys Ile Val Lys Thr Thr Ile Thr Gly Leu Gly Leu Leu
1               5                   10                  15

Leu Pro Phe Tyr Ala Ser Met Ser Phe Gly Met Ser Asn Thr Leu Ala
            20                  25                  30

Asn Gln Val Ser Pro Ile Ser Phe Gly Val Leu Tyr Lys Leu Ser His
        35                  40                  45

Pro Phe Phe Asn Asn Phe Ser Ile Glu Glu Thr Gln Ile Leu His Asp
    50                  55                  60

Val Ala Thr Glu Arg Val Val Gly Leu Lys His Asp Leu Leu Glu Ser
65                  70                  75                  80

Ala Asp Lys Leu Val Asp Asn Leu Tyr Asn Phe Asp Leu Ser Glu Asp
                85                  90                  95

Tyr Val Pro Lys Tyr Asp Asn Ser Leu Phe Gly Leu Ser Phe Phe Ile
            100                 105                 110

Gly Tyr Ser Phe Gln Asn Phe Arg Ile Glu Leu Glu Ser Phe Tyr Glu
        115                 120                 125

Lys Phe Asp Val Gln Asp Thr Lys Ser His Ile Val Asp Asp Asn Tyr
    130                 135                 140

Arg Tyr Phe Ala Leu Tyr Arg His Gly Pro Ala Lys His Ile Asn Tyr
145                 150                 155                 160

Val Thr Leu Lys Asn Asp Gly Ile Glu Leu Asn Ser Val Met Leu Asn
                165                 170                 175

Ile Cys Tyr Asp Phe Thr Leu Asn Asn Thr Tyr Ile Thr Pro Phe Ser
            180                 185                 190

Cys Val Gly Ile Gly Gly Asp Ile Ile Ser Ile Phe Asn Thr Val Lys
        195                 200                 205

Val Lys Ile Ala Ala Gln Ala Lys Val Gly Val Asn Tyr Leu Ile Ser
    210                 215                 220

Glu Arg Ile Ser Leu Phe Val Asp Gly Tyr Tyr His Gly Val Ile Asp
225                 230                 235                 240

Asn Glu Tyr Ser Asn Ile Pro Val Gln Tyr Pro Arg Asn Leu Phe Tyr
                245                 250                 255

Ala Pro Lys Val Thr Ser Ala Leu Ala Asn Leu Asp Ile Gly Tyr Phe
            260                 265                 270

Gly Ala Glu Ile Gly Met Lys Val Phe Ile
        275                 280

<210> SEQ ID NO 247
<211> LENGTH: 293
<212> TYPE: PRT
<213> ORGANISM: Ehrlichia ewingii

<400> SEQUENCE: 247

Met Ile Lys Phe Ser Ser Val Gly Val Thr Leu Ser Leu Ala Thr Leu
1               5                   10                  15

Leu Ser His Asn Ala Leu Ser Ser Pro Ile Pro Ile Asp Phe Ser Asn
            20                  25                  30

Glu Ser Glu Met Val Gly Phe Tyr Ala Ser Ala His Tyr Asn Leu Glu

```
        35                  40                  45

Leu Pro Met Phe Ser Pro Ile Ser Val Lys Tyr Lys Ser Thr Gly Asn
    50                  55                  60

Ser Glu Ala Asp Lys Ser Glu Lys Glu Leu Thr Leu Phe Thr Leu Lys
65                  70                  75                  80

Glu Ser Thr Gln Ala Pro Asp Phe Thr Lys Lys Glu Thr Phe Asn Asp
                85                  90                  95
Lys Ser Gly Tyr Lys Pro Val Tyr Asn Arg Asn Tyr Thr Gly Phe Ser
            100                 105                 110

Gly Ala Val Gly Tyr Ser Gly Gly Gly Ile Arg Val Glu Ile Glu Gly
        115                 120                 125

Ala Phe Thr Arg Phe Asp Val Asp Lys Gln Lys His Thr His Pro Asp
    130                 135                 140

Asn His Arg Tyr Phe Ala Ser Cys Thr Glu Gln Glu Met Lys Pro Ala
145                 150                 155                 160
Gln Gln Asn Gly Ser Ser Lys Asp Gly Asn Tyr Val Val Met Lys Asn
                165                 170                 175
Glu Gly Phe Lys Ala Ile Ser Leu Thr Phe Asn Val Cys Tyr Asp Met
            180                 185                 190
Ile Val Ser Asn Ser Ser Leu Ile Pro Ser Ala Cys Val Gly Ile Gly
        195                 200                 205

Gln Gly Ile Thr Asn Phe Leu Gly Ala Thr Asn Ile His Thr Ile Phe
    210                 215                 220

Gln Ala Lys Leu Gly Leu Gly Phe Ser Ile Ser Pro Lys Thr Ile Leu
225                 230                 235                 240
Phe Ala Asn Gly Tyr Tyr Val Lys Thr Lys Asp Asp Ala Phe Thr Asn
                245                 250                 255

Leu Thr Val Gln Tyr Pro Val Lys Leu Thr Ser Pro Pro Thr His Ile
            260                 265                 270
Asp Pro Val Val Tyr Phe His Ser Asp Tyr Cys Gly Gly Glu Val Gly
        275                 280                 285

Leu Arg Phe Ile Leu
    290

<210> SEQ ID NO 248
<211> LENGTH: 272
<212> TYPE: PRT
<213> ORGANISM: Ehrlichia ewingii

<400> SEQUENCE: 248

Met Ser Tyr Lys Lys Val Ile Phe Trp Ile Ile Leu Phe Leu Thr Pro
1               5                   10                  15

Gly Ala Ser Leu Ser Gln Gly Leu Asn Asp Asn Ile Phe Lys Asn Phe
            20                  25                  30

Tyr Val Gly Val Gln Tyr Lys Pro Ala Ile His His Leu Ser His Leu
        35                  40                  45

Ile Ile Lys Glu Thr Ser Lys Asp Thr Ile Gly Ile Phe Ala Leu Lys
    50                  55                  60

Lys Asp Ala Ser Leu Pro Thr Asp Ile Lys Lys Asn Ser Asn Leu Asn
65                  70                  75                  80

Ile Arg Tyr Asn Pro His Tyr Glu Asn Asn Asn Ser Gly Phe Ser Gly
                85                  90                  95

Leu Leu Gly Tyr His Tyr Asn Asn Asn Phe Arg Ile Glu Ser Glu Ile
            100                 105                 110
```

-continued

Ser Tyr Glu Ile Phe Pro Leu Lys Asn Glu Gly Tyr Lys Ile Thr Gly
115 120 125

Val Glu Gln His Phe Ala Leu Ala Ser Glu Leu Asp Thr Asn Gly Asn
130 135 140

Gln Pro Lys Thr Asp Lys Tyr Val Thr Ile Ile Asn Asp Gly Ile Arg
145 150 155 160

Ala Thr Ser Val Leu Ile Asn Ala Cys Tyr Asp Gly Ile Asp Ile Lys
165 170 175

Lys Asn Asn Ile Val Val Tyr Ser Cys Ile Gly Leu Gly Ala Asp Ile
180 185 190

Val Asp Phe Leu Ser Lys Tyr Asn Thr Lys Leu Ser Tyr Gln Gly Lys
195 200 205

Leu Gly Leu Ser Tyr Pro Ile Ser Leu Lys Ile Ile Leu Phe Ala Glu
210 215 220

Gly Tyr Tyr His Gly Leu Leu Gly Asn Val Phe Asn Asn Val Pro Val
225 230 235 240

Asn Tyr Pro Thr Asp Asn Asn Thr Thr Lys Thr Thr Val Ser Ala Ile
245 250 255

Leu Asn Ile Arg Tyr Tyr Gly Gly Ser Val Gly Val Arg Phe Ile Leu
260 265 270

<210> SEQ ID NO 249
<211> LENGTH: 284
<212> TYPE: PRT
<213> ORGANISM: Ehrlichia ewingii

<400> SEQUENCE: 249

Met Asn Tyr Ala Lys Val Phe Ile Leu Met Phe Val Ile Leu Phe Leu
1 5 10 15

Pro Ser Ser Ser Leu Leu Ala Leu Glu Asn Asn Leu Ser Gly Gly Val
20 25 30

Gly His Ile Tyr Ile Ser Gly Gln Tyr Lys Pro Ser Ile Pro Gln Phe
35 40 45

Asn Lys Phe Ser Met Glu Glu Ala Thr Ile Gly Ala Val Ile Pro Lys
50 55 60

Ser Leu Lys Gln Asp Ala Glu Asp Ile Thr Leu Ser Ile Leu Ala Leu
65 70 75 80

Ser Thr Asn Phe Thr Leu Pro Tyr Asp Pro Lys Tyr Lys Lys Ser Leu
85 90 95

Leu Gly Leu Gly Gly Thr Ile Gly Tyr Ala Ile Asn Asn Phe Arg Ile
100 105 110

Glu Leu Glu Thr Phe Tyr Glu Lys Phe Asn Val Ser Ala Pro Ser Gly
115 120 125

Tyr Asp Asp Asn Ile Tyr Ala Tyr Phe Ser Ile Glu Val Pro Gln Leu
130 135 140

Arg Ser Leu Pro Tyr His Tyr Thr Met Lys Asn Thr Gly Ile Ile Leu
145 150 155 160

Ser Pro Val Leu Ala Asn Ile Cys Tyr Asp Ile Asn Lys Lys Gln Leu
165 170 175

Arg Asn Val Ser Pro Tyr Leu Cys Leu Gly Phe Gly Val Asp Leu Ile
180 185 190

Asp Phe Leu Asp Lys Val Ser Phe Lys Phe Ser Tyr Gln Ala Lys Leu
195 200 205

Gly Val Ser Tyr Leu Ile Ser Pro Asn Leu Ala Phe Phe Ile Asp Gly
210 215 220

```
Ser Phe His Arg His Leu Gly Asn Gln Phe Ser Asp Leu Leu Leu Asp
225                 230                 235                 240

Tyr Pro Ser Tyr Tyr Arg Ser Leu Thr Ser Leu Ser Asp Asn Asp Pro
                245                 250                 255

Asn Arg Ile Leu Pro Phe Thr Ser Ala Ser Ala Lys Leu Asn Ile Asn
            260                 265                 270

Phe Phe Ser Ala Asn Ile Gly Ile Arg Phe Ile Phe
        275                 280

<210> SEQ ID NO 250
<211> LENGTH: 293
<212> TYPE: PRT
<213> ORGANISM: Ehrlichia ewingii
<400> SEQUENCE: 250

Met Phe Met Lys Lys Leu Tyr Tyr Leu Asn Phe Thr Val Leu Val Leu
 1               5                  10                  15

Thr Val Tyr Leu Phe Pro Ser Phe Val Phe Ser Met Gln Gly Arg Ser
            20                  25                  30

Asn Ile Thr Gly Ser Tyr Ile Thr Val Ser Tyr Gln Pro Ser Met Ser
        35                  40                  45

Asn Phe Arg Asn Phe His Ile Lys Glu Thr Asn Phe Asp Thr Lys Asp
    50                  55                  60

Pro Ile Gly Leu Ile Arg Ser Ala Arg Ser Thr Glu Pro Ser Val Leu
65                  70                  75                  80

Lys Ile Asn Thr His Phe Tyr Lys Pro Gln Gln Ser Asp Ser Tyr Lys
                85                  90                  95

Ser Tyr Gly Asn Asp Leu Leu Gly Phe Ser Thr Ser Ile Gly Leu Leu
            100                 105                 110

Val Lys Asn Leu Arg Met Glu Phe Glu Gly Ser Tyr Lys Lys Phe Asp
        115                 120                 125

Ile Lys Arg Leu Val Asn Tyr Ala Ser Arg Asp Gly His Arg Tyr Phe
    130                 135                 140

Ala Ile Pro Arg Asp Thr Phe Phe Asn Asn Ser Ile Pro Tyr Ala Phe
145                 150                 155                 160

Asn Ala Tyr Thr Val Ala Lys Asn Asn Gly Leu Ser Ile Ile Ser Asn
                165                 170                 175

Met Ile Asn Leu Cys Tyr Glu Ser Ile Lys Tyr Asn Asn Phe Met Pro
            180                 185                 190

Tyr Ile Cys Leu Gly Ala Gly Gly Asp Phe Ile Glu Leu Phe Asp Ser
        195                 200                 205

Met Arg Ile Lys Phe Ala Tyr Gln Gly Lys Leu Gly Val Ser Tyr Pro
    210                 215                 220

Leu Thr Ser Asn Leu Val Leu Ala Ile Ser Gly Gln Tyr His Lys Val
225                 230                 235                 240

Val Gly Asp Lys Phe Lys Phe Leu Pro Leu Met Leu Ser Pro Ser Thr
                245                 250                 255

Pro Arg Arg Arg Ile Pro Pro Gln Ser Ser Ser Glu Val Gln Asp Ala
            260                 265                 270

Thr Gly Leu Leu Thr Leu Asp Leu Gly Tyr Phe Ser Ala Asp Ile Gly
        275                 280                 285

Leu Arg Phe Met Phe
    290
```

<210> SEQ ID NO 251
<211> LENGTH: 272
<212> TYPE: PRT
<213> ORGANISM: Ehrlichia ewingii

<400> SEQUENCE: 251

| Met | Asn | Asn | Lys | Lys | Ser | His | Val | Ile | Cys | Met | Leu | Ile | Phe | Leu | Leu |
|---|---|---|---|---|---|---|---|---|---|---|---|---|---|---|---|
| 1 | | | | 5 | | | | | 10 | | | | | 15 | |

| Leu | Pro | Met | Lys | Ser | Phe | Ser | Val | Leu | Ile | Asp | Thr | Thr | Glu | Lys | Asp |
|---|---|---|---|---|---|---|---|---|---|---|---|---|---|---|---|
| | | | 20 | | | | | 25 | | | | | 30 | | |

| Tyr | Ala | Ser | Asn | Val | Tyr | Ile | Ser | Ser | Gln | Tyr | Lys | Pro | Ser | Phe | Ser |
|---|---|---|---|---|---|---|---|---|---|---|---|---|---|---|---|
| | | 35 | | | | | 40 | | | | | 45 | | | |

| Asn | Phe | Arg | Ser | Phe | Ser | Ile | Gln | Glu | Ile | Asn | Ser | Lys | Thr | Lys | Asn |
|---|---|---|---|---|---|---|---|---|---|---|---|---|---|---|---|
| | 50 | | | | | 55 | | | | | 60 | | | | |

| Ser | Ile | Ala | Leu | Glu | Lys | Pro | Ile | Glu | Ser | Asn | Ser | Asn | Ile | Leu | Lys |
|---|---|---|---|---|---|---|---|---|---|---|---|---|---|---|---|
| 65 | | | | | 70 | | | | | 75 | | | | | 80 |

| Ser | Asn | Ala | His | Ile | Ile | Val | Pro | His | Asn | Ile | Gln | Phe | Gln | Asp | Asn |
|---|---|---|---|---|---|---|---|---|---|---|---|---|---|---|---|
| | | | | 85 | | | | | 90 | | | | | 95 | |

| Thr | Ile | Ser | Phe | Ser | Gly | Ala | Val | Gly | Tyr | Ser | Ser | Lys | Gly | Leu | Arg |
|---|---|---|---|---|---|---|---|---|---|---|---|---|---|---|---|
| | | | | 100 | | | | | 105 | | | | | 110 | |

| Leu | Glu | Leu | Glu | Ser | Ala | Tyr | Glu | Glu | Phe | Tyr | Thr | Lys | Glu | Leu | Asn |
|---|---|---|---|---|---|---|---|---|---|---|---|---|---|---|---|
| | | | 115 | | | | | 120 | | | | | 125 | | |

| Ser | Ser | Ser | Leu | Ile | Ser | Ser | Asn | Asn | His | Tyr | Thr | Gln | Leu | Tyr | Glu |
|---|---|---|---|---|---|---|---|---|---|---|---|---|---|---|---|
| | 130 | | | | | 135 | | | | | 140 | | | | |

| Ala | Asn | Phe | Gln | Asn | Phe | Ala | Thr | Ser | Arg | Leu | Ser | Ile | Thr | Ser | Phe |
|---|---|---|---|---|---|---|---|---|---|---|---|---|---|---|---|
| 145 | | | | | 150 | | | | | 155 | | | | | 160 |

| Ile | Ile | Asn | Thr | Cys | Tyr | Asp | Ile | Leu | Ile | Gly | Ser | Ser | Pro | Val | Met |
|---|---|---|---|---|---|---|---|---|---|---|---|---|---|---|---|
| | | | | 165 | | | | | 170 | | | | | 175 | |

| Pro | Tyr | Ile | Cys | Thr | Gly | Ile | Gly | Gly | Asp | Ile | Ile | Arg | Leu | Phe | Asn |
|---|---|---|---|---|---|---|---|---|---|---|---|---|---|---|---|
| | | | 180 | | | | | 185 | | | | | 190 | | |

| Thr | Thr | Tyr | Leu | Lys | Phe | Ala | Tyr | Gln | Gly | Lys | Phe | Gly | Ile | Ser | Tyr |
|---|---|---|---|---|---|---|---|---|---|---|---|---|---|---|---|
| | | 195 | | | | | 200 | | | | | 205 | | | |

| Pro | Leu | Asn | Asn | Asn | Ile | Ile | Leu | Phe | Ser | Asp | Ile | Tyr | Tyr | His | Glu |
|---|---|---|---|---|---|---|---|---|---|---|---|---|---|---|---|
| | 210 | | | | | 215 | | | | | 220 | | | | |

| Ile | Ile | Gly | Gln | Glu | Phe | Glu | Asn | Leu | Tyr | Thr | Gln | Tyr | Val | Ser | Gly |
|---|---|---|---|---|---|---|---|---|---|---|---|---|---|---|---|
| 225 | | | | | 230 | | | | | 235 | | | | | 240 |

| Ile | Asn | Ser | Leu | Gln | Glu | Ile | Thr | Ser | Val | Pro | Ala | Ser | Phe | Asn | Ile |
|---|---|---|---|---|---|---|---|---|---|---|---|---|---|---|---|
| | | | | 245 | | | | | 250 | | | | | 255 | |

| Gly | Tyr | Phe | Gly | Ser | Glu | Ile | Gly | Val | Arg | Phe | Ile | Phe | Asn | Lys | Gln |
|---|---|---|---|---|---|---|---|---|---|---|---|---|---|---|---|
| | | | 260 | | | | | 265 | | | | | 270 | | |

<210> SEQ ID NO 252
<211> LENGTH: 299
<212> TYPE: PRT
<213> ORGANISM: Ehrlichia ewingii

<400> SEQUENCE: 252

| Met | Arg | Lys | Lys | Ile | Tyr | Ser | Ile | Asn | Val | Ile | Leu | Val | Phe | Thr | Leu |
|---|---|---|---|---|---|---|---|---|---|---|---|---|---|---|---|
| 1 | | | | 5 | | | | | 10 | | | | | 15 | |

| Leu | Leu | Leu | Ser | Ile | Gln | Ser | Phe | Ala | Ile | Ser | Ile | Asp | Asn | Asn | Ile |
|---|---|---|---|---|---|---|---|---|---|---|---|---|---|---|---|
| | | | 20 | | | | | 25 | | | | | 30 | | |

| Ile | Asp | Gln | Asn | Leu | Gly | Leu | Tyr | Leu | Ser | Ala | Gln | Tyr | Lys | Pro | Ser |
|---|---|---|---|---|---|---|---|---|---|---|---|---|---|---|---|
| | | 35 | | | | | 40 | | | | | 45 | | | |

| Ile | Ser | His | Phe | Lys | Asn | Phe | Ser | Val | Gln | Glu | Val | Asn | Lys | Lys | Val |
|---|---|---|---|---|---|---|---|---|---|---|---|---|---|---|---|
| | 50 | | | | | 55 | | | | | 60 | | | | |

| Asp | Leu | Ile | Ala | Leu | Lys | Asn | Asp | Val | Thr | His | Ile | Thr | Glu | Glu | Ile |
|---|---|---|---|---|---|---|---|---|---|---|---|---|---|---|---|

```
65                  70                  75                  80

Leu Lys Asp Pro Thr Asn Phe Asn Thr His Tyr Ser Ala Lys Phe Lys
                85                  90                  95

Asn Ser Phe Thr Gly Phe Ser Gly Ala Val Gly Tyr Tyr Ser Ala Gln
            100                 105                 110

Gly Pro Arg Leu Glu Val Glu Gly Phe Tyr Glu Asn Phe Asp Ile Thr
        115                 120                 125

Asp Cys Ser Asn Cys Thr Ile Asn Asp Ala Asn Arg Tyr Leu Ala Leu
    130                 135                 140

Ala Arg Glu Lys Asp Asn Asn Gln Val Gln Pro Lys Ala His Asp Ser
145                 150                 155                 160

Ser Ser Thr Asp Ser Asn Asn Ser Ser Asn Asn Thr Lys Lys Ser Tyr
                165                 170                 175

Phe Thr Phe Met Lys Asn Asn Gly Ile Ser Ile Ala Ser Val Met Ile
            180                 185                 190

Asn Gly Cys Tyr Asp Phe Ser Leu Asn Asn Ile Lys Ile Ser Pro Tyr
        195                 200                 205

Val Cys Ala Gly Ile Gly Gly Asp Phe Ile Glu Phe Phe Glu Val Met
    210                 215                 220

His Ile Lys Phe Ser Tyr Gln Gly Lys Leu Gly Val Ser Tyr Leu Ile
225                 230                 235                 240

Ser Pro Ser Ile Ser Leu Phe Val Asp Gly Tyr Tyr His Ser Val Ile
                245                 250                 255

Asn Asn Lys Phe Lys Asn Leu His Val Thr Tyr Ala Tyr Ile Leu Lys
            260                 265                 270

Asp Ser Pro Thr Ile Thr Ser Ala Ile Ala Gln Leu Asn Ile Gly Tyr
        275                 280                 285

Phe Gly Gly Glu Val Gly Leu Arg Phe Val Phe
    290                 295

<210> SEQ ID NO 253
<211> LENGTH: 284
<212> TYPE: PRT
<213> ORGANISM: Ehrlichia ewingii

<400> SEQUENCE: 253

Met Ser Asn Lys Lys Lys Phe Thr Ile Gly Thr Val Leu Val Ser Leu
1               5                   10                  15

Leu Ala Phe Leu Pro Thr Tyr Ser Phe Ser Ala Pro Ile Ser Asn Asn
            20                  25                  30

Ser Glu Asp Asn Ile Phe Gly Leu Tyr Ile Ala Gly Gln Tyr Arg Pro
        35                  40                  45

Gly Val Ser His Phe Ser Gly Phe Gly Val Thr Glu Thr Asn Phe Ala
    50                  55                  60

Thr Gln Lys Leu Met Arg Val Lys Lys Asp Ser Lys Glu Gly Leu Pro
65                  70                  75                  80

Asn Ile Leu Lys Ser Lys Asp Asn Phe Thr Glu Pro Tyr Val Ala Lys
                85                  90                  95

Phe Gln Asp Asn Ala Val Ser Phe Ser Gly Ala Ile Gly Tyr Ser Tyr
            100                 105                 110

Pro Glu Gly Leu Arg Leu Glu Ile Glu Gly Ser Tyr Glu Thr Phe Asp
        115                 120                 125

Val Lys Asp Pro Lys Asp Cys Ser Val Lys Asp Ala Phe Arg His Leu
    130                 135                 140
```

```
Ala Leu Val Arg Glu Leu Asp Thr Gly Leu Ser Met Pro Lys Glu Lys
145                 150                 155                 160

Lys Tyr Thr Val Met Arg Asn Asn Gly Leu Ser Ile Ala Ser Ile Leu
                165                 170                 175

Ile Asn Gly Cys Tyr Asp Phe Asp Phe Asp Asn Leu Ile Val Ser Pro
            180                 185                 190

Tyr Val Cys Leu Gly Ile Gly Glu Asp Phe Ile Glu Phe Phe Asp Val
        195                 200                 205

Leu His Ile Lys Phe Ala Tyr Gln Gly Lys Leu Gly Ile Ser Tyr Glu
    210                 215                 220

Leu Ser Pro Arg Ile Asn Val Phe Ala Asp Gly Tyr Tyr His Lys Val
225                 230                 235                 240

Ile Gly Asn Gln Phe Lys Asn Leu Asn Val Asn His Val Val Glu Leu
                245                 250                 255

Asp Asp Phe Pro Lys Val Thr Ser Ala Val Ala Thr Leu Asn Val Gly
            260                 265                 270

Tyr Phe Gly Gly Glu Val Gly Val Arg Phe Ile Phe
        275                 280

<210> SEQ ID NO 254
<211> LENGTH: 281
<212> TYPE: PRT
<213> ORGANISM: Ehrlichia ewingii

<400> SEQUENCE: 254

Met Ser Asn Lys Lys Ile Phe Ser Ile Ile Gly Gln Ala Leu Thr Cys
 1               5                  10                  15

Leu Val Leu Phe Ser Pro Ile Tyr Ser Phe Ser Glu Ser Asn His Tyr
            20                  25                  30

Asp Lys Ser Leu Tyr Val Ala Gly Gln Tyr Lys Ser Ser Leu Ser His
        35                  40                  45

Phe Thr Asn Phe Ser Val Arg Glu Thr Asp Ile Asn Thr Lys Gly Leu
    50                  55                  60

Phe Lys Leu Gly His Gly Val Thr Leu Val Glu Glu Asp Ile Lys Asn
65                  70                  75                  80

His Leu Gln Phe Thr Ile Pro His Ser Val Ala Phe Lys Asn Asn Phe
                85                  90                  95

Ala Asn Phe Ser Ala Ala Val Gly Tyr Ile Ser Pro Gly Gly Pro Arg
            100                 105                 110

Val Glu Ile Glu Gly Ser Tyr Glu Asn Phe Asp Val Lys Asp Leu Lys
        115                 120                 125

Asn Cys Thr Ile Gln Asp Ala Cys Arg Tyr Leu Ser Leu Ala Arg Glu
    130                 135                 140

Ile Cys Lys Glu Asn Asp Lys Pro Thr Pro Lys Glu Lys Lys Tyr Val
145                 150                 155                 160

Val Met Arg Asn Asp Gly Ile Ser Ile Thr Ser Val Thr Ile Asn Gly
                165                 170                 175

Cys Tyr Asp Phe Ser Ile Asn Lys Leu Pro Lys Ile Ser Pro Tyr Ile
            180                 185                 190

Cys Ala Gly Phe Gly Gly Asp Phe Ile Glu Phe Phe Asp Ser Val Arg
        195                 200                 205

Val Lys Phe Ala Tyr Gln Ser Lys Leu Gly Ile Asn Tyr Ser Leu Ser
    210                 215                 220

Ser Asn Phe Ile Leu Phe Val Asp Gly Tyr Tyr His Arg Val Ile Gly
225                 230                 235                 240
```

```
Asn Gln Phe Lys Asn Leu Asn Val Gln Asn Met Phe Asp Ser Asn Glu
                245                 250                 255

Pro Tyr Val Thr Ser Ala Ile Ala Thr Leu Asn Ile Glu His Phe Gly
            260                 265                 270

Gly Gly Phe Gly Leu Arg Phe Ile Phe
        275                 280

<210> SEQ ID NO 255
<211> LENGTH: 280
<212> TYPE: PRT
<213> ORGANISM: Ehrlichia ewingii

<400> SEQUENCE: 255

Met Arg Lys Lys Ser Phe Ile Ile Ile Gly Thr Val Leu Ile Cys Leu
1               5                   10                  15

Leu Ser Pro Pro Asn Ile Ser Phe Ser Glu Val Ile Thr His Asn Asp
            20                  25                  30

Asn Lys His Pro Gly Ile Tyr Val Ser Gly Gln Tyr Lys Pro Gly Ile
        35                  40                  45

Ser His Leu Arg Lys Phe Ser Val Lys Glu Thr Asn Ala Thr Thr Val
    50                  55                  60

Gln Leu Val Gly Leu Asn Tyr Thr Ala Ala Pro Ile Asp Asp Ile Lys
65                  70                  75                  80

Thr Ser Ser Lys Phe Asp Thr Pro Tyr Thr Ile Ala Phe Gln Asn Asn
                85                  90                  95

Ile Ile Ser Phe Ser Ala Ala Ile Gly Tyr Ser His Ala Lys Gly Leu
            100                 105                 110

Arg Ile Glu Leu Glu Gly Ser Tyr Glu Glu Phe Asp Val Thr Asp Pro
        115                 120                 125

Gly Asn Tyr Thr Ile Lys Asp Ala Tyr Arg Tyr Phe Ala Ile Ala Arg
    130                 135                 140

Glu Met Asn Ser Ser Asn Asn Gln Pro Lys Asp Lys Gln Phe Thr
145                 150                 155                 160

Val Met Arg Asn Asp Gly Val Ser Ile Val Ser Phe Met Phe Asn Gly
                165                 170                 175

Cys Tyr Asp Phe Pro Leu Gly Ile Leu Glu Ile Ser Pro Tyr Ile Cys
            180                 185                 190

Ala Gly Ile Gly Gly Asp Phe Ile Glu Phe Asp Ala Leu His Ile
        195                 200                 205

Lys Pro Ala Tyr Gln Gly Lys Leu Gly Leu Asn Tyr Pro Leu Phe Ser
210                 215                 220

Lys Val Ser Leu Phe Ile Asp Gly Tyr Tyr His Lys Val Ile Gly Gln
225                 230                 235                 240

Gln Phe Lys His Leu Asn Val Gln His Val Val Thr Leu Asp Thr Pro
                245                 250                 255

Lys Ile Ala Ser Val Val Ala Thr Leu Asp Val Ser Tyr Phe Gly Gly
            260                 265                 270

Glu Ile Gly Met Arg Leu Ile Phe
        275                 280

<210> SEQ ID NO 256
<211> LENGTH: 290
<212> TYPE: PRT
<213> ORGANISM: Ehrlichia ewingii

<400> SEQUENCE: 256
```

```
Met Asn Asn Lys Lys Met Phe Ser Ile Ile Gly Ile Ser Leu Leu Ala
1               5                   10                  15

Asn Leu Leu Leu Leu Pro Asn Met Ser Phe Ala Lys Asn Asn Tyr Ser
            20                  25                  30

Tyr Ile Asn Pro Val Leu Tyr Ile Ser Gly Gln Tyr Arg Pro Gly Val
        35                  40                  45

Ser His Phe Ser Gln Phe Ser Val Arg Glu Thr His Tyr Asp Thr Gln
    50                  55                  60

Leu Leu Ala Glu Leu Lys Lys Glu Val Gly Ser Val Thr Asn Thr Val
65                  70                  75                  80

Ile Gln Ala Tyr Ala Asn Tyr Asn Val Pro Ser Gln Ala Pro Phe Ser
                85                  90                  95

His Thr Tyr Val Ala Glu Phe Glu Asp Asn Thr Ile Ser Phe Ser Gly
            100                 105                 110

Ala Val Gly Phe Ser Tyr Ser Glu Gly Pro Arg Ile Glu Ile Glu Phe
        115                 120                 125

Ser Tyr Glu Glu Phe Asp Val Lys Asn Ser Gly His Ser Ser Ile Asp
    130                 135                 140

Ala His Arg Tyr Phe Ala Leu Leu Arg His Ser Asn Asn Gly Asn Thr
145                 150                 155                 160

Gln Gln Asn Pro Phe Ala Val Met Arg Asn Asn Gly Leu Phe Ile Gly
                165                 170                 175

Ser Val Ala Ile Asn Ser Cys Tyr Asp Phe Ile Leu Asp Asp Thr Pro
            180                 185                 190

Ala Leu Pro Tyr Val Cys Gly Gly Ile Gly Gly Asp Phe Ile Glu Phe
        195                 200                 205

Phe Asp Glu Leu His Val Lys Leu Ala Tyr Gln Gly Lys Ile Gly Ile
    210                 215                 220

Ser Tyr Pro Ile His Ser Lys Val Ser Thr Phe Val Asp Val Tyr Tyr
225                 230                 235                 240

His Arg Val Ile Asn Asn Lys Phe Lys Asn Leu His Val Gln Tyr Val
                245                 250                 255

Asn Thr Thr Thr Ser Gln Ala Ile Asn Pro Gln Ile Thr Ser Ala Val
            260                 265                 270

Ala Thr Leu Asn Val Gly Tyr Phe Gly Ile Glu Ile Gly Ala Arg Leu
        275                 280                 285

Thr Phe
    290
```

<210> SEQ ID NO 257
<211> LENGTH: 298
<212> TYPE: PRT
<213> ORGANISM: Ehrlichia ewingii

<400> SEQUENCE: 257

```
Met Asn Asn Lys Asn Arg Phe Thr Ala Ile Gly Val Ala Leu Thr Cys
1               5                   10                  15

Leu Leu Leu Leu Pro Asn Val Ser Phe Ser Glu Thr Thr Ile Ile Asn
            20                  25                  30

Gln Pro Ser Gly Leu Tyr Ile Ser Gly Gln Tyr Lys Pro Ser Val Ser
        35                  40                  45

Val Phe Ser Asp Phe Ser Val Lys Glu Ala Asn Val Ala Thr Lys His
    50                  55                  60

Leu Ile Ala Leu Lys Lys Ser Val Asp Ser Ile Asn Ala Glu Lys Ala
```

```
 65                  70                  75                  80

Thr Pro His Asn Gln Gly Leu Gly Lys Pro Asp Asn Phe Asn Ile Pro
                85                  90                  95

Tyr Lys Val Glu Phe Glu Asp Asn Ala Val Ser Phe Ser Gly Val Ile
            100                 105                 110

Gly Tyr Ser Phe Pro Glu Gly Pro Arg Ile Glu Ile Glu Thr Ser Tyr
        115                 120                 125

Glu Glu Phe Asp Val Lys Asn Pro Gly Gly Tyr Thr Leu Asn Asp Ala
    130                 135                 140

Phe Arg Tyr Phe Ala Leu Ala Arg Glu Ile Glu Ser Asp Gln Asn Lys
145                 150                 155                 160

Phe Gln Pro Lys Asn Ala Asn Ser Asn Ser Ser Asn Lys Ile Tyr His
                165                 170                 175

Thr Val Met Arg Asn Asp Gly Ile Ser Val Leu Ser Asn Met Ile Asn
            180                 185                 190

Ile Cys Tyr Asp Phe Ser Leu Asp Asn Leu Pro Val Leu Pro Tyr Ile
        195                 200                 205

Cys Gly Gly Thr Gly Val Asp Thr Ile Glu Phe Phe Asp Ser Leu His
    210                 215                 220

Ile Lys Leu Ala Gly Gln Ala Lys Ile Gly Ile Thr Tyr Pro Leu Ser
225                 230                 235                 240

Ser Asn Ile Asn Leu Phe Ala Gly Gly Tyr Tyr His Lys Val Ile Gly
                245                 250                 255

Asn Arg Phe Lys Asn Leu Lys Val Gln His Ile Ala Glu Leu Asn Asp
            260                 265                 270

Ala Pro Lys Val Thr Ser Ala Val Ala Thr Leu Asn Ile Ser Tyr Phe
        275                 280                 285

Gly Gly Glu Ile Gly Ala Arg Phe Ile Phe
    290                 295

<210> SEQ ID NO 258
<211> LENGTH: 302
<212> TYPE: PRT
<213> ORGANISM: Ehrlichia ewingii

<400> SEQUENCE: 258

Met Glu Ile Ser Met Ser Asn Lys Lys Lys Leu Phe Thr Ile Ser Thr
 1               5                  10                  15

Ala Leu Tyr Leu Leu Leu Ser Pro Asn Ile Ser Phe Ser Glu Thr Ile
            20                  25                  30

Val Asp Asp Ile Asp Arg Gln Phe Arg Leu Tyr Ile Ser Gly Gln Tyr
        35                  40                  45

Lys Pro Ser Leu Ser Val Phe Ser Asn Phe Ser Val Lys Glu Thr Asn
    50                  55                  60

Val Thr Thr Lys Tyr Leu Thr Ala Leu Lys Lys Asp Ala Asp Pro Thr
 65                  70                  75                  80

Glu Lys Thr Gly Ser Thr Pro His Glu Lys Gly Leu Gly Lys Pro Asp
                85                  90                  95

Asn Phe Asn Ile Pro Tyr Lys Val Glu Phe Glu Asp Asn Ala Val Ser
            100                 105                 110

Phe Ser Gly Ala Val Gly Phe Ser Tyr Pro Glu Gly Leu Arg Ile Glu
        115                 120                 125

Ile Glu Ala Ser Tyr Glu Glu Phe Asp Val Lys Asn Pro Gly Gly Tyr
    130                 135                 140
```

```
Thr Ile Ser Asn Ala Phe Arg Tyr Phe Ala Leu Val Arg Glu Ser Glu
145                 150                 155                 160

Ser Ser Lys Glu Pro Gln Pro Lys Asn Pro Asn Ser Ala Gly Asn Asn
                165                 170                 175

Lys Ile Phe His Thr Val Met Arg Asn Asp Gly Val Ala Ile Ser Ser
            180                 185                 190

Ile Thr Ile Asn Gly Cys Tyr Asp Phe Ser Leu Ser Gln Leu Pro Val
        195                 200                 205

Leu Pro Tyr Ile Cys Gly Gly Ile Gly Ile Asp Thr Ile Asp Phe Phe
    210                 215                 220

Asp Ala Leu His Ile Lys Phe Ala Gly Gln Gly Lys Leu Gly Ile Thr
225                 230                 235                 240

Tyr Pro Leu Ser Gly Asn Ile Asn Leu Phe Ala Asp Gly Tyr Tyr His
                245                 250                 255

Lys Val Ile Ser Asn Gln Phe Lys Asn Leu Asn Val Gln His Val Ala
            260                 265                 270

Glu Leu Asn Asp Asp Pro Lys Val Thr Ser Ala Val Ala Thr Leu Asn
        275                 280                 285

Ile Ser Tyr Phe Gly Gly Glu Ile Gly Val Arg Tyr Ile Phe
    290                 295                 300

<210> SEQ ID NO 259
<211> LENGTH: 285
<212> TYPE: PRT
<213> ORGANISM: Ehrlichia ewingii

<400> SEQUENCE: 259

Met Asn Tyr Asn Lys Ile Leu Val Arg Ser Ala Leu Ile Ser Leu Met
 1               5                  10                  15

Thr Val Leu Pro Tyr Gln Ser Phe Ala Asp Pro Met Asn Ser Asn Asp
            20                  25                  30

Val Ser Ile Asn Asp Ser Lys Glu Gly Phe Tyr Ile Ser Ala Lys Tyr
        35                  40                  45

Ser Pro Ser Ile Pro Tyr Ile Arg Lys Phe Ser Ala Val Glu Thr Pro
    50                  55                  60

Ile Glu Gly Ala Ile Ser Pro Thr Lys Lys Val Leu Gly Leu Asn Lys
65                  70                  75                  80

Gly Gly Ser Ile Ala Asn Ser His Asp Phe Ser Lys Ile Asp Pro Ser
                85                  90                  95

Leu Asp Phe His Asn Asn Leu Ile Ser Gly Phe Ser Gly Ser Ile Gly
            100                 105                 110

Tyr Ala Met Asp Gly Pro Arg Ile Glu Ile Glu Ala Thr Tyr Gln Lys
        115                 120                 125

Phe His Pro Lys Asn Pro Asp Asn Asn Asp Thr Asp Ser Ser Asp His
    130                 135                 140

Tyr Lys Tyr Tyr Gly Leu Phe Arg Glu Gly Thr Pro Gln Glu Glu Glu
145                 150                 155                 160

His Arg Tyr Val Val Leu Lys Asn Glu Gly Leu Thr Phe Met Ser Leu
                165                 170                 175

Thr Val Asn Ala Cys Tyr Asp Ile Val Ala Glu Gly Ile Pro Phe Ile
            180                 185                 190

Pro Tyr Ala Cys Val Gly Ile Gly Ser Asp Leu Ile Asp Ile Phe Asn
        195                 200                 205

Asp Lys Asn Leu Lys Phe Ala Tyr Gln Gly Lys Val Gly Ile Ser Tyr
    210                 215                 220
```
Pro Ile Thr Ser Glu Val Ser Ala Phe Ile Gly Gly Tyr Tyr His Gly
225 230 235 240

Ile Ile Gly Asn Lys Phe Asn Lys Leu Pro Val Lys Thr Pro Val Thr
245 250 255

Leu Asp Thr Ala Pro Gln Thr Thr Ser Ala Ser Val Glu Leu Asp Thr
260 265 270

Gly Phe Phe Gly Gly Glu Ile Gly Val Ser Phe Ser Phe
275 280 285

<210> SEQ ID NO 260
<211> LENGTH: 278
<212> TYPE: PRT
<213> ORGANISM: Ehrlichia ewingii

<400> SEQUENCE: 260

Met Asn Cys Lys Lys Ile Phe Ile Thr Ser Ala Leu Met Ser Leu Val
1 5 10 15

Ser Phe Ile Pro Cys Ile Ser Phe Ser Asn Pro Met Gln Asp Asn Asn
20 25 30

Ile Val Gly Asn Phe Tyr Val Ser Gly Lys Tyr Met Pro Thr Ile Ser
35 40 45

His Phe Asp Asn Phe Ser Ala Lys Glu Asp Thr Ile Glu Thr Ile Ala
50 55 60

Thr Phe Gly Leu Ser Lys Thr Tyr Asn Arg Ser Ser Pro Ile His Ser
65 70 75 80

Asp Phe Thr Asp Ser Lys Tyr Ser Phe Lys Tyr Glu Asn Asn Pro Phe
85 90 95

Leu Gly Phe Ala Gly Ala Val Gly Tyr Ser Met Glu Gly Leu Arg Leu
100 105 110

Glu Phe Glu Ile Ser Tyr Glu Lys Phe Asp Val Lys Asn Pro Asp Asn
115 120 125

Ser Tyr Ser Asn Gly Ala His Met Tyr Tyr Ala Leu Ser Arg Lys Asp
130 135 140

Asn Ala Asn Ile Gly Thr Thr Pro Gln Asp Lys Lys Tyr Val Tyr Ile
145 150 155 160

Lys Asn Glu Gly Leu Thr Asp Ile Ser Leu Met Leu Asn Ala Cys Tyr
165 170 175

Asp Val Ile Ser Glu Gly Ile Ser Phe Val Pro Tyr Ile Cys Ala Gly
180 185 190

Ile Gly Ser Asp Phe Ile Ser Met Phe Asp Ile Thr Ser Pro Lys Leu
195 200 205

Ser Tyr Gln Gly Lys Leu Gly Ile Ser Tyr Ser Ile Asn Pro Glu Met
210 215 220

Ser Val Phe Ile Gly Gly His Phe His Lys Val Ile Gly Asp Gln Phe
225 230 235 240

Lys Asp Ile Thr Pro Leu Lys Pro Asn Gly Ile Glu Asn Thr Thr Ala
245 250 255

Thr His Val Leu Val Thr Leu His Met Cys His Phe Gly Ala Glu Ile
260 265 270

Gly Gly Arg Phe Thr Phe
275

<210> SEQ ID NO 261
<211> LENGTH: 282
<212> TYPE: PRT

<213> ORGANISM: Ehrlichia ewingii

<400> SEQUENCE: 261

```
Met Asn Cys Lys Lys Val Phe Ile Thr Ser Ala Leu Ile Ser Phe Ile
 1               5                  10                  15

Cys Phe Leu Pro Gly Val Ser Phe Ser Asn Thr Ile Gln Asp Asn Asn
             20                  25                  30

Ile Val Gly Asn Phe Tyr Ile Ser Gly Lys Tyr Met Pro Thr Val Ser
         35                  40                  45

His Phe Gly Asn Phe Ser Ala Lys Glu Glu Lys Ala Glu Thr Lys Lys
     50                  55                  60

Thr Phe Gly Leu Glu Lys Asn Tyr Asp Gly Ala Lys Ile Glu Asp Asn
 65                  70                  75                  80

Gln Val Gln Asn Lys Phe Thr Ile Ser Asn Tyr Ser Phe Lys Tyr Glu
                 85                  90                  95

Asp Asn Pro Phe Leu Gly Phe Ala Gly Ala Ile Gly Tyr Ser Met Glu
            100                 105                 110

Gly Pro Arg Ile Glu Leu Glu Val Ser Tyr Glu Thr Phe Asn Val Lys
        115                 120                 125

Asn Gln Asp Asn Ser Tyr Lys Asn Asp Ala His Met Tyr Tyr Leu Leu
    130                 135                 140

Ala Arg Glu Val Asp Ser Ser Ser Pro Thr Lys Pro Gln Val Asn Lys
145                 150                 155                 160

Ser Val Leu Leu Lys Asn Glu Gly Leu Thr Asp Phe Ser Ile Met Leu
                165                 170                 175

Asn Ala Cys Tyr Asp Ile Ile Thr Asp Asn Ile Pro Phe Ser Pro Tyr
            180                 185                 190

Ile Cys Ala Gly Val Gly Ala Asp Leu Val Ser Met Phe Asn Ser Ile
        195                 200                 205

Asn Pro Lys Leu Ala Tyr Gln Gly Lys Leu Gly Ile Ser Tyr Ser Ile
    210                 215                 220

Ser Pro Glu Val Ser Ala Phe Ile Gly Gly His Phe His Lys Val Ile
225                 230                 235                 240

Gly Asn Glu Phe Lys Asp Ile Ala Thr Ile Leu Pro Ser Gly Ser Ser
                245                 250                 255

Ile Lys Asp Asn Gln Tyr Ala Ile Val Thr Leu Ser Val Cys His Phe
            260                 265                 270

Gly Val Glu Ile Gly Gly Arg Val Ser Phe
        275                 280
```

<210> SEQ ID NO 262
<211> LENGTH: 272
<212> TYPE: PRT
<213> ORGANISM: Ehrlichia ewingii

<400> SEQUENCE: 262

```
Met Asn Tyr Lys Lys Phe Val Leu Ser Val Ala Leu Ser Thr Leu Phe
 1               5                  10                  15

Ser Phe Leu Pro Asp Ser Ser Phe Ser Asp Val Val Val Ser Glu Glu
             20                  25                  30

Lys Arg Gly Phe Tyr Val Gly Thr Gln Tyr Arg Val Gly Val Pro Asn
         35                  40                  45

Phe Ser Asn Phe Ser Ala Ala Glu Thr Ile Pro Gly Leu Thr Lys Lys
     50                  55                  60

Ile Phe Ala Leu Ser Tyr Asp Ala Thr Asp Ile Thr Lys Glu Thr Ser
```

65 70 75 80

Phe Lys Gln Ala Tyr Asp Pro Thr Tyr Ala Ser Ser Phe Asn Ser Phe
85 90 95

Ser Gly Val Met Gly Cys Tyr Phe Asn Ser Met Arg Ile Glu Phe Glu
100 105 110

Gly Ser Tyr Ser His Phe Glu Ser Glu Arg Gln Phe Tyr Arg Glu Gly
115 120 125

Ser Asn Asn Tyr Lys Phe Phe Ala Leu Ser Arg Glu Glu Thr Ile Thr
130 135 140

Ser Lys Lys Phe Val Val Leu Glu Asn Asn Gly Val Ile Asp Arg Ser
145 150 155 160

Leu Asn Val Asn Phe Cys Tyr Asp Ile Thr Arg Gly Asp Val Pro Leu
165 170 175

Ala Pro Tyr Val Cys Ala Gly Val Gly Ala Asp Tyr Ile Lys Phe Leu
180 185 190

Gly Ile Ser Leu Pro Lys Phe Ser Tyr Gln Val Lys Phe Gly Val Asn
195 200 205

Tyr Pro Val Lys Ser Asn Ile Met Leu Phe Gly Gly Gly Tyr Tyr His
210 215 220

Lys Val Val Gly Ser Lys Tyr Glu Arg Val Glu Ile Ala Tyr His Pro
225 230 235 240

Ser Ile Glu Glu Ala Pro Lys Ile Thr Ser Ala Ser Ala Asn Leu Asn
245 250 255

Thr Asp His Phe Gly Cys Glu Val Gly Ile Arg Phe Ala Phe Ile Asn
260 265 270

<210> SEQ ID NO 263
<211> LENGTH: 282
<212> TYPE: PRT
<213> ORGANISM: Ehrlichia ewingii

<400> SEQUENCE: 263

Met Lys Tyr Lys Ile Val Lys Thr Thr Ile Thr Gly Leu Gly Leu Leu
1 5 10 15

Leu Pro Phe Tyr Ala Ser Met Ser Phe Gly Met Ser Asn Thr Leu Ala
20 25 30

Asn Gln Val Ser Pro Ile Ser Phe Gly Val Leu Tyr Lys Leu Ser His
35 40 45

Pro Phe Phe Asn Asn Phe Ser Ile Glu Glu Thr Gln Ile Leu His Asp
50 55 60

Val Ala Thr Glu Arg Val Val Gly Leu Lys His Asp Leu Leu Glu Ser
65 70 75 80

Ala Asp Lys Leu Val Asp Asn Leu Tyr Asn Phe Asp Leu Ser Glu Asp
85 90 95

Tyr Val Pro Lys Tyr Asp Asn Ser Leu Phe Gly Leu Ser Phe Phe Ile
100 105 110

Gly Tyr Ser Phe Gln Asn Phe Arg Ile Glu Leu Glu Ser Phe Tyr Glu
115 120 125

Lys Phe Asp Val Gln Asp Thr Lys Ser His Ile Val Asp Asp Asn Tyr
130 135 140

Arg Tyr Phe Ala Leu Tyr Arg His Gly Pro Ala Lys His Ile Asn Tyr
145 150 155 160

Val Thr Leu Lys Asn Asp Gly Ile Glu Leu Asn Ser Val Met Leu Asn
165 170 175

```
Ile Cys Tyr Asp Phe Thr Leu Asn Asn Thr Tyr Ile Thr Pro Phe Ser
            180                 185                 190

Cys Val Gly Ile Gly Gly Asp Ile Ile Ser Ile Phe Asn Thr Val Lys
        195                 200                 205

Val Lys Ile Ala Ala Gln Ala Lys Val Gly Val Asn Tyr Leu Ile Ser
    210                 215                 220

Glu Arg Ile Ser Leu Phe Val Asp Gly Tyr Tyr His Gly Val Ile Asp
225                 230                 235                 240

Asn Glu Tyr Ser Asn Ile Pro Val Gln Tyr Pro Arg Asn Leu Phe Tyr
                245                 250                 255

Ala Pro Lys Val Thr Ser Ala Leu Ala Asn Leu Asp Ile Gly Tyr Phe
            260                 265                 270

Gly Ala Glu Ile Gly Met Lys Val Phe Ile
        275                 280

<210> SEQ ID NO 264
<211> LENGTH: 282
<212> TYPE: PRT
<213> ORGANISM: Ehrlichia ewingii

<400> SEQUENCE: 264

Met Lys Cys Lys Ile Thr Lys Ile Ala Ile Ile Met Leu Gly Leu Leu
1               5                   10                  15

Leu Pro Phe Gln Ala Phe Ser Ala Ser Leu Val Ser Asp Ala Ser Asp
            20                  25                  30

Ser His Thr Lys Ser Val Ser Leu Ser Ala Ser Tyr Lys Leu Ser Thr
        35                  40                  45

Pro Phe Phe Asn His Phe Leu Ile Arg Glu Thr Asn Leu Thr Ser Gly
    50                  55                  60

Ile Ile Ala Asn Lys Arg Val Leu Gly Leu Lys Asn Asp Ile Leu Ile
65                  70                  75                  80

Asn Ala Asp Glu Ala Ile Lys Asn Leu Ser Asn Phe Asp Phe Ser Glu
                85                  90                  95

Asp Tyr Val Pro Lys Tyr Lys Asn Ser Leu Tyr Gly Leu Ser Phe Leu
            100                 105                 110

Phe Gly Tyr Ser Phe Lys Asn Leu Lys Val Glu Leu Glu Gly Leu Tyr
        115                 120                 125

Glu Ser Phe Asp Val Arg Asp Thr Lys Asn His Ile Ile Asp Asn Asn
    130                 135                 140

Tyr Arg Tyr Phe Ala Leu Ser Lys Gln Asp Asn Leu Asn Ser Asp Tyr
145                 150                 155                 160

Val Thr Leu Ile Asn Asn Gly Val Lys Leu Tyr Ser Val Ile Leu Asn
                165                 170                 175

Ile Cys Tyr Asp Phe Ile Gly Lys Asn Thr Ser Leu Thr Pro Phe Leu
            180                 185                 190

Cys Val Gly Ile Gly Glu Asp Ile Ile Asn Ile Phe Asp Ala Val Arg
        195                 200                 205

Phe Lys Pro Ala Phe His Ala Lys Met Gly Phe Asn Tyr Arg Ile Ser
    210                 215                 220

Glu Arg Ala Phe Leu Phe Met Asp Met Tyr Tyr His Lys Ile Ile Gly
225                 230                 235                 240

Asn Gln Tyr Ser Ser Ile Ser Val Lys Tyr Pro Lys Val Leu Val Phe
                245                 250                 255

Pro Ser Thr Arg Ser Ser Val Leu Ala Glu Leu Asp Ile Gly Tyr Leu
            260                 265                 270
```

```
Gly Ser Glu Val Gly Ile Arg Ile Phe Ile
        275                 280
```

<210> SEQ ID NO 265
<211> LENGTH: 307
<212> TYPE: PRT
<213> ORGANISM: Ehrlichia ewingii

<400> SEQUENCE: 265

```
Met Phe Tyr Thr Asn Ile Tyr Ile Leu Ala Cys Ile Tyr Phe Ala Leu
  1               5                  10                  15

Pro Leu Leu Ile Tyr Phe His Tyr Phe Arg Cys Asn Met Asn Cys
             20                  25                  30

Lys Lys Ile Leu Ile Thr Thr Ala Leu Ile Ser Leu Met Tyr Ser Ile
         35                  40                  45

Pro Ser Ile Ser Phe Ser Asp Thr Ile Gln Asp Gly Asn Met Gly Gly
     50                  55                  60

Asn Phe Tyr Ile Ser Gly Lys Tyr Val Pro Ser Val Ser His Phe Gly
 65                  70                  75                  80

Ser Phe Ser Ala Lys Glu Glu Ser Lys Ser Thr Val Gly Val Phe Gly
                 85                  90                  95

Leu Lys His Asp Trp Asp Gly Ser Pro Ile Leu Lys Asn Lys His Ala
            100                 105                 110

Asp Phe Thr Val Pro Asn Tyr Ser Phe Arg Tyr Glu Asn Asn Pro Phe
        115                 120                 125

Leu Gly Phe Ala Gly Ala Ile Gly Tyr Ser Met Gly Gly Pro Arg Ile
    130                 135                 140

Glu Phe Glu Ile Ser Tyr Glu Ala Phe Asp Val Lys Ser Pro Asn Ile
145                 150                 155                 160

Asn Tyr Gln Asn Asp Ala His Arg Tyr Cys Ala Leu Ser His His Thr
                165                 170                 175

Ser Ala Ala Met Glu Ala Asp Lys Phe Val Phe Leu Lys Asn Glu Gly
            180                 185                 190

Leu Ile Asp Ile Ser Leu Ala Ile Asn Ala Cys Tyr Asp Ile Ile Asn
        195                 200                 205

Asp Lys Val Pro Val Ser Pro Tyr Ile Cys Ala Gly Ile Gly Thr Asp
    210                 215                 220

Leu Ile Ser Met Phe Glu Ala Thr Ser Pro Lys Ile Ser Tyr Gln Gly
225                 230                 235                 240

Lys Leu Gly Ile Ser Tyr Ser Ile Asn Pro Glu Thr Ser Val Phe Ile
                245                 250                 255

Gly Gly His Phe His Arg Ile Ile Gly Asn Glu Phe Arg Asp Ile Pro
            260                 265                 270

Ala Ile Val Pro Ser Asn Ser Thr Thr Ile Ser Gly Pro Gln Phe Ala
        275                 280                 285

Thr Val Thr Leu Asn Val Cys His Phe Gly Leu Glu Leu Gly Gly Arg
    290                 295                 300

Phe Asn Phe
305
```

<210> SEQ ID NO 266
<211> LENGTH: 280
<212> TYPE: PRT
<213> ORGANISM: Ehrlichia ewingii

<400> SEQUENCE: 266

```
Met Asn Tyr Lys Lys Ile Leu Val Arg Ser Ala Leu Ile Ser Leu Met
1               5                   10                  15

Ser Ile Leu Pro Tyr Gln Ser Phe Ala Asp Pro Val Gly Ser Arg Thr
            20                  25                  30

Asn Asp Asn Lys Glu Gly Phe Tyr Ile Ser Ala Lys Tyr Asn Pro Ser
        35                  40                  45

Ile Ser His Phe Arg Lys Phe Ser Ala Glu Glu Thr Pro Ile Asn Gly
    50                  55                  60

Thr Asn Ser Leu Thr Lys Lys Val Phe Gly Leu Lys Lys Asp Gly Asp
65                  70                  75                  80

Ile Thr Lys Lys Asp Asp Phe Thr Arg Val Ala Pro Gly Ile Asp Phe
                85                  90                  95

Gln Asn Asn Leu Ile Ser Gly Phe Ser Gly Ser Ile Gly Tyr Ser Met
            100                 105                 110

Asp Gly Pro Arg Ile Glu Leu Glu Ala Ala Tyr Gln Gln Phe Asn Pro
        115                 120                 125

Lys Asn Thr Asp Asn Asn Asp Thr Asp Asn Gly Glu Tyr Tyr Lys His
    130                 135                 140

Phe Ala Leu Ser Arg Lys Asp Ala Met Glu Asp Gln Gln Tyr Val Val
145                 150                 155                 160

Leu Lys Asn Asp Gly Ile Thr Phe Met Ser Leu Met Val Asn Thr Cys
                165                 170                 175

Tyr Asp Ile Thr Ala Glu Gly Val Ser Phe Val Pro Tyr Ala Cys Ala
            180                 185                 190

Gly Ile Gly Ala Asp Leu Ile Thr Ile Phe Lys Asp Leu Asn Leu Lys
        195                 200                 205

Phe Ala Tyr Gln Gly Lys Ile Gly Ile Ser Tyr Pro Ile Thr Pro Glu
    210                 215                 220

Val Ser Ala Phe Ile Gly Gly Tyr Tyr His Gly Val Ile Gly Asn Lys
225                 230                 235                 240

Phe Glu Lys Ile Pro Val Ile Thr Pro Val Val Leu Asn Asp Ala Pro
                245                 250                 255

Gln Thr Thr Ser Ala Ser Val Thr Leu Asp Val Gly Tyr Phe Gly Gly
            260                 265                 270

Glu Ile Gly Met Arg Phe Thr Phe
        275                 280

<210> SEQ ID NO 267
<211> LENGTH: 279
<212> TYPE: PRT
<213> ORGANISM: Ehrlichia ewingii

<400> SEQUENCE: 267

Met Asn Lys Lys Lys Ile Ile Thr Val Gly Thr Thr Leu Ala Tyr Leu
1               5                   10                  15

Leu Leu Ser Pro Asn Ile Ser Phe Ser Glu Val Ile Asn Asn Asp Thr
            20                  25                  30

Asp Lys Tyr Ser Arg Leu Tyr Ile Ser Gly Gln Tyr Lys Pro Gly Phe
        35                  40                  45

Ser Tyr Phe Asn Lys Phe Ser Val Arg Glu Thr Asp His Phe Thr Lys
    50                  55                  60

Ala Leu Ile Gly Leu Arg His Asp Ala Ile Ser Thr Lys Asn Leu Thr
65                  70                  75                  80

Thr Asn Thr Asp Phe Asn Thr Leu Tyr Lys Val Thr Phe Gln Asn Asn
```

```
                85                  90                  95

Ile Ile Ser Phe Ser Gly Ala Ile Gly Tyr Ser Asp Ser Thr Gly Val
            100                 105                 110

Arg Phe Glu Leu Glu Gly Ser Tyr Glu Glu Phe Asp Val Thr Asp Pro
        115                 120                 125

Gly Asp Cys Ile Ile Lys Asp Thr Tyr Arg Tyr Phe Ala Leu Ala Arg
    130                 135                 140

Lys Thr Ser Gly Asn His Pro Asn Asp Asn Gly Glu Tyr Thr Val Met
145                 150                 155                 160

Arg Asn Asp Gly Val Ser Ile Thr Ser Val Ile Phe Asn Gly Cys Tyr
                165                 170                 175

Asp Leu Ser Leu Lys Glu Leu Glu Ile Ser Pro Tyr Val Cys Ile Gly
            180                 185                 190

Ile Gly Gly Asp Phe Ile Glu Phe Phe Asp Ala Leu His Ile Lys Leu
        195                 200                 205

Ala Tyr Gln Gly Lys Leu Gly Ile Ser Tyr Ser Phe Ser Thr Arg Thr
    210                 215                 220

Asn Leu Phe Ile Asp Cys Tyr Tyr His Arg Val Ile Gly Asn Gln Phe
225                 230                 235                 240

Asn Asn Leu Asn Val Gln His Val Val Glu Leu Thr Glu Ala Pro Lys
                245                 250                 255

Ala Thr Ser Ala Ile Ala Thr Leu Asn Val Ser Tyr Phe Gly Gly Glu
            260                 265                 270

Val Gly Ile Arg Leu Met Phe
        275

<210> SEQ ID NO 268
<211> LENGTH: 289
<212> TYPE: PRT
<213> ORGANISM: Ehrlichia ewingii

<400> SEQUENCE: 268

Met Asn Ser Lys Lys Thr Phe Ser Ile Leu Gly Ser Ile Leu Ile Cys
 1               5                  10                  15

Leu Ala Ala Cys Leu Pro Ile Gln Ser Phe Ser Glu Ser Ser Asn Val
            20                  25                  30

Thr Tyr Asn Thr Lys His Thr Gly Leu Tyr Ile Ser Gly Leu Tyr Lys
        35                  40                  45

Pro Ser Val Ser His Phe Ser Asp Phe Ser Ile Lys Glu Thr Tyr Thr
    50                  55                  60

Asn Thr Glu Ala Leu Phe Gly Leu Lys Gln Asp Ile Ser Ser Ile Leu
65                  70                  75                  80

Arg Asn Lys Glu Thr Thr Gln Tyr Asn Asn Asn Phe Asn Val Pro Tyr
                85                  90                  95

Thr Ala Lys Phe Gln Asp Asp Phe Ala Ser Phe Ser Ile Ala Val Gly
            100                 105                 110

Tyr Ile Ala Asn Asn Gly Pro Arg Ile Glu Ile Glu Gly Ser Tyr Glu
        115                 120                 125

Glu Phe Asp Val Lys Asn Pro Gly Asn Tyr Thr Thr Ile Asp Ala His
    130                 135                 140

Arg Tyr Ile Ala Leu Ala Arg Glu Lys Thr Ser Tyr Tyr Leu Ser Ser
145                 150                 155                 160

Pro Lys Glu Asn Lys Tyr Val Ile Ile Lys Asn Asn Gly Ile Ser Ile
                165                 170                 175
```

-continued

Val Ser Ile Ile Ile Asn Gly Cys Tyr Asp Ile Ser Leu Asn Asp Ser
               180                 185                 190

Lys Val Ser Pro Tyr Ile Cys Thr Gly Phe Gly Gly Asp Phe Ile Glu
            195                 200                 205

Phe Phe Ser Ala Ile Arg Phe Lys Phe Ala Tyr Gln Gly Lys Ile Gly
        210                 215                 220

Ile Ser Tyr Ser Leu Ser Ser Asn Ile Ile Leu Phe Thr Asp Gly Tyr
225                 230                 235                 240

Tyr His Lys Val Ile Asn Ser Gln Phe Lys Asn Leu Asn Val Glu His
            245                 250                 255

Val Val Asn Glu Leu Thr Thr Asp Pro Lys Val Thr Ser Ala Thr Ala
        260                 265                 270

Phe Leu Asn Ile Glu Tyr Phe Gly Gly Glu Phe Gly Leu Lys Phe Ile
275                 280                 285

Phe

<210> SEQ ID NO 269
<211> LENGTH: 278
<212> TYPE: PRT
<213> ORGANISM: Ehrlichia ewingii

<400> SEQUENCE: 269

Met Asn Asn Lys Lys Ser Leu Leu Ile Gly Thr Ile Leu Leu Ser Leu
1               5                   10                  15

Phe Ser Ser Leu Pro Ile Lys Ala Phe Ser Val Ile Asn His Ser Asp
            20                  25                  30

Ile Ser Ser Asn Val Asn Gly Leu Tyr Phe Thr Gly Gln Tyr Arg Pro
        35                  40                  45

Ala Val Ser His Phe Ser Gly Phe Thr Val Arg Glu Thr Asn Ile Ala
    50                  55                  60

Thr Gln Gln Leu Val Ser Leu Asn Thr Asn Lys Asn Glu Asn His Ile
65                  70                  75                  80

Ile Glu Arg Thr Asn Phe Ser Gly Ile Tyr Thr Ala Lys Phe Gln Asp
                85                  90                  95

Asn Ala Ala Ser Phe Ser Gly Ala Ile Gly Tyr Ser Tyr Pro Glu Gly
            100                 105                 110

Leu Lys Phe Glu Ile Glu Ile Ser Tyr Glu Lys Phe Gly Val Lys Ser
        115                 120                 125

Thr Lys Asn Tyr Gln Ser Thr Asn Ala Val Ile Phe Ala Leu Ala Arg
130                 135                 140

Gln Thr Thr Ser Ser Asn Pro Ser Asp Asn Lys Tyr Val Val Met Lys
145                 150                 155                 160

Asn Ser Gly Leu Ser Val Ala Ser Val Met Ile Asn Gly Cys Tyr Asn
                165                 170                 175

Met Ser Phe Tyr Asn Leu Val Val Ser Pro Tyr Ile Cys Ala Gly Ile
            180                 185                 190

Gly Glu Asp Phe Ile Glu Phe Asp Thr Leu Tyr Ile Lys Leu Ala
        195                 200                 205

Tyr Gln Gly Lys Leu Gly Val Asn Tyr Ser Leu Ser Ser Arg Phe Asn
    210                 215                 220

Ile Phe Ala Asp Met Tyr Tyr His Lys Val Ile Gly Asn Gln Phe Lys
225                 230                 235                 240

Asn Leu Asn Val Ile His Ala Val Ala Leu Asp Thr Phe Pro Lys Val
                245                 250                 255

Thr Ser Ala Ile Ala Thr Leu Asn Val Ala Tyr Phe Gly Gly Glu Val
            260                 265                 270

Gly Ile Arg Phe Ile Leu
        275

<210> SEQ ID NO 270
<211> LENGTH: 289
<212> TYPE: PRT
<213> ORGANISM: Ehrlichia ewingii

<400> SEQUENCE: 270

Met Leu Gln Arg Leu Asn Phe Ile Asn Ile Ile Leu Ala Phe Leu Leu
1               5                   10                  15

Leu Leu Phe Pro Phe Gln Ser Phe Thr Leu Tyr Ile His Asp His Glu
            20                  25                  30

Ile Thr Gln Asn Val Gly Leu Tyr Ile Ser Ser Gln Tyr Lys Pro Ser
        35                  40                  45

Ile Pro Tyr Phe Lys Asn Phe Leu Ile Glu Glu Asn Ser His Lys Thr
    50                  55                  60

Val Glu Leu Met Gly Leu Ala Asn Asp Val Thr His Val Thr Glu Tyr
65                  70                  75                  80

Val Leu Lys Asp Asn Thr Lys Phe Asn Thr Pro Tyr Ser Ala Lys Phe
                85                  90                  95

Arg Asn Ser Leu Ile Asn Leu Ser Gly Ala Ile Gly Tyr Tyr Ser Gly
            100                 105                 110

Gln Gly Pro Arg Leu Glu Ile Glu Gly Ser Tyr Glu Asn Phe Asp Val
        115                 120                 125

Ala Ser Cys Lys Asn Cys Pro Val Lys Asn Ala Asn Arg Tyr Ile Ala
    130                 135                 140

Leu Val Arg Asp Lys Lys Pro Gly Asn Ile Tyr Pro Gln Asp His Ser
145                 150                 155                 160

His Ser Asn Met Ser Tyr Tyr Thr Phe Ile Lys Asn Asn Gly Ile Ser
                165                 170                 175

Ile Leu Ser Val Met Ile Asn Gly Cys Tyr Asp Ile Ala Phe Ser Asn
            180                 185                 190

Val Lys Ile Ser Pro Tyr Val Cys Ala Gly Ile Gly Gly Asp Phe Ile
        195                 200                 205

Thr Leu Phe Glu Thr Met His Ile Lys Phe Ala Tyr Gln Gly Lys Phe
    210                 215                 220

Gly Ile Ser Tyr Leu Val Ser Pro Ser Ile Ser Ile Phe Ala Asn Gly
225                 230                 235                 240

His Tyr His Lys Val Met Asp Asn Val Phe Lys Asn Leu His Val Lys
                245                 250                 255

Tyr Ile Tyr Lys Leu Gln Asp Ala Pro Thr Ile Thr Ser Ala Arg Ala
            260                 265                 270

Lys Leu Arg Ile Gly Tyr Phe Gly Ser Glu Val Gly Val Arg Phe Val
        275                 280                 285

Phe

<210> SEQ ID NO 271
<211> LENGTH: 264
<212> TYPE: PRT
<213> ORGANISM: Ehrlichia ewingii

<400> SEQUENCE: 271

Met Tyr Asn Ile Ile Asn Tyr Val Ile Lys Tyr Thr Ile Ala Leu Ala

-continued

```
               1               5                  10                 15
             Phe Leu Leu Leu Pro Arg Val Ser Phe Ser Ile Leu Ile Gly Asn Ile
                             20                 25                 30

Glu Lys Ser Ile Lys Leu Leu Ser Val His Ile Asn Ser Gln Tyr Lys
                             35                 40                 45

Pro Ser Ile Ser Gln Ile Ser Asn Tyr Leu Ile Gln Glu Asn Asn Ser
              50                 55                 60

Lys Glu Lys Lys Ile Asn Ile Leu Asn Leu Ser Asn Asn Thr Ile Thr
              65                 70                 75                 80

Tyr Asn Met Gln Leu Glu Asn Ser Thr Thr Asn Phe Arg Phe Ile Ile
                             85                 90                 95

Gly Tyr Phe Phe Lys Arg Leu Arg Phe Ala Val Glu Asp Ser Tyr Glu
                             100                105                110

Glu Phe His Ile Lys Asp Asn Asp Ser Leu Lys Ala Asn Leu Ser Lys
                             115                120                125

Tyr Ser Tyr Lys Met Tyr Asn Glu Asp Phe Gln Asn Phe Thr Ile Ala
              130                135                140

Thr Asp Asn Lys Leu Ser Ile Thr Ser Ala Ile Val Asn Ile Cys Tyr
             145                 150                155                160

Asp Ile Leu Ile Asn Asn Thr Thr Val Leu Pro His Leu Cys Thr Ala
                             165                170                175

Val Gly Ile Cys Ser Thr Gly Phe Phe Asn Asp Met Arg Phe Lys Leu
                             180                185                190

Leu Tyr Gln Arg Lys Ile Gly Leu Gly Tyr Leu Ile Asn Ser Asn Val
                             195                200                205

Met Leu Phe Phe Asn Val Tyr Tyr His Lys Val Met Arg Asn Lys Leu
              210                215                220

Lys Asn Leu Leu Thr Gln Tyr Ser Val Asp Ile Asn Ala Phe Leu Asp
             225                 230                235                240

Ala Ile Thr Val Leu Ala Asn Thr Asp Ile Gly Tyr Phe Gly Ser Glu
                             245                250                255

Val Gly Val Arg Phe Ile Phe Asn
                             260
```

<210> SEQ ID NO 272
<211> LENGTH: 283
<212> TYPE: PRT
<213> ORGANISM: Ehrlichia ewingii

<400> SEQUENCE: 272

```
             Met Tyr Lys Leu Tyr Tyr Leu Ser Phe Ile Ile Ser Leu Ala Gln Leu
              1               5                  10                 15

Leu Phe Ser Gly Phe Ala Phe Ser Ile Asp Lys Asn Asn Asn Ile His
                             20                 25                 30

Gly Ser Tyr Ile Thr Ile Lys Tyr Gln Pro Thr Ile Ser Asn Phe Lys
                             35                 40                 45

Asn Phe His Ile Lys Glu Thr Asp Phe Asp Thr Glu Asp Pro Ile Gly
              50                 55                 60

Phe Asp Ile Ile Ala Pro Asn Thr Asn Phe Asp Phe Lys His Asn
              65                 70                 75                 80

Tyr Asn Phe Ser Val Leu Tyr His Lys Asp Ser Tyr Lys Phe Tyr Glu
                             85                 90                 95

Asn Asp Leu Ser Gly Leu Ala Leu Ser Ile Gly Leu Leu Val Lys Asn
                             100                105                110
```

```
Leu Arg Ile Glu Phe Glu Gly Ser Tyr Lys Asn Phe Asp Thr Lys Arg
        115                 120                 125

Leu Ala Tyr Tyr His Ser Arg Glu Gly His Lys Phe Ala Ile Pro
    130                 135                 140

Arg Thr Ser Asn Phe Gly Val Ile Pro Asn Glu Asp Asn Tyr Thr Val
145                 150                 155                 160

Ala Lys Asn Asn Gly Ile Ser Ile Ile Ser Asn Ile Ile Asn Leu Cys
                165                 170                 175

Ser Glu Thr Lys Phe Lys Asn Phe Thr Pro Tyr Ile Cys Leu Gly Ile
            180                 185                 190

Gly Gly Asp Phe Ile Glu Ile Phe Asp Val Met Arg Val Lys Phe Thr
        195                 200                 205

Tyr Gln Gly Lys Val Gly Ile Ser Tyr Pro Ile Thr Pro Lys Leu Val
    210                 215                 220

Leu Ser Ile Ser Gly Gln Tyr His Lys Val Ile Gly Asn Lys Phe Lys
225                 230                 235                 240

Phe Leu Pro Leu Ile Gln Pro Val Ala Leu Lys Arg Thr Asp Asn Ser
                245                 250                 255

Pro Glu Asp Lys Asp Val Thr Ala Leu Leu Thr Leu Asp Leu Glu His
            260                 265                 270

Phe Ser Ser Glu Ile Gly Leu Ser Phe Ile Phe
        275                 280

<210> SEQ ID NO 273
<211> LENGTH: 316
<212> TYPE: PRT
<213> ORGANISM: Ehrlichia ewingii

<400> SEQUENCE: 273

Met Asn Tyr Ala Lys Val Phe Ile Leu Val Cys Ile Ile Phe Leu Phe
1               5                   10                  15

Pro Ser Leu Ser Phe Ala Thr Asn Asn Tyr Phe Val His Glu Ile
            20                  25                  30

Gly Lys Ser Ile Gly His Phe Tyr Ile Gly Val Gln Tyr Lys Pro Gly
        35                  40                  45

Thr Pro His Phe Asn Arg Phe Ser Ile Ala Asp Asp Ser Thr Phe Asn
    50                  55                  60

Leu Leu Ala Ile Ser His Thr Lys Asp Tyr Leu Phe Ser Tyr Ser Thr
65                  70                  75                  80

Glu Val Arg Gly Leu Phe Ser Leu Pro Gln Glu Gln Gln Asn Leu Leu
                85                  90                  95

His Tyr Ala Thr Gly Gly Ser Thr Thr Leu Asn Thr Leu Lys Asp Ser
            100                 105                 110

Asn Lys Phe Ile Pro Gly Tyr Asn Pro Thr Tyr Thr Asp Asn Leu Leu
        115                 120                 125

Gly Val Gly Gly Ile Val Gly Tyr Ser Ile Asn Asn Leu Arg Ile Glu
    130                 135                 140

Leu Glu Ala Phe Tyr Glu Lys Phe Asn Ile Lys Ala Pro Thr Gly Tyr
145                 150                 155                 160

Asn Tyr Asp Thr Glu Tyr Phe Ile Ala Thr Val Val Tyr Lys Gly
                165                 170                 175

Lys Thr Lys Pro Val His Tyr His Cys Met Lys Asn Thr Gly Ile Ile
            180                 185                 190

Leu Ser Ser Phe Leu Val Asn Thr Cys Tyr Asp Phe Thr Leu Lys Ile
        195                 200                 205
```

```
Ala Lys Lys Ile Ala Pro Tyr Leu Cys Leu Gly Val Gly Gly Asp Phe
    210                 215                 220

Ile Asp Phe Leu Gly Gln Thr Arg Leu Lys Ala Ser Tyr Gln Ala Lys
225                 230                 235                 240

Ala Gly Leu Ser Tyr Ala Ile Ser Pro Asn Leu Thr Phe Phe Val Asp
                245                 250                 255

Gly Ser Phe His Gly Tyr Met Asn Asn Gln Phe Pro Gly Leu Leu Val
            260                 265                 270

Asp Tyr Pro Thr Asp Ile Ser Val Ser Met Pro Ser Gly Asp Asn Ala
        275                 280                 285

Thr Ala Tyr Ser Glu Phe Thr Thr Met Leu Ala Lys Leu Asn Met Ile
    290                 295                 300

Phe Leu Ala Gly Ser Ile Gly Ile Arg Phe Ile Ser
305                 310                 315

<210> SEQ ID NO 274
<211> LENGTH: 275
<212> TYPE: PRT
<213> ORGANISM: Ehrlichia ewingii

<400> SEQUENCE: 274

Met Asn Asn Lys Leu Ser Leu Leu Tyr Ile Ala Leu Ile Leu Phe Thr
 1               5                  10                  15

Ser His Val Ser Ser Ala Leu Val Leu Asn Asp His Asn Leu Val Tyr
            20                  25                  30

Phe Gly Ile Gln Tyr Lys Pro Ala Arg His His Leu Ser Asn Leu Leu
        35                  40                  45

Ile Lys Glu Ser Lys Ser Asp Val Val Glu Val Leu Ala Leu Lys Tyr
     50                  55                  60

Asp Ala Ile Gly Ser Pro Leu Asp Ser Thr Lys Glu Val Asn Asn Phe
 65                  70                  75                  80

Thr Ile Lys Tyr Asn Pro His Tyr Asp Asn Asn Arg Leu Gly Phe Ser
                 85                  90                  95

Val Ile Phe Gly Tyr Tyr Tyr Asn Lys Asn Phe Arg Ile Glu Ser Glu
            100                 105                 110

Ile Ser His Glu Ile Phe Gln Leu Lys Asn Glu Gly His Lys Arg Val
        115                 120                 125

Gly Phe Glu Lys Tyr Phe Ala Leu Lys Phe Ala Pro Pro Ser Ser Thr
    130                 135                 140

Gln Gly Tyr Arg His Val Thr Leu Ile Asn Asn Gly Ile Ser Thr Thr
145                 150                 155                 160

Ser Ala Leu Ile Asn Ala Cys Tyr Asp Val Leu Ile Pro Ala His Asn
                165                 170                 175

Ile Ile Thr Tyr Ser Cys Leu Gly Phe Gly Ile Asp Ile Val Asp Phe
            180                 185                 190

Leu Ser Lys Tyr Thr Thr Lys Phe Ser His Gln Gly Lys Leu Gly Ala
        195                 200                 205

Ser Tyr Pro Ile Ser His Arg Met Ser Val Phe Thr Glu Val Tyr Tyr
    210                 215                 220

His Gly Leu Phe Gly Lys Lys Phe Glu Gln Leu Pro Leu Asn Tyr Asn
225                 230                 235                 240

Ala Asn Thr Ser Pro Pro Gln Gln Pro Pro His Val His Thr Thr Ala
                 245                 250                 255

Ser Ala Ile Leu Ser Ile Gly Tyr Tyr Gly Gly Ser Val Gly Ile Lys
```

```
                    260                 265                 270

Phe Ile Leu
        275

<210> SEQ ID NO 275
<211> LENGTH: 296
<212> TYPE: PRT
<213> ORGANISM: Ehrlichia ewingii

<400> SEQUENCE: 275

Met Lys Leu Leu Tyr His Leu Asp Asn Ile Met Ile Lys Phe Ser Ala
 1               5                  10                  15

Ile Gly Ile Val Phe Ser Phe Ile Ala Leu Phe Ala Pro Asn Ala Phe
             20                  25                  30

Pro Ser Pro Val Pro Ile Asp Phe Ser Asn Glu Ser Glu Met Ala Gly
         35                  40                  45

Phe Tyr Ala Ser Ala Gln Tyr Asn Ile Gly Phe Pro Arg Phe Ser Pro
     50                  55                  60

Ile Ser Ala Lys Tyr Lys Thr Asp Glu Lys Ser Glu Lys Glu Leu Thr
 65                  70                  75                  80

Leu Phe Ser Leu Lys Glu Glu Thr Glu Thr Ile Asp Leu Lys Lys Ala
                 85                  90                  95

Gly Asp Phe Lys Lys Gly Tyr Ser Pro Val Tyr Asn Arg Asn Tyr Thr
            100                 105                 110

Gly Phe Ser Gly Ala Ile Gly Tyr Ser Gly Gly Leu Arg Val Glu
        115                 120                 125

Leu Glu Gly Ser Phe Thr Arg Phe Asp Val Asp Lys Gln Lys Tyr Lys
130                 135                 140

Asn Pro Asp Gly His Arg Tyr Phe Ala Leu Ser Lys Asp Ser Glu Ile
145                 150                 155                 160

Gln Asn Ser Ser Ser Gly Ser Ser Asn Asn Lys Asp Tyr Val Val
                165                 170                 175

Met Lys Asn Glu Gly Phe Asn Ala Ile Ser Leu Met Phe Asn Ala Cys
            180                 185                 190

Tyr Asp Met Ile Ile Gly Asn Ser Ser Leu Val Pro Asn Ala Cys Ile
        195                 200                 205

Gly Ile Gly Gln Gly Ile Ile Arg Phe Leu Gly Gly Thr Asn Ile His
    210                 215                 220

Thr Leu Phe Lys Ala Lys Leu Gly Leu Gly Phe Leu Ile Ser Pro Lys
225                 230                 235                 240

Thr Ile Leu Phe Ala Asn Gly Tyr Tyr Val Lys Ala Lys Asp Asn Ala
                245                 250                 255

Phe Thr Asn Leu Ser Val Gln Tyr Pro Val Glu Ile Ser Ala Ala Pro
            260                 265                 270

Lys His Ile Asp Pro Ile Val Tyr Phe Asn Ala Asp Asn Tyr Gly Cys
        275                 280                 285

Glu Val Gly Leu Arg Phe Ile Leu
    290                 295

<210> SEQ ID NO 276
<211> LENGTH: 280
<212> TYPE: PRT
<213> ORGANISM: Ehrlichia ewingii

<400> SEQUENCE: 276

Met Asn Cys Lys Lys Ile Leu Ile Thr Thr Ala Leu Met Ser Leu Met
```

```
              1               5                   10                  15
            Tyr Tyr Ala Pro Ser Ile Ser Phe Ser Asp Thr Ile Gln Asp Asp Asn
                            20                  25                  30
            Thr Gly Ser Phe Tyr Ile Ser Gly Lys Tyr Val Pro Ser Val Ser His
                        35                  40                  45
            Phe Gly Val Phe Ser Ala Lys Glu Glu Arg Asn Ser Thr Val Gly Val
             50                  55                  60
            Phe Gly Leu Lys His Asp Trp Asn Gly Thr Ile Ser Asn Ser Ser
             65                  70                  75                  80
            Pro Glu Asn Ile Phe Thr Val Gln Asn Tyr Ser Phe Lys Tyr Glu Asn
                            85                  90                  95
            Asn Pro Phe Leu Gly Phe Ala Gly Ala Ile Gly Tyr Ser Met Gly Gly
                            100                 105                 110
            Pro Arg Ile Glu Leu Glu Val Leu Tyr Glu Thr Phe Asp Val Lys Asn
                            115                 120                 125
            Gln Asn Asn Asn Tyr Lys Asn Gly Ala His Arg Tyr Cys Ala Leu Ser
                    130                 135                 140
            His His Ser Ser Ala Thr Asn Met Ser Ser Ala Ser Asn Lys Phe Val
            145                 150                 155                 160
            Phe Leu Lys Asn Glu Gly Leu Ile Asp Leu Ser Phe Met Ile Asn Ala
                            165                 170                 175
            Cys Tyr Asp Ile Ile Glu Gly Met Pro Phe Ser Pro Tyr Ile Cys
                        180                 185                 190
            Ala Gly Val Gly Thr Asp Val Val Ser Met Phe Glu Ala Ile Asn Pro
                    195                 200                 205
            Lys Ile Ser Tyr Gln Gly Lys Leu Gly Leu Gly Tyr Ser Ile Ser Ser
                210                 215                 220
            Glu Ala Ser Val Phe Ile Gly Gly His Phe His Arg Val Ile Gly Asn
            225                 230                 235                 240
            Glu Phe Arg Asp Ile Pro Ala Met Val Pro Ser Gly Ser Asn Leu Pro
                            245                 250                 255
            Glu Asn Gln Phe Ala Ile Val Thr Leu Asn Val Cys His Phe Gly Leu
                            260                 265                 270
            Glu Leu Gly Gly Arg Phe Asn Phe
                            275                 280

<210> SEQ ID NO 277
<211> LENGTH: 275
<212> TYPE: PRT
<213> ORGANISM: Ehrlichia ewingii

<400> SEQUENCE: 277

Met Val Ile Lys Met Asn Tyr Lys Arg Phe Val Gly Val Thr Leu
             1               5                   10                  15
            Ser Thr Phe Val Phe Phe Leu Ser Asp Gly Ala Phe Ser Asp Ala Asn
                            20                  25                  30
            Phe Ser Glu Gly Arg Arg Gly Leu Tyr Ile Gly Ser Gln Tyr Lys Val
                        35                  40                  45
            Gly Ile Pro Asn Phe Ser Asn Phe Ser Ala Glu Glu Thr Ile Pro Gly
             50                  55                  60
            Ile Thr Lys Lys Ile Phe Ala Leu Gly Leu Asp Lys Ser Glu Ile Asn
             65                  70                  75                  80
            Thr His Ser Asn Phe Thr Arg Ser Tyr Asp Pro Thr Tyr Ala Ser Ser
                            85                  90                  95
```

```
Phe Ala Gly Phe Ser Gly Ile Ile Gly Tyr Tyr Val Asn Asp Phe Arg
            100                 105                 110

Val Glu Phe Glu Gly Ser Tyr Glu Asn Phe Glu Pro Glu Arg Gln Trp
        115                 120                 125

Tyr Pro Glu Asn Ser Gln Ser Tyr Lys Phe Phe Ala Leu Ser Arg Asn
    130                 135                 140

Ala Thr Asn Ser Asp Asn Lys Phe Ile Val Leu Glu Asn Asn Gly Val
145                 150                 155                 160

Ala Asp Lys Ser Leu Asn Val Asn Val Cys Tyr Asp Ile Ala Ser Gly
                165                 170                 175

Ser Ile Pro Leu Ala Pro Tyr Met Cys Ala Gly Val Gly Ala Asp Tyr
            180                 185                 190

Ile Lys Phe Leu Gly Ile Ser Leu Pro Lys Phe Ser Tyr Gln Val Lys
        195                 200                 205

Phe Gly Val Asn Tyr Pro Leu Asn Val Asn Thr Met Leu Phe Gly Gly
    210                 215                 220

Gly Tyr Tyr His Lys Val Val Gly Asp Arg Tyr Glu Arg Val Glu Ile
225                 230                 235                 240

Ala Tyr His Pro Thr Ala Leu Ser Asp Val Pro Arg Thr Thr Ser Ala
                245                 250                 255

Ser Ala Thr Leu Asn Thr Asp Tyr Phe Gly Trp Glu Ile Gly Phe Arg
            260                 265                 270

Phe Ala Leu
        275

<210> SEQ ID NO 278
<211> LENGTH: 283
<212> TYPE: PRT
<213> ORGANISM: Ehrlichia ewingii

<400> SEQUENCE: 278

Met Asn Cys Lys Lys Val Phe Thr Ile Ser Ala Leu Ile Ser Ser Ile
 1               5                  10                  15

Tyr Phe Leu Pro Asn Val Ser Tyr Ser Asn Pro Val Tyr Gly Asn Ser
            20                  25                  30

Met Tyr Gly Asn Phe Tyr Ile Ser Gly Lys Tyr Met Pro Ser Val Pro
        35                  40                  45

His Phe Gly Ile Phe Ser Ala Glu Glu Glu Lys Lys Lys Thr Thr Val
     50                  55                  60

Val Tyr Gly Leu Lys Glu Asn Trp Ala Gly Asp Ala Ile Ser Ser Gln
 65                  70                  75                  80

Ser Pro Asp Asp Asn Phe Thr Ile Arg Asn Tyr Ser Phe Lys Tyr Ala
                85                  90                  95

Ser Asn Lys Phe Leu Gly Phe Ala Val Ala Ile Gly Tyr Ser Ile Gly
            100                 105                 110

Ser Pro Arg Ile Glu Val Glu Met Ser Tyr Glu Ala Phe Asp Val Lys
        115                 120                 125

Asn Pro Gly Asp Asn Tyr Lys Asn Gly Ala Tyr Arg Tyr Cys Ala Leu
    130                 135                 140

Ser His Gln Asp Asp Ala Asp Asp Asp Met Thr Ser Ala Thr Asp Lys
145                 150                 155                 160

Phe Val Tyr Leu Ile Asn Glu Gly Leu Leu Asn Ile Ser Phe Met Thr
                165                 170                 175

Asn Ile Cys Tyr Glu Thr Ala Ser Lys Asn Ile Pro Leu Ser Pro Tyr
            180                 185                 190
```

```
Ile Cys Ala Gly Ile Gly Thr Asp Leu Ile His Met Phe Glu Thr Thr
            195                 200                 205

His Pro Lys Ile Ser Tyr Gln Gly Lys Leu Gly Leu Ala Tyr Phe Val
    210                 215                 220

Ser Ala Glu Ser Ser Val Ser Phe Gly Ile Tyr Phe His Lys Ile Ile
225                 230                 235                 240

Asn Asn Lys Phe Lys Asn Val Pro Ala Met Val Pro Ile Asn Ser Asp
                245                 250                 255

Glu Ile Val Gly Pro Gln Phe Ala Thr Val Thr Leu Asn Val Cys Tyr
                260                 265                 270

Phe Gly Leu Glu Leu Gly Cys Arg Phe Asn Phe
            275                 280

<210> SEQ ID NO 279
<211> LENGTH: 276
<212> TYPE: PRT
<213> ORGANISM: Ehrlichia ewingii

<400> SEQUENCE: 279

Met Asn Cys Lys Lys Ile Leu Ile Thr Thr Thr Leu Val Ser Leu Thr
1               5                   10                  15

Ile Leu Leu Pro Gly Ile Ser Phe Ser Lys Pro Ile His Glu Asn Asn
                20                  25                  30

Thr Thr Gly Asn Phe Tyr Ile Ile Gly Lys Tyr Val Pro Ser Ile Ser
            35                  40                  45

His Phe Gly Asn Phe Ser Ala Lys Glu Glu Lys Asn Thr Thr Thr Gly
        50                  55                  60

Ile Phe Gly Leu Lys Glu Ser Trp Thr Gly Gly Ile Ile Leu Asp Lys
65                  70                  75                  80

Glu His Ala Ala Phe Asn Ile Pro Asn Tyr Ser Phe Lys Tyr Glu Asn
                85                  90                  95

Asn Pro Phe Leu Gly Phe Ala Gly Val Ile Gly Tyr Ser Ile Gly Ser
                100                 105                 110

Pro Arg Ile Glu Phe Glu Val Ser Tyr Glu Thr Phe Asp Val Gln Asn
            115                 120                 125

Pro Gly Asp Lys Phe Asn Asn Asp Ala His Lys Tyr Cys Ala Leu Ser
        130                 135                 140

Asn Asp Ser Ser Lys Thr Met Lys Ser Gly Lys Phe Val Phe Leu Lys
145                 150                 155                 160

Asn Glu Gly Leu Ser Asp Ile Ser Leu Met Leu Asn Val Cys Tyr Asp
                165                 170                 175

Ile Ile Asn Lys Arg Met Pro Phe Ser Pro Tyr Ile Cys Ala Gly Ile
                180                 185                 190

Gly Thr Asp Leu Ile Phe Met Phe Asp Ala Ile Asn His Lys Ala Ala
            195                 200                 205

Tyr Gln Gly Lys Leu Gly Phe Asn Tyr Pro Ile Ser Pro Glu Ala Asn
        210                 215                 220

Ile Ser Met Gly Val His Phe His Lys Val Thr Asn Asn Glu Phe Arg
225                 230                 235                 240

Val Pro Val Leu Leu Thr Ala Gly Gly Leu Ala Pro Asp Asn Leu Phe
                245                 250                 255

Ala Ile Val Lys Leu Ser Ile Cys His Phe Gly Leu Glu Phe Gly Tyr
                260                 265                 270

Arg Val Ser Phe
```

<210> SEQ ID NO 280
<211> LENGTH: 293
<212> TYPE: PRT
<213> ORGANISM: Ehrlichia ewingii

<400> SEQUENCE: 280

Met Asn Asn Lys Leu Lys Phe Thr Ile Ile Asn Thr Val Leu Val Cys
1 5 10 15

Leu Leu Ser Leu Pro Asn Ile Ser Ser Ser Lys Ala Ile Asn Asn Asn
20 25 30

Ala Lys Lys Tyr Tyr Gly Leu Tyr Ile Ser Gly Gln Tyr Lys Pro Ser
35 40 45

Val Ser Val Phe Ser Asn Phe Ser Val Lys Glu Thr Asn Val Ile Thr
50 55 60

Lys Asn Leu Ile Ala Leu Lys Lys Asp Val Asp Ser Ile Glu Thr Lys
65 70 75 80

Thr Asp Ala Ser Val Gly Ile Ser Asn Pro Ser Asn Phe Thr Ile Pro
85 90 95

Tyr Thr Ala Val Phe Gln Asp Asn Ser Val Asn Phe Asn Gly Thr Ile
100 105 110

Gly Tyr Thr Phe Ala Glu Gly Thr Arg Val Glu Ile Glu Gly Ser Tyr
115 120 125

Glu Glu Phe Asp Val Lys Asn Pro Gly Gly Tyr Thr Leu Ser Asp Ala
130 135 140

Tyr Arg Tyr Phe Ala Leu Ala Arg Glu Met Lys Gly Asn Ser Phe Thr
145 150 155 160

Pro Lys Glu Lys Val Ser Asn Ser Ile Phe His Thr Val Met Arg Asn
165 170 175

Asp Gly Leu Ser Ile Ile Ser Val Ile Val Asn Val Cys Tyr Asp Phe
180 185 190

Ser Leu Asn Asn Leu Ser Ile Ser Pro Tyr Ile Cys Gly Gly Ala Gly
195 200 205

Val Asp Ala Ile Glu Phe Phe Asp Val Leu His Ile Lys Phe Ala Tyr
210 215 220

Gln Ser Lys Leu Gly Ile Ala Tyr Ser Leu Pro Ser Asn Ile Ser Leu
225 230 235 240

Phe Ala Ser Leu Tyr Tyr His Lys Val Met Gly Asn Gln Phe Lys Asn
245 250 255

Leu Asn Val Gln His Val Ala Glu Leu Ala Ser Ile Pro Lys Ile Thr
260 265 270

Ser Ala Val Ala Thr Leu Asn Ile Gly Tyr Phe Gly Gly Glu Ile Gly
275 280 285

Ala Arg Leu Thr Phe
290

<210> SEQ ID NO 281
<211> LENGTH: 294
<212> TYPE: PRT
<213> ORGANISM: Ehrlichia ewingii

<400> SEQUENCE: 281

Met Ala Asn Phe Met Tyr Lys Lys Tyr Lys Leu Met Thr Ala Gly Val
1 5 10 15

Val Leu Phe His Met Leu Phe Leu Pro His Val Ser Phe Ala Lys Asn

```
                20                  25                  30

Thr Asn Ser Asn Lys Leu Gly Leu Tyr Ile Ser Gly Gln Tyr Asn Pro
            35                  40                  45

Ser Val Ser Val Phe Ser Asn Phe Ser Ala Lys Glu Thr Asn Val His
        50                  55                  60

Thr Val Gln Leu Met Ala Leu Lys Lys Asp Ile Asp Ser Ile Glu Val
 65                  70                  75                  80

Asp Thr Gly Asn Ser Ala Gly Ile Ser Lys Pro Gln Asn Phe Thr Val
                85                  90                  95

Leu Tyr Thr Pro Lys Phe Gln Asp Asn Val Ala Gly Leu Ser Gly Ala
            100                 105                 110

Leu Gly Phe Phe Tyr Ser Lys Gly Leu Arg Ile Glu Met Gly Phe Ser
        115                 120                 125

Tyr Glu Lys Phe Asp Ala Lys Asp Leu Gly Tyr Thr Lys Ile Lys
        130                 135                 140

Asp Ala Tyr Arg Tyr Phe Ala Leu Val Arg Glu Met His Val Ser Leu
145                 150                 155                 160

Ile Tyr Pro Lys Asp Asn Asn Thr Gly Thr His Tyr Thr Val Met Arg
                165                 170                 175

Asn Asp Gly Ile Ser Ile Ser Ser Ala Thr Val Asn Gly Cys Tyr Asp
            180                 185                 190

Phe Phe Phe Pro Ser Leu Ser Leu Ser Pro Tyr Met Cys Ile Gly Ile
        195                 200                 205

Gly Ile Asp Ala Ile Glu Phe Leu Asn Ala Leu His Ile Lys Phe Ala
    210                 215                 220

Cys Gln Gly Lys Leu Gly Val Thr Tyr Ser Val Ser Pro Asn Val Asn
225                 230                 235                 240

Leu Phe Ala Asp Gly Tyr Tyr His Lys Val Met Gly Asn Lys Phe Lys
                245                 250                 255

Asn Leu Pro Val Gln Tyr Val Asn Thr Leu Glu Glu Tyr Pro Arg Val
            260                 265                 270

Thr Ser Ala Ile Ala Thr Leu Asp Ile Gly Tyr Leu Gly Gly Glu Ile
        275                 280                 285

Gly Ile Arg Phe Ile Phe
    290

<210> SEQ ID NO 282
<211> LENGTH: 296
<212> TYPE: PRT
<213> ORGANISM: Ehrlichia ewingii

<400> SEQUENCE: 282

Met Gly Asn Ser Met Asn Asn Lys Ser Gln Phe Leu Ile Arg Phe Ile
 1               5                  10                  15

Phe Leu Thr Cys Met Leu Ser Leu Pro Asn Ile Ser Leu Ser Lys Val
                20                  25                  30

Asn Asn Glu Lys His Ser Gly Leu Tyr Ile Ser Gly Gln Tyr Lys Pro
            35                  40                  45

Ser Val Ser Val Phe Ser Asn Phe Ser Val Lys Glu Thr Asn Phe His
        50                  55                  60

Thr Lys His Leu Ile Ala Leu Lys Gln Asp Val Asp Ser Val Glu Ile
 65                  70                  75                  80

Asp Thr Gly Ser Asn Thr Ala Gly Ile Ser Asn Pro Ser Asn Phe Thr
                85                  90                  95
```

Ile Pro Tyr Thr Ala Glu Phe Gln Asp Asn His Thr Asn Cys Asn Gly
                100                 105                 110

Ser Ile Gly Tyr Ala Phe Ala Glu Gly Pro Arg Ile Glu Ile Glu Leu
            115                 120                 125

Ser Tyr Glu Lys Phe Asp Val Lys Asn Pro Thr Gly Tyr Thr Thr Val
        130                 135                 140

Lys Asp Ala Tyr Arg Tyr Phe Ala Leu Ala Arg Glu Ile Asn Ile Ser
145                 150                 155                 160

Leu Phe Gln Pro Lys Gln Lys Glu Gly Ser Gly Ile Tyr His Val Val
                165                 170                 175

Met Lys Asn Asp Gly Leu Ser Ile Leu Ser Asn Ile Val Asn Ile Cys
            180                 185                 190

Tyr Asp Phe Ser Leu Asn Asn Leu Pro Ile Ser Pro Tyr Leu Cys Gly
        195                 200                 205

Gly Met Gly Ile Asn Ala Ile Glu Phe Phe Asp Ala Leu His Val Lys
    210                 215                 220

Phe Ala Tyr Gln Ser Lys Ala Gly Ile Ser Tyr Gln Leu Leu Arg Lys
225                 230                 235                 240

Ile Asn Leu Phe Ile Asp Val Tyr Tyr Gln Val Ile Ser Asn Lys
                245                 250                 255

Phe Lys Asn Leu Lys Val Gln His Val His Glu Leu Lys Asp Asn Pro
            260                 265                 270

Lys Val Thr Ser Ala Val Ala Thr Leu Asp Ile Ala Tyr Phe Gly Ser
        275                 280                 285

Glu Ala Gly Ile Arg Ile Ile Phe
    290                 295

<210> SEQ ID NO 283
<211> LENGTH: 299
<212> TYPE: PRT
<213> ORGANISM: Ehrlichia ewingii

<400> SEQUENCE: 283

Met Asn Ser Lys Ser Lys Phe Phe Thr Ile Cys Thr Ser Leu Ile Cys
1               5                   10                  15

Leu Leu Ser Ser Pro Asn Thr Ser Leu Ser Asn Phe Ile Gly Asn Ser
            20                  25                  30

Thr Lys His Ser Gly Leu Tyr Val Ser Gly Gln Tyr Lys Pro Ser Val
        35                  40                  45

Ser Ile Phe Ser Lys Phe Ser Val Lys Glu Thr Asn Thr His Thr Val
    50                  55                  60

Gln Leu Val Ala Leu Lys Lys Asp Val Asn Ser Ile Ser Met Asn Ile
65                  70                  75                  80

Ser Asn Gly Ala Thr Gly Ile Ser Lys Ala Thr Asn Phe Asn Leu Pro
                85                  90                  95

Tyr Val Ala Glu Phe Gln Asp Asn Ala Phe Asn Phe Ser Gly Ala Ile
            100                 105                 110

Gly Tyr Ser Leu Phe Glu Gln Leu Asn Ile Glu Val Glu Gly Ser Tyr
        115                 120                 125

Glu Glu Phe Asp Ala Lys Asn Pro Gly Gly Tyr Ile Leu Asn Asp Ala
    130                 135                 140

Phe Arg Tyr Phe Ala Leu Ala Arg Glu Met Gly Gln Glu Lys Asn Asp
145                 150                 155                 160

Asn Lys His Leu Ser Pro Lys Glu Glu His Asp Ile Ser Lys Thr Tyr
                165                 170                 175

```
Tyr Thr Val Met Arg Asn Asn Gly Leu Ser Ile Leu Ser Ile Met Ile
            180                 185                 190

Asn Gly Cys Tyr Asn Leu Pro Leu Asn Asp Leu Ser Ile Ser Pro Tyr
        195                 200                 205

Phe Cys Thr Gly Ile Gly Val Asp Ala Ile Glu Phe Phe Asp Ala Leu
    210                 215                 220

His Leu Lys Leu Ala Leu Gln Ser Lys Ile Gly Ala Thr Tyr Gln Leu
225                 230                 235                 240

Ser Asp Asn Ile Ser Leu Phe Thr Asn Gly Tyr Tyr His Gln Val Ile
                245                 250                 255

Gly Asp Gln Phe Lys Asn Leu Lys Val Gln Tyr Ile Gly Glu Leu Lys
            260                 265                 270

Glu Asn Pro Lys Ile Thr Ser Ala Val Ala Thr Leu Asn Val Gly Tyr
        275                 280                 285

Phe Gly Gly Glu Ile Gly Val Arg Leu Thr Leu
    290                 295

<210> SEQ ID NO 284
<211> LENGTH: 281
<212> TYPE: PRT
<213> ORGANISM: Ehrlichia ewingii

<400> SEQUENCE: 284

Met Asn Asn Lys Arg Asn Phe Phe Leu Ile Gly Met Ser Leu Leu Ile
 1               5                  10                  15

Asn Leu Leu Leu Pro Ile Asp Ala Ser Ser Met Glu Val His Asn Tyr
            20                  25                  30

Thr His Phe Lys Pro Arg Leu Tyr Ile Ser Gly Gln Tyr Arg Pro Gly
        35                  40                  45

Val Ser His Phe Ser Lys Phe Ser Val Lys Glu Thr His Cys Asn Thr
    50                  55                  60

Val Gln Leu Val Gly Leu Thr Lys Asp Ile Lys Val Thr Asn Asn Ser
65                  70                  75                  80

Ser Ile Asn Thr Asn Thr Ser Phe Asn Phe Pro Tyr Val Ala Glu Phe
                85                  90                  95

Gln Asp Asn Ala Met Ser Phe Ser Gly Ala Ile Gly Cys Phe Tyr Ser
            100                 105                 110

Glu Asn Phe Arg Ile Glu Val Glu Ala Ser Tyr Glu Glu Phe Asp Val
        115                 120                 125

Lys Asn Pro Glu Gly Ser Thr Thr Asp Ser Tyr Arg Tyr Phe Ala Leu
    130                 135                 140

Ala Arg Gly Met Asp Gly Asn Asn Ile Pro Thr Ser Gln Lys Phe Thr
145                 150                 155                 160

Val Met Arg Asn Asp Gly Leu Leu Ile Ser Ser Val Met Ile Asn Gly
                165                 170                 175

Cys Tyr Asn Val Ile Leu Asn Asp Ile Gln Ala Glu Pro Tyr Ile Cys
            180                 185                 190

Ala Gly Leu Gly Gly Asp Phe Ile Glu Phe Phe Asn Gly Phe His Val
        195                 200                 205

Lys Leu Ala Tyr Gln Gly Lys Val Gly Ile Ser Tyr Gln Ile Phe Pro
    210                 215                 220

Glu Val Arg Leu Phe Ile Asp Gly Tyr Tyr His Lys Val Lys Gly Asn
225                 230                 235                 240

Lys Phe Lys Asn Leu His Val Gln His Val Gly Ala Leu Ala Ala Leu
```

```
                        245                 250                 255
Pro Lys Val Thr Ser Ala Val Ala Thr Leu Asn Ile Gly Tyr Phe Gly
                260                 265                 270
Cys Glu Ala Gly Val Arg Phe Ile Phe
                275                 280
```

<210> SEQ ID NO 285
<211> LENGTH: 288
<212> TYPE: PRT
<213> ORGANISM: Ehrlichia ewingii

<400> SEQUENCE: 285

```
Met Asn Cys Lys Arg Phe Phe Ile Ala Ser Ala Leu Ile Ser Leu Met
1               5                   10                  15
Ser Phe Leu Pro Ser Val Ser Phe Ser Glu Ser Ile His Glu Asp Asn
                20                  25                  30
Ile Asn Gly Asn Phe Tyr Ile Ser Ala Lys Tyr Met Pro Ser Ala Ser
                35                  40                  45
His Phe Gly Val Phe Ser Val Lys Glu Glu Lys Asn Thr Thr Thr Gly
        50                  55                  60
Val Phe Gly Leu Lys Gln Asp Trp Asp Gly Ala Thr Ile Lys Asp Ala
65                  70                  75                  80
Ser Ser Ser His Thr Ile Asp Pro Ser Thr Ile Phe Ser Ile Ser Asn
                85                  90                  95
Tyr Ser Phe Lys Tyr Glu Asn Asn Pro Phe Leu Gly Phe Ala Gly Ala
                100                 105                 110
Ile Gly Tyr Ser Met Gly Gly Pro Arg Val Glu Phe Glu Val Ser Tyr
            115                 120                 125
Glu Ile Phe Asp Val Lys Asn Gln Gly Asn Ser Tyr Lys Asn Asp Ala
130                 135                 140
His Lys Tyr Cys Ala Leu Ser Arg His Thr Gly Gly Met Pro Gln Ala
145                 150                 155                 160
Gly His Gln Asn Lys Phe Val Phe Leu Lys Asn Glu Gly Leu Leu Asp
                165                 170                 175
Ile Ser Leu Met Ile Asn Ala Cys Tyr Asp Ile Thr Ile Asp Ser Met
                180                 185                 190
Pro Phe Ser Pro Tyr Ile Cys Ala Gly Ile Gly Ser Asp Leu Val Ser
                195                 200                 205
Met Phe Glu Thr Thr Asn Pro Lys Ile Ser Tyr Gln Gly Lys Leu Gly
        210                 215                 220
Val Ser Tyr Ser Ile Ser Pro Glu Ala Ser Val Phe Val Gly Gly His
225                 230                 235                 240
Phe His Arg Val Ile Gly Asn Glu Phe Lys Asp Ile Pro Ala Ile Thr
                245                 250                 255
Pro Ala Gly Ala Thr Glu Ile Lys Gly Thr Gln Phe Thr Thr Val Thr
                260                 265                 270
Leu Asn Ile Cys His Phe Gly Leu Glu Leu Gly Gly Arg Phe Thr Phe
                275                 280                 285
```

<210> SEQ ID NO 286
<211> LENGTH: 287
<212> TYPE: PRT
<213> ORGANISM: Ehrlichia ewingii

<400> SEQUENCE: 286

Met Lys Tyr Lys Lys Thr Phe Thr Val Thr Ala Leu Val Leu Leu Thr

-continued

```
1               5                   10                  15

Ser Phe Thr His Phe Ile Pro Phe Tyr Ser Pro Ala Arg Ala Ser Thr
            20                  25                  30

Ile His Asn Phe Tyr Ile Ser Gly Lys Tyr Met Pro Thr Ala Ser His
        35                  40                  45

Phe Gly Ile Phe Ser Ala Lys Glu Glu Gln Ser Phe Thr Lys Val Leu
    50                  55                  60

Val Gly Leu Asp Gln Arg Leu Ser His Asn Ile Ile Asn Asn Asn Asp
65                  70                  75                  80

Thr Ala Lys Ser Leu Lys Val Gln Asn Tyr Ser Phe Lys Tyr Lys Asn
                85                  90                  95

Asn Pro Phe Leu Gly Phe Ala Gly Ala Ile Gly Tyr Ser Ile Gly Asn
            100                 105                 110

Ser Arg Ile Glu Leu Glu Val Ser His Glu Ile Phe Asp Thr Lys Asn
        115                 120                 125

Pro Gly Asn Asn Tyr Leu Asn Asp Ser His Lys Tyr Cys Ala Leu Ser
    130                 135                 140

His Gly Ser His Ile Cys Ser Asp Gly Asn Ser Gly Asp Trp Tyr Thr
145                 150                 155                 160

Ala Lys Thr Asp Lys Phe Val Leu Leu Lys Asn Glu Gly Leu Leu Asp
                165                 170                 175

Val Ser Phe Met Leu Asn Ala Cys Tyr Asp Ile Thr Thr Glu Lys Met
            180                 185                 190

Pro Phe Ser Pro Tyr Ile Cys Ala Gly Ile Gly Thr Asp Leu Ile Ser
        195                 200                 205

Met Phe Glu Thr Thr Gln Asn Lys Ile Ser Tyr Gln Gly Lys Leu Gly
    210                 215                 220

Leu Asn Tyr Thr Ile Asn Ser Arg Val Ser Val Phe Ala Gly Gly His
225                 230                 235                 240

Phe His Lys Val Ile Gly Asn Glu Phe Lys Gly Ile Pro Thr Leu Leu
                245                 250                 255

Pro Asp Gly Ser Asn Ile Lys Val Gln Gln Ser Ala Thr Val Thr Leu
            260                 265                 270

Asp Val Cys His Phe Gly Leu Glu Ile Gly Ser Arg Phe Phe Phe
        275                 280                 285

<210> SEQ ID NO 287
<211> LENGTH: 271
<212> TYPE: PRT
<213> ORGANISM: Ehrlichia ewingii

<400> SEQUENCE: 287

Met Asn Tyr Lys Lys Phe Val Val Gly Val Ala Leu Ala Thr Leu Leu
1               5                   10                  15

Ser Phe Leu Pro Asp Asn Ser Phe Ser Asp Ala Asn Val Pro Glu Gly
            20                  25                  30

Arg Lys Gly Phe Tyr Val Gly Thr Gln Tyr Lys Val Gly Val Pro Asn
        35                  40                  45

Phe Ser Asn Phe Ser Ala Glu Glu Thr Leu Pro Gly Leu Thr Lys Ser
    50                  55                  60

Ile Phe Ala Leu Gly Leu Asp Lys Ser Ser Ile Ser Asp His Ala Gly
65                  70                  75                  80

Phe Thr Gln Ala Tyr Asn Pro Thr Tyr Ala Ser Asn Phe Ala Gly Phe
                85                  90                  95
```

-continued

```
Gly Gly Val Ile Gly Tyr Tyr Val Asn Asp Phe Arg Val Glu Phe Glu
            100                 105                 110

Gly Ala Tyr Glu Asn Phe Glu Pro Glu Arg Gln Trp Tyr Pro Glu Gly
        115                 120                 125

Gly Glu Ser His Lys Phe Phe Ala Leu Ser Arg Glu Ser Thr Val Gln
    130                 135                 140

Asp Asn Lys Phe Ile Val Leu Glu Asn Asp Gly Val Ile Asp Lys Ser
145                 150                 155                 160

Leu Asn Val Asn Phe Cys Tyr Asp Ile Ala His Gly Ser Ile Pro Leu
                165                 170                 175

Ala Pro Tyr Met Cys Ala Gly Val Gly Ala Asp Tyr Ile Lys Phe Leu
            180                 185                 190

Gly Ile Ser Leu Pro Lys Phe Ser Tyr Gln Val Lys Phe Gly Val Asn
        195                 200                 205

Tyr Pro Val Ser Val Asn Val Met Leu Phe Gly Gly Gly Tyr Tyr His
    210                 215                 220

Lys Val Ile Gly Asn Arg Tyr Glu Arg Val Glu Ile Ala Tyr His Pro
225                 230                 235                 240

Ala Thr Leu Thr Asn Val Pro Lys Thr Thr Ser Ala Ser Ala Thr Leu
                245                 250                 255

Asp Thr Asp Tyr Phe Gly Trp Glu Val Gly Met Arg Phe Thr Leu
            260                 265                 270
```

<210> SEQ ID NO 288
<211> LENGTH: 278
<212> TYPE: PRT
<213> ORGANISM: Ehrlichia ewingii

<400> SEQUENCE: 288

```
Met Arg Tyr Arg Ile Ser Val Ile Ile Leu Met Leu Leu Leu Val Pro
 1               5                  10                  15

Cys Cys Cys Phe Ser Gly Ser Leu Asp Val Ser Asp Ser Leu Asn Ser
            20                  25                  30

Arg Leu Lys Pro Val Phe Leu Gly Ile Ser Tyr Lys Leu Ser Ala Pro
        35                  40                  45

Leu Phe Ser Ser Phe Ser Ile Gly Glu Thr Tyr Arg Ile Asn Gly Val
    50                  55                  60

Lys Thr Asp Arg Val Val Gly Leu Lys Ser Asp Ile Leu Leu Asp Ala
 65                  70                  75                  80

Asp Lys Ala Met Lys Asp Phe Asn Asn Phe Asn Phe Ser Glu Glu Tyr
                85                  90                  95

Val Pro Lys Tyr Asp Asn Asn Ile Phe Gly Leu Ser Phe Ile Phe Gly
            100                 105                 110

Tyr Ser Phe Arg Asn Leu Arg Val Glu Leu Glu Gly Ser Tyr Lys Lys
        115                 120                 125

Phe Asp Val Ile Asp Thr Arg Asn His Leu Val Asp Asn Asn Tyr Arg
    130                 135                 140

His Ile Ala Leu Val Arg Ser Asn Pro Pro Thr Leu Tyr Asp Tyr Phe
145                 150                 155                 160

Val Leu Lys Asn Asp Gly Val Glu Phe Tyr Ser Thr Ile Leu Asn Ile
                165                 170                 175

Cys Tyr Asp Phe Ala Val Asp Thr Asn Ile Val Pro Phe Ser Cys Val
            180                 185                 190

Gly Ile Gly Glu Asp Ile Ile Lys Ile Phe Asp Ser Ile Arg Phe Lys
        195                 200                 205
```

```
Pro Ser Phe Asn Ser Lys Leu Gly Ile Asn Tyr Leu Met Ser Gln Asp
    210                 215                 220

Met Leu Leu Phe Phe Asp Val Tyr Tyr His Arg Val Val Gly Asn Glu
225                 230                 235                 240

Tyr Asn Asn Ile Pro Val Gln Tyr Val Ser Leu Pro Asn Pro Leu Asn
                245                 250                 255

Ile Ser Thr Ala Ala Lys Leu Asp Met Glu Tyr Phe Gly Ala Glu Ile
            260                 265                 270

Gly Ile Lys Val Phe Val
        275

<210> SEQ ID NO 289
<211> LENGTH: 281
<212> TYPE: PRT
<213> ORGANISM: Ehrlichia ewingii

<400> SEQUENCE: 289

Met Asn Tyr Lys Lys Val Phe Ile Thr Ser Ala Leu Ile Ser Leu Ile
1               5                   10                  15

Ser Ser Leu Pro Gly Val Ser Phe Ser Asp Pro Ala Gly Ser Gly Ile
            20                  25                  30

Asn Gly Asn Phe Tyr Ile Ser Gly Lys Tyr Met Pro Ser Ala Ser His
        35                  40                  45

Phe Gly Val Phe Ser Ala Lys Glu Glu Arg Asn Thr Thr Val Gly Val
    50                  55                  60

Phe Gly Leu Lys Gln Asn Trp Asp Gly Ser Ala Ile Ser Asn Ser Ser
65                  70                  75                  80

Pro Asn Asp Val Phe Thr Val Ser Asn Tyr Ser Phe Lys Tyr Glu Asn
                85                  90                  95

Asn Pro Phe Leu Gly Phe Ala Gly Ala Ile Gly Tyr Ser Met Asp Gly
            100                 105                 110

Pro Arg Ile Glu Leu Glu Val Ser Tyr Glu Thr Phe Asp Val Lys Asn
        115                 120                 125

Gln Gly Asn Asn Tyr Lys Asn Glu Ala His Arg Tyr Cys Ala Leu Ser
    130                 135                 140

His Asn Ser Ala Ala Asp Met Ser Ser Ala Ser Asn Asn Phe Val Phe
145                 150                 155                 160

Leu Lys Asn Glu Gly Leu Leu Asp Ile Ser Phe Met Leu Asn Ala Cys
                165                 170                 175

Tyr Asp Val Val Gly Glu Gly Ile Pro Phe Ser Pro Tyr Ile Cys Ala
            180                 185                 190

Gly Ile Gly Thr Asp Leu Val Ser Met Phe Glu Ala Thr Asn Pro Lys
        195                 200                 205

Ile Ser Tyr Gln Gly Lys Leu Gly Leu Ser Tyr Ser Ile Ser Pro Glu
    210                 215                 220

Ala Ser Val Phe Ile Gly Gly His Phe His Lys Val Ile Gly Asn Glu
225                 230                 235                 240

Phe Arg Asp Ile Pro Thr Ile Pro Thr Gly Ser Thr Leu Ala Gly
                245                 250                 255

Lys Gly Asn Tyr Pro Ala Ile Val Ile Leu Asp Val Cys His Phe Gly
            260                 265                 270

Ile Glu Leu Gly Gly Arg Phe Ala Phe
        275                 280
```

```
<210> SEQ ID NO 290
<211> LENGTH: 297
<212> TYPE: PRT
<213> ORGANISM: Ehrlichia ewingii

<400> SEQUENCE: 290
```

Met Glu Asn Leu Met Asn Lys Lys Asn Lys Phe Phe Thr Ile Ser Thr
1               5                   10                  15

Ala Met Val Cys Leu Leu Leu Leu Pro Gly Ile Ser Phe Ser Glu Thr
            20                  25                  30

Ile Asn Asn Ser Ala Lys Lys Gln Pro Gly Leu Tyr Ile Ser Gly Gln
        35                  40                  45

Tyr Lys Pro Ser Val Ser Val Phe Ser Asn Phe Ser Val Lys Glu Thr
    50                  55                  60

Asn Val Pro Thr Lys Gln Leu Ile Ala Leu Lys Lys Asp Ile Asn Ser
65                  70                  75                  80

Val Ala Val Gly Ser Asn Ala Thr Thr Gly Ile Ser Asn Pro Gly Asn
                85                  90                  95

Phe Thr Ile Pro Tyr Thr Ala Glu Phe Gln Asp Asn Val Ala Asn Phe
            100                 105                 110

Asn Gly Ala Val Gly Tyr Ser Phe Pro Asp Ser Leu Arg Ile Glu Ile
        115                 120                 125

Glu Gly Phe His Glu Lys Phe Asp Val Lys Asn Pro Gly Gly Tyr Thr
    130                 135                 140

Gln Val Lys Asp Ala Tyr Arg Tyr Phe Ala Leu Ala Arg Asp Leu Lys
145                 150                 155                 160

Asp Gly Phe Phe Glu Pro Lys Ala Glu Asp Thr Gly Val Tyr His Thr
                165                 170                 175

Val Met Lys Asn Asp Gly Leu Ser Ile Leu Ser Thr Met Val Asn Val
            180                 185                 190

Cys Tyr Asp Phe Ser Val Asp Glu Leu Pro Val Leu Pro Tyr Ile Cys
        195                 200                 205

Ala Gly Met Gly Ile Asn Ala Ile Glu Phe Phe Asp Ala Leu His Val
    210                 215                 220

Lys Phe Ala Tyr Gln Gly Lys Leu Gly Ile Ser Tyr Gln Leu Phe Thr
225                 230                 235                 240

Lys Val Asn Leu Phe Leu Asp Gly Tyr Tyr His Gln Val Ile Gly Asn
                245                 250                 255

Gln Phe Lys Asn Leu Asn Val Asn His Val Tyr Thr Leu Lys Glu Ser
            260                 265                 270

Pro Lys Val Thr Ser Ala Val Ala Thr Leu Asp Ile Ala Tyr Phe Gly
        275                 280                 285

Gly Glu Val Gly Ile Arg Phe Thr Phe
    290                 295

```
<210> SEQ ID NO 291
<211> LENGTH: 283
<212> TYPE: PRT
<213> ORGANISM: Ehrlichia ewingii

<400> SEQUENCE: 291
```

Met Asn Tyr Lys Lys Ile Phe Val Ser Ser Ala Leu Ile Ser Leu Met
1               5                   10                  15

Ser Ile Leu Pro Tyr Gln Ser Phe Ala Asp Pro Val Thr Ser Asn Asp
            20                  25                  30

Thr Gly Ile Asn Asp Ser Arg Glu Gly Phe Tyr Ile Ser Val Lys Tyr

```
                35                  40                  45
Asn Pro Ser Ile Ser His Phe Arg Lys Phe Ser Ala Glu Glu Ala Pro
 50                  55                  60

Ile Asn Gly Asn Thr Ser Ile Thr Lys Lys Val Phe Gly Leu Lys Lys
 65                  70                  75                  80

Asp Gly Asp Ile Ala Gln Ser Ala Asn Phe Asn Arg Thr Asp Pro Ala
                 85                  90                  95

Leu Glu Phe Gln Asn Asn Leu Ile Ser Gly Phe Ser Gly Ser Ile Gly
                100                 105                 110

Tyr Ala Met Asp Gly Pro Arg Ile Glu Leu Glu Ala Ala Tyr Gln Lys
                115                 120                 125

Phe Asp Ala Lys Asn Pro Asp Asn Asn Asp Thr Asn Ser Gly Asp Tyr
130                 135                 140

Tyr Lys Tyr Phe Gly Leu Ser Arg Glu Asp Ala Ile Ala Asp Lys Lys
145                 150                 155                 160

Tyr Val Val Leu Lys Asn Glu Gly Ile Thr Phe Met Ser Leu Met Val
                165                 170                 175

Asn Thr Cys Tyr Asp Ile Thr Ala Glu Gly Val Pro Phe Ile Pro Tyr
                180                 185                 190

Ala Cys Ala Gly Val Gly Ala Asp Leu Ile Asn Val Phe Lys Asp Phe
                195                 200                 205

Asn Leu Lys Phe Ser Tyr Gln Gly Lys Ile Gly Ile Ser Tyr Pro Ile
210                 215                 220

Thr Pro Glu Val Ser Ala Phe Ile Gly Gly Tyr Tyr His Gly Val Ile
225                 230                 235                 240

Gly Asn Asn Phe Asn Lys Ile Pro Val Ile Thr Pro Val Val Leu Glu
                245                 250                 255

Gly Ala Pro Gln Thr Thr Ser Ala Leu Val Thr Ile Asp Thr Gly Tyr
                260                 265                 270

Phe Gly Gly Glu Val Gly Val Arg Phe Thr Phe
                275                 280

<210> SEQ ID NO 292
<211> LENGTH: 280
<212> TYPE: PRT
<213> ORGANISM: Ehrlichia ewingii

<400> SEQUENCE: 292

Met Asn Cys Lys Lys Phe Phe Ile Thr Thr Ala Leu Ala Leu Pro Met
  1                   5                  10                  15

Ser Phe Leu Pro Gly Ile Leu Leu Ser Glu Pro Val Gln Asp Asp Ser
                 20                  25                  30

Val Ser Gly Asn Phe Tyr Ile Ser Gly Lys Tyr Met Pro Ser Ala Ser
                 35                  40                  45

His Phe Gly Val Phe Ser Ala Lys Glu Glu Lys Asn Pro Thr Val Ala
                 50                  55                  60

Leu Tyr Gly Leu Lys Gln Asp Trp Asn Gly Val Ser Ala Ser Ser His
 65                  70                  75                  80

Ala Asp Ala Asp Phe Asn Asn Lys Gly Tyr Ser Phe Lys Tyr Glu Asn
                 85                  90                  95

Asn Pro Phe Leu Gly Phe Ala Gly Ala Ile Gly Tyr Ser Met Gly Gly
                100                 105                 110

Pro Arg Ile Glu Phe Glu Val Ser Tyr Glu Thr Phe Asp Val Lys Asn
                115                 120                 125
```

```
Gln Gly Gly Asn Tyr Lys Asn Asp Ala His Arg Tyr Cys Ala Leu Asp
    130                 135                 140

Arg Lys Ala Ser Ser Thr Asn Ala Thr Ala Ser His Tyr Val Leu Leu
145                 150                 155                 160

Lys Asn Glu Gly Leu Leu Asp Ile Ser Leu Met Leu Asn Ala Cys Tyr
                165                 170                 175

Asp Val Val Ser Glu Gly Ile Pro Phe Ser Pro Tyr Ile Cys Ala Gly
            180                 185                 190

Val Gly Thr Asp Leu Ile Ser Met Phe Glu Ala Ile Asn Pro Lys Ile
        195                 200                 205

Ser Tyr Gln Gly Lys Leu Gly Leu Ser Tyr Ser Ile Asn Pro Glu Ala
    210                 215                 220

Ser Val Phe Val Gly Gly His Phe His Lys Val Ala Gly Asn Glu Phe
225                 230                 235                 240

Arg Asp Ile Ser Thr Leu Lys Ala Phe Ala Thr Pro Ser Ser Ala Ala
                245                 250                 255

Thr Pro Asp Leu Ala Thr Val Thr Leu Ser Val Cys His Phe Gly Val
            260                 265                 270

Glu Leu Gly Gly Arg Phe Asn Phe
        275                 280

<210> SEQ ID NO 293
<211> LENGTH: 286
<212> TYPE: PRT
<213> ORGANISM: Ehrlichia ewingii

<400> SEQUENCE: 293

Met Asn Cys Glu Lys Phe Phe Ile Thr Thr Ala Leu Thr Leu Leu Met
 1               5                  10                  15

Ser Phe Leu Pro Gly Ile Ser Leu Ser Asp Pro Val Gln Asp Asp Asn
            20                  25                  30

Ile Ser Gly Asn Phe Tyr Ile Ser Gly Lys Tyr Met Pro Ser Ala Ser
        35                  40                  45

His Phe Gly Val Phe Ser Ala Lys Glu Glu Arg Asn Thr Thr Val Gly
    50                  55                  60

Val Phe Gly Ile Glu Gln Asp Trp Asp Arg Cys Val Ile Ser Arg Thr
65                  70                  75                  80

Thr Leu Ser Asp Ile Phe Thr Val Pro Asn Tyr Ser Phe Lys Tyr Glu
                85                  90                  95

Asn Asn Leu Phe Ser Gly Phe Ala Gly Ala Ile Gly Tyr Ser Met Asp
            100                 105                 110

Gly Pro Arg Ile Glu Leu Glu Val Ser Tyr Glu Ala Phe Asp Val Lys
        115                 120                 125

Asn Gln Gly Asn Asn Tyr Lys Asn Glu Ala His Arg Tyr Tyr Ala Leu
    130                 135                 140

Ser His Leu Leu Gly Thr Glu Thr Gln Ile Asp Gly Ala Gly Ser Ala
145                 150                 155                 160

Ser Val Phe Leu Ile Asn Glu Gly Leu Leu Asp Lys Ser Phe Met Leu
                165                 170                 175

Asn Ala Cys Tyr Asp Val Ile Ser Glu Gly Ile Pro Phe Ser Pro Tyr
            180                 185                 190

Ile Cys Ala Gly Ile Gly Ile Asp Leu Val Ser Met Phe Glu Ala Ile
        195                 200                 205

Asn Pro Lys Ile Ser Tyr Gln Gly Lys Leu Gly Leu Ser Tyr Pro Ile
    210                 215                 220
```

```
Ser Pro Glu Ala Ser Val Phe Ile Gly Gly His Phe His Lys Val Ile
225                 230                 235                 240

Gly As

<213> ORGANISM: Ehrlichia ewingii

<400> SEQUENCE: 295

Met Asn Cys Lys Lys Phe Phe Ile Thr Thr Thr Leu Val Ser Leu Met
1               5                   10                  15

Ser Phe Leu Pro Gly Ile Ser Phe Ser Asp Ala Val Gln Asn Asp Asn
            20                  25                  30

Val Gly Gly Asn Phe Tyr Ile Ser Gly Lys Tyr Val Pro Ser Val Ser
        35                  40                  45

His Phe Gly Val Phe Ser Ala Lys Gln Glu Arg Asn Thr Thr Thr Gly
    50                  55                  60

Val Phe Gly Leu Lys Gln Asp Trp Asp Gly Ser Thr Ile Ser Lys Asn
65                  70                  75                  80

Ser Pro Glu Asn Thr Phe Asn Val Pro Asn Tyr Ser Phe Lys Tyr Glu
                85                  90                  95

Asn Asn Pro Phe Leu Gly Phe Ala Gly Ala Val Gly Tyr Leu Met Asn
            100                 105                 110

Gly Pro Arg Ile Glu Leu Glu Met Ser Tyr Glu Thr Phe Asp Val Lys
        115                 120                 125

Asn Gln Gly Asn Asn Tyr Lys Asn Asp Ala His Lys Tyr Tyr Ala Leu
    130                 135                 140

Thr His Asn Ser Gly Gly Lys Leu Ser Asn Ala Gly Asp Lys Phe Val
145                 150                 155                 160

Phe Leu Lys Asn Glu Gly Leu Leu Asp Ile Ser Leu Met Leu Asn Ala
                165                 170                 175

Cys Tyr Asp Val Ile Ser Glu Gly Ile Pro Phe Ser Pro Tyr Ile Cys
            180                 185                 190

Ala Gly Val Gly Thr Asp Leu Ile Ser Met Phe Glu Ala Ile Asn Pro
        195                 200                 205

Lys Ile Ser Tyr Gln Gly Lys Leu Gly Leu Ser Tyr Ser Ile Ser Pro
    210                 215                 220

Glu Ala Ser Val Phe Val Gly Gly His Phe His Lys Val Ile Gly Asn
225                 230                 235                 240

Glu Phe Arg Asp Ile Pro Ala Met Ile Pro Ser Thr Ser Thr Leu Thr
                245                 250                 255

Gly Asn His Phe Thr Ile Val Thr Leu Ser Val Cys His Phe Gly Val
            260                 265                 270

Glu Leu Gly Gly Arg Phe Asn Phe
        275                 280

<210> SEQ ID NO 296
<211> LENGTH: 298
<212> TYPE: PRT
<213> ORGANISM: Ehrlichia ewingii

<400> SEQUENCE: 296

Met Asn His Lys Ser Met Leu Phe Thr Ile Gly Thr Ala Leu Ile Ser
1               5                   10                  15

Leu Leu Ser Leu Pro Asn Val Ser Phe Ser Gly Ile Ile Asn Asn Asn
            20                  25                  30

Ala Asn Asn Leu Gly Ile Tyr Ile Ser Gly Gln Tyr Lys Pro Ser Val
        35                  40                  45

Ser Val Phe Ser Asn Phe Ser Val Lys Glu Thr Asn Phe Thr Thr Gln
    50                  55                  60

Gln Leu Val Ala Leu Lys Lys Asp Ile Asp Ser Val Asp Ile Ser Thr

```
 65                  70                  75                  80

Asn Ala Asp Ser Gly Ile Asn Asn Pro Gln Asn Phe Thr Ile Pro Tyr
                85                  90                  95

Ile Pro Lys Phe Gln Asp Asn Ala Ala Ser Phe Ser Gly Ala Leu Gly
            100                 105                 110

Phe Phe Tyr Ala Arg Gly Leu Arg Leu Glu Met Glu Gly Ser Tyr Glu
        115                 120                 125

Glu Phe Asp Val Lys Asn Pro Gly Gly Tyr Thr Lys Val Lys Asp Ala
    130                 135                 140

Tyr Arg Tyr Phe Ala Leu Ala Arg Glu Met Gln Ser Gly Gln Thr Cys
145                 150                 155                 160

Pro Lys His Lys Glu Thr Ser Gly Ile Gln Pro His Gly Ile Tyr His
                165                 170                 175

Thr Val Met Arg Asn Asp Gly Val Ser Ile Ser Ser Val Ile Ile Asn
            180                 185                 190

Gly Cys Tyr Asn Phe Thr Leu Ser Asn Leu Pro Ile Ser Pro Tyr Met
        195                 200                 205

Cys Val Gly Met Gly Ile Asp Ala Ile Gln Phe Phe Asp Ser Leu His
    210                 215                 220

Ile Lys Phe Ala His Gln Ser Lys Leu Gly Ile Thr Tyr Pro Leu Ser
225                 230                 235                 240

Ser Asn Val His Leu Phe Ala Asp Ser Tyr Tyr His Lys Val Ile Gly
                245                 250                 255

Asn Lys Phe Lys Asn Leu Arg Val Gln His Val Tyr Glu Leu Gln Gln
            260                 265                 270

Val Pro Lys Val Thr Ser Ala Val Ala Thr Leu Asp Ile Gly Tyr Phe
        275                 280                 285

Gly Gly Glu Val Gly Val Arg Phe Ile Leu
    290                 295

<210> SEQ ID NO 297
<211> LENGTH: 298
<212> TYPE: PRT
<213> ORGANISM: Ehrlichia ewingii

<400> SEQUENCE: 297

Met Ile Leu Ile Asn Met Lys Leu Phe Tyr His Leu Asp Asn Ile Met
 1              5                   10                  15

Thr Lys Phe Ser Ala Ile Gly Ile Val Leu Ser Leu Val Thr Leu Phe
            20                  25                  30

Ala Cys Asn Val Phe Ala Ser Pro Ile Pro Ile Asp Phe Ser Asn Glu
        35                  40                  45

Ser Glu Thr Ala Gly Phe Tyr Ala Ser Gly His Tyr Asn Ile Gln Phe
     50                  55                  60

Pro Arg Phe Ser Pro Ile Ser Val Lys Tyr Lys Thr Asp Glu Asn Thr
 65                  70                  75                  80

Glu Lys Glu Leu Thr Leu Phe Thr Leu Lys Glu Ser Thr Asp Thr Pro
                85                  90                  95

Thr Phe Lys Gln Lys Ser Glu Phe Asn Asp Lys Lys Gly Tyr Ser Pro
            100                 105                 110

Ile Tyr Asn Arg Asn Tyr Thr Gly Phe Ser Gly Ala Ile Gly Tyr Ser
        115                 120                 125

Gly Gly Gly Leu Arg Val Glu Leu Glu Gly Ala Phe Thr Arg Phe Asp
    130                 135                 140
```

```
Val Asp Lys Gln Lys Tyr Lys Lys Asp Asn Tyr Arg Tyr Phe Ala Leu
145                 150                 155                 160

Cys Lys Lys Asp Ser Ile Glu Ser Thr Asp Asn Ser Asn Gly Asn His
                165                 170                 175

Val Val Met Lys Asn Glu Gly Phe Arg Val Ile Ser Leu Thr Phe Asn
            180                 185                 190

Ala Cys Tyr Asp Met Ile Val Ser Asn Ser Ser Leu Val Pro Ser Ala
        195                 200                 205

Cys Ile Gly Ile Gly Gln Gly Ile Thr Asn Phe Leu Gly Gly Thr Asn
    210                 215                 220

Ile His Thr Leu Phe Lys Ala Lys Leu Gly Leu Gly Phe Leu Ile Ser
225                 230                 235                 240

Pro Lys Thr Val Ile Phe Ala Asn Gly Tyr Tyr Val Lys Thr Lys Asp
                245                 250                 255

Asn Ser Phe Thr Asn Leu Ser Val Gln Tyr Pro Leu Glu Leu Lys Glu
            260                 265                 270

Ala Pro Lys His Ile Asp Pro Ile Ala Cys Phe Asn Ala Asp Asn Tyr
        275                 280                 285

Gly Gly Glu Val Gly Leu Arg Phe Ile Leu
    290                 295

<210> SEQ ID NO 298
<211> LENGTH: 284
<212> TYPE: PRT
<213> ORGANISM: Ehrlichia ewingii

<400> SEQUENCE: 298

Met Ser Lys Arg Ser Asn Arg Lys Phe Val Leu Trp Val Met Leu Ile
 1               5                  10                  15

Leu Phe Thr Pro His Ile Ser Leu Ala Ser Val Leu Asn Asp His Asn
            20                  25                  30

Ser Met Tyr Val Gly Ile Gln Tyr Lys Pro Ala Arg Gln His Leu Ser
        35                  40                  45

Lys Leu Leu Ile Lys Glu Ser Ala Ala Asn Thr Val Glu Val Phe Gly
    50                  55                  60

Leu Lys Lys Asp Leu Leu Asn Asp Leu Leu Thr Gly Ile Lys Asp Asn
65                  70                  75                  80

Thr Asn Phe Asn Ile Lys Tyr Asn Pro Tyr Tyr Glu Asn Asn Arg Leu
                85                  90                  95

Gly Phe Ser Gly Ile Phe Gly Tyr Tyr Tyr Asn Lys Asn Phe Arg Ile
            100                 105                 110

Glu Ser Glu Leu Ser Tyr Glu Thr Phe His Ile Lys Asn Asn Gly Tyr
        115                 120                 125

Lys Arg Ile Asp Cys Glu Lys His Phe Ala Leu Ala Lys Glu Ile Ser
    130                 135                 140

Gly Gly Ser Asn Asn Pro Ala Asn Asn Lys Tyr Val Thr Leu Ile Asn
145                 150                 155                 160

Asn Gly Ile Ser Leu Thr Ser Ala Leu Ile Asn Val Cys Tyr Asp Val
                165                 170                 175

Asp Gly Leu Lys His Asn Ile Ile Thr Tyr Ser Cys Leu Gly Phe Gly
            180                 185                 190

Val Asp Thr Ile Asp Phe Leu Ser Lys Tyr Thr Thr Lys Phe Ser Tyr
        195                 200                 205

Gln Gly Lys Leu Gly Ala Ser Tyr Thr Val Ser Pro Gln Val Ser Val
    210                 215                 220
```

Phe Ile Glu Gly Tyr Tyr His Gly Leu Phe Gly Lys Lys Phe Glu Lys
225                 230                 235                 240

Ile Pro Val Asn Tyr Pro Cys Asp Tyr Pro Ser Thr Pro Pro Asn
            245                 250                 255

Ser Lys Pro His Val His Thr Thr Ala Leu Ala Met Leu Ser Ile Gly
            260                 265                 270

Tyr Tyr Gly Gly Ser Ile Gly Ile Lys Phe Ile Leu
        275                 280

<210> SEQ ID NO 299
<211> LENGTH: 285
<212> TYPE: PRT
<213> ORGANISM: Ehrlichia ewingii

<400> SEQUENCE: 299

Met Gln Lys Leu Tyr Ile Ser Phe Ile Ile Leu Ser Gly Leu Leu Leu
1               5                   10                  15

Pro Lys Tyr Val Phe Cys Met His Gln Asn Asn Asn Ile Asp Gly Ser
            20                  25                  30

Tyr Val Thr Ile Lys Tyr Gln Leu Thr Thr Pro His Phe Lys Asn Phe
        35                  40                  45

Tyr Ile Lys Glu Thr Asp Phe Asp Thr Gln Glu Pro Ile Gly Leu Ala
    50                  55                  60

Lys Ile Thr Ala Asn Thr Lys Phe Asp Thr Leu Lys Glu Asn Phe Ser
65                  70                  75                  80

Phe Ser Pro Leu His Gln Thr Asp Ser Tyr Lys Ser Tyr Gln Asn Asp
                85                  90                  95

Leu Leu Gly Ile Gly Leu Ser Val Gly Leu Phe Val Lys Ser Phe Arg
            100                 105                 110

Ile Glu Phe Glu Gly Ala Tyr Lys Asn Phe Asn Thr Lys Arg Leu Ala
        115                 120                 125

Arg Tyr Lys Ser Lys Asp Gly Tyr Lys Tyr Phe Ala Ile Pro Arg Lys
    130                 135                 140

Ser Glu His Gly Phe Leu Asp Asn Thr Phe Gly Tyr Thr Val Ala Lys
145                 150                 155                 160

Asn Asn Gly Ile Ser Ile Ile Ser Asn Ile Ile Asn Leu Cys Ser Glu
                165                 170                 175

Thr Lys Tyr Lys Ala Phe Thr Pro Tyr Ile Cys Ile Gly Val Gly Gly
            180                 185                 190

Asp Phe Ile Glu Ile Phe Asp Val Met Arg Ile Lys Phe Ala Tyr Gln
        195                 200                 205

Gly Lys Val Gly Val Ser Tyr Pro Ile Thr Ser Lys Leu Ile Leu Ser
    210                 215                 220

Ile Asn Gly Gln Tyr His Lys Val Ile Gly Asn Lys Phe Glu Leu Leu
225                 230                 235                 240

Pro Val Tyr Gln Pro Val Glu Leu Lys Arg Leu Val Thr Asn Lys Thr
                245                 250                 255

Ser Lys Asp Ile Asp Gln Asp Val Thr Ala Ser Leu Thr Leu Asn Leu
            260                 265                 270

Glu His Phe Ser Ser Glu Ile Gly Leu Ser Phe Ile Phe
        275                 280                 285

<210> SEQ ID NO 300
<211> LENGTH: 297
<212> TYPE: PRT

<213> ORGANISM: Ehrlichia ewingii

<400> SEQUENCE: 300

```
Met Ser Tyr Ala Lys Val Phe Ile Leu Ile Cys Leu Ile Leu Leu Val
1               5                   10                  15
Pro Ser Leu Ser Phe Ala Ile Val Asn Asn Asp Phe Leu Lys Asp Asn
            20                  25                  30
Ile Gly His Phe Tyr Ile Gly Gly Gln Tyr Lys Pro Gly Val Pro Arg
        35                  40                  45
Phe Asn Arg Phe Leu Val Thr Asn Asn Ile Arg Glu Leu Met Ser
    50                  55                  60
Ser Asp Glu Glu Cys Arg Ser Thr Ile Pro His Met Val Gln Ser Val
65                  70                  75                  80
Ala Gln Gly Thr Leu Pro Pro Glu Ala Leu Glu Glu Leu Ala Lys Gly
                85                  90                  95
Leu Leu His Gly Gly Tyr Leu Phe Phe Thr Leu Pro Tyr Asn Pro Thr
            100                 105                 110
Tyr Lys Lys Asn Leu Leu Gly Ala Gly Gly Val Ile Gly Tyr Ser Thr
        115                 120                 125
Thr His Phe Arg Val Glu Val Glu Ala Phe Tyr Glu Lys Phe Asn Leu
    130                 135                 140
Thr Ala Pro Ala Gly Tyr Leu His Lys Asn Phe Tyr Glu Tyr Phe Ala
145                 150                 155                 160
Leu Ala Thr Thr Met Asp Thr Lys His Pro His Gln Ser Ala Glu Asp
                165                 170                 175
Lys Tyr Tyr Tyr Met Lys Asn Thr Gly Ile Thr Leu Ser Pro Phe Ile
            180                 185                 190
Ile Asn Ala Cys Tyr Asp Phe Ile Leu Lys Lys Thr Arg Asn Val Ala
        195                 200                 205
Pro Tyr Leu Cys Leu Gly Val Gly Gly Asn Phe Ile Asp Phe Leu Asp
    210                 215                 220
Gln Val Ser Phe Lys Phe Ala Tyr Gln Ala Lys Val Gly Ile Ser Tyr
225                 230                 235                 240
Phe Val Ser Pro Asn Ile Ala Phe Phe Ile Asp Gly Ser Phe His Gly
                245                 250                 255
His Leu Asn Asn Gln Phe Ser Asp Leu Pro Val Val Asp Tyr Ser Ser
            260                 265                 270
Ser Gly Phe Pro Thr Ile Ser Ala Lys Phe Asn Ala Asn Phe Leu Thr
        275                 280                 285
Ser Ser Ile Gly Ile Arg Phe Ile Ser
    290                 295
```

<210> SEQ ID NO 301
<211> LENGTH: 291
<212> TYPE: PRT
<213> ORGANISM: Ehrlichia ewingii

<400> SEQUENCE: 301

```
Met Asn Lys Lys Asn Lys Phe Ile Ile Ala Thr Ala Leu Val Tyr Leu
1               5                   10                  15
Leu Ser Leu Pro Ser Val Ser Phe Ser Glu Val Thr Asn Ser Ser Ile
            20                  25                  30
Lys Lys His Ser Gly Leu Tyr Ile Ser Gly Gln Tyr Lys Pro Ser Val
        35                  40                  45
Ser Val Phe Ser Ser Phe Ser Ile Lys Glu Thr Asn Thr Ile Thr Lys
```

```
     50                  55                  60

Asn Leu Ile Ala Leu Lys Lys Asp Ile Asn Ser Leu Glu Val Asn Ala
 65                  70                  75                  80

Asp Ala Ser Gln Gly Ile Ser His Pro Gly Asn Phe Thr Ile Pro Tyr
                 85                  90                  95

Ile Ala Ala Phe Glu Asp Asn Ala Phe Asn Phe Asn Gly Ala Ile Gly
            100                 105                 110

Tyr Ile Thr Glu Gly Leu Arg Ile Glu Ile Glu Gly Ser Tyr Glu Glu
        115                 120                 125

Phe Asp Ala Lys Asn Pro Gly Gly Tyr Gly Leu Asn Asp Ala Phe Arg
    130                 135                 140

Tyr Phe Ala Leu Ala Arg Asp Met Glu Ser Asn Lys Phe Gln Pro Lys
145                 150                 155                 160

Ala Gln Ser Ser Gln Lys Val Phe His Thr Val Met Lys Ser Asp Gly
                165                 170                 175

Leu Ser Ile Ile Ser Ile Met Val Asn Gly Cys Tyr Asp Phe Ser Ser
            180                 185                 190

Asp Asn Leu Leu Val Ser Pro Tyr Ile Cys Gly Gly Ile Gly Val Asp
        195                 200                 205

Ala Ile Glu Phe Phe Asp Ala Leu His Ile Lys Leu Ala Cys Gln Ser
    210                 215                 220

Lys Leu Gly Ile Thr Tyr Gln Leu Ser Tyr Asn Ile Ser Leu Phe Ala
225                 230                 235                 240

Asp Gly Tyr Tyr His Gln Val Ile Gly Asn Gln Phe Arg Asn Leu Asn
                245                 250                 255

Val Gln His Val Ala Glu Leu Asn Asp Ala Pro Lys Val Thr Ser Ala
            260                 265                 270

Val Ala Thr Leu Asn Val Gly Tyr Phe Gly Ala Glu Val Gly Val Arg
        275                 280                 285

Phe Ile Phe
    290

<210> SEQ ID NO 302
<211> LENGTH: 272
<212> TYPE: PRT
<213> ORGANISM: Ehrlichia ewingii

<400> SEQUENCE: 302

Met Tyr Met Tyr Asn Lys Lys His Tyr Cys Tyr Ile Val Thr Tyr Val
 1               5                  10                  15

Ile Thr Leu Phe Phe Leu Leu Leu Pro Ile Glu Ser Leu Ser Ala Leu
            20                  25                  30

Ile Gly Asn Val Glu Lys Asp Leu Lys Val Ser Ser Thr Tyr Val Ser
        35                  40                  45

Ser Gln Tyr Lys Pro Ser Ile Phe His Phe Arg Asn Phe Ser Ile Gln
     50                  55                  60

Glu Ser His Pro Lys Lys Ser Ser Glu Glu Phe Lys Lys Ile Lys Ala
 65                  70                  75                  80

Asn Leu Asn Asn Ile Leu Lys Ser Asn Ala Tyr Asn Leu Gln Phe Gln
                 85                  90                  95

Asp Asn Thr Thr Ser Phe Ser Gly Thr Ile Gly Tyr Phe Ser Lys Gly
            100                 105                 110

Leu Arg Leu Glu Ala Glu Gly Cys Tyr Gln Glu Phe Asn Val Lys Asn
        115                 120                 125
```

```
Ser Asn Asn Ser Leu Ile Ile Ser Ser Asn Lys Tyr His Ser Arg Ile
    130                 135                 140

His Asp Glu Asn Tyr Ala Ile Thr Thr Asn Asn Lys Leu Ser Ile Ala
145                 150                 155                 160

Ser Ile Met Val Asn Thr Cys Tyr Asp Ile Ser Ile Asn Asn Thr Ser
                165                 170                 175

Ile Val Pro Tyr Leu Cys Thr Gly Ile Gly Glu Asp Leu Val Gly Leu
            180                 185                 190

Phe Asn Thr Ile His Phe Lys Leu Ala Tyr Gln Gly Lys Val Gly Met
        195                 200                 205

Ser Tyr Leu Ile Asn Asn Asn Ile Leu Leu Phe Ser Asp Ile Tyr Tyr
    210                 215                 220

His Lys Val Met Gly Asn Arg Phe Lys Asn Leu Tyr Met Gln Tyr Val
225                 230                 235                 240

Ala Asp Pro Asn Ile Ser Glu Glu Thr Ile Pro Ile Leu Ala Lys Leu
                245                 250                 255

Asp Ile Gly Tyr Phe Gly Ser Glu Ile Gly Ile Arg Phe Met Phe Asn
            260                 265                 270

<210> SEQ ID NO 303
<211> LENGTH: 295
<212> TYPE: PRT
<213> ORGANISM: Ehrlichia ewingii

<400> SEQUENCE: 303

Met Thr Lys Lys Phe Asn Phe Val Asn Val Ile Leu Thr Phe Leu Leu
 1               5                  10                  15

Phe Leu Phe Pro Leu Lys Ser Phe Thr Thr Tyr Ala Asn Asn Asn Thr
            20                  25                  30

Ile Thr Gln Lys Val Gly Leu Tyr Ile Ser Gly Gln Tyr Lys Pro Ser
        35                  40                  45

Ile Pro His Phe Lys Asn Phe Ser Val Glu Glu Asn Asp Lys Val Val
    50                  55                  60

Asp Leu Ile Gly Leu Thr Thr Asp Val Thr Tyr Ile Thr Glu His Ile
 65                  70                  75                  80

Leu Arg Asp Asn Thr Lys Phe Asn Thr His Tyr Ile Ala Lys Phe Lys
                85                  90                  95

Asn Asn Phe Ile Asn Phe Ser Ser Ala Ile Gly Tyr Tyr Ser Gly Gln
            100                 105                 110

Gly Pro Arg Leu Glu Ile Glu Ser Ser Tyr Gly Asp Phe Asp Val Val
        115                 120                 125

Asn Tyr Lys Asn Tyr Ala Val Gln Asp Val Asn Arg Tyr Phe Ala Leu
    130                 135                 140

Val Arg Glu Lys Asn Gly Ser Asn Phe Ser Pro Lys Pro His Glu Thr
145                 150                 155                 160

Ser Gln Pro Ser Asp Ser Asn Pro Lys Lys Ser Phe Tyr Thr Leu Met
                165                 170                 175

Lys Asn Asn Gly Val Phe Val Ala Ser Val Ile Ile Asn Gly Cys Tyr
            180                 185                 190

Asp Phe Ser Phe Asn Asn Thr Thr Ile Ser Pro Tyr Val Cys Ile Gly
        195                 200                 205

Val Gly Gly Asp Phe Ile Glu Phe Phe Glu Val Met His Ile Lys Phe
    210                 215                 220

Ala Cys Gln Ser Lys Val Gly Ile Ser Tyr Pro Ile Ser Pro Ser Ile
225                 230                 235                 240
```

```
Thr Ile Phe Ala Asp Ala His Tyr His Lys Val Ile Asn Asn Lys Phe
                245                 250                 255

Asn Asn Leu His Val Lys Tyr Ser Tyr Glu Leu Lys Asn Ser Pro Thr
            260                 265                 270

Ile Thr Ser Ala Thr Ala Lys Leu Asn Ile Glu Tyr Phe Gly Gly Glu
        275                 280                 285

Val Gly Met Arg Phe Ile Phe
    290                 295

<210> SEQ ID NO 304
<211> LENGTH: 279
<212> TYPE: PRT
<213> ORGANISM: Ehrlichia ewingii

<400> SEQUENCE: 304

Met Ser Lys Lys Lys Phe Ile Thr Ile Gly Thr Val Leu Ala Ser Leu
 1               5                  10                  15

Leu Ser Phe Leu Ser Ile Glu Ser Phe Ser Ala Ile Asn His Asn His
             20                  25                  30

Thr Gly Asn Asn Thr Ser Gly Ile Tyr Ile Thr Gly Gln Tyr Arg Pro
         35                  40                  45

Gly Val Ser His Phe Ser Asn Phe Ser Val Lys Glu Thr Asn Val Asp
     50                  55                  60

Thr Ile Gln Leu Val Gly Tyr Lys Lys Ser Ala Ser Ser Ile Asp Pro
 65                  70                  75                  80

Asn Thr Tyr Ser Asn Phe Gln Gly Pro Tyr Thr Val Thr Phe Gln Asp
                 85                  90                  95

Asn Ala Ala Ser Phe Ser Gly Ala Ile Gly Tyr Ser Tyr Pro Glu Ser
            100                 105                 110

Leu Arg Leu Glu Leu Glu Gly Ser Tyr Glu Lys Phe Asp Val Lys Asp
        115                 120                 125

Pro Lys Asp Tyr Ser Ala Lys Asp Ala Phe Arg Phe Phe Ala Leu Ala
    130                 135                 140

Arg Asn Thr Ser Thr Thr Val Pro Asp Ala Gln Lys Tyr Thr Val Met
145                 150                 155                 160

Lys Asn Asn Gly Leu Ser Val Ala Ser Ile Met Ile Asn Gly Cys Tyr
                165                 170                 175

Asp Leu Ser Phe Asn Asn Leu Val Val Ser Pro Tyr Ile Cys Ala Gly
            180                 185                 190

Ile Gly Glu Asp Phe Ile Glu Phe Phe Asp Thr Leu His Ile Lys Leu
        195                 200                 205

Ala Tyr Gln Gly Lys Leu Gly Ile Ser Tyr Tyr Phe Phe Pro Lys Ile
    210                 215                 220

Asn Val Phe Ala Gly Gly Tyr Tyr His Arg Val Ile Gly Asn Lys Phe
225                 230                 235                 240

Lys Asn Leu Asn Val Asn His Val Val Thr Leu Asp Glu Phe Pro Lys
                245                 250                 255

Ala Thr Ser Ala Val Ala Thr Leu Asn Val Ala Tyr Phe Gly Gly Glu
            260                 265                 270

Ala Gly Val Lys Phe Thr Phe
        275

<210> SEQ ID NO 305
<211> LENGTH: 283
<212> TYPE: PRT
```

<213> ORGANISM: Ehrlichia ewingii

<400> SEQUENCE: 305

Met Ser Ala Lys Lys Leu Phe Ile Ile Gly Ser Val Leu Val Cys
1 5 10 15

Leu Val Ser Tyr Leu Pro Thr Lys Ser Leu Ser Asn Leu Asn Asn Ile
20 25 30

Asn Asn Asn Thr Lys Cys Thr Gly Leu Tyr Val Ser Gly Gln Tyr Lys
35 40 45

Pro Thr Val Ser His Phe Ser Asn Phe Ser Leu Lys Glu Thr Tyr Thr
50 55 60

Asp Thr Lys Glu Leu Leu Gly Leu Ala Lys Asp Ile Lys Ser Ile Thr
65 70 75 80

Asp Ile Thr Thr Asn Lys Lys Phe Asn Ile Pro Tyr Asn Thr Lys Phe
85 90 95

Gln Asp Asn Ala Val Ser Phe Ser Ala Ala Val Gly Tyr Ile Ser Gln
100 105 110

Asp Ser Pro Arg Val Glu Val Glu Trp Ser Tyr Glu Glu Phe Asp Val
115 120 125

Lys Asn Pro Gly Asn Tyr Val Val Ser Glu Ala Phe Arg Tyr Ile Ala
130 135 140

Leu Ala Arg Gly Ile Asp Asn Leu Gln Lys Tyr Pro Glu Thr Asn Lys
145 150 155 160

Tyr Val Val Ile Lys Asn Asn Gly Leu Ser Val Ala Ser Ile Ile Ile
165 170 175

Asn Gly Cys Tyr Asp Phe Ser Leu Asn Asn Leu Lys Val Ser Pro Tyr
180 185 190

Ile Cys Val Gly Phe Gly Gly Asp Ile Ile Glu Phe Phe Ser Ala Val
195 200 205

Ser Phe Lys Phe Ala Tyr Gln Gly Lys Val Gly Ile Ser Tyr Pro Leu
210 215 220

Phe Ser Asn Met Ile Ile Phe Ala Asp Gly Tyr Tyr His Lys Val Ile
225 230 235 240

Gly Asn Lys Phe Asn Asn Leu Asn Val Gln His Val Val Ser Leu Asn
245 250 255

Ser His Pro Lys Ser Thr Phe Ala Val Ala Thr Leu Asn Val Glu Tyr
260 265 270

Phe Gly Ser Glu Phe Gly Leu Lys Phe Ile Phe
275 280

<210> SEQ ID NO 306
<211> LENGTH: 275
<212> TYPE: PRT
<213> ORGANISM: Ehrlichia ewingii

<400> SEQUENCE: 306

Met Ser Lys Lys Asn Phe Ile Thr Ile Gly Ala Thr Leu Ile His Met
1 5 10 15

Leu Leu Pro Asn Ile Ser Phe Pro Glu Thr Ile Asn Asn Asn Thr Asp
20 25 30

Lys Leu Ser Gly Leu Tyr Ile Ser Gly Gln Tyr Lys Pro Gly Ile Ser
35 40 45

His Phe Ser Lys Phe Ser Val Lys Glu Ile Tyr Asn Asp Asn Ile Gln
50 55 60

Leu Ile Gly Leu Arg His Asn Ala Ile Ser Thr Ser Thr Leu Asn Ile

```
                65                  70                  75                  80
Asn Thr Asp Phe Asn Ile Pro Tyr Lys Val Thr Phe Gln Asn Asn Ile
                    85                  90                  95

Thr Ser Phe Ser Gly Ala Ile Gly Tyr Ser Asp Pro Thr Gly Ala Arg
                100                 105                 110

Phe Glu Leu Glu Gly Ser Tyr Glu Glu Phe Asp Val Thr Asp Pro Gly
                115                 120                 125

Asp Cys Leu Ile Lys Asp Thr Tyr Arg Tyr Phe Ala Leu Ala Arg Asn
130                 135                 140

Pro Ser Gly Ser Ser Pro Thr Ser Asn Asn Tyr Thr Val Met Arg Asn
145                 150                 155                 160

Asp Gly Val Ser Ile Thr Ser Val Ile Phe Asn Gly Cys Tyr Asp Ile
                165                 170                 175

Phe Leu Lys Asp Leu Glu Val Ser Pro Tyr Val Cys Val Gly Val Gly
                180                 185                 190

Gly Asp Phe Ile Glu Phe Phe Asp Ala Leu His Ile Lys Leu Ala Tyr
                195                 200                 205

Gln Gly Lys Leu Gly Ile Asn Tyr His Leu Ser Thr Gln Ala Ser Val
                210                 215                 220

Phe Ile Asp Gly Tyr Tyr His Lys Val Ile Gly Asn Gln Phe Asn Asn
225                 230                 235                 240

Leu Asn Val Gln His Val Ala Ser Thr Asp Phe Gly Pro Val Tyr Ala
                245                 250                 255

Val Ala Thr Leu Asn Ile Gly Tyr Phe Gly Gly Glu Ile Gly Ile Arg
                260                 265                 270

Leu Thr Phe
        275

<210> SEQ ID NO 307
<211> LENGTH: 285
<212> TYPE: PRT
<213> ORGANISM: Ehrlichia ewingii

<400> SEQUENCE: 307

Met Asn Asn Arg Lys Ser Phe Phe Ile Ile Gly Ala Ser Leu Leu Ala
1               5                   10                  15

Ser Leu Leu Phe Thr Ser Glu Ala Ser Ser Thr Gly Asn Val Ser Asn
                20                  25                  30

His Thr Tyr Phe Lys Pro Arg Leu Tyr Ile Ser Gly Gln Tyr Arg Pro
                35                  40                  45

Gly Val Ser His Phe Ser Lys Phe Ser Val Lys Glu Thr Asn Tyr Asn
            50                  55                  60

Thr Thr Gln Leu Val Gly Leu Lys Lys Asp Ile Ser Val Ile Gly Asn
65                  70                  75                  80

Ser Asn Ile Thr Thr Tyr Thr Asn Phe Asn Phe Pro Tyr Ile Ala Glu
                85                  90                  95

Phe Gln Asp Asn Ala Ile Ser Phe Ser Gly Ala Ile Gly Tyr Leu Tyr
                100                 105                 110

Ser Glu Asn Phe Arg Ile Glu Val Glu Ala Ser Tyr Glu Glu Phe Asp
                115                 120                 125

Val Lys Asn Pro Glu Gly Ser Ala Thr Asp Ala Tyr Arg Tyr Phe Ala
130                 135                 140

Leu Ala Arg Ala Met Asp Gly Thr Asn Lys Ser Ser Pro Asp Asp Thr
145                 150                 155                 160
```

```
Arg Lys Phe Thr Val Met Arg Asn Asp Gly Leu Ser Ile Ser Ser Val
                165                 170                 175

Met Ile Asn Gly Cys Tyr Asn Phe Thr Leu Asp Asp Ile Pro Val Val
            180                 185                 190

Pro Tyr Val Cys Ala Gly Ile Gly Gly Asp Phe Ile Glu Phe Phe Asn
        195                 200                 205

Asp Leu His Val Lys Phe Ala His Gln Gly Lys Val Gly Ile Ser Tyr
    210                 215                 220

Ser Ile Ser Pro Glu Val Ser Leu Phe Leu Asn Gly Tyr Tyr His Lys
225                 230                 235                 240

Val Thr Gly Asn Arg Phe Lys Asn Leu His Val Gln His Val Ser Asp
                245                 250                 255

Leu Ser Asp Ala Pro Lys Phe Thr Ser Ala Val Ala Thr Leu Asn Val
            260                 265                 270

Gly Tyr Phe Gly Gly Glu Ile Gly Val Arg Phe Ile Phe
        275                 280                 285

<210> SEQ ID NO 308
<211> LENGTH: 300
<212> TYPE: PRT
<213> ORGANISM: Ehrlichia ewingii

<400> SEQUENCE: 308

Met Lys Lys Lys Asn Gln Phe Ile Thr Ile Ser Thr Ile Leu Val Cys
1               5                   10                  15

Leu Leu Ser Leu Ser Asn Ala Ser Leu Ser Asn Thr Thr Asn Ser Ser
            20                  25                  30

Thr Lys Lys Gln Phe Gly Leu Tyr Val Ser Gly Gln Tyr Lys Pro Ser
        35                  40                  45

Val Ser Ile Phe Ser Asn Phe Ser Val Lys Glu Thr Asn Phe Pro Thr
    50                  55                  60

Lys Tyr Leu Ala Ala Leu Lys Lys Asp Ile Asn Ser Val Glu Phe Asp
65                  70                  75                  80

Asp Ser Val Thr Ala Gly Ile Ser Tyr Pro Leu Asn Phe Ser Thr Pro
                85                  90                  95

Tyr Ile Ala Val Phe Gln Asp Asn Ile Ser Asn Phe Asn Gly Ala Ile
            100                 105                 110

Gly Tyr Thr Phe Val Glu Gly Pro Arg Ile Glu Ile Glu Gly Ser Tyr
        115                 120                 125

Glu Glu Phe Asp Val Lys Asp Pro Gly Arg Tyr Thr Glu Ile Gln Asp
    130                 135                 140

Ala Tyr Arg Tyr Phe Ala Leu Ala Arg Asp Ile Asp Ser Ile Pro Thr
145                 150                 155                 160

Ser Pro Lys Asn Arg Thr Ser His Asp Gly Asn Ser Ser Tyr Lys Val
                165                 170                 175

Tyr His Thr Val Met Lys Asn Glu Gly Leu Ser Ile Ile Ser Ile Met
            180                 185                 190

Val Asn Gly Cys Tyr Asp Phe Ser Ser Asp Asn Leu Ser Ile Leu Pro
        195                 200                 205

Tyr Val Cys Gly Gly Ile Gly Val Asn Ala Ile Glu Phe Phe Asp Ala
    210                 215                 220

Leu His Val Lys Phe Ala Cys Gln Gly Lys Leu Gly Ile Thr Tyr Pro
225                 230                 235                 240

Leu Ser Ser Asn Val Ser Leu Phe Ala Gly Gly Tyr Tyr His Gln Val
                245                 250                 255
```

-continued

Met Gly Asn Gln Phe Lys Asn Leu Asn Val Gln His Val Ala Glu Leu
          260                 265                 270

Asn Asp Ala Pro Lys Val Thr Ser Ala Val Ala Thr Leu Asp Ile Gly
          275                 280                 285

Tyr Phe Gly Gly Glu Ile Gly Ala Arg Leu Ile Phe
          290                 295             300

<210> SEQ ID NO 309
<211> LENGTH: 285
<212> TYPE: PRT
<213> ORGANISM: Ehrlichia ewingii

<400> SEQUENCE: 309

Met Asp Lys Glu Met Asn Tyr Lys Glu Phe Val Leu Gly Val Thr Leu
1               5                   10                  15

Ser Ala Leu Leu Phe Ser Leu Leu Pro Glu Arg Ala Ile Ser Asp Met
            20                  25                  30

Asp Val Ser Glu Asn Arg Ser Arg Phe Tyr Ala Gly Val Gln Tyr Arg
        35                  40                  45

Thr Gly Ile Pro Asn Phe Asp Asn Phe Ser Ala Ser Glu Thr Ile Pro
    50                  55                  60

Gly Leu Thr Lys Gly Val Tyr Gly Leu Asp Leu Asp Leu Ser Lys Ser
65                  70                  75                  80

Asp Ile Thr Lys Arg Ala Asn Phe Thr Arg Leu Tyr Asn Pro Thr Tyr
                85                  90                  95

Ser Thr Ser Ser Thr Gly Ile Gly Gly Met Phe Gly Tyr Tyr Phe Asp
            100                 105                 110

Asn Ile Arg Met Glu Phe Glu Thr Ser Tyr Ser Ser Phe Gly Ile Glu
        115                 120                 125

Arg Gln Trp Tyr Pro Glu Gly Ser Gln Ser His Lys Phe Cys Ala Val
    130                 135                 140

Ser Arg Gln Asp Asn Ala Ala Pro Asn Thr Asp Ser Ser Asn Asn Asn
145                 150                 155                 160

Asp Phe Val Val Leu Glu Asn Asn Gly Val Lys Ile Arg Thr Leu His
                165                 170                 175

Val Asn Phe Cys Tyr Asp Val Ala His Gly Asn Ile Pro Leu Ala Pro
            180                 185                 190

Tyr Val Cys Ala Gly Ile Gly Gly Asp Tyr Val Lys Phe Ile Gly Val
        195                 200                 205

Ser Leu Pro Lys Phe Ser Tyr Gln Leu Lys Phe Gly Val Asn Tyr Pro
    210                 215                 220

Leu Ser Ile Arg Thr Met Leu Phe Gly Gly Tyr Tyr His Lys Val
225                 230                 235                 240

Met Gly Ser Lys Tyr Asp Arg Val Lys Val Val Tyr His Pro Val Gln
                245                 250                 255

Leu Asn Thr Val Pro Lys Met Thr Phe Val Ser Ala Asn Leu Asp Ile
            260                 265                 270

Asp Tyr Phe Gly Cys Glu Val Gly Ile Arg Phe Phe Leu
        275                 280                 285

<210> SEQ ID NO 310
<211> LENGTH: 282
<212> TYPE: PRT
<213> ORGANISM: Ehrlichia ewingii

<400> SEQUENCE: 310

Met Asn Tyr Lys Lys Ile Leu Val Arg Ser Ala Leu Ile Ser Leu Met
1               5                   10                  15

Ser Phe Leu Pro Tyr Gln Ser Phe Ala Glu Pro Val Ser Ser Asn Asn
            20                  25                  30

Ile Gly Asn Glu Asn Ala Lys Glu Gly Phe Tyr Ile Ser Ala Lys Tyr
        35                  40                  45

Asn Pro Ser Ile Pro His Phe Arg Lys Phe Ser Ala Glu Glu Thr Pro
    50                  55                  60

Val Tyr Gly Lys Asp Ser Pro Thr Lys Lys Val Phe Gly Leu Lys Lys
65              70                  75                  80

Glu Gly Ser Ile Thr Lys Tyr Ser Asp Phe Thr Arg Thr Asp Ile Ser
                85                  90                  95

Phe Glu Gly Gln Asn Asn Phe Ile Ser Gly Phe Ser Gly Ser Ile Gly
            100                 105                 110

Tyr Ile Met Asp Gly Pro Arg Val Glu Ile Glu Ala Ala Tyr Gln Lys
        115                 120                 125

Phe Asn Pro Lys Asn Pro Ala Asn Glu Thr Asp Thr Ser Asp Tyr Tyr
    130                 135                 140

Lys His Tyr Gly Leu Ser Arg Ala Glu Thr Met Thr Asp Lys Lys Tyr
145                 150                 155                 160

Val Val Leu Thr Asn Asn Gly Val Thr Phe Ser Ser Leu Met Phe Asn
                165                 170                 175

Ala Cys Tyr Asp Ile Thr Ala Glu Gly Val Pro Phe Ile Pro Tyr Ala
            180                 185                 190

Cys Ala Gly Ile Gly Ala Asp Leu Ile Ser Ile Phe Asp Asp Ile Asn
        195                 200                 205

Leu Lys Phe Ala Tyr Gln Gly Lys Ile Gly Ile Ser Tyr Pro Ile Thr
    210                 215                 220

Pro Glu Ile Ser Ala Phe Ile Gly Gly Tyr Tyr His Gly Val Ile Gly
225                 230                 235                 240

Asn Lys Tyr Asn Lys Val Pro Val Lys Leu Pro Val Thr Leu Thr Asp
                245                 250                 255

Ala Pro Gln Ser Thr Ser Ala Ser Val Thr Leu Asp Ala Gly Tyr Phe
            260                 265                 270

Gly Gly Glu Leu Gly Val Arg Phe Thr Phe
        275                 280

<210> SEQ ID NO 311
<211> LENGTH: 257
<212> TYPE: PRT
<213> ORGANISM: Ehrlichia ewingii

<400> SEQUENCE: 311

Met Asn Asn Lys Asn Ser Ile Thr Lys Val Tyr Ile Val Thr Ile Leu
1               5                   10                  15

Ser Phe Ile Leu Leu Pro Ile Gln Ser Phe Ser Ala Leu Ile Gly Asn
20 25 30

Ile Thr Lys Asn Glu Glu Tyr Ser Asn Val Tyr Ile Thr Ser Gln Leu
35 40 45

Lys Pro Thr Val Leu Tyr Phe Lys Asp Phe Ser Leu Lys Glu Ile Asn
50 55 60

Ala Ser His Lys Ser Asn Asp Asp Ile Ile Thr Gln His Asp Thr Lys
65 70 75 80

Phe His Asn Asn Thr Ser Ser Phe Ser Gly Ser Val Gly Tyr Ser Ser

```
                85                  90                  95

Leu Gly Leu Arg Leu Glu Leu Glu Gly Ser His Glu Lys Phe His Met
            100                 105                 110

Gln Asn Ser Asp Ile Ile Ser Lys Ile Ser Lys Tyr Gln Tyr Ser Thr
        115                 120                 125

Lys Ala Tyr Ala Ala Thr Thr Asp Asn Tyr Thr Asn Thr Asn Asn Asn
    130                 135                 140

Asn Ile Thr Leu Thr Ser Leu Met Val Asn Thr Cys Tyr Asp Ile Thr
145                 150                 155                 160

Ile Gly Asn Ser Ser Ala Val Pro Tyr Leu Cys Thr Gly Ile Gly Gly
                165                 170                 175

Asp Ile Ile Asn Ile Phe Asn Ala Thr His Leu Arg Phe Ala Tyr Gln
            180                 185                 190

Gly Lys Ile Gly Ile Ser Tyr Gln Leu Asn Asn Asn Phe Phe Leu Phe
        195                 200                 205

Ala Asp Thr Tyr Tyr His Lys Ile Met Gly Asn Lys Phe Lys Asp Leu
    210                 215                 220

Tyr Ile His Asn Ser Ser Asn Ile Thr Pro Met Leu Ala Lys Ile Asp
225                 230                 235                 240

Ile Gly Tyr Phe Gly Ser Glu Val Gly Leu Arg Ile Ile Phe Asn Lys
                245                 250                 255

Leu

<210> SEQ ID NO 312
<211> LENGTH: 293
<212> TYPE: PRT
<213> ORGANISM: Ehrlichia ewingii

<400> SEQUENCE: 312

Met Lys Lys Leu Tyr Tyr Leu Asn Phe Ile Leu Val Leu Leu Ala Thr
 1               5                  10                  15

Cys Phe Leu Pro Lys Phe Ala Phe Ser Thr Phe His Asp Thr Asn Ile
            20                  25                  30

Ala Lys Pro Tyr Ile Thr Val Asn Tyr Gln Pro Thr Val Ser Asn Phe
        35                  40                  45

Arg Asn Phe His Ile Lys Glu Thr Asn Phe Asp Thr Lys Lys Pro Ile
    50                  55                  60

Glu Val Asn Ile Asn Ser Thr Gly Ile Ser Ser Arg Tyr Phe Lys Asn
65                  70                  75                  80

Arg Glu Phe Ala Phe Tyr Ser Ser His Asn Lys His Tyr Glu Ser Tyr
                85                  90                  95

Lys Asn Asp Leu Ser Ala Phe Thr Thr Ser Ile Gly Ile Ser Leu Lys
            100                 105                 110

Asn Phe Lys Ile Glu Ala Glu Gly Ser Tyr Lys Val Phe Asp Val Phe
        115                 120                 125

Asp Phe Arg Asn Tyr Ala Ile Gln Gly Ala His Asn Ile Phe Ala Leu
    130                 135                 140

Pro Arg Glu Thr Asn Ser Tyr Gly Met Tyr Pro Leu Asp Arg Pro Ser
145                 150                 155                 160

Leu Arg Asn Lys Asn Thr Gly Tyr Thr Ile Leu Lys Asn Asn Gly Ile
                165                 170                 175

Ala Ile Ile Ser Asn Met Ile Asn Leu Cys Tyr Glu Lys Gln Ser Asn
            180                 185                 190

Asn Phe Thr Pro Tyr Ile Cys Phe Gly Ile Gly Gly Asp Phe Ile Glu
```

195                 200                 205
Ile Phe Asp Thr Thr Arg Ile Lys Ala Ala Tyr Gln Gly Lys Ile Gly
    210                 215                 220

Ile Ser Tyr Pro Leu Thr Ser Arg Thr Asn Leu Leu Ile Ser Gly Gln
225                 230                 235                 240

Tyr His Lys Val Ile Gly Asn Gln Phe Lys Glu Leu Pro Thr Leu Gln
                245                 250                 255

Ile Val Glu Leu Lys Arg Leu Pro Glu Arg Gln Pro Glu Tyr Asp Val
            260                 265                 270

Thr Ala Leu Leu Thr Leu Asp Ile Glu Tyr Phe Ser Gly Glu Val Gly
        275                 280                 285

Leu Ser Phe Thr Leu
        290

<210> SEQ ID NO 313
<211> LENGTH: 275
<212> TYPE: PRT
<213> ORGANISM: Ehrlichia ewingii

<400> SEQUENCE: 313

Met Asn Tyr Lys Asn Ile Phe Ile Leu Thr Phe Leu Ile Phe Leu Leu
1               5                   10                  15

Pro Ser Val Ser Ser Leu Ala Ser Asn Asp Asp Thr Leu Ser Pro Val
            20                  25                  30

Tyr Gln Phe Tyr Thr Ser Val Gln Tyr Lys Pro Ser Ile Ser Tyr Phe
        35                  40                  45

Ser Lys Phe Ser Pro Ser Ile Gln Asn Glu Asn Ile Val Glu Ile Leu
    50                  55                  60

Ser Leu Lys Glu Asn Leu Ser Ala Thr Ile Asn Asn Phe Asn Ile Lys
65                  70                  75                  80

Gly Gly Gln Asn Tyr Asp Ile Lys Asn Phe Ile Ser Pro Tyr Asn Pro
                85                  90                  95

Thr Tyr Lys Asn Ser Pro Leu Gly Ile Gly Gly Ala Ile Gly Val Lys
            100                 105                 110

Ser Asn Asn Tyr Arg Ile Glu Leu Glu Val Phe Tyr Glu Glu Phe Asp
        115                 120                 125

Leu Lys Val Pro Ser Glu Tyr Phe His Lys Asp Ala Tyr Lys Tyr Phe
    130                 135                 140

Ile Ile Lys Ser Thr Pro Ser His Pro His His Leu Phe Lys Asn
145                 150                 155                 160

Asn Asp Ile Thr Val Ser Pro Val Leu Ile Asn Val Cys Tyr Asp Ile
                165                 170                 175

Pro Pro Lys Asn Thr Lys Ile Phe Pro Tyr Leu Cys Phe Gly Ala Gly
            180                 185                 190

Val Asp Val Ile Asp Phe Leu Asp Lys Val His Phe Lys Val Ser Tyr
        195                 200                 205

Gln Ala Lys Ile Gly Val Ser Tyr Phe Ile Leu Pro Asn Leu Ala Leu
    210                 215                 220

Phe Val Asp Gly Ser Phe Tyr Ser His Leu Ser Asn Lys Phe Thr His
225                 230                 235                 240

Ile Pro Thr Ile Asn Ile Met Asp Pro Pro Ile Leu Pro Asp Ser Ser
                245                 250                 255

Ser Ala Lys Phe Asn Val Asn Phe Leu Ser Ser Phe Gly Ile Arg
            260                 265                 270

-continued

Phe Ile His
        275

<210> SEQ ID NO 314
<211> LENGTH: 294
<212> TYPE: PRT
<213> ORGANISM: Ehrlichia ewingii

<400> SEQUENCE: 314

Met Ser Tyr Ser Lys Phe Leu Leu Tyr Met Ala Val Ile Leu Leu Ser
 1               5                  10                  15

Pro Tyr Val Ser Leu Ala Val Asn Leu Asn Glu Asn Ile Tyr Lys Gly
            20                  25                  30

Phe Tyr Ala Gly Ile Gln Tyr Lys Pro Ala Lys Tyr His Leu Ser Tyr
        35                  40                  45

Leu Asp Leu Lys Glu Asp Gly Tyr Asn Thr Ile Asp Ala Phe Ala Leu
    50                  55                  60

Lys Lys Phe Ser Glu Ile Lys Lys Asn Ile Gln Ile Asp Asn Thr Thr
65                  70                  75                  80

Leu Ala Ala Thr Leu Val Ser Ala Asn Asn Phe Thr Ile Gly Tyr Asn
                85                  90                  95

Pro His Tyr Lys Asn Ser Tyr Leu Gly Ile Ser Gly Ala Leu Gly Tyr
            100                 105                 110

Tyr Tyr His Asn Gly Phe Arg Val Glu Ser Glu Ile Ser Ser Glu Arg
        115                 120                 125

Phe Leu Leu Lys Asn Glu Gly Tyr Lys Ile Leu Asp His Glu Lys Tyr
    130                 135                 140

Phe Val Leu Ala Arg Ser Ala Ser Gly Asn Gly Arg Ile Thr Arg Val
145                 150                 155                 160

Phe Ser Pro Asn Glu Asn Glu Tyr Val Ile Leu Met Asn Asp Gly Ile
                165                 170                 175

Arg Ser Thr Ser Leu Ile Phe Asn Ala Cys Tyr Asp Thr Asn Ile Asn
            180                 185                 190

Ile His Gly Leu Ile Thr Tyr Ser Cys Val Gly Phe Gly Ala Asp Leu
        195                 200                 205

Val Asp Phe Leu Gly Lys Tyr Ser Leu Lys Pro Ser Tyr Gln Thr Lys
    210                 215                 220

Leu Gly Ile Ser Tyr Pro Val Ser Ser Asn Ile Ile Ala Ile Ala Glu
225                 230                 235                 240

Gly Tyr Tyr His Gly Leu Leu Ser Arg Arg Phe Asp Lys Ile Pro Val
                245                 250                 255

Asn Ser Tyr Ala Ile Gln Ser Pro Leu Asn Ser Val Asp Thr Thr Ala
            260                 265                 270

Ser Ala Leu Leu Asn Ile Arg Tyr Tyr Gly Gly Ser Ile Gly Val Arg
        275                 280                 285

Phe Ile Leu Gly Ser Leu
    290

<210> SEQ ID NO 315
<211> LENGTH: 309
<212> TYPE: PRT
<213> ORGANISM: Ehrlichia ewingii

<400> SEQUENCE: 315

Met Asp Asn Val Met Val Lys Phe Ser Cys Leu Gly Phe Ala Leu Ser
 1               5                  10                  15

```
Leu Val Thr Leu Val Met Ala His Asn Ala Phe Ser Ser Pro Leu Pro
            20                  25                  30

Val Asp Phe Ser Asn Glu Ser Glu Met Val Gly Phe Tyr Thr Ser Gly
        35                  40                  45

Gln Tyr Ser Ile Glu Val Pro Lys Phe Ser Ala Ile Ser Ala Lys Tyr
    50                  55                  60

Lys His Glu Lys Gln Asp Lys Glu Leu Thr Leu Phe Ser Leu Lys Glu
65                  70                  75                  80

Glu Asn Thr Glu Leu Lys Leu Asn Asp Lys Asp Gln Phe Lys Lys Gly
                85                  90                  95

Tyr Asn Pro Val Tyr Asn Arg Asn Tyr Thr Gly Phe Ser Gly Ala Ile
            100                 105                 110

Gly Tyr Ser Gly Gly Gly Leu Arg Ile Glu Leu Glu Gly Ala Phe Thr
        115                 120                 125

Lys Phe Asp Val Asp Lys Gln Lys Tyr Lys Phe Gln Asp Asn Tyr Arg
    130                 135                 140

Tyr Phe Ala Leu Ser Lys Asp Glu Glu Ile Ser Gly Gln Pro Asp Lys
145                 150                 155                 160

Pro Thr Pro Ala Pro Glu Pro Gln Pro Ala Pro Ala Pro Ala Pro Gln
                165                 170                 175

Pro Ser Pro Lys Thr Thr Thr Gly Tyr Asn Tyr Val Thr Ala Lys Asn
            180                 185                 190

Glu Gly Leu Ser Ile Ile Ser Leu Thr Leu Asn Ala Cys Tyr Asp Val
        195                 200                 205

Ile Ile Gly Asn Ser Gln Leu Ile Pro Ser Val Cys Ile Gly Ile Gly
    210                 215                 220

Gln Gly Ile Thr Asn Phe Leu Gly Val Ile Asn Ile Lys Thr Ile Tyr
225                 230                 235                 240

Lys Ala Lys Val Gly Val Gly Phe Leu Leu Ser Pro Lys Thr Ile Ile
                245                 250                 255

Phe Val Asn Gly Tyr Tyr Val Lys Val Pro Asn Asp Ser Phe Lys Asn
            260                 265                 270

Val Ser Ile Gln Tyr Gln His Glu Leu Glu Lys Asp Pro Lys His Ile
        275                 280                 285

Glu Pro Ile Ile Phe Phe Asn Ser Asp Tyr Tyr Gly Gly Glu Val Gly
    290                 295                 300

Leu Arg Phe Ile Leu
305
```

<210> SEQ ID NO 316
<211> LENGTH: 306
<212> TYPE: PRT
<213> ORGANISM: Ehrlichia ewingii

<400> SEQUENCE: 316

```
Met Lys Asn Lys Leu Ile Ala Thr Gly Ile Val Leu Thr Leu Leu Ser
1               5                   10                  15

Phe Ile Pro Asn Ile Ser Phe Ser Glu Ile Thr His Asn Asn Thr Glu
            20                  25                  30

Ile Arg Tyr Ser Ile Tyr Ile Ser Gly Gln Tyr Lys Pro Ser Val Ser
        35                  40                  45

Asn Phe Ser Asn Phe Ser Val Lys Glu Thr Asn Thr Asn Thr Glu Asn
    50                  55                  60

Leu Val Ala Thr Lys Gln Asp Ile Ala Pro Leu Asp Ile Asp Ala Gly
65                  70                  75                  80
```

Leu Val Thr Pro Lys Pro Pro Gln Lys Ser Gln Lys Ile Tyr Lys Gly
85 90 95

Leu Arg Glu Ser Thr Asn Phe Asn His Pro Tyr Thr Ala Glu Phe Gln
100 105 110

Asp Asn Asn Ile Ser Phe Gly Gly Ala Ile Gly Tyr Ser Ser Thr Lys
115 120 125

Gly Thr Arg Val Glu Leu Glu Gly Ser Tyr Glu Phe Phe Asp Val Lys
130 135 140

Asp Pro Ile Gly His Lys Leu His Asp Ala His Arg Tyr Phe Ala Leu
145 150 155 160

Ala Arg Ala Met Asn Lys Tyr Lys Pro Phe Glu Pro Lys Arg Gln Tyr
165 170 175

Glu Leu Arg Thr His His Thr Val Met Arg Asn Asp Gly Val Tyr Ile
180 185 190

Ser Ser Ile Met Leu Asn Gly Cys Tyr Asp Phe Ser Ile Asn Glu Leu
195 200 205

Lys Ile Ser Pro Tyr Met Cys Val Gly Ile Gly Ile Asn Ala Ile Glu
210 215 220

Phe Phe Asp Ala Leu His Leu Lys Leu Ala Tyr Gln Gly Lys Phe Gly
225 230 235 240

Ile Ser Tyr Pro Ile Ser Asn Asn Ile Lys Leu Phe Ala Asp Gly Tyr
245 250 255

Tyr Tyr Lys Val Thr Asp Asn Lys Phe Lys Asn Leu Lys Val Ile His
260 265 270

Val Ala Asp Leu Asn Asn Thr Pro Leu Val Thr Ser Ala Ile Ala Thr
275 280 285

Leu Asn Val Glu Tyr Phe Gly Gly Glu Ile Gly Ile Arg Phe Gly Leu
290 295 300

Lys Leu
305

<210> SEQ ID NO 317
<211> LENGTH: 315
<212> TYPE: PRT
<213> ORGANISM: Ehrlichia ewingii

<400> SEQUENCE: 317

Met Thr Asn Lys Leu Thr Phe Thr Gly Thr Val Leu Ala Leu Leu Leu
1 5 10 15

Cys Ile Pro Asn Thr Ser Phe Ser Glu Ile Lys Tyr Asn Asn Asn Thr
20 25 30

His Ile Gln Tyr Ser Ile Tyr Val Ser Gly Gln Tyr Lys Pro Ser Val
35 40 45

Ser Asn Phe Arg Asn Phe Ser Val Lys Glu Thr Asn Thr Tyr Thr Lys
50 55 60

Asn Leu Ile Gly Val Lys Lys Asp Ile Thr Ser Leu Glu Val His Thr
65 70 75 80

Asn Asn Asn Lys Pro Ile Val Ser Arg Arg Asn Pro Asn Pro Gly Pro
85 90 95

Thr Ile Lys Ala Thr Gly Ile Ser His Pro Ser Asn Phe Asn Ile Pro
100 105 110

Tyr Asn Pro Glu Phe Gln Asp Asn Ile Ile Asn Phe Ser Gly Thr Ile
115 120 125

Gly Tyr Gln Phe Ser Lys Ser Lys Arg Ile Glu Ile Glu Gly Ser Tyr

```
            130                 135                 140
Lys Ile Phe Asp Val Lys Asp Pro Gly Gly Tyr Met Leu Tyr Asp Ala
145                 150                 155                 160

Tyr Arg Tyr Phe Ala Leu Ala Arg Glu Met Asn Asp Thr Lys Phe Glu
                165                 170                 175

Pro Lys Pro Tyr Gln Leu Asp Asn Val Phe Asn Asn Phe Tyr His Thr
                180                 185                 190

Val Met Lys Asn Thr Gly Leu Ser Ile Ile Ser Val Met Ile Asn Gly
                195                 200                 205

Cys His Asp Phe His Val Asn Glu Leu Lys Ile Ser Pro Tyr Ile Cys
                210                 215                 220

Ala Gly Val Gly Ile Asn Thr Ile Glu Phe Phe Asp Thr Ser His Ile
225                 230                 235                 240

Lys Phe Ala Tyr Gln Gly Lys Ile Gly Ile Ser Tyr Pro Leu Ser Asn
                245                 250                 255

Asn Ile Lys Val Phe Ser Asn Gly Tyr Tyr His Lys Val Ala Gly Asn
                260                 265                 270

Lys Phe Lys Asn Leu Glu Val Ile His Val Ala Asn Leu His Asn Ala
                275                 280                 285

Pro Trp Tyr Thr Ser Ala Ile Ala Thr Leu Asn Ile Gly Tyr Phe Gly
                290                 295                 300

Ala Glu Val Gly Ile Arg Leu Gly Leu Lys Leu
305                 310                 315

<210> SEQ ID NO 318
<211> LENGTH: 297
<212> TYPE: PRT
<213> ORGANISM: Ehrlichia ewingii

<400> SEQUENCE: 318

Met Arg Ile Phe Met Lys Ser Lys Ile Ile Phe Thr Asn Ile Val Leu
1               5                   10                  15

Thr Phe Ile Leu Ser Ile Pro Ser Ile Ser His Ala Glu Ile Leu Asn
                20                  25                  30

Lys Asp Thr Gly Lys Tyr Asn Asn Ile Tyr Leu Ser Thr Gln Tyr Lys
                35                  40                  45

Pro Ala Ile Pro Val Phe Asn Asn Phe Ser Val Ser Glu Lys Asp Gln
            50                  55                  60

Asn Thr Ala Leu Leu Val Ala Leu Thr Ser Asp Ile Asn Asn Thr Asn
65                  70                  75                  80

Ile Asn Asn Asn Glu Lys Ile Ser Leu Pro Gln His Phe Thr Thr Pro
                85                  90                  95

Tyr His Ala Gln Phe Gln Asn Ser Ile Ile Ser Phe Ser Gly Thr Ile
                100                 105                 110

Gly Gln Tyr Leu Pro Lys Asn Leu Arg Val Glu Ile Glu Gly Ser Tyr
                115                 120                 125

Lys Ser Phe Asp Val Lys Asn Pro Gly Tyr Tyr Asp Val Asn Asp Ala
                130                 135                 140

Tyr Arg Tyr Phe Ala Leu Ala Arg Asp Val Lys Asn Asn Ser Tyr Gln
145                 150                 155                 160

Pro Gln Asp Asn Lys Thr Asn Asn Thr Thr Asn Leu Ala Tyr Tyr Thr
                165                 170                 175

Ile Met Lys Asn Tyr Gly Val Ser Ile Met Ser Val Leu Leu Asn Gly
                180                 185                 190
```

```
Cys Tyr Asp Ile Ser Val Asp Lys Leu Lys Ala Ser Pro Tyr Ile Cys
            195                 200                 205

Leu Gly Ile Gly Val Asp Thr Ile Glu Phe Phe Glu Thr Leu His Ile
    210                 215                 220

Lys Phe Ala Tyr Gln Cys Lys Val Gly Ile Ser Tyr Leu Ile Leu Pro
225                 230                 235                 240

Gln Val Ser Leu Phe Ala Asp Gly Tyr Tyr His Lys Val Lys Asn Asn
                245                 250                 255

Gln Phe Lys Asn Leu Asn Thr Ile Gln Val Arg Met Leu Ala Asn Asn
            260                 265                 270

Pro Lys Ile Thr Tyr Ala Ala Thr Leu Asn Ile Ser Tyr Phe Gly
        275                 280                 285

Ala Glu Ile Gly Ala Arg Phe Thr Phe
    290                 295
```

<210> SEQ ID NO 319
<211> LENGTH: 295
<212> TYPE: PRT
<213> ORGANISM: Ehrlichia ewingii

<400> SEQUENCE: 319

```
Met Asn Lys Asn Arg Lys Leu Ile Leu Asn Thr Ala Leu Val Phe Ser
1               5                   10                  15

Leu Leu Ser Phe Leu Pro His Gln Val Leu Ser Ile Pro Ile Asn Asn
            20                  25                  30

Ser Ile Ser Lys Tyr Ser Gly Ile Tyr Phe Ser Gly Ser Tyr Lys Leu
        35                  40                  45

Glu Phe Pro Leu Leu Asp Asn Phe Ser Ile Lys Glu Thr Thr Ser Asn
    50                  55                  60

Thr Lys Gln Val Ile Gly Leu Ser Lys Lys Glu Ala Lys Val Arg
65                  70                  75                  80

Asp Ile Leu Ser Tyr His Ala Ala Phe Asn Glu Pro Tyr Thr Pro Ile
                85                  90                  95

Phe Gln Asn Thr Val Ser Gly Phe Ser Gly Thr Val Gly Tyr Ser Tyr
            100                 105                 110

Thr Asn Lys Leu Arg Ser Glu Ile Glu Val Ser Tyr Glu Lys Phe Asp
        115                 120                 125

Ala Glu Ile Pro Glu Gly Ser Ile Tyr Asp Asp Tyr Ile Glu Asp Thr
    130                 135                 140

Tyr Arg Tyr Phe Ala Leu Ala Arg Glu Thr Ser Ser Ser Leu Ser Lys
145                 150                 155                 160

Thr Thr Pro Lys Tyr Asn His Tyr Ile Ile Met Lys Asn Asn Gly Val
                165                 170                 175

Ser Ile Thr Ser Leu Met Val Asn Asn Cys Tyr Gln Phe Ser Thr Ser
            180                 185                 190

Gln Ser Asn Lys Ile Leu Pro Tyr Ile Cys Gly Gly Val Gly Thr Asp
        195                 200                 205

Leu Val His Phe Phe Asn Lys Leu His Ile Lys Leu Ala Cys Gln Val
    210                 215                 220

Lys Leu Gly Thr Ser Tyr Ser Leu Ser Pro His Tyr Gln Leu Phe Ala
225                 230                 235                 240

Asn Val Tyr Tyr His Glu Val Ile Gly Asn Tyr Phe Asn Lys Leu Lys
                245                 250                 255

Pro Ile Arg Thr Val Leu Pro Arg Asn Thr Thr Ser Thr Glu Leu Ser
            260                 265                 270
```

```
Asn Val Ser Ala Thr Ser Thr Leu Asn Ile Ser Tyr Phe Gly Ser Glu
        275                 280                 285

Ile Gly Leu Arg Phe Ile Leu
        290                 295

<210> SEQ ID NO 320
<211> LENGTH: 283
<212> TYPE: PRT
<213> ORGANISM: Ehrlichia ewingii

<400> SEQUENCE: 320

Met Gly Lys Phe Met Asn Tyr Lys Asn Thr Leu Leu Gly Ile Met Leu
  1               5                  10                  15

Ala Leu Ser Leu Leu Pro Thr Lys Ser Phe Ser Glu Ser Ile Ser Asn
             20                  25                  30

Asn Asp Asn Ser Gln Asn Phe Lys Leu Tyr Ile Ser Gly Gln Tyr Lys
         35                  40                  45

Pro Gly Val Pro Lys Phe Asn Asn Phe Ser Ala Lys Glu Thr Asn Val
     50                  55                  60

Lys Thr Gln Lys Leu Leu Gly Leu Leu Ser Gly Thr Ser Arg Lys Ile
 65                  70                  75                  80

Asp Lys Tyr Lys Asp Phe Ser Asn Thr Tyr Ile Pro Asp Phe Gln Asp
                 85                  90                  95

Ser Ser Thr Gly Phe Gly Ala Ala Val Gly Tyr Ile Ser Tyr Lys Gly
            100                 105                 110

Ile Arg Phe Glu Ile Glu Ser Ser Tyr Glu Glu Phe Gln Val Asn Ile
        115                 120                 125

His Asp Asn Cys Glu Gly Thr Ile Glu Pro Cys Arg Tyr Phe Ala Leu
    130                 135                 140

Ala Arg Ser Val Gly Arg Arg Gly Trp Pro Asp Gln Asn Asn Tyr Thr
145                 150                 155                 160

Val Met Lys Asn Thr Gly Leu Ser Met Thr Ser Val Met Phe Asn Gly
                165                 170                 175

Cys Tyr Asn Ile Met Ser Asn Lys Leu Glu Ile Ser Pro Tyr Ile Cys
            180                 185                 190

Ile Gly Ile Gly Gly Asp Phe Ile Asp Phe Phe Asp Ser Thr His Ile
        195                 200                 205

Lys Leu Ala Tyr Gln Gly Lys Leu Gly Ile Ser Tyr Ser Leu Leu Pro
    210                 215                 220

Asp Val Thr Leu Phe Val Asp Gly Tyr Tyr His Arg Ile Ala Asn Asn
225                 230                 235                 240

Gln Phe Lys Asn Leu Asn Val Leu Gln Pro Val Glu Leu Lys Tyr Glu
                245                 250                 255

Pro Lys Ile Thr Ser Ala Thr Ala Thr Met Asn Val Thr Tyr Phe Gly
            260                 265                 270

Gly Glu Val Gly Ile Arg Phe Ile Phe Asn Ser
        275                 280

<210> SEQ ID NO 321
<211> LENGTH: 282
<212> TYPE: PRT
<213> ORGANISM: Ehrlichia ewingii

<400> SEQUENCE: 321

Met Asn Lys Asn Lys Ser Ile Ile Ile Gly Thr Ala Leu Thr Phe Leu
  1               5                  10                  15
```

```
Leu Ala Phe Ser Pro Ile Glu Ser Phe Ser Ala Asn Gln Thr Asp Glu
            20                  25                  30

Thr Ile Pro Ile Thr Ala Pro Ile Ser Gly Ile Tyr Phe Thr Gly Gln
        35                  40                  45

Tyr Lys Pro Gly Ile Ser Asn Phe Ser Asn Phe Ser Ala Lys Glu Thr
    50                  55                  60

Asn Tyr Asn Thr Gln Lys Leu Val Arg Leu Lys Lys Asp Ala Lys Glu
65                  70                  75                  80

Ser Asn Leu Leu Gly Val Asn Thr Asn Phe Glu Asp Thr Tyr Ser Val
                85                  90                  95

Lys Phe Gln Asn Asn Ile Ile Ser Phe Ser Gly Ile Ile Gly Tyr Ala
            100                 105                 110

Thr Ser Lys Gly Ile Arg Leu Glu Ile Glu Gly Ala Tyr Glu Ser Phe
        115                 120                 125

Asp Val Lys Ser Pro Val Gly Tyr Ser Lys Asp Asn Ala Tyr Tyr Arg
    130                 135                 140

Tyr Phe Ala Leu Ala Arg Ser Met Thr Lys Glu Asn Pro Lys Glu Phe
145                 150                 155                 160

Thr Val Met Lys Asn Asn Gly Leu Ser Val Ala Ser Ile Met Ile Asn
                165                 170                 175

Gly Cys Tyr Asp Phe Ala Leu Asp Asp Phe Ala Leu Ser Pro Tyr Ile
            180                 185                 190

Cys Ala Gly Ile Gly Glu Asp Phe Ile Glu Phe Phe Asp Ala Leu His
        195                 200                 205

Ile Lys Ile Ala Tyr Gln Gly Lys Leu Gly Ile Ser Tyr Arg Glu Ser
    210                 215                 220

Pro Lys Ile Ser Leu Phe Ile Asp Gly Tyr Tyr His His Ile Ile Gly
225                 230                 235                 240

Asn Gln Phe Lys Asn Leu Ser Val His His Ala Val Glu Leu Ser Glu
                245                 250                 255

Phe Pro Lys Asn Ser Ser Ala Val Ala Thr Leu Asp Ile Gly Tyr Leu
            260                 265                 270

Gly Gly Glu Val Gly Ala Arg Phe Ile Phe
        275                 280

<210> SEQ ID NO 322
<211> LENGTH: 289
<212> TYPE: PRT
<213> ORGANISM: Ehrlichia ewingii

<400> SEQUENCE: 322

Met Lys Lys Lys Ile Asn Ile Leu Asn Val Ile Leu Leu Ala Ser Leu
1               5                   10                  15

Ser Ala Phe Leu Ser Thr Lys Ser Ser Ala Val Ser Leu Asp Asn Ile
            20                  25                  30

Glu Ser Pro Gln Ile Tyr Leu Gly Thr Asn Tyr Lys Leu Ser Ile Ser
        35                  40                  45

His Phe Thr Asn Phe Ser Val Gln Glu Thr Asn Gln Thr Val Asp Ile
    50                  55                  60

Ile Gly Leu Lys Ser Asn Val Pro Asn Thr Glu Asp Asp Ile Leu Lys
65                  70                  75                  80

Thr Ala Lys Asn Phe Asn Thr Gln Tyr Asn Pro Ile Phe Lys Asn Asn
                85                  90                  95

Phe Thr Gly Phe Ser Gly Ala Leu Gly Tyr Tyr Ser Gly Lys Gly Leu
```

```
            100                 105                 110
Arg Leu Glu Leu Glu Ala Ser Tyr Gln Asp Phe Asp Val Lys Lys Ser
        115                 120                 125

Lys Asn Tyr Lys Thr Asn Asp Ala His Arg Tyr Phe Ala Leu Val Arg
    130                 135                 140

Asn Lys Asp Asp Lys Ala Phe Gln Pro Gln Asp Val Leu Tyr Arg
145                 150                 155                 160

Lys Arg Tyr Arg Ser Phe Tyr Ser Phe Met Arg Asn Asp Gly Ile Ser
                165                 170                 175

Ile Ala Ser Val Met Phe Asn Gly Cys Tyr Asp Leu Pro Phe Ser Asn
            180                 185                 190

Phe Lys Val Ser Ser Tyr Ala Cys Ile Gly Ile Gly Gly Asp Phe Ile
        195                 200                 205

Glu Phe Phe Glu Ala Met Lys Val Lys Phe Ala Tyr Gln Ala Lys Leu
    210                 215                 220

Gly Ile Ser Tyr Tyr Ile Ser Pro Ser Val Asn Leu Phe Ala Asp Thr
225                 230                 235                 240

Tyr Tyr His Lys Ser Val Gly Asn Gln Phe Lys Asn Leu Arg Val Gln
                245                 250                 255

Tyr Ala His Thr Leu Arg Leu Thr Pro Ile Phe Thr Ser Ala Ile Ala
            260                 265                 270

Lys Leu Asn Ile Gly Tyr Phe Gly Gly Glu Val Gly Phe Arg Phe Ile
        275                 280                 285

Phe

<210> SEQ ID NO 323
<211> LENGTH: 290
<212> TYPE: PRT
<213> ORGANISM: Ehrlichia ewingii

<400> SEQUENCE: 323

Met Asn Cys Lys Lys Ile Phe Ile Thr Ser Thr Leu Ile Ser Leu Val
1               5                   10                  15

Ser Phe Leu Pro Gly Val Ser Phe Ser Asp Val Ile Gln Glu Asp Ser
            20                  25                  30

Asn Pro Ala Gly Ser Val Tyr Ile Ser Ala Lys Tyr Met Pro Thr Ala
        35                  40                  45

Ser His Phe Gly Lys Met Ser Ile Lys Glu Asp Ser Lys Asn Thr Gln
    50                  55                  60

Thr Val Phe Gly Leu Lys Lys Asp Trp Asp Gly Val Lys Val Pro Thr
65                  70                  75                  80

Ser Glu Asn Thr Asn Tyr Ser Ser Leu Phe Thr Glu Lys Asp Tyr Ser
                85                  90                  95

Phe Arg Tyr Glu Asn Asn Pro Phe Leu Gly Phe Ala Gly Ala Ile Gly
            100                 105                 110

Tyr Ser Met Asn Gly Pro Arg Ile Glu Phe Glu Val Ser Tyr Glu Thr
        115                 120                 125

Phe Asp Val Lys Asn Pro Gly Gly Asn Tyr Lys Asn Asp Ala His Met
    130                 135                 140

Tyr Cys Ala Leu Asp Thr Ala Gln Gln Ser Ala Thr Asn Gly Ala Thr
145                 150                 155                 160

Leu Ala Ser Ser Val Met Ile Lys Asn Glu Asn Leu Thr Asn Ile Ser
                165                 170                 175

Leu Met Leu Asn Ala Cys Tyr Asp Ile Met Leu Asp Gly Met Pro Val
```

```
                    180                 185                 190
Ser Pro Tyr Val Cys Ala Gly Ile Gly Thr Asp Leu Val Ser Val Ile
        195                 200                 205

Asn Ala Thr Asn Pro Lys Leu Ser Tyr Gln Gly Lys Leu Gly Ile Ser
    210                 215                 220

Tyr Ser Ile Asn Ser Glu Ala Ser Ile Phe Ile Gly Gly His Phe His
225                 230                 235                 240

Arg Val Ile Gly Asn Glu Phe Lys Asp Ile Ala Thr Leu Lys Ile Phe
            245                 250                 255

Thr Ala Thr Asn Lys Val Ser Thr Val Ala Asn Pro Gly Phe Ala Ser
            260                 265                 270

Ala Thr Leu Asp Val Cys His Phe Gly Ile Glu Ile Gly Gly Arg Phe
        275                 280                 285

Ile Phe
    290
```

EHRLICHIA EWINGII PROTEINS, NUCLEIC ACIDS, AND METHODS OF THEIR USE

RELATED APPLICATIONS

This application is a divisional of U.S. patent application Ser. No. 12/115,490, filed May 5, 2008, now U.S. Pat. No. 8,784,828, which claims priority to US Provisional Application Ser. No. 60/916,227, filed May 4, 2007; and U.S. Provisional Application Ser. No. 61/016,348, filed Dec. 21, 2007; the entire contents of which are incorporated herein by reference.

GOVERNMENT RIGHTS

This invention was made, at least in part, with federal funding from the National Institutes of Health Grant R01A147407. The United States Government may have certain rights in this invention.

BACKGROUND

*Ehrlichia ewingii*, a tick-transmitted rickettsia previously known only as a canine pathogen, is the most recently recognized human granulocytic ehrlichiosis agent. Granulocyte-tropic *Ehrlichia* was first reported by Dr. S. A. Ewing in 1971 in a dog from Arkansas and was thought to be a granulocytic variant of *Ehrlichia canis*. Granulocyte-tropic *Ehrlichia* was recognized as a separate species in 1992, based on 16S rRNA gene sequence comparison and named as *Ehrlichia ewingii* in honor of Dr. S. A. Ewing. Since then, canine infection with *E. ewingii* has been reported in several states in the U.S. and recently from Africa. Clinical signs in dogs infected with *E. ewingii* are fever, lethargy, anorexia, lameness, and polyarthritis, accompanied with mild thromobocytopenia and mild anemia. In 1999, human infection with *E. ewingii* was documented. Since 1996, retrospectively, approximately 10 confirmed cases of human granulocytic ehrlichiosis caused by *E. ewingii* infection have been identified in Missouri and Oklahoma.

Diagnosis of *E. ewingii* infections has proven difficult. *E. ewingii* has yet to be cultivated, and there is no serologic test available to diagnose *E. ewingii* infection. Clinical signs of patients infected with *E. ewingii*, such as fever, headache, myalgia, leukopenia, and thrombocytopenia are similar to those of human monocytic ehrlichiosis caused by *E. chaffeensis* and human granulocytic anaplasmosis caused by *A. phagocytophilum*. Hence, clinical features alone cannot distinguish these causative agents. Further complicating the diagnosis of ehrlichiosis infections, *E. ewingii* and *E. chaffeensis* also share the same vector tick species and animal reservoirs. Experimentally, the Lone star tick (*Amblyomma americanum*) has been shown to be a competent vector, although bacterial DNA has been detected in other species of ticks. White-tailed deer (*Odocoileus virginianus*) is considered to be an important reservoir for *E. ewingii* and dogs are also possible reservoirs. Consequently, *E. ewingii* and *E. chaffeensis* have similar seasonal and geographic distributions. While bacteria have been seen on blood smears from infected animals and humans, and detected by PCR in the blood and tick specimens, to date *E. ewingii* remains uncultivable and a stable laboratory isolate is not available. PCR tests based on the *E. ewingii*-specific partial sequence of a 16S rRNA gene and a partial p28-19 sequence have been reported (Gusa, A. A., et al. 2001. *J. Clin Microbiol* 39:3871-3876). Yet, sensitivities and specificities of *E. ewingii* PCR tests in clinical specimens are unknown, as there are no other definitive tests with which to compare. The microscopic observation of morulae in Romanovsky dye-stained peripheral blood granulocytes provides definitive proof of ehrlichial infections. Unfortunately, this test cannot be used as a single diagnostic test for *E. ewingii* infection because it cannot distinguish *E. ewingii* morulae from other granulocytic agents, such as *A. phagocytophilum*. Furthermore, negative results from Romanovsky dye-staining cannot rule out *E. ewingii* infection, owing to high false-negative rates caused by sample conditions and the low sensitivity of the assay. These setbacks in prior diagnostic testing necessitate an additional test to properly identify *E. ewingii* infection.

SUMMARY

Provided herein is an isolated *E. ewingii* (EE) polypeptide that includes an amino acid sequence of a mature EE protein or a functional derivative thereof. The mature EE protein is selected from the group consisting of: (1) amino acid 24 to 293 of SEQ ID NO 3 corresponding to a mature OMP-1-1 protein encoded by nucleotide 67203-1484 of SEQ ID NO: 1; (2) amino acid -22 to 272 of SEQ ID NO: 4 corresponding to a mature OMP-1-2 protein encoded by nucleotide 2116-2871 of SEQ ID NO: 1; (3) amino acid 24 to 284 of SEQ ID NO: 6 corresponding to a mature OMP-1-3 protein encoded by nucleotide 3610-4395 of SEQ ID NO: 1; (4) amino acid 28 to 293 of SEQ ID NO: 7 corresponding to a mature OMP-1-4 protein encoded by nucleotide 4486-5286 of SEQ ID NO: 1; (5) amino acid 24 to 272 of SEQ ID NO: 8 corresponding to a mature OMP-1-5 protein encoded by nucleotide 5380-6129 of SEQ ID NO: 1; (6) amino acid 26 to 299 of SEQ ID NO: 9 corresponding to a mature OMP-1-6 protein encoded by nucleotide 6216-7040 of SEQ ID NO: 1; (7) amino acid 27 to 284 of SEQ ID NO: 10 corresponding to a mature OMP-1-7 protein encoded by nucleotide 7145-7921 of SEQ ID NO: 1; (8) amino acid 29 to 243 of SEQ ID NO: 11 corresponding to a mature OMP-1-8 protein encoded by nucleotide 8032-8679 of SEQ ID NO: 1; (9) amino acid 28 to 281 of SEQ ID NO: 12 corresponding to a mature OMP-1-9 protein encoded by nucleotide 8772-9536 of SEQ ID NO: 1; (10) amino acid 26 to 280 of SEQ ID NO: 13 corresponding to a mature OMP-1-10 protein encoded by nucleotide 9620-10387 of SEQ ID NO: 1; (11) amino acid 28 to 290 of SEQ ID NO: 14 corresponding to a mature OMP-1-11 protein encoded by nucleotide 10477-11268 of SEQ ID NO: 1; (12) amino acid 27 to 298 of SEQ ID NO: 15 corresponding to a mature OMP-1-12 protein encoded by nucleotide 11370-12188 of SEQ ID NO: 1; (13) amino acid 30 to 302 of SEQ ID NO: 16 corresponding to a mature OMP-1-13 protein encoded by nucleotide 12292-13113 Of SEQ ID NO: 1; (14) amino acid 26 to 285 of SEQ ID NO: 17 corresponding to a mature OMP-1-14 protein encoded by nucleotide 14530-15312 of SEQ ID NO: 1; (15) amino acid 26 to 278 of SEQ ID NO: 18 corresponding to a mature OMP-1-15 protein encoded by nucleotide 15689-16450 of SEQ ID NO: 1; (16) amino acid 26 to 282 of SEQ ID NO: 19 corresponding to a mature OMP-1-16 protein encoded by nucleotide 16861-17634 of SEQ ID NO: 1; (17) amino acid 26 to 272 of SEQ ID NO: 20 corresponding to a mature OMP-1-17 protein encoded by nucleotide 18479-19222 of SEQ ID NO: 1; (18) amino acid 33 to 282 of SEQ ID NO: 21 corresponding to a mature OMP-1-18 protein encoded by nucleotide 19558-20310 of SEQ ID NO: 1; or (19) amino acid 24 to 282 of SEQ ID NO: 22 corresponding to a mature OMP-1-19 protein encoded by nucleotide 21188-21967 of SEQ ID NO: 1. Excluded from the isolated polypeptide sequence are the sequence SEQ ID NO: 128, 130, 132, 134, 136; or any fragment thereof. Each EE polypeptide has a specific binding affinity for an anti-*E. ewingii* antibody.

In some embodiments, the functional derivative of the EE protein comprises a sequence which is at least 85%, 90%, 95%, or 98% identical to one of the sequences (1)-(19), described above.

In some embodiments, the functional derivative comprises an immunoreactive fragment that has a length of from 6 amino acids to less than the full length of the EE protein and comprises at least 6 consecutive amino acids of one or more sequences selected from the group consisting of: (1) SEQ ID NO: 137-155; (2) SEQ ID NO: 156-173; (3) SEQ ID NO: 174-191; (4) SEQ ID NO: 192-208; (5) SEQ ID NO: 209-227; and (6) any combination of the sequences (1)-(5). Each immunoreactive fragment has a specific binding affinity for an anti-*E. ewingii* antibody.

In some embodiments, the EE polypeptide comprises a sequence selected from the group consisting of (1) SEQ ID NO: 3 corresponding to an immature OMP-1-1 protein; (2) SEQ ID NO: 4 corresponding to an immature OMP-1-2 protein; (3) SEQ ID NO: 6 corresponding to an immature OMP-1-3 protein; (4) SEQ ID NO: 7 corresponding to an immature OMP-1-4 protein; (5) SEQ ID NO: 8 corresponding to an immature OMP-1-5 protein; (6) SEQ ID NO: 9 corresponding to an immature OMP-1-6 protein; (7) SEQ ID NO: 10 corresponding to an immature OMP-1-7 protein; (8) SEQ ID NO: 11 correspoding to an immature OMP-1-8 protein; (9) SEQ ID NO: 12 corresponding to an immature OMP-1-9 protein; (10) SEQ ID NO: 13 corresponding to an immature OMP-1-10 protein; (11) SEQ ID NO: 14 corresponding to an immature OMP-1-11 protein; (12) SEQ ID NO: 15 corresponding to an immature OMP-1-12 protein; (13) SEQ ID NO: 16 corresponding to an immature OMP-1-13 protein; (14) SEQ ID NO: 17 corresponding to an immature OMP-1-14 protein; (15) SEQ ID NO: 18 corresponding to an immature OMP-1-15 protein; (16) SEQ ID NO: 19 corresponding to an immature OMP-1-16; (17) SEQ ID NO: 20 corresponding to an immature OMP-1-17 protein; (18) SEQ ID NO: 21corresponding to an immature OMP-1-18 protein; and (19) SEQ ID NO: 22 corresponding to an immature OMP-1-19 protein.

Also provided herein is an isolated polynucleotide encoding an *E. ewingii* (EE) protein, or a functional derivative thereof. The EE protein is selected from the group consisting of: (1) a mature OMP-1-1 protein encoded by nucleotide 672-1484 of SEQ ID NO: 1; (2) a mature OMP-1-2 protein encoded by nucleotide 2116-2871 of SEQ ID NO: 1; (3) a mature OMP-1-3 protein encoded by nucleotide 3610-4395 of SEQ ID NO: 1; (4) a mature OMP-1-4 protein encoded by nucleotide 4486-5286 of SEQ ID NO: 1; (5) a mature OMP-1-5 protein encoded by nucleotide 5380-6129 of SEQ ID NO: 1; (6) a mature OMP-1-6 protein encoded by nucleotide 6216-7040 of SEQ ID NO: 1; (7) a mature OMP-1-7 protein encoded by nucleotide 7145-7921 of SEQ ID NO: 1; (8) a mature OMP-1-8 protein encoded by nucleotide 8032-8679 of SEQ ID NO: 1; (9) a mature OMP-1-9 protein encoded by nucleotide 8772-9536 of SEQ ID NO: 1; (10) a mature OMP-1-10 protein encoded by nucleotide 9620-10387 of SEQ ID NO: 1; (11) a mature OMP-1-11 protein encoded by nucleotide 10477-11268 of SEQ ID NO: 1; (12) a mature OMP-1-12 protein encoded by nucleotide 11370-12188 of SEQ ID NO: 1; (13) a mature OMP-1-13 protein encoded by nucleotide 12292-13113 of SEQ ID NO: 1; (14) a mature OMP-1-14 protein encoded by nucleotide 14530-15312 of SEQ ID NO: 1; (15) a mature OMP-1-15 protein encoded by nucleotide 15689-16450 of SEQ ID NO: 1; (16) a mature OMP-1-16 protein encoded by nucleotide 16861-17634 of SEQ ID NO: 1; (17) a mature OMP-1-17 protein encoded by nucleotide 18479-19222 of SEQ ID NO: 1; (18) a mature OMP-1-18 protein encoded by nucleotide 19558-20310 of SEQ ID NO: 1; and (19) a mature OMP-1-19 protein encoded by nucleotide 21188-21967 of SEQ ID NO: 1. The functional derivative should not have the sequence SEQ ID NO: 128, 130, 132, 134, 136; or any fragment thereof; and each functional derivative should have a specific binding affinity for an anti-*E. ewingii* antibody.

In some embodiments, the functional derivative encoded by the polynucleotide comprises a sequence which is at least 85%, 90%, 95% or 98% identical to the sequence (1)-(19), as described above.

In some embodiments, the functional derivative encoded by the polynucleotide comprises an immunoreactive fragment that has a length of from 6 amino acids to less than the full length of the EE protein and comprises: 6 or more consecutive amino acids from the following sequences: (1) SEQ ID NO: 137-155; (2) SEQ ID NO: 156-173; (3) SEQ ID NO: 174-191; (4) SEQ ID NO: 192-208; (5) SEQ ID NO: 209-227; or (6) any combination of the sequences (1)-(5); wherein each immunoreactive fragment has a specific binding affinity for an anti-*E. ewingii* antibody.

In other embodiments, the EE protein encoded by the polynucleotide comprises a sequence selected from the group consisting of: (1) SEQ ID NO: 3 corresponding to an immature OMP-1-1 protein; (2) SEQ ID NO: 4 corresponding to an immature OMP-1-2 protein; (3) SEQ ID NO: 6 corresponding to an immature OMP-1-3 protein; (4) SEQ ID NO: 7 corresponding to an immature OMP-1-4 protein; (5) SEQ ID NO: 8 corresponding to an immature OMP-1-5 protein; (6) SEQ ID NO: 9 corresponding to an immature OMP-1-6 protein; (7) SEQ ID NO: 10 corresponding to an immature OMP-1-7 protein; (8) SEQ ID NO: 11 corresponding to an immature OMP-1-8 protein; (9) SEQ ID NO: 12 corresponding to an immature OMP-1-9 protein; (10) SEQ ID NO: 13 corresponding to an immature OMP-1-10 protein; (11) SEQ ID NO: 14 corresponding to an immature OMP-1-11 protein; (12) SEQ ID NO: 15 corresponding to an immature OMP-1-12 protein; (13) SEQ ID NO: 16 corresponding to an immature OMP-1-13 protein; (14) SEQ ID NO: 17 corresponding to an immature OMP-1-14 protein; (15) SEQ ID NO: 18 corresponding to an immature OMP-1-15 protein; (16) SEQ ID NO: 19 corresponding to an immature OMP-1-16; (17) SEQ ID NO: 20 corresponding to an immature OMP-1-17 protein; (18) SEQ ID NO: 21 corresponding to an immature OMP-1-18 protein; (19) SEQ ID NO: 22 corresponding to an immature OMP-1-19 protein.

In one embodiment, the polynucleotide comprises a portion of the nucleotide sequence SEQ ID NO: 1.

The invention also relates to a kit for detecting antibodies specific for *E. ewingii* (EE), the kit comprising an isolated EE polypeptide as described herein.

Also provided herein is a method for detecting antibodies specific for *E. ewingii* (EE). The method includes: (a) contacting a test sample with one or more isolated EE polypeptides, as described herein, under conditions that allow polypeptide/antibody complexes to form; and (b) assaying for the formation of a complex between antibodies in the test sample and the one or more EE polypeptides; wherein the formation of the complex is an indication that antibodies specific for *E. ewingii* are present in the test sample.

Also provided are isolated antibodies having specific binding affinity to an isolated EE polypeptide, as described herein.

Also provided is an immunogenic composition comprising one or more isolated *E. ewingii* OMP proteins, or immunogenic fragments or variants thereof, or a fusion protein containing same, and a pharmaceutically acceptable carrier. Such a composition is capable of producing antibodies specific to *E. ewingii* in a subject to whom the immunogenic composition has been administered. The isolated *E. ewingii* OMP protein for use in such a composition is selected from the group consisting of: (1) amino acid 24 to 293 of SEQ ID NO: 3 corresponding to a mature OMP-1-1 protein; (2) amino acid 22 to 272 of SEQ ID NO: 4 corresponding to a mature OMP-1-2 protein; (3) amino acid 24 to 284 of SEQ ID NO: 6 corresponding to a mature OMP-1-3 protein; (4) amino acid 28 to 293 of SEQ ID NO: 7 corresponding to a mature OMP-1-4 protein; (5) amino acid 24 to 272 of SEQ ID NO: 8 corresponding to a mature OMP-1-5 protein; (6) amino acid 26 to 299 of SEQ ID NO: 9 corresponding to a mature OMP-1-6 protein; (7) amino acid 27 to 284 of SEQ ID NO: 10 corresponding to a mature OMP-1-7 protein; (8) amino acid 29 to 243 of SEQ ID NO: 11 corresponding to a mature OMP-1-8 protein; (9) amino acid 28 to 281 of SEQ ID NO: 12 corresponding to a mature OMP-1-9 protein; (10) amino acid 26 to 280 of SEQ ID NO: 13 corresponding to a mature OMP-1-10 protein; (11) amino acid 28 to 290 of SEQ ID NO: 14 corresponding to a mature OMP-1-11 protein; (12) amino acid 27 to 298 of SEQ ID NO: 15 corresponding to a mature OMP-1-12 protein; (13) amino acid 30 to 302 of SEQ ID NO: 16 corresponding to a mature OMP-1-13 protein; (14) amino acid 26 to 285 of SEQ ID NO: 17 corresponding to a mature OMP-1-14 protein; (15) amino acid 26 to 278 of SEQ ID NO: 18 corresponding to a mature OMP-1-15 protein; (16) amino acid 26 to 282 of SEQ ID NO: 19 corresponding to a mature OMP-1-16 protein; (17) amino acid 26 to 272 of SEQ ID NO: 20 corresponding to a mature OMP-1-17 protein; (18) amino acid 33 to 282 of SEQ ID NO: 21 corresponding to a mature OMP-1-18 protein; and (19) amino acid 24 to 282 of SEQ ID NO: 22 corresponding to a mature OMP-1-19 protein.

In one embodiment, the fusion protein in such a composition comprises an isolated *E. ewingii* OMP protein, or immunogenic fragment or variant thereof, and an N-terminal or C-terminal peptide or tag.

DETAILED DESCRIPTION

Figure 1:
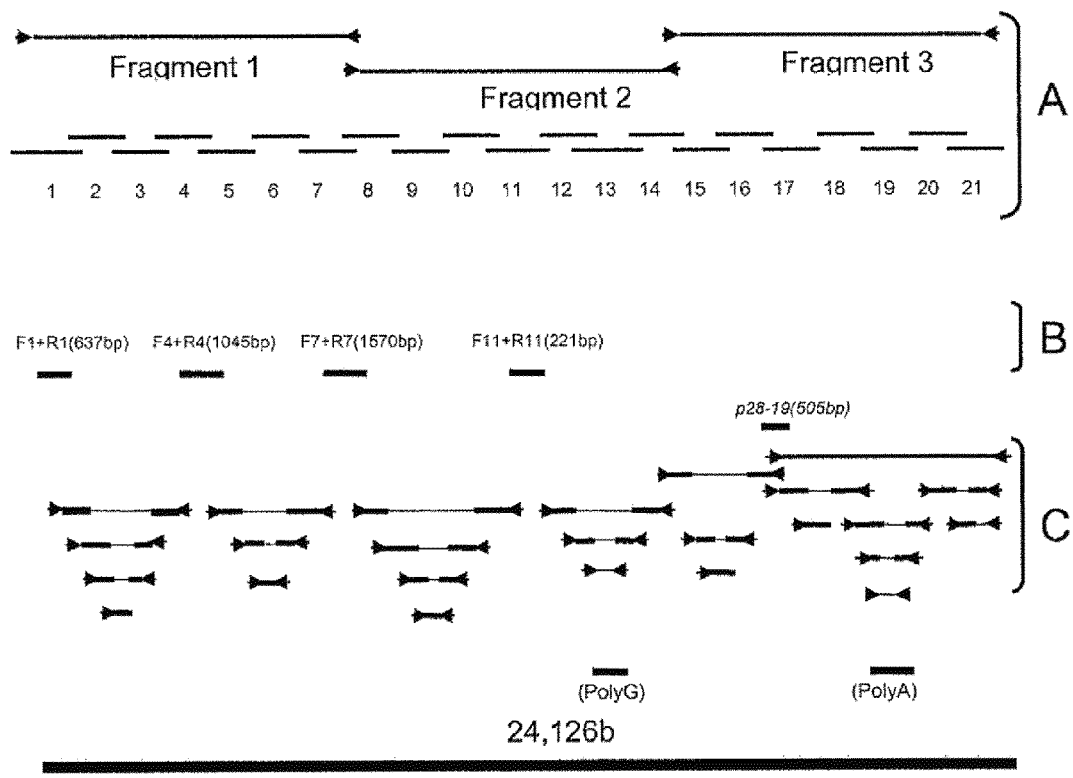
FIG. 1. Strategy of *E. ewingii* omp-1 cluster sequencing. *E. chaffeensis* omp-1 and *E. canis* p30 were aligned to design 21 pairs of degenerate primers. The OMP-1 multigene locus was divided into three fragments each composed of seven shorter fragments (A). The initial nested touch-down PCRs generated four specific sequences within fragments 1 and 2 (B). Two fragments were amplified by nested touchdown PCR within fragment 3 using the p28-19 sequence and degenerate primers. Specific primers were designed to close all gaps (C). Two poly A/T and G/C regions were cloned into a TA vector and sequenced. The final sequence (24,126 bp) was assembled using SeqMan program in the DNASTAR software.

The present invention will now be described with occasional reference to some specific embodiments disclosed herein. This invention may, however, be embodied in different forms and should not be construed as limited to the embodiments set forth herein. Rather, these embodiments are provided so that this disclosure will be thorough and complete, and will fully convey the scope to those skilled in the art.

Unless otherwise defined, all technical and scientific terms used herein have the same meaning as commonly understood by one of ordinary skill in the art to which this invention belongs. The terminology used in the description herein is for describing particular embodiments only and is not intended to be limiting. As used in the description and the appended claims, the singular forms "a," "an," and "the" are intended to include the plural forms as well, unless the context clearly indicates otherwise. All publication, patent applications, patents, and other references mentioned herein are incorporated by reference in their entirety.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope are approximations, the numerical values set forth in the specific examples are reported as precisely as possible. Any numerical values, however, inherently contain certain errors necessarily resulting from error found in their respective measurements.

DEFINITIONS

A "polynucleotide" or "nucleic acid molecule," as is generally understood and used herein, refers to a polymer of nucleotides, and includes but should not be limited to DNA and RNA.

"Recombinant DNA" is any DNA molecule formed by joining DNA segments from different sources and produced using "recombinant DNA" technology (also known as "molecular genetic engineering").

A "DNA segment or fragment," as is generally understood and used herein, refers to a molecule comprising a linear stretch of nucleotides wherein the nucleotides are present in a sequence that can encode, through the genetic code, a molecule comprising a linear sequence of amino acid residues that is referred to as a protein, a protein fragment or a polypeptide.

"Gene" refers to a DNA sequence related to a single polypeptide chain or protein, and as used herein includes the 5' and 3' untranslated ends. The polypeptide can be encoded by a full-length sequence or any portion of the coding sequence, so long as the functional activity (i.e. immunoreactivity or immunogenicity) of the protein is retained.

"Complementary," as used herein, refers to the natural binding of polynucleotides under permissive salt and temperature conditions by base pairing.

"Complementary DNA" or "cDNA" refers to recombinant nucleic acid molecules synthesized by reverse transcription of messenger RNA ("mRNA").

Open Reading Frame ("ORF"). A series of codons (base triplets) which can be translated into a protein without any termination codons interrupting the relevant reading frames. An ORF can be evidence that a DNA sequence is part of a gene.

Restriction Endonuclease. A "restriction endonuclease" (also "restriction enzyme") is an enzyme that has the capacity to recognize a specific base sequence (usually 4, 5, or 6 base pairs in length) in a DNA molecule, and to cleave the DNA molecule at every place where this sequence appears. For example, EcoRI recognizes the base sequence GAATTC/CTTAAG.

Restriction Fragment. The DNA molecules produced by digestion with a restriction endonuclease are referred to as "restriction fragments." Any given genome can be digested by a particular restriction endonuclease into a discrete set of restriction fragments.

Agarose Gel Electrophoresis. To determine the length of restriction fragments, an analytical method for fractionating double-stranded DNA molecules on the basis of size is required. The most commonly used technique (though not the only one) for achieving such a fractionation is "agarose gel electrophoresis." The principle of this method is that DNA molecules migrate through the gel as though it were a sieve that retards the movement of the largest molecules to the greatest extent and the movement of the smallest molecules to the least extent. Note that the smaller the DNA fragment, the greater the mobility under electrophoresis in the agarose gel.

The DNA fragments fractionated by "agarose gel electrophoresis" can be visualized directly by a staining procedure if the number of fragments included in the pattern is small. The DNA fragments of genomes can be visualized successfully. However, most genomes, including the human genome, contain far too many DNA sequences to produce a simple pattern of restriction fragments. For example, the human genome is digested into approximately 1,000,000 different DNA fragments by EcoRI. In order to visualize a small subset of these fragments, a methodology referred to as the Southern hybridization procedure can be applied.

Southern Transfer Procedure. The purpose of the "Southern transfer procedure" (also "Southern blotting") is to physically transfer DNA fractionated by agarose gel electrophoresis onto a nitrocellulose filter paper or another appropriate surface or method, while retaining the relative positions of DNA fragments resulting from the fractionation procedure. The methodology used to accomplish the transfer from agarose gel to nitrocellulose involves drawing the DNA from the gel into the nitrocellulose paper by capillary action or electrophoretic transfer.

Nucleic Acid Hybridization. "Nucleic acid hybridization" depends on the principle that two single-stranded nucleic acid molecules that have complementary base sequences will reform the thermodynamically favored double-stranded structure if they are mixed under the proper conditions. The double-stranded structure will be formed between two complementary single-stranded nucleic acids even if one is immobilized on a nitrocellulose filter. In the Southern hybridization procedure, the latter situation occurs. As noted previously, the DNA of the test sample to be tested is digested with a restriction endonuclease, fractionated by agarose gel electrophoresis, converted to the single-stranded form, and transferred to nitrocellulose paper, making it available for reannealing to the hybridization probe. Examples of hybridization conditions can be found in Ausubel, F. M. et al., Current Protocols in Molecular Biology, John Wiley & Sons, Inc., New York, N.Y. (1989). For example, a nitrocellulose filter is incubated overnight at 68° C. with labeled probe in a solution containing 50% formamide, high salt (either 5×SSC[20×: 3M NaCl/0.3M trisodium citrate] or 5×SSPE [20×: 3.6M NaCl/0.2M $NaH_2PO_4$/0.02M EDTA, pH 7.7]), 5×Denhardt's solution, 1% SDS, and 100 µg/ml denatured salmon sperm DNA. This is followed by several washes in 0.2×SSC/0.1% SDS at a temperature selected based on the desired stringency: room temperature (low stringency), 42° C. (moderate stringency) or 68° C. (high stringency). The temperature selected is determined based on the melting temperature (Tm) of the DNA hybrid.

Hybridization Probe. To visualize a particular DNA sequence in the Southern hybridization procedure, a labeled DNA molecule or "hybridization probe" is reacted to the fractionated DNA bound to the nitrocellulose filter. The areas on the filter that carry DNA sequences complementary to the labeled DNA probe become labeled themselves as a consequence of the reannealing reaction. The areas of the filter that exhibit such labeling are visualized. The hybridization probe is generally produced by molecular cloning of a specific DNA sequence.

A "purified" or "isolated" polypeptide or nucleic acid is a polypeptide or nucleic acid that has been separated from a cellular component. Purified or isolated polypeptides or nucleic acids have been purified to a level of purity not found in nature.

A "mutation" is any detectable change in the genetic material which can be transmitted to daughter cells and possibly even to succeeding generations giving rise to mutant cells or mutant individuals. If the descendants of a mutant cell give rise only to somatic cells in multicellular organisms, a mutant spot or area of cells arises. "Mutations" in the germ line of sexually reproducing organisms can be transmitted by the gametes to the next generation resulting in an individual with the new mutant condition in both its somatic and germ cells.

A "mutation" can be any (or a combination of) detectable, unnatural change affecting the chemical or physical constitution, mutability, replication, phenotypic function, or recombination of one or more deoxyribonucleotides; nucleotides can be added, deleted, substituted for, inverted, or transposed to new positions with and without inversion. "Mutations" can occur spontaneously and can be induced experimentally by application of mutagens.

Oligonucleotide or Oligomer. A molecule comprised of two or more deoxyribonucleotides or ribonucleotides, preferably more than three. Its exact size will depend on many factors, which in turn depend on the ultimate function or use of the "oligonucleotide." An "oligonucleotide" can be derived synthetically or by cloning.

Sequence Amplification. A method for generating large amounts of a target sequence. In general, one or more amplification primers are annealed to a nucleic acid sequence. Using appropriate enzymes, sequences found adjacent to, or in between the primers are amplified.

Amplification Primer or "Primer". An oligonucleotide which is capable of annealing adjacent to a target sequence and serving as an initiation point for DNA synthesis when placed under conditions in which synthesis of a primer extension product which is complementary to a nucleic acid strand is initiated.

Vector. A plasmid or phage DNA or other DNA sequence into which DNA can be inserted to be cloned. The "vector" can replicate autonomously in a host cell, and can be further characterized by one or a small number of endonuclease recognition sites at which such DNA sequences can be cut in a determinable fashion and into which DNA can be inserted. The "vector" can further contain a marker suitable for use in the identification of cells transformed with the "vector". Markers, for example, are tetracycline resistance or ampicillin resistance. The words "cloning vehicle" are sometimes used for "vector."

Expression. "Expression" is the process by which a structural gene produces a polypeptide. It involves transcription of the gene into mRNA, and the translation of such mRNA into polypeptide(s).

Expression Vector. A vector or vehicle similar to a cloning vector but which is capable of expressing a gene which has been cloned into it, after transformation into a host. The cloned gene is usually placed under the control of (i.e., operably linked to) certain control sequences such as promoter sequences.

Expression control sequences will vary depending on whether the vector is designed to express the operably linked gene in a prokaryotic or eukaryotic host and can additionally contain transcriptional elements such as enhancer elements, termination sequences, tissue-specificity elements, and/or translational initiation and termination sites.

Embodiments

The omp-1 gene cluster sequence of E. ewingii (SEQ ID NO: 1) contains 23 open reading frames (ORFs), as outlines in Table 1. The ORFs encode E. ewingii (EE) outer membrane proteins (OMPs) OMP-1-1, OMP-1-2, OMP-1-3, OMP-1-4, OMP-1-5, OMP-1-6, OMP-1-7, OMP-1-8, OMP-1-9, OMP-1-10, OMP-1-11, OMP-1-12, OMP-1-13, OMP-1-14, OMP-1-15, OMP-1-16, OMP-1-17, OMP-1-18, OMP-1-19, as well as the two proteins UN2 and UN3. As used herein, the term "EE proteins" and "EE OMPs" are used interchangeably and refer to the above mentioned 19 EE OMPs of *E. ewingii* in their mature (i.e. lacking the signal peptide) as well as immature (i.e. including the signal peptide) forms, as listed in Table 1.

"EE polypeptides" include EE proteins and functional derivatives of the EE proteins, as well as fusion proteins made from such proteins or their functional derivatives. The invention also relates to isolated polynucleotides encoding EE polypeptides, probes, primers, antibodies and methods of their production, compositions containing one or more of the above mentioned molecules, as well as methods of using the probes, primers, EE polypeptides and antibodies for the purpose of diagnosis, screening, therapy and production of vaccines against *E. ewingii.*

Isolated *E. Ewingii* Polypeptides

The 24-kb omp-1 gene locus contains 23 open reading frames (ORFs), numbered ORF 1 to 23 (see Table 1). These 23 ORFs are arranged in tandem except for three ORFs (ORF 19, 20, and 21) that are in the opposite orientation (i.e. the complementary strand encodes the OMP-1-17, OMP-1-18 and OMP-1-19 proteins, respectively). Nineteen of these 23 ORFs encode outer membrane proteins (EE proteins) enumerated as *E. ewingii* (EE)OMP-1-1 to EEOMP-1-19. Two ORFs encode the proteins UN2 and UN3. The mature OMP-1 proteins of *E. ewingii* have a molecular mass of about 25.1 to 31.3 kDa; and isoelectric points of 5.03 to 9.80. The properties of the polypeptides encoded by the ORFs of the *E. ewingii* omp-1 gene cluster, including signal peptide lengths, molecular mass, and isoelectric points of mature proteins, as well as the sequence identifiers for each protein, are shown in Table 1.

TABLE 1

Properties of *E. ewingii* proteins

| OMP-1 number | ORF number | SEQ ID NO | Upstream intergenic space (bp) | Length (bp) (based on the omp-1 nucleotide sequence SEQ ID NO: 1) | AA number | signal peptide AA number | Molecular Mass[a] (Da) | PI[a] |
|---|---|---|---|---|---|---|---|---|
| NA | ORF-1 Hypothetical transcriptional regulator | 2 | NA | 357(3-359) | 118 | NA | 13687.9[b] | 7.93[b] |
| OMP-1-1 | ORF-2 | 3 | 244 | 882(603-1484) | 293 | 23 | 29848.6 | 6.38 |
| OMP-1-2 | ORF-3 | 4 | 568 | 819(2053-2871) | 272 | 21 | 28125.9 | 8.61 |
| NA | ORF-4 UN2 | 5 | 101 | 558(2973-3530) | 185 | 32 | 18000.7 | 9.80 |
| OMP-1-3 | ORF-5 | 6 | 10 | 855(3541-4395) | 284 | 23 | 29372.6 | 7.07 |
| OMP-1-4 | ORF-6 | 7 | 6 | 882(4405-5286) | 293 | 27 | 30194.6 | 9.47 |
| OMP-1-5 | ORF-7 | 8 | 24 | 819(5311-6129) | 272 | 23 | 28174.6 | 5.39 |
| OMP-1-6 | ORF-8 | 9 | 11 | 900(6141-7040) | 299 | 25 | 30194.6 | 9.47 |
| OMP-1-7 | ORF-9 | 10 | 26 | 855(7067-7921) | 284 | 26 | 28864.7 | 5.43 |
| OMP-1-8 | ORF-10 | 11 | 26 | 732(7948-8679) | 243 | 28 | 25098.4 | 7.88 |

TABLE 1-continued Properties of E. ewingii proteins

| OMP-1 number | ORF number | SEQ ID NO | Upstream intergenic space (bp) | Length (bp) (based on the omp-1 nucleotide sequence SEQ ID NO: 1) | AA number | signal peptide AA number | Molecular Mass$^a$ (Da) | PI$^a$ |
|---|---|---|---|---|---|---|---|---|
| OMP-1-9 | ORF-11 | 12 | 11 | 846(8691-9536) | 281 | 27 | 28661.4 | 7.24 |
| OMP-1-10 | ORF-12 | 13 | 8 | 843(9545-10387) | 280 | 25 | 28476.4 | 6.25 |
| OMP-1-11 | ORF-13 | 14 | 8 | 867(10396-11268) | 290 | 27 | 29488.9 | 5.90 |
| OMP-1-12 | ORF-14 | 15 | 23 | 897(11292-12188) | 298 | 26 | 30036.8 | 5.89 |
| OMP-1-13 | ORF-15 | 16 | 16 | 909(12205-13113) | 302 | 29 | 31275.1 | 5.31 |
| OMP-1-14 | ORF-16 | 17 | 1343 | 858(14455-15312) | 285 | 25 | 28864.7 | 5.03 |
| OMP-1-15 | ORF-17 | 18 | 301 | 837(15614-16450) | 278 | 25 | 28862.8 | 5.58 |
| OMP-1-16 | ORF-18 | 19 | 335 | 849(16786-17634) | 282 | 25 | 28476.0 | 5.41 |
| OMP-1-17 | ORF-19 | 20 | 769 | 819(18404-19222) | 272 | 25 | 27782.3 | 6.50 |
| OMP-1-18 | ORF-20 | 21 | 539 | 849(19462-20310) | 282 | 32 | 28603.4 | 5.08 |
| OMP-1-19 | ORF-21 | 22 | 808 | 849(21119-21967) | 282 | 23 | 30505.0 | 7.88 |
| NA | ORF-22 | 23 | 1082 | 408(23050-23457) | 135 | NA | 14800.0 | 3.85 |
| NA | ORF-23 | 24 | 390 | 285(23848-24126) | 93 | NA | 10533.3$^b$ | 9.40$^b$ |

In one aspect, the invention relates to isolated polypeptides comprising an amino acid sequence corresponding to EE proteins, or functional derivatives thereof. The isolated polypeptides of the invention expressly exclude a peptide that is the 505-bp E. ewingii p28-1 peptide deposited in GenBank accession numbers: AF287961 (SEQ ID NOS 127-128), AF287962 (SEQ ID NOS 129-130), AF287963 (SEQ ID NOS 131-132), AF287964 (SEQ ID NOS 133-134, AF287966 (SEQ ID NOS 135-136); or any fragment thereof.

The EE proteins include the immature (i.e. with the signal peptide) as well as the mature form (lacking the signal peptide) proteins of E. Ewingii, as described below and in Table 1.

In one embodiment, the polypeptide comprises the sequence of an immature OMP-1-1 protein having the amino acid sequence SEQ ID NO: 3, encoded by nucleotide 603-1484 of SEQ ID NO: 1. In another embodiment, the polypeptide comprises the sequence of a mature OMP-1-1 protein having the amino acid sequence from residue 24 to 293 of SEQ ID NO: 3, encoded by nucleotide 672-1484 of SEQ ID NO: 1.

In one embodiment, the polypeptide comprises the sequence of an immature OMP-1-2 protein having the amino acid sequence SEQ ID NO: 4, encoded by nucleotide 2053-2871 of SEQ ID NO: 1. In another embodiment, the polypeptide comprises the sequence of a mature OMP-1-2 protein having the amino acid sequence from residue 22 to 272 of SEQ ID NO: 4, encoded by nucleotide 2116-2871 of SEQ ID NO: 1.

In another embodiment, the polypeptide comprises the sequence of an immature OMP-1-3 protein having the amino acid sequence SEQ ID NO: 6, encoded by nucleotide 3541-4395 of SEQ ID NO: 1. In another embodiment, the polypeptide comprises the sequence of a mature OMP-1-3 protein having the amino acid sequence from residue 24-284 of SEQ ID NO: 6, encoded by nucleotide 3610-4395 of SEQ ID NO: 1.

In another embodiment, the polypeptide comprises the sequence of an immature OMP-1-4 protein having the amino acid sequence SEQ ID NO: 7, encoded by nucleotide 4405-5286 of SEQ ID NO: 1. In another embodiment, the polypeptide comprises the sequence of a mature OMP-1-2 protein having the amino acid sequence from residue 28 to 293 of SEQ ID NO: 7, encoded by nucleotide 4486-5286 of SEQ ID NO: 1.

In another embodiment, the polypeptide comprises the sequence of an immature OMP-1-5 protein having the amino acid sequence SEQ ID NO: 8, encoded by nucleotide 5311-6129 of SEQ ID NO: 1. In another embodiment, the polypeptide comprises the sequence of a mature OMP-1-5 protein having the amino acid sequence from residue 24 to 272 of SEQ ID NO: 8, encoded by nucleotide 5380-6129 of SEQ ID NO: 1.

In another embodiment, the polypeptide comprises the sequence of an immature OMP-1-6 protein having the amino acid sequence SEQ ID NO: 9, encoded by nucleotide 6141-7040 of SEQ ID NO: 1. In another embodiment, the polypeptide comprises the sequence of a mature OMP-1-6 protein having the amino acid sequence from residue 26 to 299 of SEQ ID NO: 9, encoded by nucleotide 6216-7040 of SEQ ID NO: 1.

In another embodiment, the polypeptide comprises the sequence of an immature OMP-1-7 protein having the amino acid sequence SEQ ID NO: 10, encoded by nucleotide 7067-7921 of SEQ ID NO: 1. In another embodiment, the polypeptide comprises the sequence of a mature OMP-1-7 protein having the amino acid sequence from residue 27 to 284 of SEQ ID NO: 10, encoded by nucleotide 7145-7921 of SEQ ID NO: 1.

In another embodiment, the polypeptide comprises the sequence of an immature OMP-1-8 protein having the amino acid sequence SEQ ID NO: 11, encoded by nucleotide 7948-8679 of SEQ ID NO: 1. In another embodiment, the polypeptide comprises the sequence of a mature OMP-1-8 protein having the amino acid sequence from residue 29 to 243 of SEQ ID NO: 11, encoded by nucleotide 8032-8679 of SEQ ID NO: 1.

In another embodiment, the polypeptide comprises the sequence of an immature OMP-1-9 protein having the amino acid sequence SEQ ID NO: 12, encoded by nucleotide 8691-9536 of SEQ ID NO: 1. In another embodiment, the polypeptide comprises the sequence of a mature OMP-1-9 protein having the amino acid sequence from residue 28 to 281 of SEQ ID NO: 12, encoded by nucleotide 8772-9536 of SEQ ID NO: 1.

In another embodiment, the polypeptide comprises the sequence of an immature OMP-1-10 protein having the amino acid sequence SEQ ID NO: 13, encoded by nucleotide 9545-10387 of SEQ ID NO: 1. In another embodiment, the polypeptide comprises the sequence of a mature OMP-1-10 protein having the amino acid sequence from residue 26 to 280 of SEQ ID NO: 13. encoded by nucleotide 9620-10387 of SEQ ID NO: 1.

In another embodiment, the polypeptide comprises the sequence of an immature OMP-1-11 protein having the amino acid sequence SEQ ID NO: 14, encoded by nucleotide 10396-11268 of SEQ ID NO: 1. In another embodiment, the polypeptide comprises the sequence of a mature OMP-1-11 protein having the amino acid sequence from residue 28 to 290 of SEQ ID NO: 14, encoded by encoded by nucleotide 10477-11268 of SEQ ID NO: 1.

In another embodiment, the polypeptide comprises the sequence of an immature OMP-1-12 protein having the amino acid sequence SEQ ID NO: 15, encoded by nucleotide 11292-12188 of SEQ ID NO: 1. In another embodiment, the polypeptide comprises the sequence of a mature OMP-1-12 protein having the amino acid sequence from residue 27 to 298 of SEQ ID NO: 15, encoded by nucleotide 11370-12188 of SEQ ID NO: 1.

In another embodiment, the polypeptide comprises the sequence of an immature OMP-1-13 protein having the amino acid sequence SEQ ID NO: 16, encoded by nucleotide 12205-13113 of SEQ ID NO: 1. In another embodiment, the polypeptide comprises the sequence of a mature OMP-1-13 protein having the amino acid sequence from residue 30 to 302 of SEQ ID NO: 16, encoded by nucleotide 12292-13113 of SEQ ID NO: 1.

In another embodiment, the polypeptide comprises the sequence of an immature OMP-1-14 protein having the amino acid sequence SEQ ID NO: 17, encoded by nucleotide 14455-15312 of SEQ ID NO: 1. In another embodiment, the polypeptide comprises the sequence of a mature OMP-1-14 protein having the amino acid sequence from residue 26 to 285 of SEQ ID NO: 17, encoded by nucleotide 14530-15312 of SEQ ID NO: 1.

In another embodiment, the polypeptide comprises the sequence of an immature OMP-1-15 protein having the amino acid sequence SEQ ID NO: 18, encoded by nucleotide 15614-16450 of SEQ ID NO: 1. In another embodiment, the polypeptide comprises the sequence of a mature OMP-1-15 protein having the amino acid sequence from residue 26 to 278 of SEQ ID NO: 18, encoded by nucleotide 15689-16450 of SEQ ID NO: 1.

In another embodiment, the polypeptide comprises the sequence of an immature OMP-1-16 protein having the amino acid sequence SEQ ID NO: 19, encoded by nucleotide 16786-17634 of SEQ ID NO: 1. In another embodiment, the polypeptide comprises the sequence of a mature OMP-1-16 protein having the amino acid sequence from residue 26 to 282 of SEQ ID NO: 19, encoded by nucleotide 16861-17634 of SEQ ID NO: 1.

In another embodiment, the polypeptide comprises the sequence of an immature OMP-1-17 protein having the amino acid sequence SEQ ID NO: 20, encoded by nucleotide 18404-19222 of SEQ ID NO: 1. In another embodiment, the polypeptide comprises the sequence of a mature OMP-1-17 protein having the amino acid sequence from residue 26 to 272 of SEQ ID NO: 20, encoded by nucleotide 18479-19222 of SEQ ID NO: 1.

In another embodiment, the polypeptide comprises the sequence of an immature OMP-1-18 protein having the amino acid sequence SEQ ID NO: 21, encoded by nucleotide 19462-20310 of SEQ ID NO: 1. In another embodiment, the polypeptide comprises the sequence of a mature OMP-1-18 protein having the amino acid sequence from residue 33 to 282 of SEQ ID NO: 21, encoded by nucleotide 19558-20310 of SEQ ID NO: 1.

In another embodiment, the polypeptide comprises the sequence of an immature OMP-1-19 protein having amino acid sequence SEQ ID NO: 22, encoded by nucleotide 21119-21967 of SEQ ID NO: 1. In another embodiment, the polypeptide comprises the sequence of a mature OMP-1-19 protein having the amino acid sequence from residue 24 to 282 of SEQ ID NO: 22, encoded by nucleotide 21188-21967 of SEQ ID NO: 1.

Figure 7:
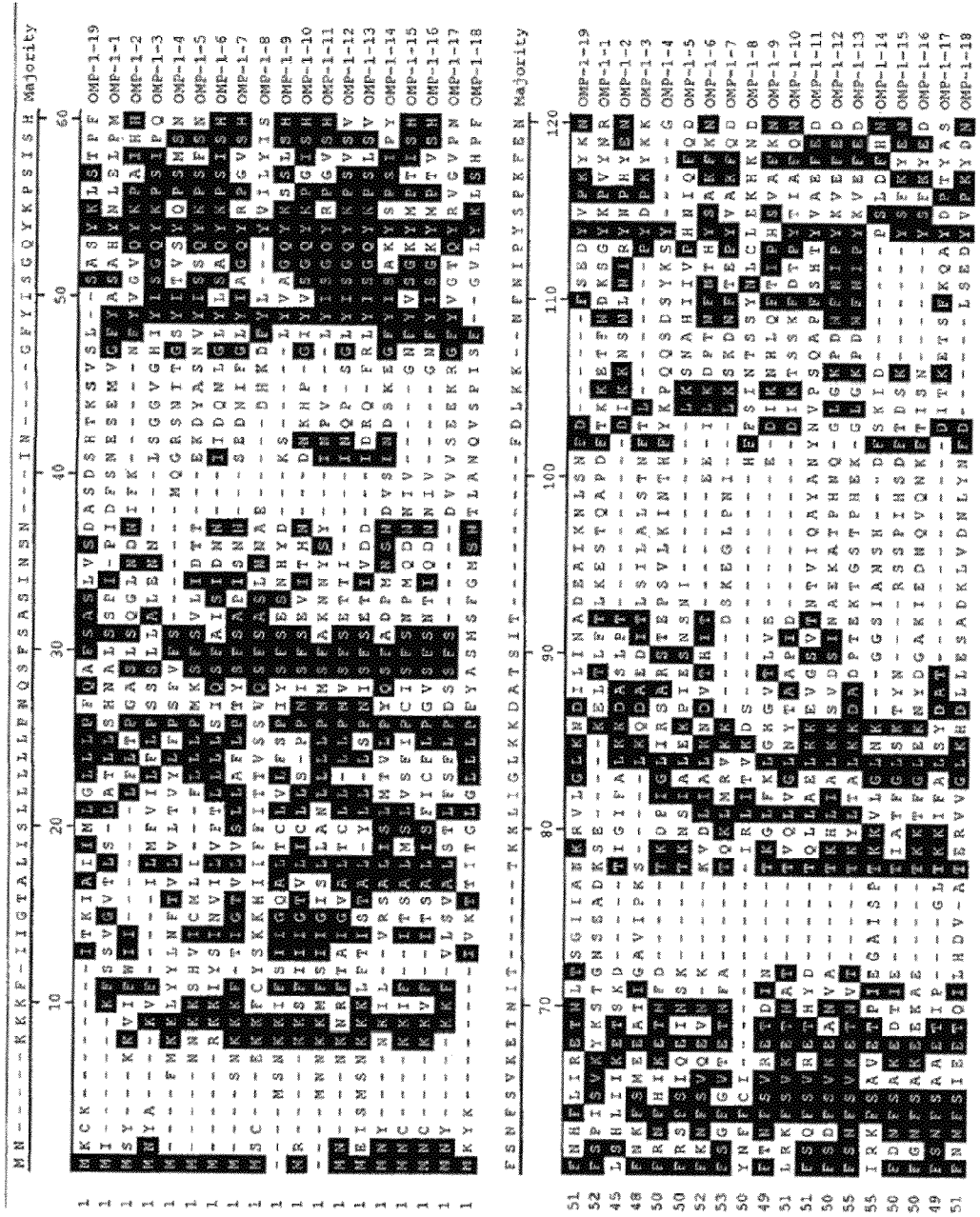
FIG. 7. Alignment of the 19 *E. ewingii* OMP-1 proteins.

Each EE OMP-1 protein has several conserved regions, with amino acid sequences that are more or less conserved between the nineteen EE OMP-1 proteins. Each EE OMP-1 protein also includes 4 variable loops, referred to hereinafter as loops 1-4, that have variable amino sequences between the nineteen EE OMP-1 proteins (FIG. 7). Tables 2-5 shows that amino acid sequence of each of the variable loops in the EE OMP-1 proteins.

TABLE 2

Sequences of variable region loop 1 in EE OMP-1-1 to OMP-1-19

| OMP # | Loop 1 | SEQ ID NO: | From aa residue # to aa residue # |
|---|---|---|---|
| OMP1-1 | SPIPIDFSNESEMV | 137 | 24 to 37 |
| OMP1-2 | QGLNDNIFKN | 138 | 22 to 31 |
| OMP1-3 | LLALENNLSGGVGHI | 139 | 21-31 |
| OMP1-4 | SFVFSMQGRSNIT | 140 | 23-35 |
| OMP1-5 | VLIDTTEKDYASNV | 141 | 24-37 |
| OMP1-6 | AISIDNNIIDQNL | 142 | 25-37 |
| OMP1-7 | PISNNSEDNIF | 143 | 28-38 |
| OMP1-8 | LNNAEDHKD | 144 | 31-39 |
| OMP1-9 | ESNHYDKSL | 145 | 28-36 |
| OMP1-10 | EVITHNDNKHPGI | 146 | 26-38 |
| OMP1-11 | AKNNYSYINPVL | 147 | 27-38 |

TABLE 2-continued

Sequences of variable region loop 1 in EE OMP-1-1 to OMP-1-19

| OMP # | Loop 1 | SEQ ID NO: | From aa residue # to aa residue # |
|---|---|---|---|
| OMP1-12 | ETTIINQPSGL | 148 | 27-37 |
| OMP1-13 | ETIVDDIDRQFRL | 149 | 30-42 |
| OMP1-14 | ADPMNSNDVSINDSKE | 150 | 25-40 |
| OMP1-15 | LVSFIPCI | 151 | 15-22 |
| OMP1-16 | FICELPGV | 152 | 15-22 |
| OMP1-17 | DVVVSEEKR | 153 | 26-34 |
| OMP1-18 | FYASMSFGMSNTLANQVSPIS | 154 | 19-39 |
| OMP1-19 | LVSDASDSHTKSVSL | 155 | 26-34 |

TABLE 3

Sequences of variable region loop 2 in EE OMP-1-1 to OMP-1-19

| OMP # | Loop 2 | SEQ ID NO: | From aa residue # to aa residue # |
|---|---|---|---|
| OMP1-1 | YKSTGNSEADKSEKELTLFTLKESTQAPDFTKKET | 156 | 59-93 |
| OMP1-2 | SKDTIGIFALKKDASLPTDIKKNS | 157 | 54-77 |
| OMP1-3 | MEEATIGAVIPKSLKQDAEDITLSILALST | 158 | 53-82 |
| OMP1-4 | FDTKDPIGLIRSARSTEPSVLKINTH | 159 | 60-85 |
| OMP1-5 | SKTKNSIALEKPIESNSNILKS | 160 | 60-81 |
| OMP1-6 | KKVDLIALKNDVTHITEEILKDP | 161 | 62-84 |
| OMP1-7 | FATQKLMRVKKDSKEGLPNILKSKD | 162 | 63-87 |
| OMP1-8 | CIIRLITVKDSHFFSINTSSYNLCLEKHKNDI | 163 | 54-85 |
| OMP1-9 | DINTKGLFKLGHGVTLVEEDIKNHLQ | 164 | 58-83 |
| OMP1-10 | ATTVQLGLNYTAAPIDDIKTSSK | 165 | 61-84 |
| OMP1-11 | HYDTQLLELKKEVGSVTNTVIQAYANYNVPSQAP | 166 | 60-94 |
| OMP1-12 | VATKHLIALKKSVDSINAEKATPHNQGLGKPD | 167 | 60-91 |
| OMP1-13 | VTTKYLTALKKDADPTEKTGSTPHEKGLGKPD | 168 | 65-96 |
| OMP1-14 | PIEGAISPTKKVLGLNKGGSIANSHDFSKIDP | 169 | 64-95 |
| OMP1-15 | DTIETIATFGLSKTYNRSSPIHSDFTDKS | 170 | 58-86 |
| OMP1-16 | — | — | — |
| OMP1-17 | IPGLTKKIFALSYDATDITKETSFKQA | 171 | 58-84 |
| OMP1-18 | QILHDVATERVVGLKHDLLESADKLVDNLYNFDLSED | 172 | 60-96 |
| OMP1-19 | LTSGIIANKRVLGLKNDILINADEAIKNLS | 173 | 61-90 |

TABLE 4

Sequences of variable region loop 3 in EE OMP-1-1 to OMP-1-19

| OMP # | Loop 3-1 | SEQ ID NO | From aa residue # to aa residue # |
|---|---|---|---|
| OMP1-1 | DKQKHTHPDNH | 174 | 136-146 |
| OMP1-2 | EGYTKITGVEQH | 175 | 122-132 |
| OMP1-3 | VSAPSGYDDNYAYSI | 176 | 123-139 |
| OMP1-4 | IKRLVNYASRDGH | 177 | 129-141 |
| OMP1-5 | ELNSSSLISSNNHYTQLYE | 178 | 126-144 |
| OMP1-6 | ITDCSNCTIN | 179 | 127-136 |
| OMP1-7 | KDPKDCSVKDAFRHL | 180 | 130-144 |
| OMP1-8 | TEDKYLTSEQEVNDY | 181 | 120-134 |
| OMP1-9 | DLKNCTIQ | 182 | 126-133 |
| OMP1-10 | TDPGNYTIK | 183 | 127-135 |
| OMP1-11 | KNSGHSSIDAHR | 184 | 136-147 |
| OMP1-12 | TLNDAF | 185 | 130-135 |
| OMP1-13 | TISNAF | 186 | 135-140 |
| OMP1-14 | KYYGLFREGTPQEEEH | 187 | 146-161 |
| OMP1-15 | SNGAHM | 188 | 121-126 |
| OMP1-16 | — | — | — |
| OMP1-17 | QFYREGSNNYKF | 189 | 123-134 |
| OMP1-18 | VQDTKSHIVDDNYR | 190 | 121-134 |
| OMP1-19 | RDTKNHIIDNN | 191 | 134-144 |

| OMP # | Loop 3-2 | SEQ ID NO: | From aa residue # to aa residue # |
|---|---|---|---|
| OMP1-1 | SCTEQEMKPAQQNGSSKDGN | 192 | 151-170 |
| OMP1-2 | LDTNGNQPKTDK | 193 | 139-150 |
| OMP1-3 | SIEVPQLRSLPYHYT | 194 | 138-152 |
| OMP1-4 | IRPDTFFNNSIPYAFNA | 195 | 146-162 |
| OMP1-5 | ANFQNFATSR | 196 | 145-154 |
| OMP1-6 | KDNNQVQPKAHDSSSTDSNNSSNNTKKSYFTF | 197 | 148-175 |
| OMP1-7 | LDTGLSMPKEKK | 198 | 150-161 |
| OMP1-8 | VNDYNIISAI | 199 | 131-140 |
| OMP1-9 | ICKENDKPTPKEKK | 200 | 145-158 |
| OMP1-10 | MNSSSNNQPKDKQFT | 201 | 146-160 |
| OMP1-11 | HSNNGNTQQNPFA | 202 | 154-166 |
| OMP1-12 | IESDQNKFQPKNANSNSSNKIYHT | 203 | 154-177 |
| OMP1-13 | SESSKEPQPKNPNSAGNNKIFHT | 204 | 159-181 |
| OMP1-14 | — | — | — |
| OMP1-15 | KDNANIGTTPQDKK | 205 | 143-156 |
| OMP1-16 | — | — | — |
| OMP1-17 | ETTISKKF | 206 | 141-148 |
| OMP1-18 | HGPAKHIN | 207 | 152-159 |
| OMP1-19 | SKQDNLNSD | 208 | 151-159 |

TABLE 5

Sequences of variable region loop 4 in EE OMP-1-1 to OMP-1-19

| OMP # | Loop 4 | SEQ ID NO | From aa residue # to aa residue # |
|---|---|---|---|
| OMP1-1 | TVQYPVKLTSPPTHIDPVVYFHSD | 209 | 258-281 |
| OMP1-2 | NYPTDNNTTKTTVSAI | 210 | 241-256 |
| OMP1-3 | LLDYPSYYRSLTSLSDNDPNRILPF | 211 | 238-262 |
| OMP1-4 | PLMLSPSTPRRRIPPQSSSEVQDATGLL | 212 | 249-276 |
| OMP1-5 | YTQYVSGINSLQEI | 213 | 234-247 |
| OMP1-6 | TYAYILKDS | 214 | 266-274 |
| OMP1-7 | NHVVELDDF | 215 | 251-259 |
| OMP1-8 | SKIHYAIILSNNKYLQNSLGDTKTNTY | 216 | 208-234 |
| OMP1-9 | QNMFDSNE | 217 | 249-256 |
| OMP1-10 | QHVVTLDT | 218 | 248-255 |
| OMP1-11 | QYVNTTTSQAIN | 219 | 254-265 |

TABLE 5-continued

Sequences of variable region loop 4 in EE OMP-1-1 to OMP-1-19

| OMP # | Loop 4 | SEQ ID NO | From aa residue # to aa residue # |
|---|---|---|---|
| OMP1-12 | QIIIAELNDA | 220 | 265-273 |
| OMP1-13 | QHVAELNDD | 221 | 269-277 |
| OMP1-14 | KTPVTLDTAPQT | 222 | 252-263 |
| OMP1-15 | DITPLKPNGIENTTATHVLV | 223 | 242-256 |
| OMP1-16 | DIATILPSGSSIKDNQY | 224 | 250-262 |
| OMP1-17 | YERVEIAYHPSIEEA | 225 | 229-245 acids of the conservative regions located between the variable loops can be changed without significantly altering the immunoreactivity of the resultant variant protein.

Variants of the EE proteins can include nonconservative as well as conservative amino acid substitutions. A conservative substitution is one in which the substituted amino acid has similar structural or chemical properties with the corresponding amino acid in the reference sequence. By way of example, conservative amino acid substitutions involve substitution of one aliphatic or hydrophobic amino acids, e.g. alanine, valine, leucine and isoleucine, with another, substitution of one hydroxyl-containing amino acid, e.g. serine and threonine, with another, substitution of one acidic residue, e.g. glutamic acid or aspartic acid, with another, replacement of one amide-containing residue, e.g. asparagine and glutamine, with another, replacement of one aromatic residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another.

The alterations are designed not to abolish the immunoreactivity of the variant EE protein with antibodies that bind to the reference protein. Guidance in determining which amino acid residues may be substituted, inserted or deleted without abolishing such immunoreactivity of the variant protein are found using computer programs well known in the art, for example, DNASTAR software.

Preparation of an EE protein variant in accordance herewith can be achieved by site-specific mutagenesis of DNA that encodes an earlier prepared variant or a nonvariant version of the protein. Site-specific mutagenesis allows the production of EE protein variants through the use of specific oligonucleotide sequences that encode the DNA sequence of the desired mutation. In general, the technique of site-specific mutagenesis is well known in the art, as exemplified by publications such as Adelman et. al., DNA 2:183 (1983) and Ausubel et al. "Current Protocols in Molecular Biology", J. Wiley & Sons, N.Y., N.Y., 1996. As will be appreciated, the site-specific mutagenesis technique can employ a phage vector that exists in both a single-stranded and double-stranded form. Typical vectors useful in site-directed mutagenesis include vectors such as the M13 phage, for example, as disclosed by Messing et al., Third Cleveland Symposium on Macromolecules and Recombinant DNA, Editor A. Walton, Elsevier, Amsterdam (1981). These phage are readibly commercially available and their use is generally well known to those skilled in the art. Alternatively, plasmid vectors that contain a single-stranded phage origin of replication (Vieira et al., Meth. Enzymol. 153:3 (1987)) can be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., Proc. Natl. Acad. Sci. (USA) 75:5765 (1978). This primer is then annealed with the single-stranded protein-sequence-containing vector, and subjected to DNA-polymerizing enzymes such as E. coli polymerase 1 Klenow fragment, to complete the synthesis of the mutation-bearing strand. Thus, a mutated sequence and the second strand bears the desired mutation. This heteroduplex vector is then used to transform appropriate cells and clones are selected that include recombinant vectors bearing the mutated sequence arrangement. After such a clone is selected, the mutated protein region can be removed and placed in an appropriate vector for protein production, generally an expression vector of the type that can be employed for transformation of an appropriate host.

Some deletions and insertions, and substitutions are not expected to product radical changes in the characteristics of EE proteins. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the native EE OMP-encoding nucleic acid, expression of the variant nucleic acid in recombinant cell culture, and, optionally, purification from the cell culture, for example, by immunoaffinity adsorption on a column (to absorb the variant by binding it to at least one remaining immune epitope). The activity of the cell lysate or purified EE OMP molecule variant is then screened in a suitable screening assay for the desired characteristic. For example, a change in the immunological character of the OMP molecule, such as affinity for a given antibody, is measured by a competitive type immunoassay. Changes in immunomodulation activity are measured by the appropriate assay. Modifications of such protein properties as redox or thermal stability, hydrophobicity, susceptibility to proteolytic degradation or the tendency to aggregate with carriers or into multimers are assayed by methods well known to the ordinarily skilled artisan.

A "fragment" is an immunoreactive fragment of an EE protein that has a length of from about 6 amoni acids to less than the full length EE protein and includes a sequence that contains at least 6 consecutive amino acids of a sequence of the EE protein. These fragments are collectively referred to herein as "EE peptides." In some embodiments, the fragment has at least 6, 7, 8, 9, 10, 11, 12, 13, 14, 15, 16, 17, 18, 19, 20, 25, 30, 35, 40, 45, 50, 60, 70, 80, 90, or 100 consecutive amino acids of an EE protein sequence. The fragment can have a length of at most, e.g., 6, 7, 8, 9, 10, 11, 12, 13, 14, 15, 16, 17, 18, 19, 20, 25, 30, 35, 40, 45, 50, 60, 70, 80, 90, 100, 120, 140, 160, 180, 200, 220, 240, 260, 280, or 300 amino acids. In some embodiments, an immunoreactive fragment has from six to sixty amino acids, from six to fifty amino acids, from ten to fifty amino acids, from six to twenty amino acids, from eight to twenty amino acids, from ten to twenty amino acids, from twelve to twenty amino acids or from twelve to seventeen amino acids. The immunoreactive fragments contemplated herein specifically exclude any fragment encoded by a 505 bp that is from nucleotide 16,918 to 17,422 of the omp-1 gene cluster sequence, SEQ ID NO: 1, previously reported as the E. ewingii p-28-1 peptide. Thus, the immunoreactive fragments as described herein specifically exclude any of the previously reported sequences for the 505-bp E. ewingii p28-1 sequence, GenBank accession numbers: AF287961 (SEQ ID NOS 127-128), AF287962 (SEQ ID NOS 129-130), AF287963 (SEQ ID NOS 131-132), AF287964 (SEQ ID NOS 133-134, AF287966 (SEQ ID NOS 135-136); or any fragment thereof.

In some embodiments, the immunoreactive peptides are from six (6) amino acids up to less than the full length EE protein, and are antigenic, i.e. are recognized by mammalian immune systems effectively. For this purpose, the peptides comprise segments that are bacterial surface exposed, rather than bacterial cytoplasmic side-exposed or embedded within the lipid bilayer membrane. Such surface exposed regions of EE proteins can be identified using computer programs using algorithms that can predict the three dimensional structure of the EE proteins based on the hydrophobicity/hydrophilicity of the amino acid regions and the repeated β sheet model.

In some embodiments, the fragments comprise a sequence that is identical to at least 6 consecutive amino acids of one or more of the variable loops depicted in Tables 2-5. In other embodiments, the fragment has a sequence that comprises at least 6 consecutive amino acids in any combination of one or more of the variable loops depicted in Tables 2-5. For example, the fragment can have a sequence from loops 1 and 2, loops 1 and 3-1, loops 1 and 3-2, loops 1 and 4, loops 2 and 3-1, loops 2 and 3-2, loops 2 and 4, loops 3-1 and 4, loops 3-2 and 4, loops 1 and 2 and 3-1, loops 1 and 2 and 3-2, loops 2 and 3-1 and 4, loops 2 and 3-2 and 4, loops 1 and 3-1 and 4, loops 1 and 3-2 and 4, loops 1 and 2 and 3-1 and 4, or loops 1 and 2 and 3-2 and 4, etc.

In some embodiments, the immunoreactive fragments (or EE peptides) include the sequences set forth in Table 6. Thus, in one embodiment, the OMP-1-1 peptide includes the sequence, SEQ ID NO: 25; the OMP-1-2 peptide includes the sequence, SEQ ID NO: 26; the OMP-1-3 peptide includes the sequence, SEQ ID NO: 27; the OMP-1-4 peptide includes the sequence, SEQ ID NO: 28; the OMP-1-5 peptide includes the sequence, SEQ ID NO: 29; the OMP-1-6 peptide includes the sequence, SEQ ID NO: 30; the OMP-1-7 peptide includes the sequence, SEQ ID NO: 31; the OMP-1-8 peptide includes the sequence, SEQ ID NO: 32; the OMP-1-9 peptide includes the sequence, SEQ ID NO: 33; the OMP-1-10 peptide includes the sequence, SEQ ID NO: 34; the OMP-1-11 peptide includes the sequence, SEQ ID NO: 35; the OMP-1-12 peptide includes the sequence, SEQ ID NO: 36; the OMP-1-13 peptide includes the sequence, SEQ ID NO: 37; the OMP-1-14 peptide includes the sequence, SEQ ID NO: 38; the OMP-1-15 peptide includes the sequence, SEQ ID NO: 39; the OMP-1-16 peptide includes the sequence, SEQ ID NO: 40; the OMP-1-17 peptide includes the sequence, SEQ ID NO: 41; the OMP-1-18 peptide includes the sequence, SEQ ID NO: 42; and the OMP-1-19 peptide includes the sequence, SEQ ID NO: 43.

TABLE 6

*E. ewingii* OMP-1 peptide sequences used in ELISA (see Example 1)

| SEQ ID NO: | OMP-1 ID | Amino acids sequence | Peptide length (amino acid position in the protein sequence) | |
|---|---|---|---|---|
| 25 | OMP-1-1 | SCTEQEMKPAQQNGSSK | 17 a.a | (151-167) |
| 26 | OMP-1-2 | EQHFALASELDTNGNQ | 16 a.a | (130-145) |
| 27 | OMP-1-3 | VSAPSGYDDNIYAYFSI | 17 a.a | (123-139) |
| 28 | OMP-1-4 | FAIPRDTFFNNSIPY | 15 a.a | (144-150) |
| 29 | OMP-1-5 | NSSSLISSNNHYTQLY | 16 a.a | (129-144) |
| 30 | OMP-1-6 | KDNNQVQPKAHDSSSTD | 17 a.a | (148-164) |
| 31 | OMP-1-7 | KDPKDCSVKDAFRHL | 15 a.a | (130-144) |
| 32 | OMP-1-8 | TEDKYLTSEQEVNDY | 15 a.a | (120-134) |
| 33 | OMP-1-9 | ICKENDKPTPKEKKY | 15 a.a | (145-159) |
| 34 | OMP-1-10 | YRYFAIAREMNSSSNNQ | 17 a.a | (137-153) |
| 35 | OMP-1-11 | KNSGHSSIDAHR | 12 a.a | (136-147) |
| 36 | OMP-1-12 | IESDQNKFQPKNANSNS | 17 a.a | (154-170) |
| 37 | OMP-1-13 | SESSKEPQPKNPNSAGN | 17 a.a | (159-175) |
| 38 | OMP-1-14 | KYYGLFREGTPQEEEH | 16 a.a | (146-161) |
| 39 | OMP-1-15 | SRKDNANIGTTPQDKK | 16 a.a | (141-156) |
| 40 | OMP-1-16 | KIEDNQVQNKFTISNY | 16 a.a | (76-91) |
| 41 | OMP-1-17 | QFYREGSNNYKF | 12 a.a | (123-134) |
| 42 | OMP-1-18 | VQDTKSHIVDDNYR | 14 a.a | (121-144) |
| 43 | OMP-1-19 | SKQDNLNSDYVTLIN | 15 a.a | (171-185) |

Also provided herein are fusion proteins in which a tag or one or more amino acids from a heterologous protein are added to the amino or carboxy terminus of the amino acid sequence of an EE protein or a functional derivative thereof. At least one of the proteins or peptides can be in a multimeric form. As used herein, the term "heterologous protein" means a protein derived from a source other than the *E. ewingii* omp-1 gene, operationally linked to a *E. ewingii* protein or a functional derivative thereof, as disclosed in the present specification, to form a chimeric or fusion *E. ewingii* protein or peptide. Typically, such additions are made to stabilize the resulting fusion protein or to simplify purification of an expressed recombinant form of the corresponding EE protein, variant, or peptide. Such tags are known in the art. Representative examples of such tags include sequences which encode a series of histidine residues, the Herpes simplex glycoprotein D, or glutathione S-transferase. Such a chimeric or fusion protein can have a variety of lengths including, but not limited to, a length of at most 100 residues, at most 200 residues, at most 300 residues, at most 400 residues, at most 500 residues, at most 800 residues or at most 1000 residues. Non-limiting examples of chimeric *E. ewingii* proteins include fusions of *E. ewingii* OMPs, or variants, or peptides: with immunogenic polypeptides, such as flagellin and cholera enterotoxin; with immunomodulatory polypeptides, such as IL-2 and B7-1; with tolerogenic polypeptides; with another *E. ewingii* OMP, or variant, or peptide; and with synthetic sequences. Other examples include linking the EE protein, or variant or peptide with an indicator reagent, an amino acid spacer, an amino acid linker, a signal sequence, a stop transfer sequence, a transmembrane domain, a protein purification ligand or a combination of thereof. The fusion proteins can have similar or substantially similar immunoreactivity to EE antibodies as the EE proteins from which they derive.

The EE polypeptides of the present invention can be used in a variety of procedures and methods, such as for the generation of antibodies, immunogenic composition and vaccines; for use in identifying pharmaceutical compositions; for studying DNA/protein interaction; as well as for diagnostic and screening methods.

Also provided are compositions of matter comprising one or more EE proteins, their functional derivatives and/or EE fusion proteins. The isolated or purified polypeptide in such compositions can be in a multimeric form and can further include a carrier. The purified polypeptide can be linked to an indicator reagent, an amino acid spacer, an amino acid linker, a signal sequence, a stop transfer sequence, a transmembrane domain, a protein purification ligand, or a combination of these. Alternatively, one or more EE proteins or peptides may be linked together.

Isolated Polynucleotides Coding for EE Polypeptides

The present invention also provides isolated polynucleotides as follows:

(a) a polynucleotide sequence encoding an immature EE protein OMP-1-1, OMP-1-2, OMP-1-3, OMP-1-4, OMP-1-5, OMP-1-6, OMP-1-7, OMP-1-8, OMP-1-9, OMP-1-10, OMP-1-11, OMP-1-12, OMP-1-13, OMP-1-14, OMP-1-15, OMP-1-16, OMP-1-17, OMP-1-18, or OMP-1-19, as described above;

(b) a polynucleotide sequence encoding a mature EE protein OMP-1-1, OMP-1-2, OMP-1-3, OMP-1-4, OMP-1-5, OMP-1-6, OMP-1-7, OMP-1-8, OMP-1-9, OMP-1-10, OMP-1-11 OMP-1-12, OMP-1-13, OMP-1-14, OMP-1-15, OMP-1-16, OMP-1-17, OMP-1-18, or OMP-1-19, as described above;

(c) a polynucleotide sequence encoding a functional derivative of an EE protein of (a) or (b) above;

(d) a polynucleotide sequence encoding a fusion protein of an EE protein or functional derivative of an EE protein;

(e) a polynucleotide sequence complementary to any of the nucleotide sequences in (a), (b), (c) or (d); and (f) a polynucleotide sequence that hybridizes under highly stringent hybridization conditions with any of the nucleotide sequences in (a), (b), (c), (d) or (e).

The EE protein encoded by the polynucleotide of the invention includes: (1) a mature OMP-1-1 protein encoded by nucleotide 672-1484 of SEQ ID NO: 1; (2) a mature OMP-1-2 protein encoded by nucleotide 2116-2871 of SEQ ID NO: 1; (3) a mature OMP-1-3 protein encoded by nucleotide 3610-4395 of SEQ ID NO: 1; (4) a mature OMP-1-4 protein encoded by nucleotide 4486-5286 of SEQ ID NO: 1; (5) a mature OMP-1-5 protein encoded by nucleotide 5380-6129 of SEQ ID NO: 1; (6) a mature OMP-1-6 protein encoded by nucleotide 6216-7040 of SEQ ID NO: 1; (7) a mature OMP-1-7 protein encoded by nucleotide 7145-7921 of SEQ ID NO: 1; (8) a mature OMP-1-8 protein encoded by nucleotide 8032-8679 of SEQ ID NO: 1; (9) a mature OMP-1-9 protein encoded by nucleotide 8772-9536 of SEQ ID NO: 1; (10) a mature OMP-1-10 protein encoded by nucleotide 9620-10387 of SEQ ID NO: 1; (11) a mature OMP-1-11 protein encoded by nucleotide 10477-11268 of SEQ ID NO: 1; (12) a mature OMP-1-12 protein encoded by nucleotide 11370-12188 of SEQ ID NO: 1; (13) a mature OMP-1-13 protein encoded by nucleotide 12292-13113 of SEQ ID NO: 1; (14) a mature OMP-1-14 protein encoded by nucleotide 14530-15312 of SEQ ID NO: 1; (15) a mature OMP-1-15 protein encoded by nucleotide 15689-16450 of SEQ ID NO: 1; (16) a mature OMP-1-16 protein encoded by nucleotide 16861-17634 of SEQ ID NO: 1; (17) a mature OMP-1-17 protein encoded by nucleotide 18479-19222 of SEQ ID NO: 1; (18) a mature OMP-1-18 protein encoded by nucleotide 19558-20310 of SEQ ID NO: 1; and (19) a mature OMP-1-19 protein encoded by nucleotide 21188-21967 of SEQ ID NO: 1.

The functional derivative encoded by the polynucleotide should not have the sequence SEQ ID NO: 128, 130,132, 134, 136; or any fragment thereof; and each functional derivative should have a specific binding affinity for an anti-*E. ewingii* antibody.

In some embodiments, the functional derivative encoded by the polynucleotide comprises a sequence which is at least 85%, 90%, 95% or 98% identical to the sequence of the mature OMP-1 protein (1)-(19), as described above.

In some embodiments, the functional derivative encoded by the polynucleotide comprises an immunoreactive fragment that has a length of from 6 amino acids to less than the full length of the EE protein and comprises 6 or more consecutive amino acids from the following sequences: (1) SEQ ID NO: 137-155; (2) SEQ ID NO: 156-173; (3) SEQ ID NO: 174-191; (4) SEQ ID NO: 192-208; (5) SEQ ID NO: 209-227; or (6) any combination of the sequences (1)-(5); wherein each immunoreactive fragment has a specific binding affinity for an anti-*E. ewingii* antibody.

In other embodiments, the EE protein encoded by the polynucleotide comprises a sequence selected from the group consisting of: (1) SEQ ID NO: 3 corresponding to an immature OMP-1-1 protein; (2) SEQ ID NO: 4 corresponding to an immature OMP-1-2 protein; (3) SEQ ID NO: 6 corresponding to an immature OMP-1-3 protein; (4) SEQ ID NO: 7 corresponding to an immature OMP-1-4 protein; (5) SEQ ID NO: 8 corresponding to an immature OMP-1-5 protein; (6) SEQ ID NO: 9 corresponding to an immature OMP-1-6 protein; (7) SEQ ID NO: 10 corresponding to an immature OMP-1-7 protein; (8) SEQ ID NO: 11 corresponding to an immature OMP-1-8 protein; (9) SEQ ID NO: 12 corresponding to an immature OMP-1-9 protein; (10) SEQ ID NO: 13 corresponding to an immature OMP-1-10 protein; (11) SEQ ID NO: 14 corresponding to an immature OMP-1-11 protein; (12) SEQ ID NO: 15 corresponding to an immature OMP-1-12 protein; (13) SEQ ID NO: 16 corresponding to an immature OMP-1-13 protein; (14) SEQ ID NO: 17 corresponding to an immature OMP-1-14 protein; (15) SEQ ID NO: 18 corresponding to an immature OMP-1-15 protein; (16) SEQ ID NO: 19 corresponding to an immature OMP-1-16; (17) SEQ ID NO: 20 corresponding to an immature OMP-1-17 protein; (18) SEQ ID NO: 21 corresponding to an immature OMP-1-18 protein; (19) SEQ ID NO: 22 corresponding to an immature OMP-1-19 protein.

In one embodiment, the polynucleotide comprises a portion of a nucleotide sequence SEQ ID NO: 1.

It is understood that the polynucleotides encoding the EE polypeptides can have a different sequence than the nucleotide sequence shown in Table 1 due to the degeneracy of the genetic code. Thus, also included within the scope of this invention are the functional equivalents of the herein-described isolated polynucleotides and derivatives thereof. For example, the nucleic acid sequences depicted in SEQ ID NO: 1 can be altered by substitutions, additions or deletions that provide for functionally equivalent molecules. Due to the degenracy of nucleotide coding sequences, other DNA sequences which encode substantially the same amino acid sequences as depicted in Tables 1-6 can be used in the practice of the present invention. These include but are not limited to nucleotide sequences comprising all or portions of SEQ ID NO: 1 that encode for EE polypeptides, which are altered by the substitution of different codons that encode a Functionally equivalent amino acid residue within the sequence.

In addition, the polynucleotide can comprise a nucleotide sequence which results from a addition, deletion or substitution of at least one nucleotide to the 5'-end and/or the 3'-end of the nucleic acid segments of SEQ ID NO: 1, or a derivative thereof. Any polynucleotide can be used in this regard, provided that its addition, deletion or substitution does not substantially alter the amino acid sequence of the EE protein, or functional derivatives or fusion proteins thereof, encoded by the polynucleotide sequence. Moreover, the polynucleotide of the present invention can, as necessary, have restriction endonuclease recognition sites added to its 5'-end and/or 3'-end. All variations of the nucleotide sequence of the EE omp-1 gene and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

Finally, the isolated polynucleotides of the invention expressly exclude any polynucleotide that encodes for a peptide that is the 505-bp *E. ewingii* p28-1 peptide deposited in GenBank accession numbers: AF287961 (SEQ ID NOS 127-128), AF287962 (SEQ ID NOS 129-130), AF287962 (SEQ ID NOS 131-132), AF287964 (SEQ ID NOS 133-134, AF287966 (SEQ ID NOS 135-136); or any fragment thereof.

Isolation of Polynucleotides

The isolated EE polynucleotides coding for EE polypeptides can be isolated from a biological sample (e.g. of mammalian or tick origin) containing EE RNA or DNA.

The polynucleotide can be isolated from a biological sample containing EE RNA using the techniques of cDNA cloning and subtractive hybridization. The polynucleotide can also be isolated from a cDNA library using a homologous probe, i.e., a probe comprising sequences substantially identical or complementary to portions or all of the polynucleotide sequence SEQ ID NO: 1; or with antibodies immunospecific for an EE OMP protein or peptide to identify clones containing such polynucleotides.

The polynucleotide can be isolated from a biological sample containing genomic DNA or from a genomic library. Suitable biological samples include, but are not limited to, whole organisms, organs, tissues, blood and cells. The method of obtaining the biological sample will vary depending upon the nature of the sample.

One skilled in the art will realize that EE polynucleotides may also be isolated from a number of infected eukaryotes (for example, mammals, birds, fish and humans) that may contain the EE protein genes.

Synthesis of Polynucleotides

Isolated polynucleotides of the present invention include those chemically synthesized. For example, a polynucleotide with the nucleotide sequence which codes for the expression product of an EE protein gene can be designed and, if necessary, divided into appropriate smaller fragments. Then an oligomer which corresponds to the polynucleotide, or to each of the divided fragments, can be synthesized. Such synthetic oligonucleotides can be prepared, for example, by the triester method of Matteucci et al., J. Am. Chem. Soc. 103:3185-3191 (1981) or by using an automated DNA synthesizer.

An oligonucleotide can be derived synthetically or by cloning. If necessary, the 5'-ends of the oligomers can be phosphorylated using T4 polynucleotide kinase. Kinasing of single strands prior to annealing or for labeling can be achieved using an excess of the enzyme. If kinasing is for the labeling of probe, the ATP can contain high specific activity radioisotopes. Then, the DNA oligomer can be subjected to annealing and ligation with T4 ligase or the like.

Also encompassed by the present invention, are single stranded polynucleotides, hereinafter referred to as antisense polynucleotides, having sequences which are complementary to the DNA and RNA sequences which encode the EE proteins and peptides, or their functional variants.

DNA Constructs Comprising a Polynucleotide Encoding an EE Polypeptide, and Cells Containing These Constructs The EE polynucleotides described herein are useful for producing the EE polypeptides. For example, an RNA molecule encoding an EE polypeptide can be used in a cell-free translation system to prepare an isolated polypeptide corresponding to an EE protein, its functional derivatives or fusion proteins. Alternatively, a DNA molecule encoding an EE polypeptide can be introduced into an expression vector and used to transform cells.

Accordingly, in another aspect, the present invention relates to an recombinant DNA molecule comprising, 5' to 3', a promoter effective to initiate transcription in a host cell and one or more of the above-described EE polynucleotides. In another embodiment, the present invention relates to a recombinant DNA molecule comprising a vector and an above-described polynucleotide.

In another embodiment, the present invention relates to a nucleic acid molecule comprising a transcriptional control region functional in a cell, a sequence complimentary to an RNA sequence encoding an amino acid sequence corresponding to an above-described EE polypeptide, and a transcriptional termination region functional in the cell.

In one embodiment, the above-described molecules are isolated and/or purified DNA molecules.

In another embodiment, the present invention relates to a cell or non-human organism that has been altered to express the EE polypeptides and so contains one or more of the above-described nucleic acid molecules.

In another embodiment, the polypeptide is purified from cells which have been altered to express the polypeptide.

As used herein, a cell, or organism, is said to be "altered to express a desired polypeptide" when the cell, or organism, through genetic manipulation, is made to produce a protein which it normally does not produce or which it normally produces at low levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression can vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the EE polypeptide coding sequence can be obtained by the above-described methods. This region can be retained for its transcriptional termination regulatory sequences, such as termination and polyadenylation. Thus, by retaining the 3'-region naturally contiguous to the DNA sequence encoding an EE protein gene, the transcriptional termination signals can be provided. Where the transcriptional termination signals are not satisfactorily functional in the expression host cell, then a 3' region functional in the host cell can be substituted.

Two DNA sequences (such as a promoter region sequence and an EE polypeptide coding sequence) are said to be operably linked if the nature of the linkage between the two DNA sequences does not (1) result in the introduction of a frame-shift mutation, (2) interfere with the ability of the promoter region sequence to direct the transcription of an EE polypeptide coding sequence, or (3) interfere with the ability of the EE polypeptide coding sequence to be transcribed by the promoter region sequence. Thus, a promoter region would be operably linked to a DNA sequence if the promoter were capable of effecting transcription of that DNA sequence.

The present invention encompasses the expression of the EE polypeptide coding sequence in either prokaryotic or eukaryotic cells. Prokaryotic hosts are, generally, the most efficient and convenient for the production of recombinant proteins and, therefore, are suitable for the expression of the EE polypeptide coding sequence.

Prokaryotes most frequently are represented by various strains of $E.\ coli$. However, other microbial strains can also be used, including other bacterial strains. In prokaryotic systems, plasmid vectors that contain replication sites and control sequences derived from a species compatible with the host can be used. Examples of suitable plasmid vectors include, but are not limited to, pBR322, pUC18, pUC19, pUC118, pUC119 and the like; suitable phage or bacteriphage vectors include λgt10, λgt11 and the like; and suitable virus vectors include pMAM-neo, pKRC and the like. In some examples, the selected vector of the present invention has the capacity to replicate in the selected host cell.

Recognized prokaryotic hosts include bacteria such as $E.\ coli$, $Bacillus$, $Streptomyces$, $Pseudomonas$, $Salmonella$, $Serratia$, and the like. However, under such conditions, the peptide will not be glycosylated. The prokaryotic host must be compatible with the replicon and control sequences in the expression plasmid.

To express EE polypeptides in a prokaryotic cells, it is necessary to operably link the EE protein coding sequence to a functional prokaryotic promoter. Such promoters can be either constitutive or regulatable (i.e., inducible or derepressible). Examples of constitutive promoters include, but are not limited to, the int promoter of bacteriophage λ, the bla promoter of the β-lactamase gene sequence of pBR322, and the CAT promoter of the chloramphenicol acetyl transferase gene sequence of pBR325, and the like. Examples of inducible prokaryotic promoters include, but are not limited to, the major right and left promoters of bacteriophage λ ($P_L$ and $P_R$), the trp, recA, lacZ, lacI, and gal promoters of $E.\ coli$, the α-amylase (Ulmanen et al., J. Bacteriol. 162:176-182 (1985)) and the ξ-28-specific promoters of $B.\ subtilis$ (Gilman et al., Gene sequence 32:11-20 (1984)), the promoters of the bacteriopages of $Bacillus$ (Gryezan, In: The Molecular Biology of the Bacilli, Academic Press, Inc., NY (1982)), and $Streptomyces$ promoters (Ward et al., Mol. Gen. Genet. 203:468-478 (1986)). Prokaryotic promoters are reviewed by Glick (J. Ind. Microbiol. 1:277-282 (1987)); Cenatiempo (Biochimie 68:505-516 (1986)); and Gottesman (Ann. Rev. Genet. 18:415-442 (1984)).

Proper expression in a prokaryotic cell may also require the presence of a ribosome binding site upstream of the gene sequence-encoding sequence. Such ribosome binding sites are disclosed, for example, by Gold et al (Ann. Rev. Microbiol. 35:365-404 (1981)).

The selection of control sequences, expression vectors, transformation methods, and the like, are dependent on the type of host cell to express the gene. As used herein, "cell", "cell line", and "cell culture" can be used interchangeably and all such designations include progeny. Thus, the words "transformants" or "transformed cells" include the primary subject cell and cultures derived therefrom, without regard to the number of transfers. It is also understood that all progeny can not be precisely identical in DNA content, due to deliberate or inadvertent mutations. However, as defined, mutant progeny have the same functionality as that of the originally transformed cell. Host cells which can be used in the expression systems of the present invention are not strictly limited, provided that they are suitable for use in the expression of the EE polypeptides of interest. Suitable hosts include eukaryotic cells.

Some examples of suitable eukaryotic hosts include, but are not limited to, yeast, fungi, insect cells, mammalian cells either in vivo, or in tissue culture. Suitable mammalian cells include HeLa cells, cells of fibroblast origin such as VERO or CHO-K1, or cells of lymphoid origin and their derivatives.

In addition, plant cells are also available as hosts, and control sequences compatible with plant cells are available, such as the cauliflower mosaic virus 35S and 19S, and nopaline synthase promoter and polyadenylation signal sequences.

Another type of host is an insect cell, for example Drosophila larvae. Using insect cells as hosts, the Drosophila alcohol dehydrogenase promoter can be used, Rubin, Science 240:1453-1459 (1988). Alternatively, baculovirus vectors can be engineered to express large amounts of EE polypeptides in insect cells (Jasny, Science 238:1653 (1987); Miller et al., In: Genetic Engineering (1986), Setlow, J. K., et al., eds., Plenum, Vol. 8, pp. 277-297).

Different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed.

Any of a series of yeast gene sequence expression systems can be utilized which incorporate promoter and termination elements from the actively expressed gene sequences coding for glycolytic enzymes. These enzymes are produced in large quantities when yeast are grown in mediums rich in glucose. Known glycolytic gene sequences can also provide very efficient transcriptional control signals.

Yeast can provide substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of EE polypeptides.

A wide variety of transcriptional and translational regulatory sequences can be employed, depending upon the nature of the host. The transcriptional and translational regulatory signals can be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, can be employed. Transcriptional initiation regulatory signals can be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

As discussed above, expression of EE polypeptides in eukaryotic hosts requires the use of eukaryotic regulatory regions. Such regions will, in general, include a promoter region sufficient to direct the initiation of RNA synthesis. Examples of eukaryotic promoters include, but are not limited to, the promoter of the mouse metallothionein 1 gene sequence (Hamer et al., J. Mol. Appl. Gen. 1:273-288 (1982)); the TK promoter of Herpes virus (McKnight, Cell 31:355-365 (1982)), the SV40 early promoter (Benoist et al., Nature (London) 290:304-310 (1981)); the yeast gal4 gene sequence promoter (Johnston et al., Proc. Natl. Acad. Sci. (USA) 79:6971-6975 (1982); Silver et al., Proc. Natl. Acad. Sci. (USA) 81:5951-5955 (1984)) and the CMV immediate-early gene promoter (Thomsen et al., Proc. Natl. Acad. Sci (USA) 81:659-663 (1984)).

As is widely known, translation of eukaryotic mRNA is initiated at the codon which encodes the first methionine. For this reason, it may be desirable to ensure that the linkage between a eukaryotic promoter and an EE polypeptide coding sequence does not contain any intervening codons which are capable of encoding a methionine (i.e., AUG). The presence of such codons results either in a formation of a fusion protein (if the AUG codon is in the same reading frame as the EE polypeptide coding sequence) or a frame-shift mutation (if the AUG codon is not in the same reading frame as the EE polypeptide coding sequence).

A nucleic acid molecule encoding an EE polypeptide and an operably linked promoter can be introduced into a recipient prokaryotic or eukaryotic cell either as a non-replicating DNA (or RNA) molecule, which can either be a linear molecule or a closed covalent circular molecule. Since such molecules are incapable of autonomous replication, the expression of the gene can occur through the transient expression of the introduced sequence. Alternatively, permanent expression can occur through the intergration of the introduced DNA sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker can provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements can also be needed for optimal synthesis of single chain binding protein mRNA. These elements can include splice signals, as well as transcription promoters, enhancer signal sequences, and termination signals. cDNA expression vectors incorporating such elements include those described by Okayama, Molec. Cell. Biol. 3:280 (1983).

In some embodiments, the introduced nucleic acid molecule will be incorporated into a plasmid or viral vector capable of autonomous replication in the recipient host. Any of a wide variety of vectors can be employed for this purpose. Factors of importance in selecting a particular plasmid or viral vector include: the ease with which recipient cells that contain the vector can be recognized and selected from those recipient cells which do not contain the vector; the number of copies of the vector which are desired in a particular host; and whether it is desirable to be able to "shuttle" the vector between host cells of different species.

Examples of prokaryotic vectors include, but are not limited to, plasmid such as those capable of replication in *E. coli* (such as, for example, pBR322, ColE1, pSC101, pACYC 184, πVX. Such plasmids are, for example, disclosed by Sambrook (Molecular Cloning: A Labroatory Manual, second edition, edited by Sambrook, Fritsch, & Maniatis, Cold Spring Harbor Laboratory, 1989), *Bacillus* plasmids include pC194, pC221, pT127, and the like. Such plasmids are disclosed by Gryezan (In: The Molecular Biology of the Bacilli, Academic Press, NY (1982), pp. 307-329). Suitable *Streptomyces* plasmids include pIJ101 (Kendall et al., J. Bacteriol. 169:4177-4183 (1987)), and *streptomyces* bacteriophages such as φC31 (Chater et al., In: Sixth International Symposium on Actinomycetales Biology, Akaderniai Kaido, Budapest, Hungary (1986), pp. 45-54). Pseudomonas plasmids are reviewed by John et al (Rev. Infect. Dis. 8:693-704 (1986)), and Izaki (Jpn. J. Bacteriol. 33:729-742 (1978)).

Examples of suitable eukaryotic plasmids include, but are not limited to, BPV, vaccinia, SV40, 2-micron circle, and the like, or their derivatives. Such plasmids are well known in the art (Botstein et al., Miami Wntr. Symp. 19:265-274 (1982); Broach, In: The Molecular Biology of the Yeast *Saccharomyces*: Life Cycle and Inheritance, Cold Spring Harbor Laboratory, Cold Spring Harbor, N.Y., p. 445-470 (1981); Broach, Cell 28:203-204 (1982); Bollon et al., J. Clin. Hematol. Oncol. 10:39-48 (1980); Maniatis, In: Cell Biology: A Comprehensive Treatise, Vol 3, Gene Sequence Expression, Academic Press, NY, pp. 563-608 (1980)).

Once the vector or nucleic acid molecule containing the construct(s) has been prepared for expression, the DNA construct(s) can be introduced into an appropriate host cell by any of a variety of suitable means, e.g., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of EE polypeptide. This can take place in the transformed cells as such, or following the induction of these cells to differentiate (for example, by administration of bromodeoxyuracil to neuroblastoma cells or the like).

Nucleic Acid Probes and Primers for the Specific Detection of *E. Ewingii*

The EE polynucleotides described herein are also useful for designing hybridization probes for isolating and identifying cDNA clones and genomic clones encoding the EE proteins, peptides or allelic forms thereof. Such hybridization techniques are known to those of skill in the art.

Therefore, in another embodiment, a nucleic acid probe is provided for the specific detection of the presence of one or more EE polynucleotides in a sample comprising the above-described isolated polynucleotides or at least a fragment thereof, which binds under stringent conditions, or highly stringent conditions, to EE polynucleotides.

The term "stringent conditions" as used herein is the binding which occurs within a range from about Tm 5° C. (5° C. below the melting temperature Tm of the probe) to about 20° C. to 25° C. below Tm. The term "highly stringent hybridization conditions" as used herein refers to conditions of: at least about 6×SSC and 1% SDS at 65° C., with a first wash for 10 minutes at about 42° C. with about 20% (v/v) formamide in 0.1×SSC, and with a subsequent wash with 0.2×SSC and 0.1% SDS at 65° C.

In one embodiment, the isolated nucleic acid probe consisting of 10 to 1000 nucleotides (for example: 10 to 500, 10 to 250, 10 to 100, 10 to 50, 10 to 35, 20 to 1000, 20 to 500, 20 to 250, 20 to 100, 20 to 50, or 20 to 35, etc.) which hybridizes preferentially to RNA or DNA of EE but not to RNA or DNA of non-EE organisms, wherein said nucleic acid probe is or is complementary to a nucleotide sequence consisting of at least 10 consecutive nucleotides, or 15, 20, 25, 30, 50, 100, 250, 500, 600, 700, 800, or 900 consecutive nucleotides, or along the entire length, of one or more of the EE polynucleotides described above.

In some embodiments, the nucleic acid probe comprises a polynucleotide sequence encoding a polypeptide that corresponds to one or more of the variable loop sequences in Tables 2-6. Such probes would hybridize with a specific polynucleotide encoding a polypeptide corresponding to a variable sequence in each EE OMP protein and so will be specific to EE, as opposed to the other *ehrlichia* species. Methods for designing probes that are specific for EE polynucleotide sequences based on the sequence alignment provided in FIG. 7 are well known in the art.

In other embodiments, the nucleic acid probe can be used to probe an appropriate chromosomal or cDNA library by usual hybridization methods to obtain another nucleic acid molecule of the present invention. A chromosomal DNA or cDNA library can be prepared from appropriate cells according to recognized methods in the art (see e.g. Molecular Cloning: A Laboratory Manual, second edition, edited by Sambrook, Fritsch, & Maniatis, Cold Spring Harbor Laboratory, 1989).

Such hybridization probes can have a sequence which is at least 90%, 95%, 98%, 99% or 100% complementary with a sequence contained within the sense strand of a DNA molecule which encodes each of the EE proteins or with a sequence contained within its corresponding antisense strand. Such hybridization probes bind to the sense or antisense strand under stringent, or highly stringent, conditions.

The term "stringent conditions" as used herein is the binding which occurs within a range from about Tm 5° C. (5° C. below the melting temperature Tm of the probe) to about 20° C. to 25° C. below Tm. The term "highly stringent hybridization conditions" as used herein refers to conditions of: at least about 6×SSC and 1% SDS at 65° C., with a first wash for 10 minutes at about 42° C. with about 20% (v/v) formamide in 0.1×SSC, and with a subsequent wash with 0.2×SSC and 0.1% SDS at 65° C.

The probes can be used in a number of assays, such as Northern assays to detect transcripts of EE omp-1 homologous genes and in Southern assays to detect EE omp-1 homologous genes. In some examples, the identity of probes which are e.g. 200 nucleotides in length and have full complementarity with a portion of the antisense strand of a double-stranded DNA molecule which encodes the EE proteins can be determined using EE protein-encoding segments of the nucleotide sequence SEQ ID NO: 1.

The hybridization probes of the present invention can be labeled by standard labeling techniques such as with a radiolabel, enzyme label, fluorescent label, biotin-avidin label, chemiluminescence, and the like. After hybridization, the probes can be visualized using known methods.

The nucleic acid probes of the present invention include RNA, as well as DNA probes, such probes being generated using techniques known in the art.

In one embodiment of the above described method, a nucleic acid probe is immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The EE polynucleotides disclosed herein are also useful for designing primers for polymerase chain reaction (PCR), a technique useful for obtaining large quantities for cDNA molecules that encode the EE polypeptides. PCR primers can also be used for diagnostic purposes.

Thus, also included are oligonucleotides that are used as primers in polymerase chain reaction (PCR) technologies to amplify transcripts of the genes which encode the EE polypeptides, or portions of such transcripts. In some examples, the primers comprise a minimum of about 12 to 15 nucleotides and a maximum of about 30 to 35 nucleotides. The primers can have a G+C content of 40% or greater. Such oligonucleotides are at least 98% complementary with a portion of the DNA strand, i.e., the sense strand, which encodes the EE protein, or a portion of its corresponding antisense strand. In some embodiments, the primer has at least 99% complementarity, or 100% complementarity, with such sense strand or its corresponding antisense strand. Primers which have 100% complementarity with the antisense strand of a double-stranded DNA molecule encoding an EE protein have a sequence which is identical to a sequence contained within the sense strand.

One skilled in the art can readily design such probes based on the sequences disclosed herein using methods of computer alignment and sequence analysis known in the art (see, for example, Molecular Cloning: A Laboratory Manual, second edition, edited by Sambrook, Fritsch, & Maniatis, Cold Spring Harbor Laboratory, 1989). For example, the identity of primers which are 15 nucleotides in length and have full complementarity with a portion of the antisense strand of a double-stranded DNA molecule which encodes the EE proteins can be determined using the EE protein segments of the nucleotide sequence, SEQ ID NO: 1.

In some embodiments, the primers have one or more of the following features: (i) the 3' end of the primer set is either C or G; (ii) at least the 3' end of each primer has the same sequence as the target DNA (or its reverse complement), i.e., the 5' end can have variations and still produce a proper PCR product; (iii) the primer is about 20 bp long; (iv) both members of a primer set are around the same length; (v) the GC total and AT total for both primers in a set are the same, or very similar; (vi) the primer should be designed after performing a BLAST search on each primer to determine if there could be alignment for amplification of an unwanted species; and/or (vii) use the formula 4×(G+C)+2×(A+T)=PCR Annealing Temperature (±5° C.) for a primer set. For example, Ohashi N, et al. (2001) Infection and Immunity, 69:2083-91, the entire contents of which are incorporated herein by reference, describes multiple primers designed to detect all 22 p30 proteins of *E. canis*. A similar strategy can be used for *E. ewingii* primer design.

Figure 8:
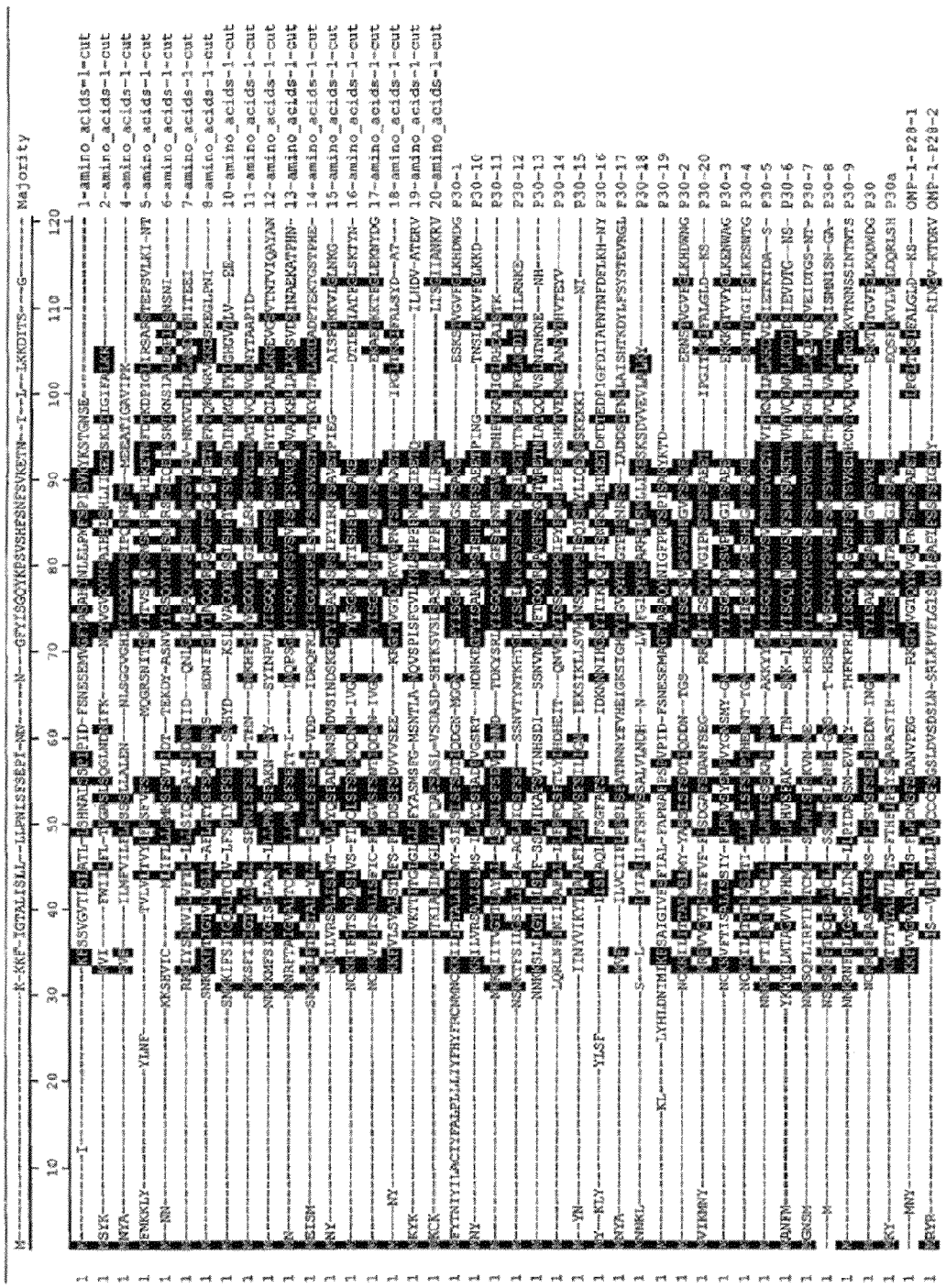
FIG. 8. Alignment of *E. ewingii* OMP-1, *E. canis* P30, *E. chaffeensis* OMP-1, and *E. ruminantium* MAP1 proteins.

In one embodiment, the primers are designed to amplify a target DNA segment that is useful for diagnostic purposes. The target sequence can have a length of 50-300 nucleotide bases, 50-200 bases, 80-200 bases, 100-300, 300-600, 600-800, 600-1000, or 800-1000 bases. In some embodiments, the target DNA comprises a polynucleotide sequence encoding a polypeptide comprising one or more of the variable loop sequences in Tables 2-6. Such primers would amplify a specific polynucleotide segment encoding a polypeptide whose sequence corresponds to a variable sequence in each EE OMP protein and so will be specific to EE, as opposed to other *ehrlichia* species. Methods for designing primers that are specific for EE polynucleotide sequences based on the sequence alignment provided in FIGS. 7 and 8 are well known in the art.

In another embodiments, the target DNA segment has a nucleotide sequence that encodes a polypeptide that is conserved among *E. ewingii* strains, but is distinct from other *Ehrlichia* strains. Examples of conserved sequences among *E. ewingii* strains are shown as darkened areas in the attached sequence alignment (FIGS. 7 and 8). Using as target DNA sequences that encode for conserved regions of EE proteins increases the sensitivity of the PCR reaction because there are more than two copies of the target sequence in the genome. This increases the PCR's sensitivity more than two fold. For example, U.S. Pat. No. 6,432,649 to Stich et al., the entire contents of which is incorporated herein by reference, describes methods of designing such primers based on sequence alignments of *E. canis* and *E. chaffeensis* for the specific diagnosis of each of these species. A similar method can be employed to design optimal primer sets for *E. ewingii* diagnosis.

In other embodiments, the primers are designed for nested PCR, or target more than two regions of the target sequence to increase sensitivity. Nested PCR is a conventional PCR with a second round of amplification using a different set of primers. This second set of primers is specific to a sequence found within the target DNA of the initial conventional PCR amplicon. The use of a second amplification step with the "nested" primer set results in a reduced background from products amplified during the initial PCR due to the nested primers' additional specificity to the region. The amount of amplicon produced is increased as a result of the second round of amplification and due to a reduction in any inhibitor concentrations. For example, the first set of primers can target variable loops 1 and 4, and the second nested primer set can target variable loops 2 or 3.

Primer design choices that can increase the PCR reaction's specificity include using primers that border the target DNA sequence together with higher annealing temperatures.

The term "primer" as used herein refers to an oligonucleotide, whether occurring naturally as in a purified restriction digest or produced synthetically, which is capable of acting an a point of initiation of synthesis when placed under conditions in which synthesis of a primer extension product complementary to a nucleic acid strand is induced. The conditions include the presence of nucleotides and an inducing agent such as a DNA polymerase and a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, the oligonucleotide primer typically contains 15-30 or more nucleotides depending on the complexity of the target sequence. Primers with fewer nucleotides may also be used.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementary with the sequence or hybridize therewith and thereby form the template for the synthesis of the extension product.

Antibodies

Also contemplated herein is an isolated or purified antibody having specific binding affinity to an EE polypeptide as described above.

An antibody that has a "specific binding affinity" to an EE polypeptide, is an antibody that binds with a substantially greater affinity to the EE polypeptide, than to an *E. canis* or *E. chaffeensis* protein.

Any of a variety of routine assays can be used for detecting antigen-antibody complexes, the presence of which is an indicator of selective binding. Such assays include, without limitation, enzyme-linked immunosorbent assays (ELISA), radioimmunoassays, western blotting, enzyme immunoassays, fluorescence immunoassays, luminescent immunoassays and the like. Methods for detecting a complex between a peptide and an antibody, and thereby identifying and antibody with specific binding affinity to an EE polypeptide are well known to those skilled in the art and are described, for example, in ANTIBODIES: A LABORATORY MANUAL (Edward Harlow & David Lane, eds., Cold Spring Harbor Laboratory Press, 2.sup.nd ed. 1998a); and USING ANTIBODIES: A LABORATORY MANUAL: PORTABLE PROTOCOL No. 1 (Edward Harlow & David Lane, Cold Spring Harbor Laboratory Press, 1998b), which are hereby incorporated by reference in their entirety.

In one embodiment, the "specific binding affinity" of an antibody is defined as an ELISA assay result, where the ratio of *E. chaffeensis* or *E. canis* polypeptide reactivity/control plasma reactivity is ~1.00, and where *E. ewingii* polypeptide reactivity yields an $OD_{405nm}$-$OD_{492nm}$ value greater than the mean $OD_{405nm}$-$OD_{492nm}$ of preinfection control plasma+ three standard deviations. In this example, the antibodies can be obtained from a subject infected with *E. ewingii*. The control plasma can include preinfection plasma, plasma from subjects infected with anything other than *E. ewingii*, or plasma from subjectes infected with *E. chaffeensis* or *E. canis*.

The EE polypeptides can be used to produce antibodies or hybridomas. One skilled in the art will recognize that if an antibody is desired, such a polypeptide would be generated as described herein and used as an immunogen.

The produced antibodies are useful research tools for diagnostic and screening purposes, for identifying cells, such as granulocytes, infected with *E. ewingii* and for purifying the major outer membrane protein of *E. ewingii* from partially purified preparations by affinity chromatography. Such antibodies are also useful for identifying bacterial colonies, particularly colonies of genetically-engineered bacteria, that are expressing the major outer membrane protein of *E. ewingii*.

The antibodies described herein can also be used in a composition to be administered to a subject in need thereof, to reduce the level of *E. ewingii* infection in the subject. Such a reduction refers to a reduction or elimination of clinical signs and symptoms of *E. ewingii* infection in the subject. Alternatively the antibody can be used to prevent infection with *E. ewingii* in a subject.

The antibodies include monoclonal and polyclonal antibodies, as well as fragments of these antibodies. The invention further includes single chain antibodies. Antibody fragments which contain the idiotype of the molecule can be generated by known techniques. For example, such fragments include but are not limited to: the $F(ab')_2$ fragment; the Fab' fragments, Fab fragments, and Fv fragments.

In one embodiment, the antibodies to EE polypeptides are produced in humans, or are "humanized" (i.e. non-immunogenic in a human) by recombinant or other technology. Humanized antibodies can be produced, for example by replacing an immunogenic portion of an antibody with a corresponding, but non-immunogenic portion (i.e. chimeric antibodies) (Robinson, R. R. et al., International Patent Publication PCT/US86/02269; Akira, K. et al., European Patent Application 184,187; Taniguchi, M., European Patent Application 171,496; Morrison, S. L., et al., European Patent Application 173,494; Neuberger, M. S. et al., PCT Application WO 86/01533; Cabilly, S. et al., European Patent Application 125,023; Better, M. et al., Science 240:1041-1043 (1988); Liu, A. Y. et al., Proc. Natl. Acad. Sci. USA 84:3439-3443 (1987); Liu, A. Y. et al., J. Immunol. 139:3521-3526 (1987); Sun, L. K. et al., Proc. Natl. Acad. Sci. USA 84:214-218 (1987); Nishimura, Y. et al., Canc. Res. 47:999-1005 (1987); Wood, C. R. et. al., Nature 314:446-449 (1985); Shaw et al., J. Natl. Cancer Inst. 80:1553-1559 (1988)). General reviews of "humanized" chimeric antibodies are provided by Morrison, S. L. (Science, 229:1202-1207 (1985)) and by Oi, V. T. et al., BioTechniques 4:214 (1986)). Suitable "humanized" antibodies can be alternatively produced by CDR or CEA substitution (Jones, P. T. et. al., Nature 321:552-525 (1986); Verhoeyan et al., Science 239:1534 (1988); Beidler, C. B. et al., J. Immunol. 141:4053-4060 (1988)).

In another embodiment, the present invention relates to a hybridoma which produces the above-described monoclonal antibody. A hybridoma is an immortalized cell line which is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam. The Netherlands (1984); St. Groth et al., J. Immunol. Methods 35:1-21 (1980)).

Any animal (mouse, rabbit, and the like) which is known to produce antibodies can be immunized with the selected polypeptide. Methods for immunization are well known in the art. Such methods include subcutaneous or interperitoneal injection of the polypeptide. One skilled in the art will recognize that the amount of polypeptide used for immunization will vary based on the animal which is immunized, the antigenicity of the polypeptide and the site of injection.

The polypeptide can be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz et al., Exp. Cell Res. 175:109-124 (1988)). Hybridomas secreting the desired antibodies are cloned and the class and subclass is determined using procedures known in the art (Campbell, Monoclonal Antibody Technology: Laboratory Techniques in Biochemistry and Molecular Biology, supra (1984)).

For polyclonal antibodies, antibody containing antisera is isolated from the immunized animal and is screened for the presence of antibodies with the desired specificity using one of the above-described procedures.

In another embodiment, the above-described antibodies are detectably labeled. Antibodies can be detectably labeled through the use of radioisotopes, affinity labels (such as biotin, avidin, and the like), enzymatic labels (such as horseradish peroxidase, alkaline phosphatase, and the like) fluorescent labels (such as FITC or rhodamine, and the like), paramagnetic atoms, and the like. Procedures for accomplishing such labeling are well-known in the art, for example, see (Stemberger et al., J. Histochem. Cytochem. 18:315 (1970); Bayer et al., Meth. Enzym. 62:308 (1979); Engval et al., Immunol. 109:129 (1972); Goding, J. Immunol. Meth. 13:215 (1976)). The labeled antibodies of the present invention can be used for in vitro, in vivo, and in situ assays to identify cells or tissues which express a specific polypeptide.

In another embodiment, the above-described antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10 (1986); Jacoby et al., Meth. Enzym. 34 Academic Press, N.Y. (1974)). The immobilized antibodies can be used for in vitro, in vivo, and in situ assays as well as in immunochromatography.

Furthermore, one skilled in the art can readily adapt currently available procedures, as well as the techniques, methods and kits disclosed above with regard to antibodies, to generate peptides capable of binding to a specific polypeptide sequence in order to generate rationally designed antipeptide peptides, for example see Hurby et al., "Application of Synthetic Peptides: Antisense Peptides", In Synthetic Peptides, A User's Guide, W. H. Freeman, NY, pp. 289-307 (1992), and Kaspczak et al., Biochemistry 28:9230-8 (1989).

Anti-peptide peptides can be generated in one of two fashions. First the anti-peptide peptides can be generated by replacing the basic amino acid residues found in the EE polypeptide sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

Diagnostic Methods

Also contemplated herein are diagnostic methods that use the EE polypeptides, EE polynucleotides, EE fusion proteins and EE antibodies described herein.

Samples used in the diagnostic methods are samples obtained from a subject that is suspected of having, or having has, *E. ewingii* infection. Subjects not infected with EE do not have EE DNA, mRNA, protein, or antibody.

The subject may be a human or any animal that can be infected with *E. ewingii*. Such subjects include, but should not be limited to, humans, horses, deer, cattle, pigs, sheep, dogs, cats and chicken.

The test sample may be a biological fluid such as serum, plasma, whole blood, urine, or saliva, or may be tissue, cells, protein or membrane or nucleic acid extract of cells, obtained from a subject. The sample used in the methods will vary based on the assay format, the detection method and the nature of the tissues, cells or extracts to be assayed.

For example, in some embodiments, it is advantageous to use more than one EE polypeptide as antigents in diagnostic methods. Since currently no *E. ewingii*-specific serodiagnosis is available, for serodiagnosis of *E. ewingii* infection in either humans and animals, use of a combination of EEOMP-1s (i.e. EE OMP-1 proteins or functional derivatives thereof) as the antigen can provide sensitive and specific serodiagnosis. Use of multiple EE polypeptides can provide more sensitive diagnosis than the use of a single EE OMP-1 antigen. Not all humans and dogs develop antibodies to every EEOMP-1 protein. Therefore, the use of a combination of EE polypeptides (e.g. a combination of EE polypeptides corresponding to all OMP-1 proteins) as antigens provides a more comprehensive coverage of antibody responses. Furthermore, the entire EEOMP-1 amino acid sequences disclosed herein can help optimize peptide antigens to provide desired specificity and sensitivity to detect potentially diverse *E. ewingii* strains in the field.

Diagnostic Methods Using EE Polypeptides and Antibodies

The present invention also provides a method for detecting the presence of antibodies specific to *E. ewingii* in a test sample. The method includes contacting a test sample suspected of comprising antibodies specific for *E. ewingii* with one or more *E. ewingii* polypeptides, as described herein, under conditions that allow polypeptide/antibody complexes to form; and assaying for the formation of a complex between antibodies in the test sample and the one or EE polypeptides. Accordingly, detecting the formation of such a complex is an indication that antibodies specific for *E. ewingii* are present in the test sample.

Another aspect provides for a method for detecting the presence of *E. ewingii* polypeptides in a test sample. The method includes contacting a test sample suspected of comprising *E. ewingii* polypeptides with one or more *E. ewingii* antibodies that specifically bind to at least one epitope of an *E. ewingii* OMP protein or peptide, as described herein, under conditions that allow polypeptide/antibody complexes to form; and assaying for the formation of a complex between polypeptides in the test sample and the one or EE antibodies. Accordingly, detecting the formation of such a complex is an indication that *E. ewingii* polypeptides are present in the test sample.

The presence of EE polypeptides, or antibodies to EE polypeptides, may indicate exposure to *E. ewingii*, the potential need for therapy of an affected subject, or EE contamination of a biological sample.

For ease of detection, the isolated EE polypeptide or antibody can be attached to a substrate such as a column, plastic dish, matrix, or membrane, such as nitrocellulose. The test sample may be untreated, subjected to precipitation, fractionation, separation, or purification before combining with the isolated polypeptide. Conditions for incubating an EE polypeptide or antibody with a test sample vary. Incubation conditions depend on the format employed in the assay, the detection methods employed, and the type and nature of the antibody used in the assay.

Interactions between antibodies and polypeptide can be detected in a number of ways well know to those skilled in the art. These include, but are not limited to, radiometric, calorimetric, or fluorometric means, size-separation, or precipitation. These assays include, but are not limited to, a microtiter plate assay, a reversible flow chromatographic binding assay, an enzyme linked immunosorbent assay, a radioimmunoassay, a hemagglutination assay, a western blot assay, a fluorescence polarization immunoassay, an indirect immunofluorescence assay, diffusion based Ouchterlony, or rocket immunofluorescent assays. Examples of such assays can be found in Chard, An Introduction to Radioimmunoassay and Related Techniques, Elsevier Science Publishers, Amsterdam, The Netherlands (1986); Bullock et al., Techniques in Immunocytochemistry, Academic Press, Orlando, Fla. Vol. 1 (1982), Vol. 2 (1983), Vol. 3 (1985); Tijssen, Practice and Theory of Enzyme Immunoassays: Laboratory Techniques in Biochemistry and Molecular Biology, Elsevier Science Publishers, Amsterdam, The Netherlands (1985). In one example, detection of the antibody-polypeptide complex is by addition of a secondary antibody that is coupled to a detectable tag, such as for example, an enzyme, fluorophore, or chromophore. Formation of the complex is indicative of the presence of *E. ewingii* proteins, or anti-*E. ewingii* antibodies in the subject from whom the test sample was obtained. Thus, the method is used to determine whether a subject is infected with *E. ewingii.*

In some embodiments, the method employs an enzyme-linked immunosorbent assay (ELISA) or a Western immunoblot procedure. Such methods are relatively simple to perform and do not require special equipment as long as membrane strips are coated with a high quality antigen. Accordingly, it is possible to use a recombinant form of the EE polypeptides since such proteins and peptides, typically, are more pure and consistent in quality than a their purified form.

Diagnostic Methods using EE Primers and Probes

The probes and primers described herein can be designed and used diagnostically for determining whether a subject has been infected with an *E. Ewingii* species. Therefore, also provided are methods of detecting the presence of EE polynucleotides in a sample.

Analysis of nucleic acid specific to EE can be by PCR techniques or hybridization techniques (see, for example, Molecular Cloning: A Laboratory Manual, second edition, edited by Sambrook, Fritsch, & Maniatis, Cold Spring Harbor Laboratory, 1989; Eremeeva et al., J. Clin. Microbiol. 32:803-810 (1994) which describes differentation among spotted fever group *Rickettsiae* species by analysis of restriction fragment length polymorphism of PCR-amplified DNA). For example, methods of using nucleic acid probes to analyze EE genomic DNA via PCR analysis have been described in Chen et al., J. Clin. Microbiol. 32:589-595 (1994).

In one embodiment, the method includes: a) contacting the sample with the above-described nucleic acid probe, under speicifc hybridization conditions such that hybridization occurs and b) detecting the presence of the probe bound to the nucleic acid molecule, wherein detecting the presence of such binding is indicative of the presence of *E. ewingii* in the sample, and therefore, the subject.

The screening and diagnostic methods of the invention that employ probes do not require that the entire EE protein coding sequence be used for the probe. Rather, it is only necessary to use a fragment or length of nucleiic acid that is sufficient to detect the presence of the EE nucleic acid in a DNA preparation from a subject.

Alternatively, in another embodiment, the method of detecting the presence of EE nucleic acid in a sample may include: a) amplifying the nucleic acid in the sample with one or more of the above-described primer sets specific for one or more portions of the EE omp-1 gene cluster, SEQ ID NO: 1 using PCR techniques and b) detecting the presence of the amplified nucleic acid molecules, wherein the presence of a PCR product having a sequence or length which corresponds to the sequence or length of the portion of the EE omp-1 gene which is located between the primer set is indicative of the presence of E. ewingii in the sample.

The resulting PCR amplification products can be seperated by size by any method, such as gel electrophoresis, and detection of an appropriately sized product indicates E. ewingii infection. One skilled in the art would select the nucleic acid probe according to techniques known in the art as described above.

Methods for preparing nucleic acid extracts of cells are well known in the art and can be readily adapted in order to obtain a sample which is compatible with the method utilized.

Kits

In another embodiment of the present invention, a kit is provided which contains all the necessary reagents to carry out the previously described methods of detection.

The kit can comprise one or more isolated EE polypeptides. For ease of detection, the polypeptides may be attached to a substrate such as a column, plastic dish, matrix, or membrane, such as nitrocellulose. The kit may further comprise a conjugate comprising a binding partner of the polypeptide. The binding partner can be a biomolecule, such as a secondary antibody, for detecting interactions between the isolated polypeptide and antibodies immuno-specific to E. ewingii, in a test sample. In some embodiments, the biomolecule is coupled to a detectable tag such as an enzyme, chromophore, fluorophore, or radio-isotope. The kit can be used by contacting a test sample with the EE polypeptide under conditions that permit formation of antigen-antibody complexes. Then the biomolecule is added and the presence or absence of any resulting antigen-antibody complexes is detected by assaying for a change in the sample, for example, by observing the formation of a precipitate in the sample, the presence of radioactivity on the substrate, or a color change in the sample or on the substrate. Detecting such a change is indicative that the test sample contains anti-E. ewingii antibodies.

In other embodiments the kit can comprise one or more of an above-described antibodies. The kit can further comprise a conjugate comprising a binding partner of the antibody. The binding partner can be a biomolecule, such as a secondary antibody, for detecting interactions between the antibodies and the EE OMP protein or peptide in the test sample. In some embodiments, the biomolecule is coupled to a detectable tag such as an enzyme, chromophore, fluorophore, or radio-isotope. The kit can be used by contacting a test sample with the EE antibody under conditions that permit formation of antigen-antibody complexes. Then the biomolecule is added and the presence or absence of any resulting antigen-antibody complexes is detected by assaying for a change in the sample, for example, by observing the formation of a precipitate in the sample, the presence of radioactivity on the substrate, or a color change in the sample or on the substrate. Detecting such a change is indicative that the test sample contains E. ewingii or components of E. ewingii.

In other embodiments, the above described kits may further comprises one or more other reagents such as: wash reagents and reagents capable of detecting the presence of bound antibodies. Examples of detection reagents include, but are not limited to, labeled secondary antibodies, or in the alternative, if the primary antibody is labeled, the chromophoric, enzymatic, or antibody binding reagents which are capable of reacting with the labeled antibody.

Also provided are kits for detecting the presence of EE nucleic acid in a sample, which include at least one of the above-described omp-1 specific nucleic acid probes or primers. In one embodiment, the kit further include: reagents for DNA extraction from the test sample, reagents for PCR amplification, wash reagents and reagents capable of detecting the presence of bound nucleic acid probe. Examples of detection reagents include, but are not limited to radiolabelled probes, enzymatic labeled probes (horseradish peroxidase, alkaline phosphatase), and affinity labeled probes (biotin, avidin, or steptavidin).

In detail, the kit may be a compartmentalized kit in which reagents are contained in separate containers. Such containers include small glass containers, plastic containers or strips of plastic or paper. Such containers allow the efficient transfer or reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which container wash reagents (such as phosphate buffered saline, Tris-buffers, and the like), and containers which contain the reagents used to detect the hybridized probe, bound antibody, amplified product, or the like.

One skilled in the art will readily recognize that the nucleic acid probes described in the present invention can readily be incorporated into one of the established kit formats which are well known in the art. One skilled in the art will readily recognize that the EE polypeptides and antibodies described in the present invention can readily be incorporated into one of the established kit formats which are well known in the art.

Immunogenic Compositions and Vaccines

The present invention also relates to immunogenic compositions comprising one or more E. ewingii OMP proteins, or immunogenic fragments and variants thereof, or a fusion protein containing same, collectively referred to herein as an "immunogenic EE polypeptide" and a pharmaceutically acceptable carrier.

The immunogenic EE polypeptides, as used herein, comprise an epitope-bearing portion of an EE OMP protein. In some embodiments, the epitope-bearing portion comprises a sequence of at least 6 consecutive amino acids within the variable loops of OMP proteins shown in Tables 2-5. Some examples of immunogenic fragments (or peptides) are shown in Table 6.

An immunogenic EE polypeptide is a polypeptide that is capable of producing antibodies with a specific binding affinity to E. ewingii in a subject to whom the immunogenic composition has been administered.

In another embodiment, the present invention relates to a vaccine comprising an immunogenic EE polypeptide, together with a pharmaceutically acceptable diluent, carrier, or excipient, wherein the immunogenic EE polypeptide is present in an amount effective to elicit a beneficial immune response in a subject to EE. The immunogenic EE polypeptide may be obtained as described above and using methods well known in the art.

In another embodiment, the present invention relates to a vaccine comprising an EE nucleic acid (e.g., DNA) or a segment thereof (e.g., a segment encoding an immunogenic EE polypeptide) together with a pharmaceutically acceptable diluent, carrier, or excipient, wherein the nucleic acid is present in an amount effective to elicit, in a subject, a beneficial immune response to EE. The EE nucleic acid may be obtained as described above and using methods well known in the art.

In a further embodiment, the present invention relates to a method of producing an immune response which recognizes EE in a host, comprising administering to the host one or more of the above-described immunogenic EE polypeptides.

In some embodiments, the host or subject to be protected is selected from the group consisting of humans, horses, deer, cattle, pigs, sheep, dogs, cats and chickens. In some embodiments, the animal is a human or a dog.

In a further embodiment, the present invention relates to a method of preventing or inhibiting chrlichiosis in a subject comprising administering to the subject the above-described vaccine, wherein the vaccine is administered in an amount effective to prevent or inhibit Ehrlichiosis. The vaccine of the invention is used in an amount effective depending on the route of administration. Although intra-nasal, subcutaneous or intramuscular routes of administration are suitable, the vaccine of the present invention can also be administered by an oral, intraperitoneal or intravenous route. One skilled in the art will appreciate that the amounts to be administered for any particular treatment protocol can be readily determined without undue experimentation. Suitable amounts are within the range of 2 µg of the EE vaccine per kg body weight to 100 micrograms per kg body weight (preferably, 2 µg to 50 µg, 2 µg to 25 µg, 5 µg to 50 µg, or 5 µg to 10 µg).

Examples of vaccine formulations including antigen amounts, route of administration and addition of adjuvants can be found in Kensil, Therapeutic Drug Carrier Systems 13:1-55 (1996), Livingston et al., Vaccine 12:1275 (1994), and Powell et al., AIDS RES, Human Retroviruses 10:5105 (1994). The vaccine of the present invention may be employed in such forms as capsules, liquid solutions, suspensions or elixirs for oral administration, or sterile liquid forms such as solutions or suspensions. Any inert carrier may be used, such as saline, phosphate-buffered saline, or any such carrier in which the vaccine has suitable solubility properties. The vaccines may be in the form of single dose preparations or in multi-dose flasks which can be used for mass vaccination programs. Reference is made to Remington's Pharmaceutical Sciences, Mack Publishing Co., Easton, Pa., Osol (ed.) (1980); and New Trends and Developments in Vaccines, Voller et al (eds.), University Park Press, Baltimore, Md. (1978), for methods of preparing and using vaccines.

The vaccines of the present invention may further comprise adjuvants which enhance production of antibodies and immune cells. Such adjuvants include, but are not limited to, various oil formulations such as Freund's complete adjuvant (CFA), the dipeptide known as MDP, saponins (ex. QS-21, U.S. Pat. No. 5,047,540), aluminum hydroxide, or lymphatic cytokines. Freund's adjuvant is an emulsion of mineral oil and water which is mixed with the immunogenic substance. Although Freund's adjuvant is powerful, it is usually not administered to humans. Instead, the adjuvant alum (aluminum hydroxide) may be used for administration to a human. Vaccine may be absorbed onto the aluminum hydroxide from which it is slowly released after injection. The vaccine may also be encapsulated within liposomes according to Fullerton, U.S. Pat. No. 4,235,877.

The present invention will be better understood by reference to the following examples which are offered by way of illustration, not limitation.

EXAMPLE—Identification of 19 Polymorphic Major Outer Membrane Protein Genes and Their Immunogenic Peptides in *Ehrlichia Ewingii*

Since ehrlichial infections induce significant antibody titers in non-immunocompromised patients, and nonexposed people seldom have antibodies reactive to *Ehrlichia* spp., serologic tests are considered reliable tests for confirmation of ehrlichioses, especially when ruling out the possibility of infection. In order to develop a serologic test using major antigens of *E. ewingii*, genes encoding these proteins must be first identified.

There are a number of challenges to sequencing genes encoding *E. ewingii* outer membrane proteins. First, *E. ewingii* DNA amount available from naturally or experimentally infected dogs is limited. Second, *E. ewingii* DNA concentration in the total DNA extracted from the blood is very low, due to a small amount of bacteria present in the blood and is difficult to enrich due to obligatory intracellular nature of this bacterium. Third, DNA sequences encoding OMP-1/P28/P30/MAP1, are too divergent to design universal primers. Prior to the instant application, only a partial sequence (505 bp) of a single member OMP-1 family p28-19 has been cloned in *E. ewingi*, and the sequence of other *E. ewingii* outer membrane proteins, or the genes encoding such proteins, remained unknown.

The purposes of the reported study were to i) determine the *E. ewingii* omp-1 gene family, ii) determine each OMP-1-specific peptide, and iii) analyze all OMP-1 synthesized peptides for antigenicity.

We systematically identified the entire *E. ewingii* OMP-1 genomic locus. Using nested touchdown PCR and a primer walking strategy, we found 19 omp-1 paralogs in *E. ewingii*. These genes are arranged in tandem downstream of trl and upstream of secA in a 24-kb genomic region. Predicted molecular masses of the 19 mature *E. ewingii* OMP-1s range from 25.1 to 31.3 kDa with isoelectric points of 5.03 to 9.80.

Those multigene family proteins are composed of conserved and unique amino acid sequences. This led to our idea that, rather than the whole OMP-1 protein, antigenic OMP-1 peptides unique to *E. ewingii* can provide better serologic diagnostic antigens. Therefore, differences of the genomic loci and sequences of *E. ewingii* omp-1s with those of *E. chaffeensis* omp-1/p28, *E. canis* p30s and *E. ruminantium* map 1 were determined to design antigenic OMP-1 peptides specific to *E. ewingii*.

Based on comparative sequence analyses among OMP-1s from *E. ewingii* and the three other *Ehrlichia* spp. (FIG. 8), each *E. ewingii* OMP-1 oligopeptide predicted to be antigenic, bacterial surface exposed, unique in comparison to the other *E. ewingii* OMP-1s, and distinct from other *Ehrlichia* spp. was synthesized to perform ELISA. Plasma from *E. ewingii*-experimentally infected dogs significantly reacted with most of the OMP-1 specific peptides, indicating that multiple OMP-1 proteins were expressed and immunogenic in infected dogs. The results support the utility of the tailored OMP-1 peptides as *E. ewingii* serologic test antigens.

MATERIALS AND METHODS

*E. ewingii* omp-1 cluster amplification, sequencing, and assembly. An EDTA-treated whole-blood specimen (~200 pl) collected in April 2005 from an 8-week-old male German Sheperd mixed breed dog in Ohio was used for DNA extraction. DNA was extracted using the QIAamp blood kit (QIAGEN, Valencia, Calif.) and used as the template for the entire amplification and sequencing process. *E. ewingii* infection of the dog was confirmed by PCR and sequencing of the 16S rRNA of *E. ewingii* as well as observation of bacterial inclusions (morulae) in granulocytes in the blood and joint fluid smear. PCR analysis showed that the dog was negative for infection by *A. phagocytophilum*, *E. chaffeensis* and *E. canis* (Qingming Xiong, Weichao Bao, and Yasuko Rikihisa, unpublished data).

The omp-1 fragments were amplified using first touchdown PCR (Roux, K. H. et al. (1997) Methods Mol. Biol. 67:39-45) with the primer pairs F1 and R7, F8 and R14, and F15 and R21 (Table 7). The PCR reaction (50 μl) included 0.5 μl template DNA corresponding to 4 μl of the original blood sample, 10 pmol of each primer, 0.2 mM deoxynucleoside triphosphate mixture, 2.5 U high-fidelity Taq polymerase (Invitrogen, Carlsbad, Calif.), and 1.5 mM MgC12. Amplification was performed with a program (94° C. for 3 min; a gradient over 10 cycles of 94° C. for 0.5 min, 64° C. for 0.5 min, and 72° C. for 2 min, the annealing temperature decreased by 1° C./cycle; 35 cycles of 94° C. for 0.5 min, 55° C. for 0.5 min, and 68° C. for 9 min; and finally 68° C. for 9 min). The nested PCRs were performed using the first PCR products as template with 21 pairs of degenerate primers, with amplicons of approximately 1,500 bp that each overlapped approximately 200 bp according to *E. chaffeensis* and *E. canis* omp-1 clusters (Table 7, FIG. 1). Conditions of the nested PCR were similar to the first PCR except that Taq polymerase was used and the elongation step was at 72° C. for 2 min. The nested PCR products were run on a 1% agarose gel with TAE buffer (40 mM Tris-acetate, 1 mM EDTA, pH 8.0). The amplified DNA fragments were recovered from the gel with the QIAEX II Gel Extraction kit (QIAGEN) and directly sequenced with the nested PCR primers (FIG. 1). For fragment 3, two touchdown PCRs with high-fidelity Taq polymerase were performed using the infected dog blood DNA as template and one of the following primer pairs: forward primer P28-19F and primer R21, or the forward primer designed based on the 3' end of fragment 2 (Specific 4F) and reverse primer P28-19R (Table 7). Nested amplification of these two PCR products and direct sequencing were used for subsequent design of new specific primers. Direct sequences obtained ranged from 250 to 800 bp. The poly G/C or A/T regions (FIG. 1) were cloned using the TA cloning kit (Invitrogen), and the plasmid inserts were sequenced. All sequencing data were assembled using the SeqMan program of DNASTAR software (DNASTAR Inc., Madison, Wis.)

TABLE 7

Primers used.

| SEQ ID NO: | Degenerate primers | | SEQ ID NO: | *E. ewingii* specific primers | |
|---|---|---|---|---|---|
| 44 | F1: | CGYATYATGAGAGGTATGAG | 86 | Specific 1F: | GTACTTTGCCATTCCCAGAGA |
| 45 | R1: | AGGRTCTATATGTTTTGGTGCT | 87 | Specific 1R: | GATCTACTCCAAACCCAAGAC |
| 46 | F2: | TTGYATTGGTATAGGGCAAGGA | 88 | Specific 1RA: | GGAATTACTGCTCCAATAGTAGC |
| 47 | R2: | CTCAAATTTTTACCRAATAAACCATG | 89 | Specific 2F: | GTTGATGGGTATTACCACAGAG |
| 48 | F3: | CRTATTCATGTTTAGGRTTTGG | 90 | Specific 2R: | CACCTAGTATTTTGCTGAAGCT |
| 49 | R3: | AGTTGCTAWAGCAAARTACTC | 91 | Specific 3F: | TTACTTACCCACTATCTGGTAAC |
| 50 | F4: | TAGAASTTGAAGCTTTTTATGAG | 92 | Specific 3R: | TAATTTCCCCTGACCTGCAAAC |
| 51 | R4: | GATATACCRTTRTTTTTTGCTACAG | 93 | Specific 0F: | CAAACCAGTTTATTGACTGGGCAT |
| 52 | F5: | AARTWCTTTGCTATACCACGTA | 94 | Specific 19F: | CAATCATGCTAAATGCATGTTATGAC |
| 53 | R5: | TCTATTTCTAYYCTTGGYCCTTG | 95 | P28 19R: | GGATTTATGCTATTAAACATTGTACAC |
| 54 | F6: | ATRGGYCTTRCAAMTGATGTTAC | 96 | Specific 0FA: | TTCAAGCTAAGCTAGGTTTAGG |
| 55 | R6: | YTTAYTCCARCTTCACCACCA | 97 | Specific 1RB: | CATATTAACTCAATCAAGTAAACACAC |
| 56 | F7: | GCARTAGCWACACTTAATGTTG | 98 | Specific 1FA: | CCTCTTACCTCAAATTTAGTTCTC |
| 57 | R7: | CCTGGTTTATATTGMCCACTT | 99 | Specific 2RA: | TTCACCTATACCTAAGCATACATAAG |
| 58 | F8: | GAGTATTTYGGTRGTGAATTTGG | 100 | Specific 3FA: | GTCATGCTATATAGATGATACTGTG |
| 59 | R8: | RAAATCTCCTCCTAKTCCTGC | 101 | Specific 4F: | TCCCTTATGTTTTTGTATTCCTATAC |

TABLE 7-continued

Primers used.

| SEQ ID NO: | Degenerate primers | | SEQ ID NO: | E. ewingii specific primers | |
|---|---|---|---|---|---|
| 60 | F9: | CTGTMATGAGAAAYGACGGGTT | 102 | Specific 4R: | CCATCCATAGCATAACCGATAC |
| 61 | R9: | TAYYAATKTCAACAGAATCAAYATC | 103 | Specific 2FA: | CTGTTATGAGAAATGACGGAGTTTC |
| 62 | F10: | CAATAYAAACCCAGTGTTTCTG | 104 | Specific 3FB: | CGTACATAGAGTGTTATAGGCAATTC |
| 63 | R10: | GRATAAGTAAYACCTAAYTTACC | 105 | Specific 0FB: | GGTTTAAGTATATGAGTTATAAGAAGGT |
| 64 | F11: | TAYRGTMAATGGCTGCTATGAT | 106 | Specific 1FB: | ATGCACAGGCATTGGTGGAGA |
| 65 | R11: | AAGTGTAGCWACTGCRGATGT | 107 | Specific 2RB: | GTATATATGCATATGTAACATGCAAG |
| 66 | F12: | TACCATMAAGTAATRGGCAATCA | 108 | Specific 19RA: | GGCATGTACTTTCCGCTGATG |
| 67 | R12: | AYTTCTCCGCCAAAGTATCCA | 109 | Specific 3RA: | CTTTACTACTTTCTGATTCACGTAC |
| 68 | F13: | GCTCCTCAAACCACATCTGC | 110 | Specific 5F: | TGCTTTTATTGGTGGGCACTTTC |
| 69 | R13: | TAKGGTTTATAGCKTCAAACATG | 111 | Specific 6R: | TAAGTTTTTGCATTATCTCGTGAAG |
| 70 | F14: | TTYTCWCCTTACATATGTGCAG | 112 | Specific 7F: | TTGCACAAAAAATCTTTGGCTCAG |
| 71 | R14: | CARTTCATATTTACACCWGAAAKAGTGAA | 113 | Specific 7R: | ATTAACGCATTTGCATGTAGTAGTGTG |
| 72 | F15: | GTWTTTAMWTTGTAKKTTTACTACTGTT | 114 | Specific 4FA: | CAAGGAAAACTAGGTATAAGTTACTC |
| 73 | R15: | CTAYCTTGGRCCACCCATTG | 115 | Specific 4RA: | AAGACTGGTATGGTAAGACTGTC |
| 74 | F16: | TAGGGTTTGCAGGAGCTATTG | 116 | Specific 6F: | ACACCCCATAACACCACTAAAAG |
| 75 | R16: | AATTTTAGGRYTTRTAGCTTCAAAC | 117 | Specific 6RA: | GTTTGTTAACTACCCTGTAAAGTC |
| 76 | F17: | TATGYGCAGGTRTTGGTACTGA | 118 | Specific 7RA: | GATAGTACAAACCTGTAAGATGTTAC |
| 77 | R17: | GAWGCTTCTGGGCTTATRGAGT | 119 | Specific 3RB: | AACCTAAATTGCCTATCGATATCATC |
| 78 | F18: | CAAATCCTAAAATTTCTTAYCAAGGA | 120 | Specific 7RB: | TCAACCGTAATATTTAGTGTAGCATC |
| 79 | R18: | TYAGTAATTTTTCAGCTGAAGAAAC | 121 | Specific 6FB: | CAATATGGCTTTTAGTATCTTGTACATC |
| 80 | F19: | GCAAAAYTGCTTGCATAWGTAG | 122 | Specific 7RD: | TACACTACTTATTGGTATTGTTGGTAG |
| 81 | R19: | ATTTYTCAGAAGARTATGTTCCA | 123 | Specific 6RA2: | TATGTTGTTTGGAGGTGGTTACTATC |
| 82 | F20: | GAGTMAAAAAYTTTAAYAATRTCTTCTC | 124 | Specific 6FA: | CCTATATCTAAGTTAGCTAATGCCGAAG |
| 83 | R20: | AAAATATCCATTRTAGCTTACCT | 125 | Specific 7RC: | TTTTTGTTTTCTGTTTTGTGTAACCTGTG |

TABLE 7-continued

Primers used.

| SEQ ID NO: | Degenerate primers | SEQ ID NO: | E. ewingii specific primers |
|---|---|---|---|
| 84 | F21: ATGWTAAATTYATGYTTAAGTTGCA | 126 | Specific 2FB: CTGGGCATTCTTCAATAGATGCTC |
| 85 | R21: SCCYGTYTTCATTTCGGATATC | | |

E. ewingii omp-1 cluster analysis. Artemis (38) was used to identify the ORFs in the newly obtained E. ewingii omp-1 cluster. The ORFs longer than 100 amino acids were blasted against the NCBI GenBank database to find homologs. The Artemis comparison tool (Carver, T. J., et al. (2005) N Engl J Med 341:148-155) was used to analyze the synteny of the E. ewingii omp-1 cluster to that of E. chaffeensis, E. canis, and E. ruminantium. To search for repeat regions in the E. ewingii omp-1 cluster and between the E. ewingii omp-1 cluster and E. chaffeensis, E. canis, or E. ruminantium's omp-1 clusters, dot plot analysis was performed with Java Dot Plot Alignments program (JDotter) http://athena.bioc.uvie.ca/index-.php.

Phylogenetic analysis. The deduced amino acid sequences of E. chaffeensis OMP1/P28s, E. canis P30s, E. ruminantium MAP1s, and E. ewingii OMP-1s were aligned using the MegAlign program of DNASTAR software. Then, phylogenetic analysis was performed with PHYLIP software (version 3.66) (Felsenstein, J. (1989) Cladistics 5:164-166). The phylogram was constructed using the Neighbor-Joining method with Kimura's formula and 1,000 bootstrap replications were conducted to evaluate the reliability of the tree (Felsenstein, J. (1989) Cladistics 5:164-166).

Peptide synthesis and peptide-pin ELISA analysis. The peptide libraries were synthesized using non-cleavable multipin synthesis technology and fluorentylmethoxycarbonyl chemistry (Mimotopes Pty. Ltd., Victoria, Australia) (Geysen, H. M. (1990) Southeast Asian J Trop Med Public Health 12:523-533). After disruption of the peptide-pins with 0.1 M sodium phosphate buffer containing 1% SDS (pH 7.2) and 0.1% β-mercaptoethanol and hot (temperature) water washes, nonspecific binding sites were blocked with 200 µl of 3% skim milk (Becton, Dickinson and Co., Sparks, Md.) in PBS/Tween-20. Blocking was carried out in 96-well plates for 1 h at room temperature. Sets of peptide-bound pins were washed once with PBS containing 0.1% (v/v) Tween-20 for 10 min and then incubated in the blocking solution (1:100 dilution) with plasma from E. ewingii- or E. chaffeensis-infected dogs, or pre-infection dogs plasma, at 4° C. overnight. Samples from dogs 2119, 2185, and 2405 were collected at days 206, 109, and 110 post-infection, respectively, with E. ewingii. Samples from dog CTUALJ (E. chaffeenis IFA titer, 1:2,560), dog 1425 (E. chaffeenis IFA titer, 1:320), and dog 3918815 (E. chaffeenis IFA titer, 1:2,560) were collected at days 41, 121, and approximately 210 post-infection, respectively, with E. chaffeensis. Dogs 2119, 2185, and 1425, and preinfection plasma from dog CTUALJ, were used as negative controls. After washing four times as described above, the peptide pins were placed in wells filled with horseradish peroxidase-labeled goat anti-dog IgG (H+L) (Kirkegaard & Perry Laboratories, Gaithersburg, Md.) diluted at 1:1,000 in PBS/Tween-20 and incubated for 1 h at room temperature. Samples were washed four times, and then the peptide pins were incubated for 20 min at room temperature with horseradish peroxidase substrate 2,2'-azido-di-(3-ethyl)-benzthiazoline-6-sulfonic acid (Sigma, St. Louis, Mo.) in 70 mM citrate buffer (pH 4.2) applied to a new plate. Absorbance at 405 and 492 nm was measured in an ELISA plate reader (Molecular Devices, Sunnyvale, Calif.). Each assay was repeated at least three times. The cut off $OD_{405nm}$-$OD_{492nm}$ value for positive reaction was set as the mean $OD_{405nm}$-$OD_{492nm}$+three standard deviations of the negative control plasma.

RESULTS

E. ewingii omp-1 cluster sequencing and assembly. Forty-two degenerate primers were initially designed based on the conserved regions of the aligned omp-1/p30 clusters of E. chaffeensis and E. canis (Table 7, FIG. 1). To efficiently utilize the limited amount of E. ewingii DNA, the putative omp-1 cluster was divided into three overlapping fragments of approximately 9 kb, estimated based on homologous regions of E. chaffeensis and E. canis. The first touchdown PCR (Roux, K. H. et al (1997) Methods Mol. Biol. 67:39-45) was designed to amplify the three putative long fragments. The PCR products were then used as templates for the 21 nested touchdown PCRs using degenerate primer pairs (Table 7, FIG. 1). As a result only four PCRs showed bands ranging from ~200 to ~1,500 bp: F1 and R1 (~700 bp), F4 and R4 (~1,000 bp), F7 and R7 (~1,500 bp), and F11 and R11 (~220 bp). The PCR products were directly sequenced. The result showed they belong to the omp-1/p28/p30 family. For regions covered by fragments 1 and 2 (FIG. 1), E. ewingii-specific omp-1 primers were designed based on the four newly obtained E. ewingii omp-1 DNA sequences (Table 7). However, because no omp-1 was amplified in fragment 3 using degenerate primers, two touchdown PCRs with high-fidelity Taq polymerase were performed using the infected dog blood DNA as template and one of the following primer pairs: forward primer P28-19F designed based on the conserved region of E. ewingii p28-19 DNA sequences (Gusa, A. A., et al. (2001) J Clin Microbiol 39:3871-3876) and primer R21, or the forward primer designed based on the 3' end of fragment 2 and reverse primer P28-19R designed based on the conserved region on the p28-19 DNA sequence. Nested amplification of these two PCR products and direct sequencing were used for subsequent design of new specific primers. This process was repeated for three fragments until we encountered the poly G/C or A/T regions in fragments 2 and 3. The poly A/T and poly C/G tracts (FIG. 1) were determined by TA cloning and sequencing 10 and 22 plasmid inserts, respectively, in each of two regions. The poly G tract and 9-13 Gs (the number of Gs was distributed among the 22 sequenced clones as follows: 9 G=1, 10 G=4, 11 G=7, 12 G=2, and 13 G=8), and was reported as 13 G according to SeqMan software. The poly A tract has 10-12 As (the number of As was distributed among the 10 sequenced clones as follows: 10 A=1, 11 A=3, 12 A=3, and 13 A=3), and was reported as 12 A according to SeqMan software. The predominant in-frame sequences in each region were deposited in GenBank. The final sequence assembled from the entire E. ewingii omp-1 locus contained 24,126 bp (GenBank accession No. EF116932). The G+C content of the E. ewingii omp-1 cluster was 28.74%, which is similar to that of E. canis, E. chaffeensis, and E. ruminantium (29.36%, 30.95%, and 27.19%, respectively). E. ruminantium is the causative agent of heartwater in ruminants in Africa and Caribbean countries. Sequence identity of the entire E. ewingii omp-1 cluster relative to E. canis, E. chaffeensis, and E. ruminantium was 28.4%, 22.2%, and 14.8%, respectively.

Features of the OMP Cluster Structure are Conserved Among the Ehrlichia Species

The Artemis software analysis showed that each of the 24 ORFs encode more than 100 amino acids in the assembled E. ewingii omp-1 DNA fragment. One of the 24 ORFs in the middle of the cluster was short (390 bp), partially overlapped with two other ORFs in the opposite orientation, and had no homolog in the GenBank database, and thus this ORF was not included in the Figures or Table 1. The 23 ORFs were numbers ORF 1 to 23. These 23 genes were arranged in tandem except for three ORFs (ORF19, 20, and 21) that were in the opposite orientation. Nineteen of these 23 ORFs encoded proteins homologous to OMP-11P28/MAP1 of E. chaffeensis, E. canis, or E. ruminantium. Most closely related proteins to each EEOMP-1 are listed in Table 8.

Figure 2:
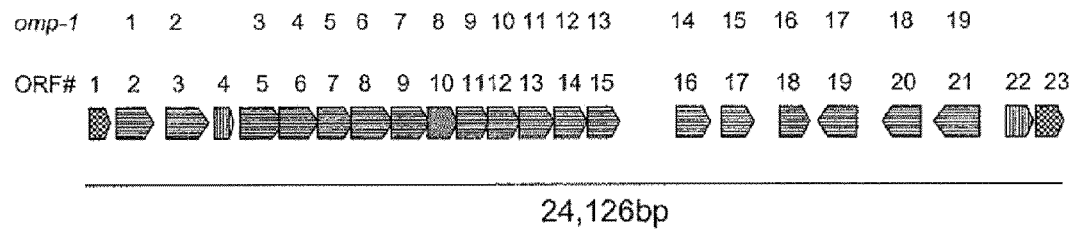
FIG. 2. Schematic representation of the organization of the *E. ewingii* omp-1 gene cluster. Genes are represented as boxes with arrows indicating their orientation. omp-1s are shown in a horizontal shading pattern. Black, white, and gray boxes show tr1, unknown genes, and secA, respectively.

We numbered them E. ewingii (EE)OMP-1-1 to EEOMP-1-19 (FIG. 2). The sequence similarity and molecular mass of EEOMP-1-8 was less than that of the other EEOMP-1s. There is a protein ortholog of EEOMP-1-8, UN3, in the E. chaffeensis and E. canis genomes with unknown function. In E. ruminantium, the EEOMP-1-8 ortholog is MAP1-9. The protein encoded by the first ORF (ORF1) is homologous to a hypothetical transcriptional regulator, and the protein encoded by the last ORF (ORF23) is homologous to SecA. Proteins encoded by the other two ORFs (ORF4 and ORF22) are most homologous to two E. chaffeensis and E. canis peptides, UN2 and UN4, with unknown function, as well as two E. ruminantium peptides, UN1 and UN2, whose function is unknown. The p28-19 505 bp sequence was a part of EEomp-1-16 (Table 1). Intergenic spaces between omp-1 genes ranged from 6 to 1,343 bp (Table 1). At the 5' half of each OMP cluster, 14 genes (un2 to EEomp-1-13 in E. ewingii) were linked by short intergenic spaces ranging from 6 to 26 bp (Table 1). Eight genes in the 3' half (EEomp-1-14 to EEomp-1-19) were connected by longer intergenic spaces ranging from 301 to 808 bp. Thus, features of the OMP cluster structure were conserved among E. ewingii, E. canis, E. chaffeensis, and E. ruminantium, with the exception of the opposite orientation of three genes, instead of one gene (E. canis and E. ruminantium) or two genes (E. chaffeensis) at the 3'end.

Figure 3:
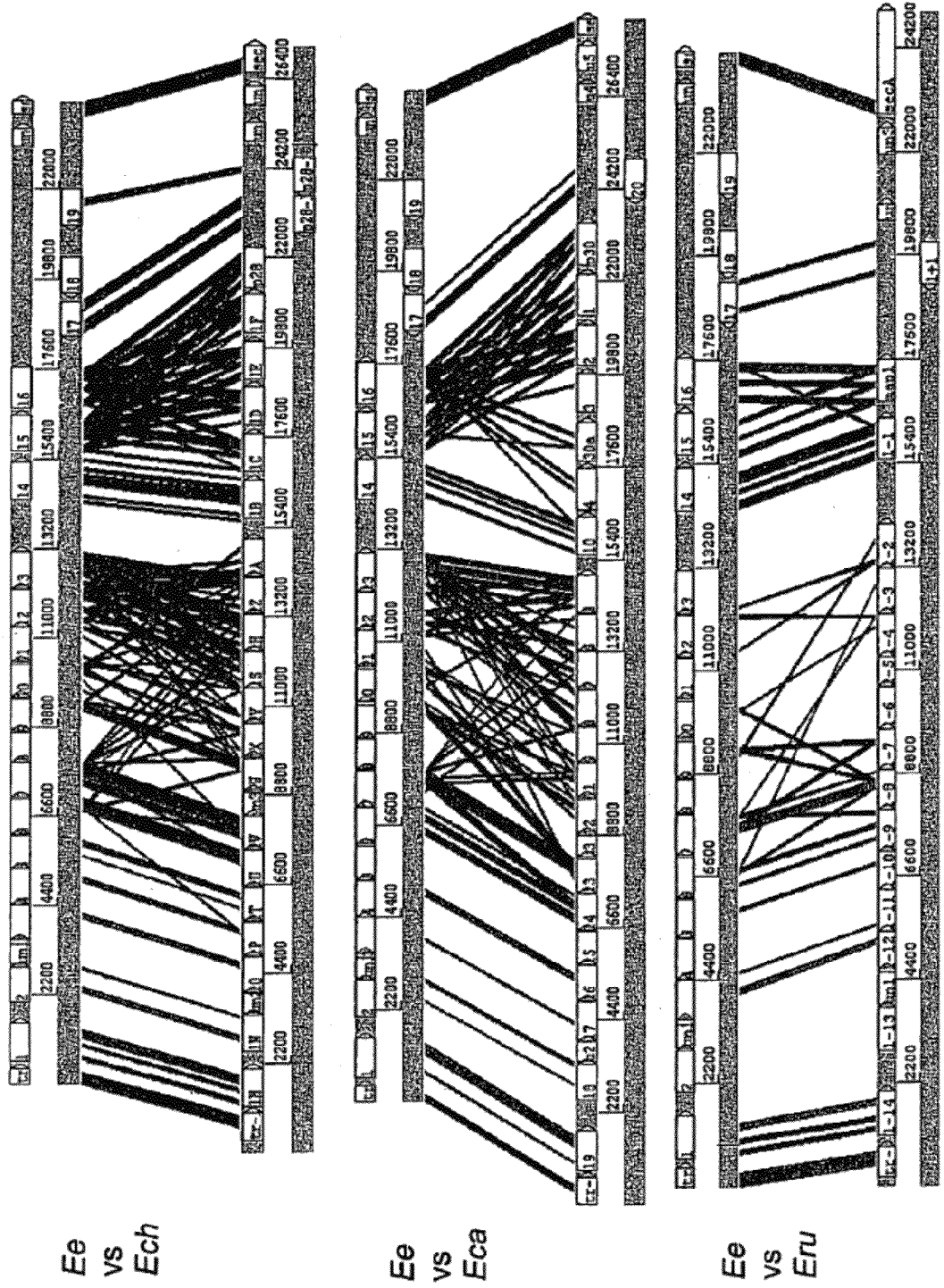
FIG. 3. Synteny analysis of the *E. ewingii* (Ee) omp-1 cluster relative to *E. chaffeensis* (Ech), *E. canis* (Eca), and *E. ruminantium* (Eru) by the Artemis comparison tool.
Figure 4:
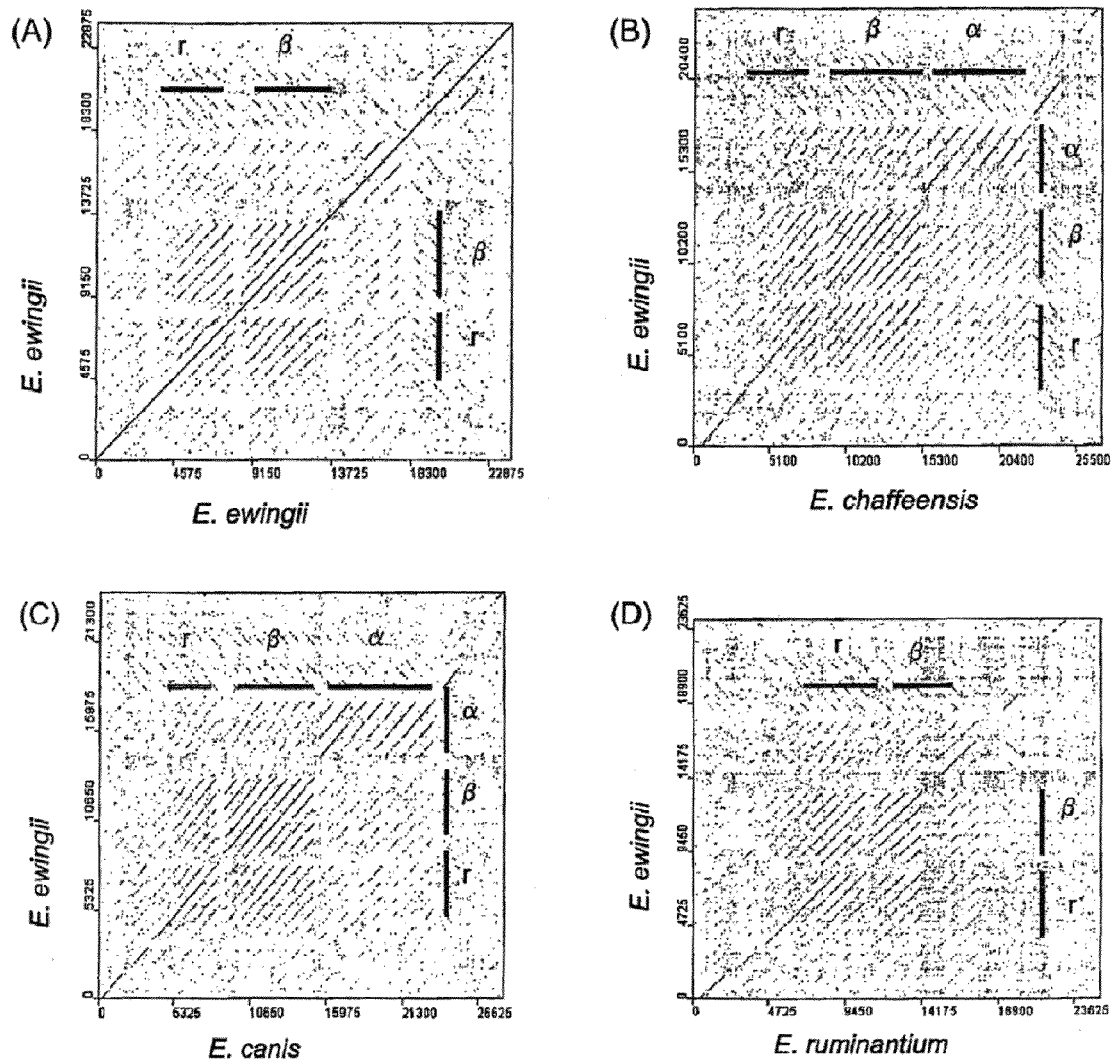
FIG. 4. Dot plot analysis of the *E. ewingii* omp-1 cluster (A), and the *E. ewingii* omp-1 cluster relative to *E. chaffeensis* (B), *E. canis* (C), or *E. ruminantium* (D). Repetitive regions consisting of multiple homologous DNA segments were analyzed using the web-based dot plot program (JDotter) (available at athena.bioc.uvic.ca/index.php. The window cutoff was set to the default. The α, β and γ repetitive regions described by Ohashi et al., 2001, *Infect Immun* 69:2083-2091, are marked by lines.

After removal of the signal peptide sequence, predicted molecular masses of mature E. ewingii OMP-is ranged from 25.1 to 31.3 kDa. The predicted signal peptides ranged from 21 to 32 amino acids. The predicted isoelectric points of the mature OMP-is were 5.03 to 9.80. Properties of the ORFs of the E. ewingii omp-1 cluster, including predicted signal peptide lengths, molecular masses of mature proteins and isoelectric points, are shown in Table 1.

omp-1/p28/map1 gene clusters display synteny at the 5' end. The synteny among entire OMP-1 gene clusters of E. ewingii and three related Ehrlichia species was analyzed by Artemis Comparison Tool, and the results are shown in FIG. 3. The genes at the 5' end of the omp-1 clusters were more highly conserved than genes in the central region or 3' end (FIG. 3). Previously we defined three repeat sequence regions, α, β and γ, in omp-1 clusters of E. chaffeensis and E. canis (Ohashi, N., et al. (2001) Infect Immun 69:2083-2091). The dot plot analysis of the E. ewingii omp-1 cluster and the dot plot between E. ewingii and E. ruminantium only revealed β and γ repeat regions (FIG. 4). The β repeat region in E. ruminantium was shorter than that of E. chaffeensis and E. canis. The dot plot analysis between E. ewingii and E. chaffeensis and between E. ewingii and E. canis showed three clear repeat regions, indicating that the α region is expanded in E. canis and E. chaffeensis.

Figure 5:
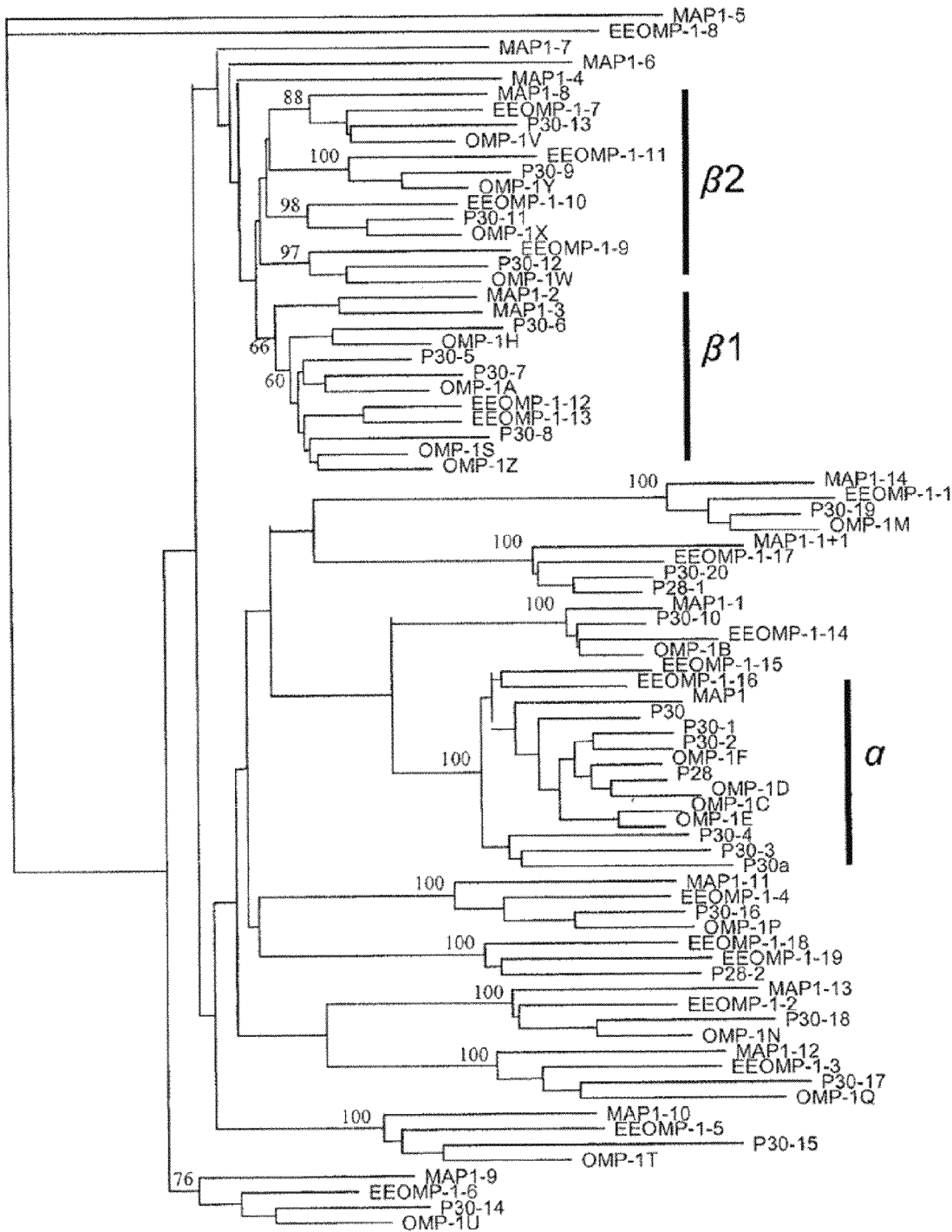
FIG. 5. Phylogram of OMP proteins of *E. ewingii*, *E. chaffeensis*, *E. canis*, and *E. ruminantium*. A total of 39 OMPs were segregated into 10 clusters with four or three *Ehrlichia* species each, but 40 remaining proteins were not. The tree was constructed using the Neighbor-Joining (NEIGHBOR program from PHYLIP) method based on the alignment generated with CLUSTAL V; 1000 bootstrap replications were performed. The nodes supported by bootstrap values greater than 60% are labeled. The OMPs encoded by the three repetitive regions in FIG. 4 are indicated by α, β1, and β2. Branch lengths are proportional to percent divergence. The calibration bar is on the lower left.

The phylogenetic analysis of all 79 OMPs of E. ewingii, E. chaffeensis, E. canis, and E. ruminantium is shown in FIG. 5. The previously defined α and β1 regions in the E. chaffeensis omp-1 cluster (Ohashi, N., et al. (2001) Infect Immun 69:2083-2091) encoded five (P28, OMP-1F, -1D, -1C, and -1E) and four (OMP-1H, -1A, -1S, and -1Z) proteins, respectively, and α and β1 regions in the E. canis p30 cluster encoded six (P30, P30-1, P30-2, P30-3, P30-4, and P30a and four (P30-6, P30-5, P30-7, and P30-8) proteins, respectively. However, in E. ewingii, the α and β1 regions each encoded two proteins (EEOMP-1-15, EEOMP-1-16 and EEOMP-1-12, EEOMP-1-13, respectively). In E. ruminantium, the α region encoded only one protein (MAP1) and the β1 region encoded two proteins (MAP1-2, MAP1-3) (FIG. 5)

EEOMP-1-8 and MAP1-5 were far removed from the remaining OMP-1s, raising the possibility that they do not belong to the OMP cluster (FIG. 5). EEOMP1-18 and EEOMP-1-19, which are encoded by genes in the reverse orientation, were clustered with P28-2, which is encoded by one of two reverse-oriented E. chaffeensis omp-1 genes. All proteins except α and β1 group proteins formed separate small clusters, including four proteins from each of the four Ehrlichia species. Each cluster of proteins is thus expected to share a common ancestor.

Previously reported 505-bp E. ewingii p28-1 sequences (GenBank accession numbers: AF287961, AF287962, AF287963, AF287964, AF287966) (Gusa, A. A., et al. (2001) J Clin Microbiol 39:3871-3876) were compared with corresponding sequences identified in the present study. The 505 bp begins at 16,918 bp and ends at 17,422 bp in the cluster, which corresponds to 75% of omp-1-16 (i.e., from 123 to 637 bp of the 849-bp omp-1-16 gene). The E. ewingii p28-1 sequences of a Missouri canine sample and an Oklahoma human sample (Gusa, A. A., et al. (2001) J Clin Mircobiol 39:3871-3876) were identical to the sequence obtained from the Ohio dog analyzed in the present study.

TABLE 8

Comparison of the most closely related E. chaffeensis and E. canis OMPs with E. ewingii OMPs

| E. ewingii OMP-1 paralogs | Most closely related Ehrlichia orthologs | % identity of orthologs |
|---|---|---|
| OMP-1-1 | OMP-1M | 66.2 |
| OMP-1-2 | OMP-1N | 51.5 |
| OMP-13 | OMP-1Q | 45.1 |
| OMP-1-4 | OMP-1P | 51.6 |
| OMP-1-5 | OMP-1T | 48.5 |
| OMP-1-6 | P30-14 | 60.9 |
| OMP-1-7 | OMP-1V | 67.4 |
| OMP-1-8 | MAP1-8 | 18.9 |
| OMP-1-9 | P30-12 | 51.6 |
| OMP-1-10 | P30-11 | 59.5 |
| OMP-1-11 | OMP-1Y | 55.8 |
| OMP-1-12 | P30-5 | 63.5 |
| OMP-1-13 | OMP-1H | 59.4 |
| OMP-1-14 | OMP-1B | 71.0 |
| OMP-1-15 | OMP-1E | 60.8 |
| OMP-1-16 | OMP-1F | 64.3 |

TABLE 8-continued

Comparison of the most closely related *E. chaffeensis* and *E. canis* OMPs with *E. ewingii* OMPs

| *E. ewingii* OMP-1 paralogs | Most closely related *Ehrlichia* orthologs | % identity of orthologs |
|---|---|---|
| OMP-1-17 | P28-1 | 69.4 |
| OMP-1-18 | P28-2 | 49.3 |
| OMP-1-19 | P28-2 | 47.1 |

*E. ewingii* OMP-1-specific peptide ELISA. Following our OMP-1 amino acid sequence alignment, repetitive sequence analysis, and phylogenic analysis results, we designed *E. ewingii* OMP-1-specific peptides for serologic tests. As OMP-1s share repetitive common or homologous amino acid sequences with OMP-1s of the same or different *Ehrlichia* sp., it is difficult to design recombinant proteins (>10 kDa) that provide *Ehrlichia* sp.-specific or gene-specific antigens. Also, to clone, express, and purify 19 recombinant OMP-1 proteins are cost and labor-prohibitive. Therefore, we designed 12-17-mer peptides specific to each of the 19 *E. ewingii* OMP-is. For this purpose, extracellular loops of the 19 *E. ewingii* OMP-1s were first predicted using the Posterior Decoding method of PRED-TMBB (http://bioinformatics.biol.uoa.gr/PRED-TMBB) (Bagos, P. G., et al. (2004) Nucleic Acids Res 32:W400-404). PRED-TMBB is a web server capable of predicting transmembrane strands and topology of β-barrel in OMPs of Gram-negative bacteria based on a Hidden Markov Model. The validity of these predictions is tested using non-homologous OMPs with structures known at atomic resolution according to the Conditional Maximum Likelihood criteria (Bagos, P. G., et al. (2004) Nucleic Acids Res 32:W400-404). Relatively highly antigenic and hydrophilic 12-17-mer peptide fragments located within one of the extracellular loops were chosen from each of the 19 EEOMP-1 amino acid sequences based on DNASTAR Protean analysis. Using the program BLAST, these peptide sequences were compared with the entire *E. ewingii* omp-1 locus and the *E. chaffeensis, E. canis* and *E. ruminantium* genome sequences to synthesize one peptide specific to each of the 19 EEOMP-1 (FIG. 8, Table 6).

Figure 6:
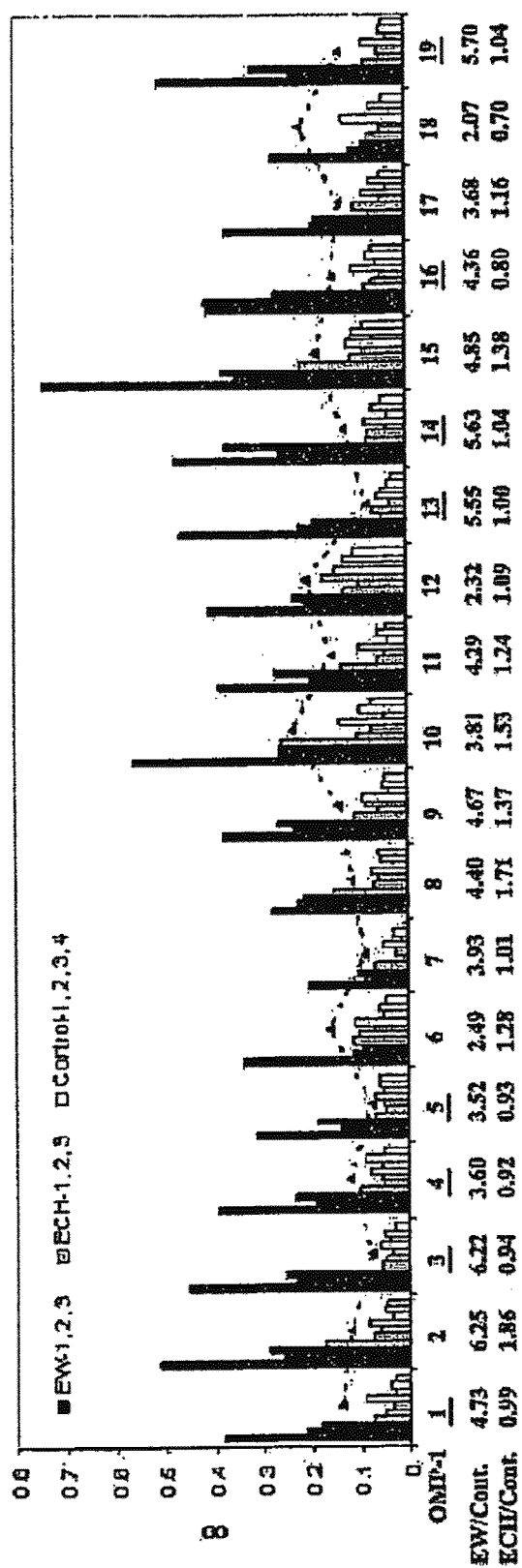
FIG. 6. ELISA analysis of *E. ewingii*- and *E. chaffeensis*-infected dogs with the 19 EEOMP-1 oligopeptides. Preinfection control and post-infection plasma from dogs were allowed to react with the 19 synthesized EEOMP-1 specific peptides. The y-axis shows $OD_{405nm}$-$OD_{492nm}$. A reaction was considered to be positive when the plasma from infected dogs yielded an $OD_{405nm}$-$OD_{492nm}$ value greater than the mean $OD_{405nm}$-$OD_{492nm}$ of preinfection control plasma+ three standard deviations (dashed line with closed triangles). Representative data of 3-5 assays is shown. Reactivity ratios of *E. ewingii*/control plasma (EW/Control) and *E. chaffeensis*/control plasma (ECH/Control) were calculated based on the averages of three EW-positive and three ECH-positive samples, respectively, to four negative control samples. EEOMP-1 peptides that showed good sensitivity and specificity for detecting *E. ewingii* infection are underlined.

Plasma from three dogs experimentally infected with *E. ewingii* and preinfection plasma from four dogs were then tested in ELISA containing the 19 EEOMP-1-specific peptides. Thirteen peptides (EEOMP-1-1, EEOMP-1-2, EEOMP-1-3, EEOMP-1-4, EEOMP-1-5, EEOMP-1-8, EEOMP-1-9, EEOMP-1-10, EEOMP-1-13, EEOMP-1-14, EEOMP-1-15, EEOMP-1-16, and EEOMP-1-19) were consistently recognized with plasma from three dogs experimentally infected with *E. ewingii* compared with preinfection dog plasma (FIG. 6).

As geographical distributions, vector ticks and animal reservoirs overlap between *E. ewingii* and *E. chaffeensis*, it is important to distinguish them by a simple assay. Therefore, we examined the immunological cross reactivity of these peptides with plasma from three dogs experimentally infected with *E. chaffeensis*. Among 13 EEOMP-1s specifically recognized in *E. ewingii*-infected dogs, EEOMP-1-8, EEOMP-1-10, and EEOMP-1-15 were recognized by one of three *E. chaffeensis*-infected dogs (FIG. 6). While more specimens need to be tested, the peptide-pin ELISA result suggests that of the remaining 10 EEOMP-1 peptides, 8 peptides (EEOMP-1-1, EEOMP-1-3, EEOMP-1-4, EEOMP-1-5, EEOMP-1-13, EEOMP-1-14, EEOMP-1-16, and EEOMP-1-19) serve as good candidate antigens for *E. ewingii* serodiagnosis based on high sensitivity (indicated by the ratio of *E. ewingii* plasma reactivity/control plasma reactivity) and good specificity (indicated by the ratio of *E. chaffeensis* plasma reactivity/control plasma reactivity, −1.00).

DISCUSSION

In the present study and for the first time, the entire 24-kb *E. ewingii* omp-1 locus containing 19 omp-1 genes was sequenced. As the only available source of *E. ewingii* DNA was a small amount of the infected dog blood specimen, we employed touchdown PCR. This method has been used previously to amplify a small amount of fragmented *Aegyptianella pullorum* DNA from archival paraffin sections on glass slides. Incorrect base calls resulting from amplification or sequencing errors have been minimized in the present study because large pools of PCR products were directly sequenced. In addition, multiple overlapping regions throughout the sequences ensure the reliability of sequencing results. So far, only a few *E. ewingii* genes, including 16S rRNA, groESL, p28-19, dsbA (GenBank Accession No. DQ902688), gltA (GenBank Accession No. DQ365879), and disulfide oxidoreductase have been reported. Applying a similar approach as used here, it would be possible to obtain DNA sequences of other genomic regions to further our understanding of this uncultivable emerging zoonotic pathogen.

Because *E. ewingii* infects granulocytes, the distinction between *E. ewingii* and a strain of *A. phagocytophilum* was unclear prior to the molecular era. However, in concordance with the 16S rRna and groESL sequence-based classification of this bacterium, our finding of the complete OMP-1 cluster structure flanked with trl and secA clearly demonstrated that *E. ewingii* belongs to the genus *Ehrlichia*. Synteny analysis suggests that the OMP clusters existed in a common ancestor of the present day four *Ehrlichia* species. Furthermore, the locus appears to have been partially scrambled as species evolved. The *E. ewingii* OMP-1 cluster has greater synteny with monocytotropic *E. chaffeensis* and *E. cards* than with the endotheliotropic *E. ruminantium*. It is possible that OMP-1s and host cell type specificity co-evolved.

The present study revealed 19 *E. ewingii* OMP-1 amino acid sequences and examples of 19 *E. ewingii* immunogenic amino acid sequences. Studies on *E. chaffeensis* have shown an important role for OMP-1/P28 outer membrane proteins in the stimulation of host immune response and protection of the host from infection. Immunization with recombinant P28 (one of the major outer membrane OMP-1/P28 family members) has been shown to protect mice from *E. chaffeensis* challenge. The monoclonal antibody against OMP-1 g (P28) mediates protection of SCID mice from *E. chaffeensis* fatal infection. While antibodies against a single OMP-1 protein confer partial protection, existence of multiple homologous surface proteins likely plays a role in the organism's evasion of host immune response. A recent proteomic study showed that 18 out of 21 *E. chaffeensis* OMP-1/P28 family proteins are indeed bacterial surface-exposed, supporting the idea of immunoevasion. The number of *E. ewingii* omp-1 genes found in the OMP-1 cluster (19 copies) was similar to that of *E. canis* (22 copies, but there is an additional locus with duplicates of three p30s) *E. chaffeensis* (22 copies), and *E. ruminantium* (16 copies). In addition, there is extensive diversification among omp-1 genes of *E. ewingii*, similar to other *Ehrlichia* spp., supporting the hypothesis that multiple omp-1/p28 paralogs present in *Ehrlichia* wp. are involved in immunoavoidance. Thus, theses studies suggest that incorporation of immunogenic peptides of multiple OMP-1s in the vaccine preparation may provide better protection against *Ehrlichia* infection than the use of a single OMP-1 in the vaccine.

Multiple OMP-1/P28 and P30 mRNAs are expressed by *E. chaffeensis* and *E. canis* during experimental infections of dogs with these bacteria. All 22 *E. chaffeensis* P28 recombinant antigens are recognized by sera from two dogs experimentally infected with *E. chaffeensis*. Similarly, the present results suggest all 19 EEOMP-1 peptides were recognized by the plasma from three *E. ewingii*-infected dogs. Thus, the lack of immunlogical cross-reactivity of *E. canis* and *E. chaffeensis* OMP-1/P28/P30 with plasma from human patients or dogs infected with *E. ewingii* in the previous studies is likely due to divergence of the amino acid sequences of the *E. ewingii* OMP-is from those of the *E. canis* and *E. chaffeensis* OMP-1/P28-P30 proteins expressed in cell culture. It is also most likely that in *E. ewingii* infected humans and dogs, different combinations of multiple OMP-1s are expressed at different stages of infection, and under different immune and health status of animals. Therefore, for serodiagnosis of *E. ewingii* infection in both humans and animals, use of a combination of EEOMP-1 peptides as serodiagnostic antigens is expected to provide more sensitive and more specific serodiagnosis with broader coverage than the use of a single EEOMP-1 antigen. Furthermore, the DNA sequence data also obtained in the present study should help refine diagnostic PCR for human and dog granulocytic ehrlichioses to make this direct test more reliable for all infective species.

The invention claimed is:

1. A method for detecting antibodies specific for *E. ewingii* (EE), comprising:
   (a) contacting a test sample with one or more isolated EE polypeptides under conditions that allow polypeptide/antibody complexes to form; and
   (b) assaying for the formation of a complex between antibodies in the test sample and the one or more EE polypeptides; wherein the formation of said complex is an indication that antibodies specific for *E. ewingii* are present in the test sample; and
   wherein at least one of the one or more EE polypeptides comprises an amino acid sequence that comprises:
   1) 6 or more consecutive amino acids of one or more amino acid sequences of variable region loops 1-4 of a mature OMP-1-19 protein encoded by nucleotide 21188-21967 of SEQ ID NO:1, or
   2) 6 or more consecutive amino acids of the amino acid sequence set forth in SEQ ID NO: 43, and
   wherein an anti-*E. ewingii* antibody has a specific binding affinity for the at least one of the one or more isolated EE polypeptides.

2. The method of claim 1, wherein the one or more amino acid sequences of the variable region loops 1-4 comprises 6 or more consecutive amino acids of an amino acid sequence that is set forth in SEQ ID NO: 155, SEQ ID NO: 173, SEQ ID NO: 191, SEQ ID NO:208 and/or SEQ ID NO:227.

3. The method of claim 1, wherein the one or more EE polypeptides comprises 6 or more consecutive amino acids of the amino acid sequence that is set forth in SEQ ID NO: 43.

4. The method of claim 1, wherein the one or more EE polypeptides comprises an amino acid sequence of a mature OMP-1-19 protein that comprises amino acids 24 to 282 of SEQ ID NO: 22.

5. The method of claim 1, wherein the one or more EE polypeptides comprises an amino acid sequence of a mature OMP-1-19 protein that consists of amino acids 24 to 282 of SEQ ID NO: 22.

6. The method of claim 1, wherein the one or more EE polypeptides further comprises an amino acid sequence that comprises 6 or more consecutive amino acids of a mature OMP-1-3 protein having the amino acid sequence from residue 24-284 of SEQ ID NO: 6, a mature OMP-1-10 protein having the amino acid sequence from residue 26 to 280 of SEQ ID NO: 13, a mature OMP-1-15 protein having the amino acid sequence from residue 26 to 278 of SEQ ID NO: 18, a mature OMP-1-16 protein having the amino acid sequence from residue 26 to 282 of SEQ ID NO: 19, or any combination thereof.

7. The method of claim 1, wherein the one or more EE polypeptides comprises an amino acid sequence that comprises 6 or more consecutive amino acids of a mature OMP-1-15 protein having the amino acid sequence from residue 26 to 278 of SEQ ID NO: 18, a mature OMP-1-19 protein having the amino acid sequence from residue 24 to 282 of SEQ ID NO: 22, or a combination thereof.

8. The method of claim 1, wherein the one or more EE polypeptides comprises an amino acid sequence that comprises 6 or more consecutive amino acids of a mature OMP-1-10 protein having the amino acid sequence from residue 26 to 280 of SEQ ID NO: 13, a mature OMP-1-15 protein having the amino acid sequence from residue 26 to 278 of SEQ ID NO: 18, a mature OMP-1-16 protein having the amino acid sequence from residue 26 to 282 of SEQ ID NO: 19, a mature OMP-1-19 protein having the amino acid sequence from residue 24 to 282 of SEQ ID NO: 22, or any combination thereof.

9. The method of claim 1, wherein the one or more EE polypeptides is operatively linked to an N-terminal or C-terminal peptide or tag.

10. The method of claim 1, wherein the one or more EE polypeptides is a recombinant form of the EE polypeptide(s).

11. The method of claim 1, wherein the isolated EE polypeptide is attached to a substrate.

12. The method of claim 11, wherein the substrate is a column, plastic dish, matrix, or membrane.

13. The method of claim 12, wherein the membrane comprises nitrocellulose.

14. The method of claim 1, wherein the test sample is untreated, or subjected to precipitation, fractionation, separation, or purification before combining with the EE polypeptide(s).

15. The method of claim 1, wherein the formation of a complex between antibodies in the test sample and the one or more EE polypeptides is detected by radiometric, calorimetric, or fluorometric means, or by size-separation or precipitation.

16. The method of claim 1, which is used in an assay format selected from the group consisting of a microtiter plate assay, a reversible flow chromatographic binding assay, an enzyme linked immunosorbent assay, a radioimmunoassay, a hemagglutination assay, a western blot assay, a fluorescence polarization immunoassay, an indirect immunofluorescence assay, a diffusion based Ouchterlony, and a rocket immunofluorescent assay.

17. The method of claim 1, wherein the formation of a complex between antibodies in the test sample and the one or more EE polypeptides is detected by addition of a secondary antibody that is coupled to a detectable tag.

18. The method of claim 17, wherein the detectable tag is an enzyme, a fluorophore, or a chromophore.

19. The method of claim 1, which is used to determine whether a subject is infected with E. ewingii.

20. The method of claim 1, wherein the subject is a human.

21. The method of claim 1, wherein the subject is an animal.

22. The method of claim 21, wherein the animal is a horse, a deer, a cattle, a pig, a sheep, a dog, a cat or a chicken.

23. The method of claim 1, wherein the one or more amino acid sequences of the variable region loops 1-4 comprises an amino acid sequence that is set forth in SEQ ID NO: 155, SEQ ID NO: 173, SEQ ID NO: 191, SEQ ID NO:208 and/or SEQ ID NO:227.

24. The method of claim 3, wherein the one or more EE polypeptides comprises the amino acid sequence that is set forth in SEQ ID NO:43.

25. The method of claim 6, wherein the one or more EE polypeptides further comprises an amino acid sequence that comprises 6 or more consecutive amino acids of the amino acid sequence set forth in SEQ ID NO: 27, the amino acid sequence set forth in SEQ ID NO: 34, the amino acid sequence set forth in SEQ ID NO: 39, the amino acid sequence set forth in SEQ ID NO: 40, or any combination thereof.

26. The method of claim 7, wherein the one or more EE polypeptides comprises an amino acid sequence that comprises 6 or more consecutive amino acids of the amino acid sequence set forth in SEQ ID NO: 39, the amino acid sequence set forth in SEQ ID NO: 43, or a combination thereof.

27. The method of claim 8, wherein the one or more EE polypeptides comprises an amino acid sequence that comprises 6 or more consecutive amino acids of the amino acid sequence set forth in SEQ ID NO: 34, the amino acid sequence set forth in SEQ ID NO: 39, the amino acid sequence set forth in SEQ ID NO: 40, the amino acid sequence set forth in SEQ ID NO: 43, or any combination thereof.

* * * * *